United States Patent
Frazier et al.

(10) Patent No.: US 10,669,336 B2
(45) Date of Patent: *Jun. 2, 2020

(54) THERAPEUTIC CD47 ANTIBODIES

(71) Applicant: Arch Oncology, Inc., St. Louis, MO (US)

(72) Inventors: William A. Frazier, St. Louis, MO (US); Pamela T. Manning, Chesterfield, MO (US); Gerhard Frey, St. Louis, MO (US); Hwai Wen Chang, St. Louis, MO (US)

(73) Assignee: Arch Oncology, Inc., St. Louis, MO (US)

( * ) Notice: Subject to any disclaimer, the term of this patent is extended or adjusted under 35 U.S.C. 154(b) by 130 days.

This patent is subject to a terminal disclaimer.

(21) Appl. No.: 15/723,523

(22) Filed: Oct. 3, 2017

(65) Prior Publication Data

US 2018/0051081 A1   Feb. 22, 2018

Related U.S. Application Data

(63) Continuation of application No. 14/737,053, filed on Jun. 11, 2015, now abandoned, which is a continuation-in-part of application No. 14/302,348, filed on Jun. 11, 2014, now abandoned, which is a continuation-in-part of application No. PCT/US2013/074766, filed on Dec. 12, 2013.

(60) Provisional application No. 61/833,691, filed on Jun. 11, 2013, provisional application No. 61/736,301, filed on Dec. 12, 2012.

(51) Int. Cl.
*C07K 16/28* (2006.01)
*A61K 39/00* (2006.01)

(52) U.S. Cl.
CPC ...... *C07K 16/2803* (2013.01); *C07K 16/2896* (2013.01); *A61K 2039/505* (2013.01); *C07K 2317/24* (2013.01); *C07K 2317/33* (2013.01); *C07K 2317/71* (2013.01); *C07K 2317/73* (2013.01); *C07K 2317/75* (2013.01); *C07K 2317/76* (2013.01); *C07K 2317/92* (2013.01)

(58) Field of Classification Search
CPC ............ C07K 16/2803; C07K 16/2896; C07K 16/00–468

See application file for complete search history.

(56) References Cited

U.S. PATENT DOCUMENTS

| | | |
|---|---|---|
| 6,261,839 B1 | 7/2001 | Multhoff |
| 7,514,229 B2 | 4/2009 | Jamieson |
| 7,531,643 B2 | 5/2009 | Fukushima |
| 7,696,325 B2 | 4/2010 | Fukushima |
| 8,101,719 B2 | 1/2012 | Kikuchi |
| 8,236,313 B2 | 8/2012 | Isenberg |
| 8,562,997 B2 | 10/2013 | Jaiswal |
| 8,728,476 B2 | 5/2014 | Van |
| 8,758,750 B2 | 6/2014 | Weissman |
| 8,759,495 B2 | 6/2014 | Boghaert |
| 8,951,527 B2 | 2/2015 | Isenberg |
| 9,017,675 B2 | 4/2015 | Liu |
| 9,045,541 B2 | 6/2015 | Eckelman |
| 9,221,908 B2 | 12/2015 | Frazier |
| 9,382,320 B2 | 7/2016 | Liu |
| 9,518,116 B2 | 12/2016 | Frazier |
| 9,518,117 B2 | 12/2016 | Frazier |
| 10,239,945 B2 | 3/2019 | Manning |
| 10,259,873 B2 | 4/2019 | Frazier |
| 2001/0041670 A1 | 11/2001 | Simantov |
| 2003/0108546 A1 | 6/2003 | Fukushima |
| 2004/0213792 A1 | 10/2004 | Clemmons |
| 2006/0088522 A1 | 4/2006 | Boghaert |
| 2007/0111238 A1 | 5/2007 | Jamieson |

(Continued)

FOREIGN PATENT DOCUMENTS

| AU | 2014201010 | 3/2014 |
|---|---|---|
| BY | 6782 C1 | 3/2005 |

(Continued)

OTHER PUBLICATIONS

Giusti, A. et al., "Somatic Diversification of S107 from an Antiphosphocholine to an Anti-DNA Autoantibody is Due to a Single Base Change in its Heavy Chain Variable Region", Proc Natl Acad Sci USA., 84(9):2926-30, (1987).

Mariuzza, R. et al., "The Structural Basis of Antigen-Antibody Recognition", Annu Rev Biophys Biophys Chem., 16:139-59, (1987).

Rudikoff, S. et al., "Single Amino Acid Substitution Altering Antigen-Binding Specificity", Proc Natl Acad Sci U S A, 79(6):1979-83, (1982).

U.S. Appl. No. 15/345,691; Final Office Action dated Jul. 12, 2018; 14 pages.

U.S. Appl. No. 15/820,054; Non-Final Office Action dated Jul. 20, 2018; 33 pages.

(Continued)

*Primary Examiner* — Jessica H Roark

(74) *Attorney, Agent, or Firm* — Dennis A. Bennett; Charles H. Rexer, Jr.

(57) ABSTRACT

Provided are monoclonal antibodies and antigen-binding fragments thereof that bind to CD47 of multiple mammalian species, block the binding of SIRPalpha and TSP1 to CD47, promote phagocytosis of susceptible cancer cells, and reverse TSP1 inhibition of nitric oxide signaling, as well as monoclonal antibodies and antigen binding fragments thereof that compete with the former for binding to CD47 and that exhibit similar biological activities. Also provided are combinations of any of the foregoing. Such antibody compounds are variously effective in 1) treating tissue ischemia and ischemia-reperfusion injury (IRI) in the setting of organ preservation and transplantation, pulmonary hypertension, sickle cell disease, myocardial infarction, stroke, and other instances of surgery and/or trauma in which IRI is a component of pathogenesis; 2) in treating autoimmune and inflammatory diseases; and 3) as anti-cancer agents for treating susceptible cancer cells, promoting their phagocytic uptake and clearance.

2 Claims, 12 Drawing Sheets

Specification includes a Sequence Listing.

(56) References Cited

U.S. PATENT DOCUMENTS

| | | |
|---|---|---|
| 2010/0173382 A1 | 7/2010 | Boghaert |
| 2010/0203559 A1 | 8/2010 | Ester |
| 2011/0117085 A1 | 5/2011 | Rotem-Yehudar |
| 2011/0177064 A1 | 7/2011 | Whiteman |
| 2013/0142786 A1 | 6/2013 | Liu |
| 2013/0224188 A1 | 8/2013 | Eckelman |
| 2014/0065169 A1 | 3/2014 | Jaiswal |
| 2014/0140989 A1 | 5/2014 | Eckelman |
| 2014/0161799 A1 | 6/2014 | Frazier |
| 2014/0161825 A1 | 6/2014 | Jaiswal |
| 2014/0199308 A1 | 7/2014 | Van |
| 2014/0294765 A1 | 10/2014 | Cojocaru |
| 2014/0363442 A1 | 12/2014 | Frazier |
| 2014/0369924 A1 | 12/2014 | Weissman |
| 2015/0030600 A1 | 1/2015 | Marks |
| 2015/0274826 A1 | 10/2015 | Frazier |
| 2016/0130336 A1 | 5/2016 | Lai |
| 2016/0137733 A1 | 5/2016 | Frazier |
| 2016/0137734 A1 | 5/2016 | Frazier |
| 2016/0289326 A1 | 10/2016 | Chao |
| 2017/0151282 A1 | 6/2017 | Discher |
| 2017/0283498 A1 | 10/2017 | Frazier |
| 2018/0057592 A1 | 3/2018 | Frazier |
| 2018/0142019 A1 | 5/2018 | Manning |
| 2018/0171014 A1 | 6/2018 | Manning |
| 2019/0112373 A1 | 4/2019 | Manning |
| 2019/0248892 A1 | 8/2019 | Frazier |
| 2019/0309066 A1 | 10/2019 | Manning |

FOREIGN PATENT DOCUMENTS

| | | |
|---|---|---|
| CN | 103665165 | 3/2014 |
| EP | 0256654 A2 | 2/1988 |
| EP | 1035132 | 9/2000 |
| EP | 1693385 | 8/2006 |
| EP | 2111869 | 10/2009 |
| JP | 2007008895 | 1/2007 |
| WO | 1999012973 | 3/1999 |
| WO | 199940940 | 8/1999 |
| WO | 199940940 A1 | 8/1999 |
| WO | 1999040940 | 8/1999 |
| WO | 200105968 A1 | 1/2001 |
| WO | 2003050295 | 6/2003 |
| WO | 2004096133 A2 | 11/2004 |
| WO | 2008043072 A2 | 4/2008 |
| WO | 2008060785 | 5/2008 |
| WO | 2008060785 A2 | 5/2008 |
| WO | 2009091547 | 7/2009 |
| WO | 2009091601 | 7/2009 |
| WO | 2009131453 A1 | 10/2009 |
| WO | 2011083140 | 7/2011 |
| WO | 2011143624 | 11/2011 |
| WO | 2011143624 A2 | 11/2011 |
| WO | 2013119714 | 8/2013 |
| WO | 2014087248 | 6/2014 |
| WO | 2014093678 | 6/2014 |
| WO | 2014093678 A2 | 6/2014 |
| WO | 2014149477 A1 | 9/2014 |
| WO | 2014093678 A3 | 11/2014 |
| WO | 2014123580 | 10/2015 |
| WO | 2015191861 A1 | 12/2015 |
| WO | 2017049251 A2 | 3/2017 |
| WO | 2018075960 | 4/2018 |
| WO | 2018175790 | 9/2018 |

OTHER PUBLICATIONS

Winkler, K. et al., "Changing the Antigen Binding Specificity by Single Point Mutations of an Anti-p24 (HIV-1) Antibody", J Immunol., 165(8):4505-14, (2000).

International Application No. PCT/US2013/074766; International Preliminary Report on Patentability, dated Jun. 16, 2015; 08 pages.

International Application No. PCT/US2015/035345; International Preliminary Report on Patentability, dated Dec. 15, 2016; 04 pages.

International Application No. PCT/US2015/035345; International Search Report and Written Opinion of the International Search Authority; dated Oct. 15, 2015; 06 pages.

International Application No. PCT/US2016/052383; International Preliminary Report on Patentability, dated Mar. 20, 2018; 11 pages.

International Application No. PCT/US2016/052383; International Search Report and Written Opinion of the International Search Authority, dated Mar. 1, 2017; 16 pages.

International Application No. PCT/US2017/057716; International Search Report and Written Opinion of the International Search Authority, dated Feb. 21, 2018; 22 pages.

U.S. Appl. No. 14/104,007; Examiner Initiated Interview Summary dated Aug. 14, 2015; 01 page.

U.S. Appl. No. 14/104,007; Notice of Allowance dated Aug. 14, 2015; 14 pages.

U.S. Appl. No. 14/302,348; Affidavit-traversing rejections or objections rule 132 dated Feb. 1, 2017; 17 pages.

U.S. Appl. No. 14/302,348; Final Office Action dated Mar. 13, 2017; 11 pages.

U.S. Appl. No. 14/302,348; Non-Final Office Action dated Aug. 1, 2016; 15 pages.

U.S. Appl. No. 14/302,348; Notice of Allowance dated Oct. 6, 2017; 02 pages.

U.S. Appl. No. 14/302,348; Notice of Allowance dated Sep. 27, 2017; 05 pages.

U.S. Appl. No. 14/737,053; Affidavit-traversing rejections or objections rule 132 dated Feb. 2, 2017; 17 pages.

U.S. Appl. No. 14/737,053; Final Office Action dated Mar. 14, 2017; 11 pages.

U.S. Appl. No. 14/737,053; Non-Final Office Action dated Aug. 2, 2016; 15 pages.

U.S. Appl. No. 14/737,053; Notice of Allowance dated Sep. 25, 2017; 05 pages.

U.S. Appl. No. 14/940,751; Notice of Allowance dated Aug. 4, 2016; 10 pages.

U.S. Appl. No. 14/940,755; Notice of Allowance dated Aug. 4, 2016; 10 pages.

U.S. Appl. No. 15/345,691; Non-Final Office Action dated Dec. 6, 2017; 16 pages.

U.S. Appl. No. 15/820,054; Application as filed dated Nov. 21, 2017; 106 pages.

U.S. Appl. No. 15/871,802; Application as filed dated Jan. 15, 2018; 170 pages.

U.S. Appl. No. 15/871,802; Non-Final Office Action dated Mar. 1, 2018; 15 pages.

Abcam anti-CD47 antibody [EPR 4150(2)] ab108415, available at www.abcam.com/cd47-antibody-epr41502-ab108415.html (last visited Jul. 20, 2015).

Ahmed et al., "Targeting Cd47 as an Apoptotic Trigger of Human Lung Carcinoma Tumors", Amer Inst Chem Eng. 2005 mtg abstract #457d.

Avent et al., "Monoclonal antibodies that recognize different membrane proteins that are deficient in Rh null, human erythrocytes", Biochem. J. (1988) 251, 499-505.

Blazar B R et al., CD47 (integrin-associated protein) engagement of dendritic cell and macrophage counterreceptors is required to prevent the clearance of donor lymphohematopoietic cells, Journal Exp. Med., vol. 194, No. 4, Aug. 20, 2001 541-549.

Brown et al., 'Integrin-associated Protein: A 50-kD Plasma Membrane Antigen Physically and Functionally Associated with Integrins', The Journal of Cell Biology, vol. 111, Dec. 1, 1990, pp. 2785-2794.

Campbell et al., 'An Ovarian Tumor Marker with Homology to Vaccinia Virus Contains an IgV-like Region and Multiple Transmembrane Domains', Cancer Research, vol. 52, Oct. 1. 1992, pp. 5416-5420.

Chao MP et al., Anti-CD47 antibody synergizes with Rituximab to promote phagocytosis and eradicate non-Hodgkin lymphoma, Cell 2010 plus supplemental info.

Chao, et al. , "The CD47-SIRP alpha Pathway in Cancer Immune Evasion and Potential Therapeutic Implications," Curr Opin Immunol., Apr. 2012; 24(2): 225-232.

(56) References Cited

OTHER PUBLICATIONS

Danielsen et al., 'Dysregulation of CD47 and the ligands thrombospondin 1 and 2 in multiple myeloma', British Journal of Haematology, 138, 756-760. (2007).
Edris B et al., Antibody therapy targeting the CD47 protein is effective in a model of aggressive metastatic leiomyosarcoma, PNAS, 2012, 6656-6661.
Epenetos et al., 'Monoclonal antibodies for imaging and therapy', Br. J. Cancer (1989), 59, 152-155.
Florian et al., 'Evaluation of normal and neoplastic human mast cells for expression of CD172a (SIRP-alpha), CD47, and SHP-1', Journal of Leukocyte Biology vol. 77, Jun. 2005.
Frazier WA et al., Therapeutic CD47 Antibodies, Vasculox Inc., US20140161799A1, Examiner initiated interview summary, Aug. 14, 2015.
Frazier WA et al., Therapeutic CD47 Antibodies, Vasculox Inc., US20140161799A1, Notice of Allowance, dated Aug. 14, 2015.
Frazier WA et al., Therapeutic CD47 Antibodies, Vasculox Inc., WO0140293678A1, International Preliminary Report on Patentability Chapter I, dated Jun. 16, 2015.
Gardai et al., 'Cell-Surface Calreticulin Initiates Clearance of Viable or Apoptotic Cells through trans-Activation of LRP on the Phagocyte', Cell, vol. 123, 321-334, Oct. 21, 2005.
Gresham et al., 'A Novel Member of the Integrin Receptor Family Mediates Arg-Gly-Asp-stimulated Neutrophil Phagocytosis', The Journal of Cell Biology, vol. 108, May 1989, 1935-1943.
Han et al., 'CD47, a Ligand for the Macrophage Fusion Receptor, Participates in Macrophage Multinucleation', The Journal of Biological Chemistry, vol. 275, No. 48, Issue of Dec. 1, pp. 37984-37992, 2000.
International Search Report, PCT Application No. PCT/US2013/074766, dated Oct. 10, 2014, 6 pgs.
Isenberg, J. et al., Treatment of Liver Ischemia/Reperfusion Injury by Limiting Thrombospondin-1/CD47 Signaling, Surgery 144(5), 752-761, 2008.
Jaiswal S et al., CD47 is upregulated on circulating hematopoietic stem cells and leukemia cells to avoid phagocytosis, Jul. 24, 2009, Cell 138, 271-285.
Jiang P et al., Integrin-associated Protein Is a Ligand for the P84 Neural Adhesion Molecule, The Journal of Biological Chemistry, vol. 274, No. 2, Issue of Jan. 8, 1999, pp. 559-562.
Kaiser et al., 'Expression of insulin-like growth factor receptors I and II in normal human lung and in lung cancer', J Cancer Res Clin Oncol (1993) 119:665-668.
Kenemans, P., CA 125 and OA 3 as target antigens for immunodiagnosis and immunotherapy in ovarian cancer, European Journal of Obstetrics & Gynecology and Reproductive Biology, 36 (1990) 221-238.
Kikuchi et al., "A bivalent single-chain Fv fragment against CD47 induces apoptosis for leukemic cells", Biochemical and Biophysical Research Communications 315 (2004) 912-918.
Kikuchi et al., "Apoptosis inducing bivalent single-chain antibody fragments against CD47 showed antitumor potency for multiple myeloma", Leukemia Research 29 (2005) 445-450.
Knapp et al., 'CD Antigens 1989', Blood, vol. 74, No. 4 (Sep.), 1989: pp. 1448-1450.
Lamy et al., 'CD47 and the 19 kDa Interacting Protein-3 (BNIP3) in T Cell Apoptosis', The Journal of Biological Chemistry, vol. 278, No. 26, Issue of Jun. 27, pp. 23915-23921, 2003.
Latour et al., "Bidirectional Negative Regulation of Human T and Dendritic Cells by CD47 and Its Cognate Receptor Signal-Regulator Protein-alpha: Down-Regulation of IL-12 Responsiveness and Inhibition of Dendritic Cell Activation", The Journal of Immunology, 2001, 167: 2547-2554.
Legrand, et al., 'Functional CD47/Signal Regulatory Protein Alpha (SIRP(alpha)) Interaction is Required for Optimal Human T- and Natural Killer—(NK) Cell Homeostasis in Vivo', Proceedings of the National Academy of Sciences, vol. 108, No. 32, 2001, pp. 13224-13229.
Lindberg et al., 'Molecular Cloning of Integrin-associated Protein: An Immunoglobulin Family Member with Multiple Membrane-spanning Domains Implicated in CvB3-dependent Ligand Binding', The Journal of Cell Biology, vol. 123, No. 2, Oct. 1993, 485-496.
Lindberg et al., 'Rh-related Antigen CD47 Is the Signal-transducer Integrin-associated Protein', The Journal of Biological Chemistry, vol. 269, No. 3, Issue of Jan. 21, pp. 1567-1570, 1994.
Lindberg F P et al., Decreased resistance to bacterial infection and granulocyte defects in IAP-deficient mice, Science New Series, vol. 274, No. 5288 (Nov. 1, 1996), pp. 795-798.
Liu et al., 'Signal Regulatory Protein (SIRP-alpha), a Cellular Ligand for CD47, Regulates Neutrophil Transmigration', The Journal of Biological Chemistry, vol. 277, No. 12, Issue of Mar. 22, pp. 10028-10036, 2002.
Liu, A. 'Differential Expression of Cell Surface Molecules in Prostate Cancer Cells', Cancer Research 60, 3429-3434, Jul. 1, 2000.
Majeti R et al., CD47 is an adverse prognostic factor and therapeutic antibody target on human acute myeloid leukemia stem cells, Cell 2009, 138, p. 286-299.
Majeti, "Monoclonal antibody therapy directed against human acute myeloid leukemia stem cells.", ONCOGENE, (Nov. 15, 2010), vol. 30, No. 9, pp. 1009-1019, XP055094665.
Manna et al, 'The Mechanism of CD47-Dependent Killing of T Cells: Heterotrimeric Gi-Dependent Inhibition of Protein Kinase A', The Journal of Immunology, (Apr. 1, 2003), vol. 170, No. 7, doi:10.4049/jimmunol.170.7.3544, ISSN 0022-1767, pp. 3544-3553, XP055116597.
Manna et al., 'CD47 Mediates Killing of Breast Tumor Cells via Gi-Dependent Inhibition of Protein Kinase A', Cancer Research 64, 1026-1036, Feb. 1, 2004.
Mateo et al., 'CD47 ligation induces caspase-independent cell death in chronic lymphocytic leukemia', Nature Medicine, vol. 5, No. 11, Nov. 1999, pp. 1277-1284.
Mawby et al., "Isolation and characterization of CD47 glycoprotein: a multispanning membrane protein which is the same as integrin-associated protein (IAP) and the ovarian tumour marker OA3", Biochem. J. (1994) 304, 525-530.
Motegi et al., "Role of CD47-SHPS-1 system in regulation of cell migration", The EMBO Journal vol. 22, No. 11, pp. 2634-2644, 2003.
"Chimeric Anti-Human Type VII Collagen Immunoglobulin G1 [Synthetic Construct]", Database Protein, NCBI, Genbank Accession No. ACN 59874.1, (Nov. 20, 2009).
"Chain L, Diels Alder Catalytic Antibody Germline Precursor", Database Protein, NCBIM Genbank Accession No. 1A4J_L, (Oct. 10, 2012).
Nishiyama et al., 'Overexpression of Integrin-associated Protein (CD47) in Rat Kidney Treated with a Renal Carcinogen, Ferric Nitrilotriacetate', Jpn. J. Cancer Res. 88, 120-128, Feb. 1997.
Obeid M et al., Ecto-calreticulin in immunogenic chemotherapy, Immunological Reviews 2007, vol. 220: 22-34.
Oldenborg PA et al., CD47-signal regulatory protein alpha (SIRPa) regulates Fcgamma and complement receptor-mediated phagocytosis, Journal Exp Med, vol. 193, No. 7, Apr. 2, 2001 p. 855-861.
Per-Arne Oldenborg et al., 'Role of CD47 as a Marker of Self on Red Blood Cells', Science vol. 288, Jun. 16, 2000, pp. 2051-2054.
Pettersen et al., 'CD99 Signals Caspase-Independent T Cell Death', The Journal of Immunology, 2001, 166: 4931-4942.
Pettersen et al., "CD47 Signals T Cell Death", The Journal of Immunology, 1999, 162: 7031-7040.
Poels et al., "Monoclonal Antibody Against Human Ovarian Tumor-Associated Antigens", JNCI, vol. 76, 1986, 781-791.
Rebres et al., "Novel CD47-Dependent Intercellular Adhesion Modulates Cell Migration", Journal of Cellular Physiology, 205:182-193 (2005).
Roberts, D. et al., The Matricellular Protein Thrombospondin-1 Globally Regulates Cardiovascular Function and Responses to Stress via CD47, Matrix Biology 31(3), 162-169, 2012.
Sagawa et al., 'A new disulfide-linked dimer of a single-chain antibody fragment against human CD47 induces apoptosis in lymphoid malignant cells via the hypoxia inducible factor-1 alpha pathway', Cancer Sci, Jun. 2011, vol. 102, No. 6, 1208-1215.

(56) References Cited

OTHER PUBLICATIONS

Samani et al., 'The Role of the IGF System in Cancer Growth and Metastasis: Overview and Recent Insights', Endocrine Reviews 28(1):20-47, (2007).
Seiffert et al., 'Human Signal-Regulatory Protein Is Expressed on Normal, but Not on Subsets of Leukemic Myeloid Cells and Mediates Cellular Adhesion Involving Its Counterreceptor CD47' Blood, vol. 94, No. 11 (Dec. 1), 1999: pp. 3633-3643.
Subramanian et al., 'Species- and cell type-specific interactions between CD47 and human SIRP-alpha', Blood, Mar. 15, 2006, vol. 107, No. 6.
Tamoto et al., 'Gene-Expression Profile Changes Correlated with Tumor Progression and Lymph Node Metastasis in Esophageal Cancer', Clinical Cancer Research, vol. 10, 3629-3638, Jun. 1, 2004.
Ticchioni et al., "Integrin-Associated Protein (CD47) Is a Comitogenic Molecule on CD3-Activated Human T Cells", The Journal of Immunology, 1997, 158: 677-684.
Uno et al., "Antitumor activity of a monoclonal antibody against CD47 in xenograft models of human leukemia", Oncology Reports 17: 1189-1194, 2007.
US20140161799A1, Examiner Initiated Interview Summary, dated Aug. 14, 2015, 1 page.
Van Ravenswaay Claasen et al., "Analysis of Production, Purification, and Cytolytic Potential of Bi-Specific Antibodies Reactive With Ovarian-Carcinoma-Associated Antigens and the T-Cell Antigen CD3", Int. J. Cancer: 55, 128-136 (1993).
Vernon-Wilson et al., 'CD47 is a ligand for rat macrophage membrane signal regulatory protein SIRP (0X41) and human Sirp alpha 1', Eur. J. Immunol. 2000. 30: 2130-2137.
Willingham S B et al., The CD47-signal regulatory protein alpha (SIRPa) interaction is a therapeutic target for human solid tumors, PNAS, Apr. 24, 2012, vol. 109, No. 17, p. 6662-6667.
WO2015191861, International Search Report and Written Opinion, dated Oct. 15, 2015, 6 pages.
Yamao T et al., Negative regulation of platelet clearance and of the macrophage phagocytic response by the transmembrane glycoprotein SHPS-1, Journal of Biological Chemistry, vol. 277, No. 42, Issue of Oct. 18, 2002, pp. 39833-9.
Zhan et al., 'Global gene expression profiling of multiple myeloma, monoclonal gammopathy of undetermined significance, and normal bone marrow plasma cells', Blood, Mar. 1, 2002, z vol. 99, No. 5.
Chao, M. et al., "Anti-CD47 antibody synergizes with rituximab to promote phagocytosis and eradicate non-Hodgkin lymphoma", Cell, 142(5):699-713, (2010).
Cioffi, M. et al., "Inhibition of CD47 Effectively Targets Pancreatic Cancer Stem Cells via Dual Mechanisms", Clinical Cancer Research, 21(10):2325-37, (2015).
Hanahan, D. et al., "The hallmarks of cancer", Cell, 100(1):57-70, (2000).
Johnstone, R. et al., "Apoptosis: A Link between Cancer Genetics and Chemotherapy", Cell, 108:153-64, (2002).
Liu, J. et al., "Pre-Clinical Development of a Humanized Anti-CD47 Antibody with Anti-Cancer Therapeutic Potential", PLoS One, 10(9):e0137345, (2015).
McKenzie, S. et al., "Apoptosis evasion: the role of survival pathways in prostate cancer progression and therapeutic resistance.", J. Cell Biochem., 97(1):18-32, (2006).
Weiskopf, K. et al., "CD47-blocking immunotherapies stimulate macrophage-mediated destruction of small-cell lung cancer", J Clin Invest., 126(7):2610-20, (2016).
Written Submission of Opposition to EP2242512 Following Preliminary Opinion on Behalf of James Roger Wilding, (Jun. 27, 2018); 13 pages.
Written Submission of Opposition to EP2242512 Following Preliminary Opinion on Behalf of Opponent Avidity IP LTD, (dated Jun. 27, 2018); 29 pages.
Written Submission of Opposition to EP2242512 Following Preliminary Opinion on Behalf of Surface Oncology, Inc., (dated Jun. 27, 2018); 21 pages.
Written Submission of Opposition to EP2242512 Following Preliminary Opinion on Behalf of the Board of Trustees of the Leland Stanford Junior University, (dated Jun. 27, 2018); 16 pages.
Written Submission of Opposition to EP2242512 Following Preliminary Opinion on Behalf of Tioma Therapeutics, Inc., (Jun. 27, 2018); 21 pages.
Zhao, X. et al., "CD47-signal regulatory protein—(SIRP) interactions form a barrier for antibody-mediated tumor cell destruction", Proceedings of the National Academy of Sciences, 108(45)18342-7, (2011).
U.S. Appl. No. 16/223,009; Non-Final Office Action dated Feb. 8, 2019; 17 pages.
U.S. Appl. No. 16/271,513; Application as filed, dated Feb. 8, 2019; 105 pages.
U.S. Appl. No. 16/288,957; Application as filed dated Feb. 28, 2019; 63 pages.
Chao, M. et al., "Therapeutic Antibody Targeting of CD47 Eliminates Human Acute Lymphoblastic Leukemia", Cancer Res., 71(4):1374-84, (2011).
International Application No. PCT/US2017/057716; International Preliminary Report on Patentability, dated Apr. 23, 2019; 16 pages.
Majeti, R. et al., "CD47 is an Adverse Prognostic Factor and Therapeutic Antibody Target on Human Acute Myeloid Leukemia Stem Cells", Cell, 138(2):286-99, (2009).
U.S. Appl. No. 15/345,691; Notice of Allowance, dated Nov. 28, 2018; 18 pages.
U.S. Appl. No. 15/820,054; Notice of Allowance, dated Nov. 7, 2018; 16 pages.
U.S. Appl. No. 15/871,802; Examiner-Initiated Interview Summary dated Oct. 26, 2018; 2 pages.
U.S. Appl. No. 15/871,802; Final Office Action dated Oct. 26, 2018; 32 pages.
U.S. Appl. No. 16/223,009; Application as filed, dated Dec. 17, 2018; 148 pages.
Akewanlop, et al., "Phagocytosis of Breast Cancer Cells Mediated by Anti-Muc-1 Monoclonal Antibody, DF3, and its Bispecific Antibody", Cancer Research, vol. 61, (May 15, 2001).
Almagro, J. et al., Humanization of antibodies, Frontiers in Bioscience 13, 1619-1633, Jan. 1, 2008.
Almagro, J. et al., Progress and Challenges in the Design and Clinical Development of Antibodies for Cancer Therapy, Front Immunol. Jan. 4, 2018;8:1751.
Baker, Monya, "Cancer and Stem Cells: Beckman Conference", Nature Reports Stem Cells, (Mar. 13, 2008).
Brown, Eric J. et al., "Integrin-Associated Protein (CD47) and it's Ligands", Trends in Cell Biology, 11(3):130-5, (2001).
Cameron, C. et al., "Myxoma Virus M128L is Expressed as a Cell Surface CD47-Like Virulence Factor that Contributes to the Downregulation of Macrophage Activation in Vivo", Virology, vol. 337, pp. 55-67 (2005).
Carter, P., Potent antibody therapeutics by design, Nature Reviews Immunology, vol. 6, 343-357, May 2006.
Chao, et al., "Targeting CD47 Eliminates Human Acute Myeloid Leu-Kemia Stem Cells", May 14, 2008, cited Jan. 3, 2017.
Chen, Thomas T. et al., "Expression and Activation of Signal Regulatory Protein Alpha on Astrocytomas", Cancer Research, 64:117-27, (2004).
Cooper, G.M., "The Development and Causes of Cancer", The Cell: A Molecular Approach, (2000), cited Jan. 3, 2017.
Finlay WJ etr al., Natural and man-made V-gene repertoires for antibody discovery, Front Immunol. Nov. 15, 2012;3:342.
Galluzzi, Lorenzo, et al, "Immunogenic cell death in cancer and infectious disease," Nature Reviews, Immunology, vol. 17, Feb. 2017.
Head, et al., "Ligation of CD47 Mediates Phosphatidylserine Expression on Erythrocytes and a Concomitant Loss of Viability in Vitro", British Journal of Haematology, 130:788-90, (2005).
Henson, Peter M. et al., "Apoptotic Cell Removal", Current Biology, 11:R795-R805, (2011).
Humana Press Inc., "Handbook of Cancer Vaccines", Humana Press Inc., 2004.

(56) References Cited

OTHER PUBLICATIONS

International Search Report and Written Opinion of the International Searching Authority for PCT/2017/057716 dated Feb. 21, 2018.
Isenberg, Jeff et al., "Differential Interactions of Thrombospondin-1,-2 and -4 with CD47 and Effects on cGMP Signaling and Ischemic Injury Response", The Journal of Biological Chemistry, vol. 284, No. 2, (Jan. 9, 2009).
Jamieson, Catriona et al., "Increased Expression of CD47 is a Constant Marker in Mouse and Human Myeloid Leukemias", Blood, vol. 106, (2005).
Kim, Min Jung et al., "Association of CD47 with Natural Killer Cell-Mediated Cytotoxicty of Head-and-Neck Squamous Cell Carcinoma Lines", Tumor Biology, 29:28-34, (2008).
Kroemer, G. et al., "Classificatio of Cell Death", Cell Death Difference, 16(1):3-11, (Jan. 2009).
L'Esperance, Sylvain et al., "Gene Expression Profiling of Paired Ovarian Tumors Obtained Prior to and Following Adjuvant Chemotherapy: Molecular Signatures of Chemoresistant Tumors", International Journal of Oncology, 29:5-24, (2006).
Majeti, et al., "Acute Myeloid Leukemia—Therapy, Excluding Transplantation", Blood, vol. 112, (Nov. 16, 2008).
Majeti, Ravindra et al., "CD47 is an Independent Prognostic Factor and Therapeutic Antibody Target on Human Acute Myeloid Leukemia Stem Cells", Blood, vol. 112, (2008).
Mughal, Tariq I. et al., "Understanding Leukemias, Lymphomas and Myelomas", Taylor & Francis, pp. 47-48, 53, (2006).
Munn, "Phagocytosis of Tumor Cells by Human Monocytes Cultured in Recombinant Macrophage Colony-Stimulating Factor", J. Exp. Med., vol. 172, (Jul. 1990).
National Cancer Institute, "Cancer Classification", cited Jan. 3, 2017.
Oldenborg, et al., "Role of CD47 in Erythroid Cells and in Autoimmunity", Leukemia & Lymphoma, 45(7):1319-27, (2004).
Olsson, et al., "Platelet Homeostasis is Regulated by Platelet Expression of CD47 Under Normal Conditions and in Passive Immune Thromocytopenia", Blood, 105(9):3577-82, (May 1, 2005).
Pietsch, et al., "Anti-Leukemic Activity and Tolerability of Anti-Human CD47 Monoclonal Antibodies", American Association of Cancer Research Abstract 2470, (Jan. 2017).
Raetz, Elizabeth A. et al., "Gene Expression Profiling Reveals Intrinsic Differences Between T-cell Acute Lymphoblastic Leukemia and T-cell Lymphoblastic Lymphoma", Pediatr. Bllod Cancer, (47):130-40, (2006).
Reichert, Janice M., "Marketed Therapeutic Antibodies Compendium", mAbs, Lades Bioscience, 4(3):413-5, (2012).
Roitt A. et al., Immunology (Published by "Mir" Publishing House, Moscow, 2000, p. 110-111.
Science Daily, "Scientists Discover New Way to Distinguish Self from Other", cited Jan. 22, 2017.
Sick E et al., CD47 update: a multifaceted actor in the tumour microenvironment of potential therapeutic interest, Br J Pharmacol. Dec. 2012;167(7): pp. 1415-1430.
Singer M. et al., Genes and Genomes (Published by "Mir" Publishing House, Moscow, 1998, vol. 1, p. 63-64.
Sonderegger S et al., Interleukin (IL)11 mediates protein secretion and modification in human extravillous trophoblasts, Hum Reprod. Oct. 2011;26(10):2841-9.
Soto-Pantoja, et al., "Inhibitory Signaling Through Signal Regulatory Protein-A is Not Sufficient to Explain the Antitumor Activities of CD47 Antibodies", PNAS, 109:E2842, (2012).
Strome, Scott et al., "A Mechanistic Perspective of Monoclonal Antibodies in Cancer Therapy Beyond Target-Related Effects", The Oncologist, vol. 12, (2007).
Submissions dated Jul. 21, 2011 filed during prosecution of U.S. Appl. No. 12/321,215, a continuation-in-part of U.S. Appl. No. 11/528,890.
Submissions of James Poole Limited of Dec. 22, 2016 on EP2282772.

Subramanian S. et al., Phylogenetic divergence of CD47 interactions with human signal regulatory protein alpha reveals locus of species specificity. Implications for the binding site, J Biol Chem. Jan. 19, 2007;282(3):1805-1818.
Takizawa, Hitoshi et al., "Macrophage Tolerance: CD47-SIRP-Alpha-Mediated Signals Matter", Nature Immunology, (8):1287-9, (2007).
Trounson, "Stem Cells, Plasticity and Cancer—Uncomfortable Bed Fellows", Development, vol. 131, (2004).
Van Beek, Ellen M. et al., "Signal Regulatory Proteins in the Immune System", J. Immunol., ISSN: 175:7781-7, (Dec. 2005).
Van Den Berg, Timo K. et al., "Innate Immune 'Self' Recognition: A Role for CD47-SIRPa Interactions in Hemotopoietic Stem Transplantation", Trends Immunology, 29(5):203-6, (Apr. 3, 2008).
Vermeer DW et al., Radiation-induced loss of cell surface CD47 enhances immune-mediated clearance of human papillomavirus-positive cancer, Int J Cancer. Jul. 2013;133(1):120-9.
Wang, Hui et al., "Attenuation of Phagocytosis of Xenogeneic Cells by Manipulating CD47", Blood, vol. 109, No. 2, (Jan. 15, 2007).
Weiskopf and Weissman, "Macrophages are Critical Effectors of Antibody Therapies for Cancer", mAbs, vol. 7, No. 2, (2015).
Weiskopf, et al., "Engineered SIRPa Variants as Immunotherapeutic Adjuvants to Anticancer Antibodies", Science, 341:88-91, (Jul. 5, 2013).
Weissman, Irving et al., "The E. Donnall Thomas Lecture; Normal and Neoplastic Stem Cells", Biol. Blood Marrow Transplant, (2008).
Wikipedia, "Cancer Immunotherapy", cited Jan. 8, 2017.
Wikipedia, "Monoclonal Antibody", cited Jan. 8, 2017.
Yang Y et al., Wogonin induced calreticulin/annexin Al exposure dictates the immunogenicity of cancer cells in a PERK/AKT dependent manner, PLoS One. 2012;7(12):e50811.
Zhao, et al., "Is Targeting of CD47-SIRPa Enough for Treating Hematopoietic Malignancy", Blood, 119:4333-4, (May 3, 2012).
Zipin-Roitman A et al., CXCL10 promotes invasion-related properties in human colorectal carcinoma cells, Cancer Res. Apr. 1, 2007;67(7):3396-405.
Anonymous, "Tumor-Toxic CD47 mAb Therapy for Leukemia: A Proof of Concept Study", retreived online at https://www.sbir.gov/print/sbirsearch/detail/677077 on Oct. 1, 2017; 3 pages, (2013).
Declaration of Henry Shelton Earp, date of signatory Dec. 21, 2016, with Exhibits HSE-1 and HSE-2; pages.
Declaration of Kristy Richards, date of signatory Dec. 20, 2016, with Exhibit KR-1; 31 pages.
Declaration of Ravindra Majeti, date of signatory Dec. 16, 2016, with exhibits RM-1 to RM-3 (D3, D3a, D3b); 86 pages.
European Patent Application No. 2240780; Register Extract, date of retrieval Nov. 26, 2016; 3 pages.
European Patent Application No. 2282772; Register Extract, date of retrieval Jan. 25, 2017; 2 pages.
International Application No. PCT/US2009/000319; Assignment Data Extract, date of retrieval Nov. 21, 2016; 1 page.
International Application No. PCT/US2009/000319; Patent Assignment Abstract of Title, date of retrieval Apr. 20, 2016; 1 page.
International Application No. PCT/US2009/000319; PCT Request form, dated Jan. 15, 2009; 6 pages.
International Application No. PCT/US2018/023860; International Preliminary Report on Patentability, dated Oct. 3, 2019; 10 pages.
International Application No. PCT/US2018/023860; International Search Report and Written Opinion of the International Searching Authority, dated Jun. 20, 2018; 14 pages.
Liu, X. et al., "CD47 Blockade Triggers T Cell-Mediated Destruction of Immunogenic Tumors", Nat Med., 21 (10):1209-15, (2015).
U.S. Appl. No. 15/723,534; Non-Final Office Action, dated Jul. 5, 2019; 54 pages.
U.S. Appl. No. 15/871,802; Non-Final Office Action, dated Jun. 4, 2019; 31 pages.
U.S. Appl. No. 16/223,009; Final Office Action, dated Jun. 4, 2019; 27 pages.
U.S. Appl. No. 16/271,513; Non-Final Office Action, dated Sep. 9, 2019; 28 pages.
U.S. Appl. No. 16/452,432; Application as filed, dated Jun. 25, 2019; 163 pages.

(56) References Cited

OTHER PUBLICATIONS

U.S. Appl. No. 61/011,324; Excerpt from the USPTO website regarding Assignments Data, date of retrieval Nov. 15, 2016; 1 page.
U.S. Appl. No. 61/189,786; Excerpt from the USPTO website regarding Assignments Data, date of retrieval Nov. 15, 2016; 1 page.

```
                         SEQUENCE LISTING

<160> NUMBER OF SEQ ID NOS: 124

<210> SEQ ID NO 1
<211> LENGTH: 16
<212> TYPE: PRT
<213> ORGANISM: Artificial Sequence
<220> FEATURE:
<223> OTHER INFORMATION: light chain complementarity determining region

<400> SEQUENCE: 1

Arg Ser Ser Gln Ser Leu Val His Ser Asn Gly Asn Thr Tyr Leu His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: light chain complementarity determining region

<400> SEQUENCE: 2

Lys Val Ser Tyr Arg Phe Ser
1               5

<210> SEQ ID NO 3
<211> LENGTH: 9
<212> TYPE: PRT
<213> ORGANISM: Artificial Sequence
<220> FEATURE:
<223> OTHER INFORMATION: light chain complementarity determining region

<400> SEQUENCE: 3
```

Ser Gln Asn Thr His Val Pro Arg Thr
1               5

<210> SEQ ID NO 4
<211> LENGTH: 10
<212> TYPE: PRT
<213> ORGANISM: Artificial Sequence
<220> FEATURE:
<223> OTHER INFORMATION: heavy chain complementarity determining region

<400> SEQUENCE: 4

Gly Tyr Thr Phe Thr Asn Tyr Tyr Val Phe
1               5                   10

<210> SEQ ID NO 5
<211> LENGTH: 17
<212> TYPE: PRT
<213> ORGANISM: Artificial Sequence
<220> FEATURE:
<223> OTHER INFORMATION: heavy chain complementarity determining region

<400> SEQUENCE: 5

Asp Ile Asn Pro Val Asn Gly Asp Thr Asn Phe Asn Glu Lys Phe Lys
1               5                   10                  15

Asn

<210> SEQ ID NO 6
<211> LENGTH: 7
<212> TYPE: PRT
<213> ORGANISM: Artificial Sequence
<220> FEATURE:
<223> OTHER INFORMATION: heavy chain complementarity determining region

<400> SEQUENCE: 6

Gly Gly Tyr Thr Met Asp Tyr
1               5

<210> SEQ ID NO 7
<211> LENGTH: 106
<212> TYPE: PRT
<213> ORGANISM: Artificial Sequence
<220> FEATURE:
<223> OTHER INFORMATION: light chain variable region

<400> SEQUENCE: 7

Asp Val Val Met Thr Gln Thr Pro Leu Ser Leu Ser Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Arg Thr Phe Gly Gln Gly
            100                 105

<210> SEQ ID NO 8
<211> LENGTH: 106
<212> TYPE: PRT

<213> ORGANISM: Artificial Sequence
<220> FEATURE:
<223> OTHER INFORMATION: light chain variable region

<400> SEQUENCE: 8

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105
```

<210> SEQ ID NO 9
<211> LENGTH: 106
<212> TYPE: PRT
<213> ORGANISM: Artificial Sequence
<220> FEATURE:
<223> OTHER INFORMATION: light chain variable region

<400> SEQUENCE: 9

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Ser Gln Asn
                85                  90                  95

Thr His Val Pro Arg Thr Phe Gly Gln Gly
            100                 105
```

<210> SEQ ID NO 10
<211> LENGTH: 106
<212> TYPE: PRT
<213> ORGANISM: Artificial Sequence
<220> FEATURE:
<223> OTHER INFORMATION: light chain variable region

<400> SEQUENCE: 10

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Arg Thr Phe Gly Gln Gly
            100                 105
```

<210> SEQ ID NO 11
<211> LENGTH: 106
<212> TYPE: PRT
<213> ORGANISM: Artificial Sequence
<220> FEATURE:
<223> OTHER INFORMATION: light chain variable region

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Tyr Arg Phe Ser Gly Ile Pro
 50                  55                  60

Ala Arg Phe Ser Gly Ser Gly Ser Gly Thr Glu Phe Thr Leu Thr Ile
 65                  70                  75                  80

Ser Ser Leu Gln Ser Glu Asp Phe Ala Val Tyr Tyr Cys Ser Gln Asn
                 85                  90                  95

Thr His Val Pro Arg Thr Phe Gly Gln Gly
            100                 105
```

<210> SEQ ID NO 12
<211> LENGTH: 106
<212> TYPE: PRT
<213> ORGANISM: Artificial Sequence
<220> FEATURE:
<223> OTHER INFORMATION: light chain variable region

<400> SEQUENCE: 12

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Tyr Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Arg Thr Phe Gly Gln Gly
            100                 105
```

<210> SEQ ID NO 13
<211> LENGTH: 106
<212> TYPE: PRT
<213> ORGANISM: Artificial Sequence
<220> FEATURE:
<223> OTHER INFORMATION: light chain variable region

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Tyr Arg Phe Ser Gly Ile Pro
    50                  55                  60

Ala Arg Phe Ser Gly Ser Gly Ser Gly Thr Glu Phe Thr Leu Thr Ile
65                  70                  75                  80

Ser Ser Leu Gln Ser Glu Asp Phe Ala Val Tyr Tyr Cys Ser Gln Asn
                85                  90                  95

Thr His Val Pro Arg Thr Phe Gly Gln Gly
            100                 105

<210> SEQ ID NO 14
<211> LENGTH: 106
<212> TYPE: PRT
<213> ORGANISM: Artificial Sequence
<220> FEATURE:
<223> OTHER INFORMATION: light chain variable region

<400> SEQUENCE: 14

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

<210> SEQ ID NO 15
<211> LENGTH: 106
<212> TYPE: PRT
<213> ORGANISM: Artificial Sequence
<220> FEATURE:
<223> OTHER INFORMATION: light chain variable region

<400> SEQUENCE: 15

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Ser Gln Asn
            85                  90                  95

Thr His Val Pro Arg Thr Phe Gly Gln Gly
            100                 105

<210> SEQ ID NO 16
<211> LENGTH: 106
<212> TYPE: PRT
<213> ORGANISM: Artificial Sequence
<220> FEATURE:
<223> OTHER INFORMATION: light chain variable region

<400> SEQUENCE: 16

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
            35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
            85                  90                  95

Thr His Val Pro Arg Thr Phe Gly Gln Gly
            100                 105

<210> SEQ ID NO 17
<211> LENGTH: 106
<212> TYPE: PRT
<213> ORGANISM: Artificial Sequence
<220> FEATURE:
<223> OTHER INFORMATION: light chain variable region

<400> SEQUENCE: 17

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
            85                  90                  95

Thr His Val Pro Arg Thr Phe Gly Gln Gly
            100                 105

<210> SEQ ID NO 18
<211> LENGTH: 106
<212> TYPE: PRT
<213> ORGANISM: Artificial Sequence
<220> FEATURE:
<223> OTHER INFORMATION: light chain variable region

<400> SEQUENCE: 18
```

```
Glu Ile Val Leu Thr Gln Ser Pro Ala Thr Leu Ser Val Ser Pro Gly
1               5                   10                  15

Glu Arg Ala Thr Leu Ser Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Glu Ala Glu Asp Ala Ala Thr Tyr Tyr Cys Ser Gln Asn
            85                  90                  95

Thr His Val Pro Arg Thr Phe Gly Gln Gly
            100                 105
```

<210> SEQ ID NO 19
<211> LENGTH: 106
<212> TYPE: PRT
<213> ORGANISM: Artificial Sequence
<220> FEATURE:
<223> OTHER INFORMATION: light chain variable region

<400> SEQUENCE: 19

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
            85                  90                  95

Thr His Val Pro Arg Thr Phe Gly Gln Gly
            100                 105
```

<210> SEQ ID NO 20
<211> LENGTH: 106
<212> TYPE: PRT
<213> ORGANISM: Artificial Sequence
<220> FEATURE:
<223> OTHER INFORMATION: light chain variable region

<400> SEQUENCE: 20

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
            85                  90                  95
```

```
Thr His Val Pro Arg Thr Phe Gly Gln Gly
            100                 105

<210> SEQ ID NO 21
<211> LENGTH: 106
<212> TYPE: PRT
<213> ORGANISM: Artificial Sequence
<220> FEATURE:
<223> OTHER INFORMATION: light chain variable region

<400> SEQUENCE: 21

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

<210> SEQ ID NO 22
<211> LENGTH: 106
<212> TYPE: PRT
<213> ORGANISM: Artificial Sequence
<220> FEATURE:
<223> OTHER INFORMATION: light chain variable region

<400> SEQUENCE: 22

Ala Ile Gln Leu Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Ser Gln Asn
                85                  90                  95

Thr His Val Pro Arg Thr Phe Gly Gln Gly
            100                 105

<210> SEQ ID NO 23
<211> LENGTH: 106
<212> TYPE: PRT
<213> ORGANISM: Artificial Sequence
<220> FEATURE:
<223> OTHER INFORMATION: light chain variable region

<400> SEQUENCE: 23

Ala Ile Gln Leu Thr Gln Ser Pro Ser Ser Leu Ser Ala Ser Val Gly
1               5                   10                  15
```

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

<210> SEQ ID NO 24
<211> LENGTH: 106
<212> TYPE: PRT
<213> ORGANISM: Artificial Sequence
<220> FEATURE:
<223> OTHER INFORMATION: light chain variable region

<400> SEQUENCE: 24

Ala Ile Gln Leu Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

<210> SEQ ID NO 25
<211> LENGTH: 106
<212> TYPE: PRT
<213> ORGANISM: Artificial Sequence
<220> FEATURE:
<223> OTHER INFORMATION: light chain variable region

<400> SEQUENCE: 25

Glu Ile Val Leu Thr Gln Ser Pro Ala Thr Leu Ser Val Ser Pro Gly
1               5                   10                  15

Glu Arg Ala Thr Leu Ser Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Glu Ala Glu Asp Ala Ala Thr Tyr Tyr Cys Ser Gln Asn
                85                  90                  95

Thr His Val Pro Arg Thr Phe Gly Gln Gly
            100                 105

```
<210> SEQ ID NO 26
<211> LENGTH: 106
<212> TYPE: PRT
<213> ORGANISM: Artificial Sequence
<220> FEATURE:
<223> OTHER INFORMATION: light chain variable region

<400> SEQUENCE: 26
```

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

```
<210> SEQ ID NO 27
<211> LENGTH: 106
<212> TYPE: PRT
<213> ORGANISM: Artificial Sequence
<220> FEATURE:
<223> OTHER INFORMATION: light chain variable region

<400> SEQUENCE: 27
```

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

```
<210> SEQ ID NO 28
<211> LENGTH: 106
<212> TYPE: PRT
<213> ORGANISM: Artificial Sequence
<220> FEATURE:
<223> OTHER INFORMATION: light chain variable region

<400> SEQUENCE: 28
```

Ala Ile Gln Leu Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

```
Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Arg Thr Phe Gly Gln Gly
            100                 105
```

<210> SEQ ID NO 29
<211> LENGTH: 106
<212> TYPE: PRT
<213> ORGANISM: Artificial Sequence
<220> FEATURE:
<223> OTHER INFORMATION: light chain variable region

<400> SEQUENCE: 29

```
Glu Ile Val Leu Thr Gln Ser Pro Ala Thr Leu Ser Val Ser Pro Gly
 1               5                  10                  15

Glu Arg Ala Thr Leu Ser Cys Arg Ser Ser Gln Ser Leu Val His Ser
                 20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
 50                  55                  60

Ser Arg Phe Ser Gly Ser Gly Ser Gly Thr Asp Phe Thr Phe Thr Ile
 65                  70                  75                  80

Ser Ser Leu Glu Ala Glu Asp Ala Ala Thr Tyr Tyr Cys Ser Gln Asn
                 85                  90                  95

Thr His Val Pro Arg Thr Phe Gly Gln Gly
            100                 105
```

<210> SEQ ID NO 30
<211> LENGTH: 106
<212> TYPE: PRT
<213> ORGANISM: Artificial Sequence
<220> FEATURE:
<223> OTHER INFORMATION: light chain variable region

<400> SEQUENCE: 30

```
Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Val His Ser
                 20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Arg Thr Phe Gly Gln Gly
            100                 105
```

<210> SEQ ID NO 31

```
<211> LENGTH: 106
<212> TYPE: PRT
<213> ORGANISM: Artificial Sequence
<220> FEATURE:
<223> OTHER INFORMATION: light chain variable region

<400> SEQUENCE: 31

Ala Ile Gln Leu Thr Gln Ser Pro Ser Ser Leu Ser Ala Ser Val Gly
1               5                   10                  15

Asp Arg Val Thr Ile Thr Cys Arg Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Ser Gln Asn
                85                  90                  95

Thr His Val Pro Arg Thr Phe Gly Gln Gly
            100                 105

<210> SEQ ID NO 32
<211> LENGTH: 319
<212> TYPE: DNA
<213> ORGANISM: Artificial Sequence
<220> FEATURE:
<223> OTHER INFORMATION: light chain variable region

<400> SEQUENCE: 32
gatgttgtta tgacccaaac tccactctcc ctgtctgtca gtcttggaga tcaagcctcc      60
atctcttgca gatctagtca gagccttgta cacagtaatg gaaacaccta tttacattgg     120
tacctgcaga agccaggcca gtctccaaag ctcctgatct acaaagtttc ctaccgattt     180
tctggggtcc cagacaggtt cagtggcagt ggatcaggga cagatttcac actcaagatc     240
agcagagtgg aggctgagga tctgggagtt tatttctgct ctcaaaatac acatgttcct     300
cggacgttcg gccaaggag                                                  319

<210> SEQ ID NO 33
<211> LENGTH: 318
<212> TYPE: DNA
<213> ORGANISM: Artificial Sequence
<220> FEATURE:
<223> OTHER INFORMATION: light chain variable region

<400> SEQUENCE: 33
gatattgtga tgacccagac tccactctcc ctgcccgtca cccctggaga gccggcctcc      60
atctcctgca gatctagtca gagccttgta cacagtaatg gaaacaccta tttacattgg     120
tatcagcaga aaccagggaa agctcctaag ctcctgatct ataaagtttc ctaccgattt     180
tctggggtcc cagacaggtt cagtggcagt gggtcaggca ctgatttcac actgaaaatc     240
agcagggtgg aggctgagga tgttggagtt tattactgtt ctcaaaatac acatgttcct     300
cggacgttcg gccaaggg                                                   318

<210> SEQ ID NO 34
<211> LENGTH: 318
<212> TYPE: DNA
<213> ORGANISM: Artificial Sequence
<220> FEATURE:
```

<223> OTHER INFORMATION: light chain variable region

<400> SEQUENCE: 34

| | |
|---|---|
| gatgttgtga tgactcagtc tccactctcc ctgcccgtca cccttggaca gccggcctcc | 60 |
| atctcctgca gatctagtca gagccttgta cacagtaatg aaacaccta tttacattgg | 120 |
| taccagcaga aacctggcca ggctcccagg ctcctcatct ataaagtttc ctaccgattt | 180 |
| tctggggtcc catcaaggtt cagcggcagt ggatctggga cagaattcac tctcaccatc | 240 |
| agcagcctgc agcctgatga ttttgcaact tattactgtt ctcaaaatac acatgttcct | 300 |
| cggacgttcg gccaaggg | 318 |

<210> SEQ ID NO 35
<211> LENGTH: 318
<212> TYPE: DNA
<213> ORGANISM: Artificial Sequence
<220> FEATURE:
<223> OTHER INFORMATION: light chain variable region

<400> SEQUENCE: 35

| | |
|---|---|
| gatgttgtga tgactcagtc tccactctcc ctgcccgtca cccttggaca gccggcctcc | 60 |
| atctcctgca gatctagtca gagccttgta cacagtaatg aaacaccta tttacattgg | 120 |
| tatcagcaga aaccagggaa agctcctaag ctcctgatct ataaagtttc ctaccgattt | 180 |
| tctggggtcc cagacaggtt cagtggcagt gggtcaggca ctgatttcac actgaaaatc | 240 |
| agcagggtgg aggctgagga tgttggagtt tattactgtt ctcaaaatac acatgttcct | 300 |
| cggacgttcg gccaaggg | 318 |

<210> SEQ ID NO 36
<211> LENGTH: 318
<212> TYPE: DNA
<213> ORGANISM: Artificial Sequence
<220> FEATURE:
<223> OTHER INFORMATION: light chain variable region

<400> SEQUENCE: 36

| | |
|---|---|
| gacatccaga tgacccagtc tccatcctcc ctgtctgcat ctgtaggaga cagagtcacc | 60 |
| atcacttgca gatctagtca gagccttgta cacagtaatg aaacaccta tttacattgg | 120 |
| tacctgcaga agccagggca gtctccacag ctcctgatct ataaagtttc ctaccgattt | 180 |
| tctgggatcc cagccaggtt cagtggcagt gggtctggga cagagttcac tctcaccatc | 240 |
| agcagcctgc agtctgaaga ttttgcagtt tattactgtt ctcaaaatac acatgttcct | 300 |
| cggacgttcg gccaaggg | 318 |

<210> SEQ ID NO 37
<211> LENGTH: 318
<212> TYPE: DNA
<213> ORGANISM: Artificial Sequence
<220> FEATURE:
<223> OTHER INFORMATION: light chain variable region

<400> SEQUENCE: 37

| | |
|---|---|
| gatattgtga tgacccagac tccactctcc ctgcccgtca cccctggaga gccggcctcc | 60 |
| atctcctgca gatctagtca gagccttgta cacagtaatg aaacaccta tttacattgg | 120 |
| tacctgcaga agccagggca gtctccacag ctcctgatct ataaagtttc ctaccgattt | 180 |
| tctggggtcc cagacaggtt cagtggcagt gggtcaggca ctgatttcac actgaaaatc | 240 |
| agcagggtgg aggctgagga tgttggagtt tattactgtt ctcaaaatac acatgttcct | 300 |

```
cggacgttcg gccaaggg                                                   318

<210> SEQ ID NO 38
<211> LENGTH: 318
<212> TYPE: DNA
<213> ORGANISM: Artificial Sequence
<220> FEATURE:
<223> OTHER INFORMATION: light chain variable region

<400> SEQUENCE: 38
gacatccaga tgacccagtc tccatcctcc ctgtctgcat ctgtaggaga cagagtcacc     60
atcacttgca gatctagtca gagccttgta cacagtaatg aaacaccta tttacattgg    120 tacctgcaga agccagggca gtctccacag ctcctgatct ataaagtttc ctaccgattt    180
tctgggatcc cagccaggtt cagtggcagt gggtctggga cagagttcac tctcaccatc    240
agcagcctgc agtctgaaga ttttgcagtt tattactgtt ctcaaaatac acatgttcct    300
cggacgttcg gccaaggg                                                   318

<210> SEQ ID NO 39
<211> LENGTH: 318
<212> TYPE: DNA
<213> ORGANISM: Artificial Sequence
<220> FEATURE:
<223> OTHER INFORMATION: light chain variable region

<400> SEQUENCE: 39
gatattgtga tgacccagac tccactctcc ctgcccgtca cccctggaga gccggcctcc     60
atctcctgca gatctagtca gagccttgta cacagtaatg aaacaccta tttacattgg    120 tacctgcaga agccagggca gtctccacag ctcctgatct ataaagtttc ctaccgattt    180
tctggggtcc cagacaggtt cagtggcagt gggtcaggca ctgatttcac actgaaaatc    240
agcagggtgg aggctgagga tgttggagtt tattactgtt ctcaaaatac acatgttcct    300
cggacgttcg gccaaggg                                                   318

<210> SEQ ID NO 40
<211> LENGTH: 318
<212> TYPE: DNA
<213> ORGANISM: Artificial Sequence
<220> FEATURE:
<223> OTHER INFORMATION: light chain variable region

<400> SEQUENCE: 40
gatattgtga tgacccagac tccactctcc ctgcccgtca cccctggaga gccggcctcc     60
atctcctgca gatctagtca gagccttgta cacagtaatg aaacaccta tttacattgg    120 tatcagcaga aaccagggaa agctcctaag ctcctgatct ataaagtttc ctaccgattt    180
tctggggtcc cagacaggtt cagtggcagt gggtcaggca ctgatttcac actgaaaatc    240
agcagggtgg aggctgagga tgttggagtt tattactgtt ctcaaaatac acatgttcct    300
cggacgttcg gccaaggg                                                   318

<210> SEQ ID NO 41
<211> LENGTH: 318
<212> TYPE: DNA
<213> ORGANISM: Artificial Sequence
<220> FEATURE:
<223> OTHER INFORMATION: light chain variable region

<400> SEQUENCE: 41
```

```
gatgttgtga tgactcagtc tccactctcc ctgcccgtca cccttggaca gccggcctcc    60
atctcctgca gatctagtca gagccttgta cacagtaatg gaaacaccta tttacattgg   120
tatcagcaga aaccagggaa agctcctaag ctcctgatct ataaagtttc ctaccgattt   180
tctggggtcc cagacaggtt cagtggcagt gggtcaggca ctgatttcac actgaaaatc   240
agcagggtgg aggctgagga tgttggagtt tattactgtt ctcaaaatac acatgttcct   300
cggacgttcg gccaaggg                                                 318
```

<210> SEQ ID NO 42
<211> LENGTH: 318
<212> TYPE: DNA
<213> ORGANISM: Artificial Sequence
<220> FEATURE:
<223> OTHER INFORMATION: light chain variable region

<400> SEQUENCE: 42

```
gatattgtga tgacccagac tccactctcc ctgcccgtca cccctggaga gccggcctcc    60
atctcctgca gatctagtca gagccttgta cacagtaatg gaaacaccta tttacattgg   120
tacctgcaga agccagggca gtctccacag ctcctgatct ataaagtttc ctaccgattt   180
tctggggtcc cagacaggtt cagtggcagt gggtcaggca ctgatttcac actgaaaatc   240
agcagggtgg aggctgagga tgttggagtt tattactgtt ctcaaaatac acatgttcct   300
cggacgttcg gccaaggg                                                 318
```

<210> SEQ ID NO 43
<211> LENGTH: 318
<212> TYPE: DNA
<213> ORGANISM: Artificial Sequence
<220> FEATURE:
<223> OTHER INFORMATION: light chain variable region

<400> SEQUENCE: 43

```
gaaattgtgt tgacacagtc tccagccacc ctgtctgtgt ctccagggga aagagccacc    60
ctctcctgca gatctagtca gagccttgta cacagtaatg gaaacaccta tttacattgg   120
taccagcaga aacctggcca ggctcccagg ctcctcatct ataaagtttc ctaccgattt   180
tctggggtcc cctcgaggtt cagtggcagt ggatctggga cagatttcac ctttaccatc   240
agtagcctgg aagctgaaga tgctgcaaca tattactgtt ctcaaaatac acatgttcct   300
cggacgttcg gccaaggg                                                 318
```

<210> SEQ ID NO 44
<211> LENGTH: 318
<212> TYPE: DNA
<213> ORGANISM: Artificial Sequence
<220> FEATURE:
<223> OTHER INFORMATION: light chain variable region

<400> SEQUENCE: 44

```
gatattgtga tgacccagac tccactctcc ctgcccgtca cccctggaga gccggcctcc    60
atctcctgca gatctagtca gagccttgta cacagtaatg gaaacaccta tttacattgg   120
tatcagcaga aaccagggaa agctcctaag ctcctgatct ataaagtttc ctaccgattt   180
tctggggtcc cagacaggtt cagtggcagt gggtcaggca ctgatttcac actgaaaatc   240
agcagggtgg aggctgagga tgttggagtt tattactgtt ctcaaaatac acatgttcct   300
cggacgttcg gccaaggg                                                 318
```

<210> SEQ ID NO 45
<211> LENGTH: 318
<212> TYPE: DNA
<213> ORGANISM: Artificial Sequence
<220> FEATURE:
<223> OTHER INFORMATION: light chain variable region

<400> SEQUENCE: 45

```
gatattgtga tgacccagac tccactctcc ctgcccgtca cccctggaga gccggcctcc      60
atctcctgca gatctagtca gagccttgta cacagtaatg gaaacaccta tttacattgg     120
tatcagcaga aaccagggaa agctcctaag ctcctgatct ataaagtttc ctaccgattt     180
tctggggtcc cagacaggtt cagtggcagt gggtcaggca ctgatttcac actgaaaatc     240
agcagggtgg aggctgagga tgttggagtt tattactgtt ctcaaaatac acatgttcct     300
cggacgttcg gccaaggg                                                   318
```

<210> SEQ ID NO 46
<211> LENGTH: 318
<212> TYPE: DNA
<213> ORGANISM: Artificial Sequence
<220> FEATURE:
<223> OTHER INFORMATION: light chain variable region

<400> SEQUENCE: 46

```
gatgttgtga tgactcagtc tccactctcc ctgcccgtca cccttggaca gccggcctcc      60
atctcctgca gatctagtca gagccttgta cacagtaatg gaaacaccta tttacattgg     120
tatcagcaga aaccagggaa agctcctaag ctcctgatct ataaagtttc ctaccgattt     180
tctggggtcc cagacaggtt cagtggcagt gggtcaggca ctgatttcac actgaaaatc     240
agcagggtgg aggctgagga tgttggagtt tattactgtt ctcaaaatac acatgttcct     300
cggacgttcg gccaaggg                                                   318
```

<210> SEQ ID NO 47
<211> LENGTH: 318
<212> TYPE: DNA
<213> ORGANISM: Artificial Sequence
<220> FEATURE:
<223> OTHER INFORMATION: light chain variable region

<400> SEQUENCE: 47

```
gccatccagt tgacccagtc tccatcctcc ctgtctgcat ctgtaggaga cagagtcacc      60
atcacttgca gatctagtca gagccttgta cacagtaatg gaaacaccta tttacattgg     120
taccagcaga aacctggcca ggctcccagg ctcctcatct ataaagtttc ctaccgattt     180
tctggggtcc catcaaggtt cagcggcagt ggatctggga cagaattcac tctcaccatc     240
agcagcctgc agcctgatga ttttgcaact tattactgtt ctcaaaatac acatgttcct     300
cggacgttcg gccaaggg                                                   318
```

<210> SEQ ID NO 48
<211> LENGTH: 318
<212> TYPE: DNA
<213> ORGANISM: Artificial Sequence
<220> FEATURE:
<223> OTHER INFORMATION: light chain variable region

<400> SEQUENCE: 48

```
gccatccagt tgacccagtc tccatcctcc ctgtctgcat ctgtaggaga cagagtcacc      60
atcacttgca gatctagtca gagccttgta cacagtaatg gaaacaccta tttacattgg     120
```

```
taccagcaga aacctggcca ggctcccagg ctcctcatct ataaagtttc ctaccgattt      180
tctggggtcc cagacaggtt cagtggcagt gggtcaggca ctgatttcac actgaaaatc      240
agcagggtgg aggctgagga tgttggagtt tattactgtt ctcaaaatac acatgttcct      300
cggacgttcg gccaaggg                                                     318

<210> SEQ ID NO 49
<211> LENGTH: 318
<212> TYPE: DNA
<213> ORGANISM: Artificial Sequence
<220> FEATURE:
<223> OTHER INFORMATION: light chain variable region

<400> SEQUENCE: 49
gccatccagt tgacccagtc tccatcctcc ctgtctgcat ctgtaggaga cagagtcacc      60
atcacttgca gatctagtca gagccttgta cacagtaatg gaaacaccta tttacattgg     120
taccagcaga aacctggcca ggctcccagg ctcctcatct ataaagtttc ctaccgattt     180
tctggggtcc cagacaggtt cagtggcagt gggtcaggca ctgatttcac actgaaaatc     240
agcagggtgg aggctgagga tgttggagtt tattactgtt ctcaaaatac acatgttcct     300
cggacgttcg gccaaggg                                                    318

<210> SEQ ID NO 50
<211> LENGTH: 318
<212> TYPE: DNA
<213> ORGANISM: Artificial Sequence
<220> FEATURE:
<223> OTHER INFORMATION: light chain variable region

<400> SEQUENCE: 50
gaaattgtgt tgacacagtc tccagccacc ctgtctgtgt ctccagggga aagagccacc      60
ctctcctgca gatctagtca gagccttgta cacagtaatg gaaacaccta tttacattgg     120
taccagcaga aacctggcca ggctcccagg ctcctcatct ataaagtttc ctaccgattt     180
tctggggtcc cctcgaggtt cagtggcagt ggatctggga cagatttcac ctttaccatc     240
agtagcctgg aagctgaaga tgctgcaaca tattactgtt ctcaaaatac acatgttcct     300
cggacgttcg gccaaggg                                                    318

<210> SEQ ID NO 51
<211> LENGTH: 318
<212> TYPE: DNA
<213> ORGANISM: Artificial Sequence
<220> FEATURE:
<223> OTHER INFORMATION: light chain variable region

<400> SEQUENCE: 51
gatgttgtga tgactcagtc tccactctcc ctgcccgtca cccttggaca gccggcctcc      60
atctcctgca gatctagtca gagccttgta cacagtaatg gaaacaccta tttacattgg     120
tatcagcaga aaccagggaa agctcctaag ctcctgatct ataaagtttc ctaccgattt     180
tctggggtcc cagacaggtt cagtggcagt gggtcaggca ctgatttcac actgaaaatc     240
agcagggtgg aggctgagga tgttggagtt tattactgtt ctcaaaatac acatgttcct     300
cggacgttcg gccaaggg                                                    318

<210> SEQ ID NO 52
<211> LENGTH: 318
<212> TYPE: DNA
<213> ORGANISM: Artificial Sequence
```

<220> FEATURE:
<223> OTHER INFORMATION: light chain variable region

<400> SEQUENCE: 52

```
gatattgtga tgacccagac tccactctcc ctgcccgtca cccctggaga gccggcctcc      60
atctcctgca gatctagtca gagccttgta cacagtaatg gaaacaccta tttacattgg     120
tacctgcaga agccagggca gtctccacag ctcctgatct ataaagtttc ctaccgattt     180
tctggggtcc cagacaggtt cagtggcagt gggtcaggca ctgatttcac actgaaaatc     240
agcagggtgg aggctgagga tgttggagtt tattactgtt ctcaaaatac acatgttcct     300
cggacgttcg gccaaggg                                                   318
```

<210> SEQ ID NO 53
<211> LENGTH: 318
<212> TYPE: DNA
<213> ORGANISM: Artificial Sequence
<220> FEATURE:
<223> OTHER INFORMATION: light chain variable region

<400> SEQUENCE: 53

```
gccatccagt tgacccagtc tccatcctcc ctgtctgcat ctgtaggaga cagagtcacc      60
atcacttgca gatctagtca gagccttgta cacagtaatg gaaacaccta tttacattgg     120
taccagcaga aacctggcca ggctcccagg ctcctcatct ataaagtttc ctaccgattt     180
tctggggtcc cagacaggtt cagtggcagt gggtcaggca ctgatttcac actgaaaatc     240
agcagggtgg aggctgagga tgttggagtt tattactgtt ctcaaaatac acatgttcct     300
cggacgttcg gccaaggg                                                   318
```

<210> SEQ ID NO 54
<211> LENGTH: 318
<212> TYPE: DNA
<213> ORGANISM: Artificial Sequence
<220> FEATURE:
<223> OTHER INFORMATION: light chain variable region

<400> SEQUENCE: 54

```
gaaattgtgt tgacacagtc tccagccacc ctgtctgtgt ctccagggga aagagccacc      60
ctctcctgca gatctagtca gagccttgta cacagtaatg gaaacaccta tttacattgg     120
taccagcaga aacctggcca ggctcccagg ctcctcatct ataaagtttc ctaccgattt     180
tctggggtcc cctcgaggtt cagtggcagt ggatctggga cagatttcac ctttaccatc     240
agtagcctgg aagctgaaga tgctgcaaca tattactgtt ctcaaaatac acatgttcct     300
cggacgttcg gccaaggg                                                   318
```

<210> SEQ ID NO 55
<211> LENGTH: 318
<212> TYPE: DNA
<213> ORGANISM: Artificial Sequence
<220> FEATURE:
<223> OTHER INFORMATION: light chain variable region

<400> SEQUENCE: 55

```
gatattgtga tgacccagac tccactctcc ctgcccgtca cccctggaga gccggcctcc      60
atctcctgca gatctagtca gagccttgta cacagtaatg gaaacaccta tttacattgg     120
tatcagcaga aaccagggaa agctcctaag ctcctgatct ataaagtttc ctaccgattt     180
tctggggtcc cagacaggtt cagtggcagt gggtcaggca ctgatttcac actgaaaatc     240
```

```
agcagggtgg aggctgagga tgttggagtt tattactgtt ctcaaaatac acatgttcct    300
cggacgttcg gccaaggg                                                  318
```

<210> SEQ ID NO 56
<211> LENGTH: 318
<212> TYPE: DNA
<213> ORGANISM: Artificial Sequence
<220> FEATURE:
<223> OTHER INFORMATION: light chain variable region

<400> SEQUENCE: 56

```
gccatccagt tgacccagtc tccatcctcc ctgtctgcat ctgtaggaga cagagtcacc     60
atcacttgca gatctagtca gagccttgta cacagtaatg gaaacaccta tttacattgg    120
taccagcaga aacctggcca ggctcccagg ctcctcatct ataaagtttc ctaccgattt    180
tctggggtcc catcaaggtt cagcggcagt ggatctggga cagaattcac tctcaccatc    240
agcagcctgc agcctgatga ttttgcaact tattactgtt ctcaaaatac acatgttcct    300
cggacgttcg gccaaggg                                                  318
```

<210> SEQ ID NO 57
<211> LENGTH: 109
<212> TYPE: PRT
<213> ORGANISM: Artificial Sequence
<220> FEATURE:
<223> OTHER INFORMATION: heavy chain variable region

<400> SEQUENCE: 57

Glu Val Gln Leu Gln Gln Phe Gly Ala Glu Leu Val Lys Pro Gly Ala
1               5                   10                  15

Ser Met Lys Leu Ser Cys Lys Ala Ser Gly Tyr Thr Phe Thr Asn Tyr
            20                  25                  30

Tyr Val Phe Trp Val Lys Gln Arg Pro Gly Gln Gly Leu Glu Trp Ile
        35                  40                  45

Gly Asp Ile Asn Pro Val Asn Gly Asp Thr Asn Phe Asn Glu Lys Phe
    50                  55                  60

Lys Asn Lys Ala Thr Leu Thr Val Asp Lys Ser Ser Thr Thr Thr Tyr
65                  70                  75                  80

Leu Gln Leu Ser Ser Leu Thr Ser Glu Asp Ser Ala Val Tyr Tyr Cys
                85                  90                  95

Thr Arg Gly Gly Tyr Thr Met Asp Tyr Trp Gly Gln Gly
            100                 105

<210> SEQ ID NO 58
<211> LENGTH: 109
<212> TYPE: PRT
<213> ORGANISM: Artificial Sequence
<220> FEATURE:
<223> OTHER INFORMATION: heavy chain variable region

<400> SEQUENCE: 58

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Thr Met Asp Tyr Trp Gly Gln Gly
            100                 105

<210> SEQ ID NO 59
<211> LENGTH: 109
<212> TYPE: PRT
<213> ORGANISM: Artificial Sequence
<220> FEATURE:
<223> OTHER INFORMATION: heavy chain variable region

<400> SEQUENCE: 59

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Thr Met Asp Tyr Trp Gly Gln Gly
            100                 105

<210> SEQ ID NO 60
<211> LENGTH: 109
<212> TYPE: PRT
<213> ORGANISM: Artificial Sequence
<220> FEATURE:
<223> OTHER INFORMATION: heavy chain variable region

<400> SEQUENCE: 60

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 61
<211> LENGTH: 109
<212> TYPE: PRT
<213> ORGANISM: Artificial Sequence
<220> FEATURE:
<223> OTHER INFORMATION: heavy chain variable region

<400> SEQUENCE: 61

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Pro Gly Lys Gly Leu Glu Trp Val
        35                  40                  45

Ser Asp Ile Asn Pro Val Asn Gly Asp Thr Asn Phe Asn Glu Lys Phe
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 62
<211> LENGTH: 109
<212> TYPE: PRT
<213> ORGANISM: Artificial Sequence
<220> FEATURE:
<223> OTHER INFORMATION: heavy chain variable region

<400> SEQUENCE: 62

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Pro Gly Lys Gly Leu Glu Trp Val
        35                  40                  45

Ser Asp Ile Asn Pro Val Asn Gly Asp Thr Asn Phe Asn Glu Lys Phe
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 63
<211> LENGTH: 109
<212> TYPE: PRT
<213> ORGANISM: Artificial Sequence
<220> FEATURE:
<223> OTHER INFORMATION: heavy chain variable region

<400> SEQUENCE: 63

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Leu Thr Ile Ser Lys Asp Thr Ser Lys Asn Gln Val Val
65                  70                  75                  80

```
Leu Thr Met Thr Asn Met Asp Pro Val Asp Thr Ala Thr Tyr Tyr Cys
                85                  90                  95

Ala Arg Gly Gly Tyr Thr Met Asp Tyr Trp Gly Gln Gly
            100                 105
```

<210> SEQ ID NO 64
<211> LENGTH: 109
<212> TYPE: PRT
<213> ORGANISM: Artificial Sequence
<220> FEATURE:
<223> OTHER INFORMATION: heavy chain variable region

<400> SEQUENCE: 64

```
Gln Val Gln Leu Gln Glu Ser Gly Pro Gly Leu Val Lys Pro Gly Ala
1               5                   10                  15

Thr Val Lys Ile Ser Cys Lys Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
            100                 105
```

<210> SEQ ID NO 65
<211> LENGTH: 109
<212> TYPE: PRT
<213> ORGANISM: Artificial Sequence
<220> FEATURE:
<223> OTHER INFORMATION: heavy chain variable region

<400> SEQUENCE: 65

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Tyr Thr Phe Thr Asn Tyr
            20                  25                  30

Tyr Val Phe Trp Ile Arg Gln Ser Pro Ser Arg Gly Leu Glu Trp Leu
        35                  40                  45

Gly Asp Ile Asn Pro Val Asn Gly Asp Thr Asn Phe Asn Glu Lys Phe
    50                  55                  60

Lys Asn Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Thr Met Asp Tyr Trp Gly Gln Gly
            100                 105
```

<210> SEQ ID NO 66
<211> LENGTH: 109
<212> TYPE: PRT
<213> ORGANISM: Artificial Sequence
<220> FEATURE:
<223> OTHER INFORMATION: heavy chain variable region

<400> SEQUENCE: 66

```
Gln Val Gln Leu Gln Glu Ser Gly Pro Gly Leu Val Lys Pro Ser Gln
```

```
                1               5                          10                            15
            Thr Leu Ser Leu Thr Cys Thr Val Ser Gly Tyr Thr Phe Thr Asn Tyr
                            20                          25                          30

Tyr Val Phe Trp Val Arg Gln Ala Arg Gly Gln Arg Leu Glu Trp Ile
                        35                          40                          45

Gly Asp Ile Asn Pro Val Asn Gly Asp Thr Asn Phe Asn Glu Lys Phe
                    50                          55                          60

Lys Asn Arg Leu Thr Ile Ser Lys Asp Thr Ser Lys Asn Gln Val Val
            65                          70                          75                          80

Leu Thr Met Thr Asn Met Asp Pro Val Asp Thr Ala Thr Tyr Tyr Cys
                                    85                          90                          95

Ala Arg Gly Gly Tyr Thr Met Asp Tyr Trp Gly Gln Gly
                                100                         105
```

<210> SEQ ID NO 67
<211> LENGTH: 109
<212> TYPE: PRT
<213> ORGANISM: Artificial Sequence
<220> FEATURE:
<223> OTHER INFORMATION: heavy chain variable region

<400> SEQUENCE: 67

```
            Gln Val Gln Leu Gln Glu Ser Gly Pro Gly Leu Val Lys Pro Ser Gln
            1               5                          10                            15

Thr Leu Ser Leu Thr Cys Thr Val Ser Gly Tyr Thr Phe Thr Asn Tyr
                            20                          25                          30

Tyr Val Phe Trp Val Arg Gln Ala Arg Gly Gln Arg Leu Glu Trp Ile
                        35                          40                          45

Gly Asp Ile Asn Pro Val Asn Gly Asp Thr Asn Phe Asn Glu Lys Phe
                    50                          55                          60

Lys Asn Arg Leu Thr Ile Ser Lys Asp Thr Ser Lys Asn Gln Val Val
            65                          70                          75                          80

Leu Thr Met Thr Asn Met Asp Pro Val Asp Thr Ala Thr Tyr Tyr Cys
                                    85                          90                          95

Ala Arg Gly Gly Tyr Thr Met Asp Tyr Trp Gly Gln Gly
                                100                         105
```

<210> SEQ ID NO 68
<211> LENGTH: 109
<212> TYPE: PRT
<213> ORGANISM: Artificial Sequence
<220> FEATURE:
<223> OTHER INFORMATION: heavy chain variable region

<400> SEQUENCE: 68

```
            Gln Val Gln Leu Gln Glu Ser Gly Pro Gly Leu Val Lys Pro Gly Ala
            1               5                          10                            15

Thr Val Lys Ile Ser Cys Lys Val Ser Gly Tyr Thr Phe Thr Asn Tyr
                            20                          25                          30

Tyr Val Phe Trp Val Arg Gln Ala Arg Gly Gln Arg Leu Glu Trp Ile
                        35                          40                          45

Gly Asp Ile Asn Pro Val Asn Gly Asp Thr Asn Phe Asn Glu Lys Phe
                    50                          55                          60

Lys Asn Arg Val Thr Ile Thr Ala Asp Lys Ser Thr Ser Thr Ala Tyr
            65                          70                          75                          80

Met Glu Leu Ser Ser Leu Arg Ser Glu Asp Thr Ala Val Tyr Tyr Cys
                                    85                          90                          95
```

Ala Arg Gly Gly Tyr Thr Met Asp Tyr Trp Gly Gln Gly
            100                 105

<210> SEQ ID NO 69
<211> LENGTH: 109
<212> TYPE: PRT
<213> ORGANISM: Artificial Sequence
<220> FEATURE:
<223> OTHER INFORMATION: heavy chain variable region

<400> SEQUENCE: 69

Gln Val Gln Leu Gln Glu Ser Gly Pro Gly Leu Val Lys Pro Gly Ala
1               5                   10                  15

Thr Val Lys Ile Ser Cys Lys Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 70
<211> LENGTH: 109
<212> TYPE: PRT
<213> ORGANISM: Artificial Sequence
<220> FEATURE:
<223> OTHER INFORMATION: heavy chain variable region

<400> SEQUENCE: 70

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Asn Tyr
            20                  25                  30

Tyr Val Phe Trp Ile Arg Gln Ser Pro Ser Arg Gly Leu Glu Trp Leu
        35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 71
<211> LENGTH: 109
<212> TYPE: PRT
<213> ORGANISM: Artificial Sequence
<220> FEATURE:
<223> OTHER INFORMATION: heavy chain variable region

<400> SEQUENCE: 71

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr

```
            20                  25                  30

Tyr Val Phe Trp Val Arg Gln Ala Arg Gly Gln Arg Leu Glu Trp Ile
            35                  40                  45

Gly Asp Ile Asn Pro Val Asn Gly Asp Thr Asn Phe Asn Glu Lys Phe
            50                  55                  60

Lys Asn Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Thr Met Asp Tyr Trp Gly Gln Gly
            100                 105

<210> SEQ ID NO 72
<211> LENGTH: 109
<212> TYPE: PRT
<213> ORGANISM: Artificial Sequence
<220> FEATURE:
<223> OTHER INFORMATION: heavy chain variable region

<400> SEQUENCE: 72

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
            35                  40                  45

Gly Asp Ile Asn Pro Val Asn Gly Asp Thr Asn Phe Asn Glu Lys Phe
            50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Gly Tyr Thr Met Asp Tyr Trp Gly Gln Gly
            100                 105

<210> SEQ ID NO 73
<211> LENGTH: 109
<212> TYPE: PRT
<213> ORGANISM: Artificial Sequence
<220> FEATURE:
<223> OTHER INFORMATION: heavy chain variable region

<400> SEQUENCE: 73

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
            35                  40                  45

Gly Asp Ile Asn Pro Val Asn Gly Asp Thr Asn Phe Asn Glu Lys Phe
            50                  55                  60

Lys Asn Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Thr Met Asp Tyr Trp Gly Gln Gly
            100                 105
```

```
<210> SEQ ID NO 74
<211> LENGTH: 109
<212> TYPE: PRT
<213> ORGANISM: Artificial Sequence
<220> FEATURE:
<223> OTHER INFORMATION: heavy chain variable region

<400> SEQUENCE: 74

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asn Tyr
            20                  25                  30

Tyr Val Phe Trp Ile Arg Gln Pro Pro Gly Lys Gly Leu Glu Trp Ile
        35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 75
<211> LENGTH: 109
<212> TYPE: PRT
<213> ORGANISM: Artificial Sequence
<220> FEATURE:
<223> OTHER INFORMATION: heavy chain variable region

<400> SEQUENCE: 75

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Asn Tyr
            20                  25                  30

Tyr Val Phe Trp Ile Arg Gln Ser Pro Ser Arg Gly Leu Glu Trp Leu
        35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 76
<211> LENGTH: 109
<212> TYPE: PRT
<213> ORGANISM: Artificial Sequence
<220> FEATURE:
<223> OTHER INFORMATION: heavy chain variable region

<400> SEQUENCE: 76

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Asn Tyr
            20                  25                  30

Tyr Val Phe Trp Ile Arg Gln Ser Pro Ser Arg Gly Leu Glu Trp Leu
```

```
            35                  40                  45
Gly Asp Ile Asn Pro Val Asn Gly Asp Thr Asn Phe Asn Glu Lys Phe
 50                  55                  60
Lys Asn Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Gly Gly Tyr Thr Met Asp Tyr Trp Gly Gln Gly
             100                 105

<210> SEQ ID NO 77
<211> LENGTH: 109
<212> TYPE: PRT
<213> ORGANISM: Artificial Sequence
<220> FEATURE:
<223> OTHER INFORMATION: heavy chain variable region

<400> SEQUENCE: 77

Gln Ile Thr Leu Lys Glu Ser Gly Pro Thr Leu Val Lys Pro Thr Gln
  1               5                  10                  15
Thr Leu Thr Leu Thr Cys Thr Phe Ser Gly Tyr Thr Phe Thr Asn Tyr
                 20                  25                  30
Tyr Val Phe Trp Val Arg Gln Ala Pro Gly Gln Gly Leu Glu Trp Met
             35                  40                  45
Gly Asp Ile Asn Pro Val Asn Gly Asp Thr Asn Phe Asn Glu Lys Phe
 50                  55                  60
Lys Asn Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Gly Gly Tyr Thr Met Asp Tyr Trp Gly Gln Gly
             100                 105

<210> SEQ ID NO 78
<211> LENGTH: 109
<212> TYPE: PRT
<213> ORGANISM: Artificial Sequence
<220> FEATURE:
<223> OTHER INFORMATION: heavy chain variable region

<400> SEQUENCE: 78

Gln Val Gln Leu Gln Glu Ser Gly Pro Gly Leu Val Lys Pro Ser Gln
  1               5                  10                  15
Thr Leu Ser Leu Thr Cys Thr Val Ser Gly Tyr Thr Phe Thr Asn Tyr
                 20                  25                  30
Tyr Val Phe Trp Val Arg Gln Ala Arg Gly Gln Arg Leu Glu Trp Ile
             35                  40                  45
Gly Asp Ile Asn Pro Val Asn Gly Asp Thr Asn Phe Asn Glu Lys Phe
 50                  55                  60
Lys Asn Arg Leu Thr Ile Ser Lys Asp Thr Ser Lys Asn Gln Val Val
 65                  70                  75                  80
Leu Thr Met Thr Asn Met Asp Pro Val Asp Thr Ala Thr Tyr Tyr Cys
                 85                  90                  95
Ala Arg Gly Gly Tyr Thr Met Asp Tyr Trp Gly Gln Gly
             100                 105

<210> SEQ ID NO 79
<211> LENGTH: 109
```

```
<212> TYPE: PRT
<213> ORGANISM: Artificial Sequence
<220> FEATURE:
<223> OTHER INFORMATION: heavy chain variable region

<400> SEQUENCE: 79

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Gly Tyr Thr Met Asp Tyr Trp Gly Gln Gly
            100                 105

<210> SEQ ID NO 80
<211> LENGTH: 109
<212> TYPE: PRT
<213> ORGANISM: Artificial Sequence
<220> FEATURE:
<223> OTHER INFORMATION: heavy chain variable region

<400> SEQUENCE: 80

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Gly Tyr Thr Met Asp Tyr Trp Gly Gln Gly
            100                 105

<210> SEQ ID NO 81
<211> LENGTH: 109
<212> TYPE: PRT
<213> ORGANISM: Artificial Sequence
<220> FEATURE:
<223> OTHER INFORMATION: heavy chain variable region

<400> SEQUENCE: 81

Gln Val Gln Leu Gln Glu Ser Gly Pro Gly Leu Val Lys Pro Gly Ala
1               5                   10                  15

Thr Val Lys Ile Ser Cys Lys Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
```

```
                    50                  55                  60
Lys Asn Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Tyr Thr Met Asp Tyr Trp Gly Gln Gly
            100                 105
```

<210> SEQ ID NO 82
<211> LENGTH: 327
<212> TYPE: DNA
<213> ORGANISM: Artificial Sequence
<220> FEATURE:
<223> OTHER INFORMATION: heavy chain variable region

<400> SEQUENCE: 82

```
gaggtccagc tgcagcagtt tggggctgaa ctggtgaagc ctggggcttc aatgaagttg      60
tcctgcaagg cttctggcta caccttcacc aactactatg tattctgggt gaaacagagg     120
cctggacaag gccttgagtg gattggagac attaatcctg tcaatggtga ctactaattc    180
aatgagaaat tcaagaacaa ggccacactg actgtagaca gtcctccac cacaacatac     240
ttgcaactca gcagcctgac atctgaggac tctgcggtct attactgtac aagaggggt    300
tatactatgg actactgggg tcaagga                                        327
```

<210> SEQ ID NO 83
<211> LENGTH: 327
<212> TYPE: DNA
<213> ORGANISM: Artificial Sequence
<220> FEATURE:
<223> OTHER INFORMATION: heavy chain variable sequence

<400> SEQUENCE: 83

```
caggtgcagc tgcaggagtc gggcccagga ctggtgaagc cttcacagac cctgtccctc      60
acctgcactg tctctggcta caccttcacc aactactatg tattctgggt gcgacaggct    120
cgtggacaac gccttgagtg gataggtgac attaatcctg tcaatggtga ctactaattc    180
aatgagaaat tcaagaacag agtcaccatc tcagccgaca gtccatcag caccgcctac    240
ctgcagtgga gcagcctgaa ggcctcggac accgccatgt attactgtgc gagaggggt    300
tatactatgg actactgggg ccaggga                                       327
```

<210> SEQ ID NO 84
<211> LENGTH: 327
<212> TYPE: DNA
<213> ORGANISM: Artificial Sequence
<220> FEATURE:
<223> OTHER INFORMATION: heavy chain variable sequence

<400> SEQUENCE: 84

```
caggtgcagc tgcaggagtc gggcccagga ctggtgaagc cttcacagac cctgtccctc      60
acctgcactg tctctggcta caccttcacc aactactatg tattctgggt gcgacaggct    120
cgtggacaac gccttgagtg gataggtgac attaatcctg tcaatggtga ctactaattc    180
aatgagaaat tcaagaacag agtcaccatc tcagccgaca gtccatcag caccgcctac    240
ctgcagtgga gcagcctgaa ggcctcggac accgccatgt attactgtgc gagaggggt    300
tatactatgg actactgggg ccaggga                                       327
```

<210> SEQ ID NO 85

```
<211> LENGTH: 327
<212> TYPE: DNA
<213> ORGANISM: Artificial Sequence
<220> FEATURE:
<223> OTHER INFORMATION: heavy chain variable sequence

<400> SEQUENCE: 85
gaagtgcagc tggtgcagtc tggagcagag gtgaaaaagc ccggggagtc tctgaggatc      60
tcctgtaagg gttctggcta caccttcacc aactactatg tattctgggt gcgacaggct     120
cgtggacaac gccttgagtg gataggtgac attaatcctg tcaatggtga tactaacttc     180
aatgagaaat tcaagaacag agtcacgatt accgcggaca atccacgag cacagcctac      240 atggagctga gcagcctgag atctgaggac acggccgtgt attactgtgc gagaggggt      300 tatactatgg actactgggg ccaggga                                         327

<210> SEQ ID NO 86
<211> LENGTH: 327
<212> TYPE: DNA
<213> ORGANISM: Artificial Sequence
<220> FEATURE:
<223> OTHER INFORMATION: heavy chain variable region

<400> SEQUENCE: 86
caggtgcagc tgcaggagtc gggcccagga ctggtgaagc cttcacagac cctgtccctc      60
acctgcactg tctctggcta caccttcacc aactactatg tattctgggt ccgccaggct     120
ccagggaagg ggctggagtg ggtcagtgac attaatcctg tcaatggtga tactaacttc     180
aatgagaaat tcaagaacag agtcaccata tcagtagaca cgtccaagaa ccagttctcc     240
ctgaagctga gctctgtgac cgccgcggac acggctgtgt attactgtgc gagaggggt      300 tatactatgg actactgggg ccaggga                                         327

<210> SEQ ID NO 87
<211> LENGTH: 327
<212> TYPE: DNA
<213> ORGANISM: Artificial Sequence
<220> FEATURE:
<223> OTHER INFORMATION: heavy chain variable region

<400> SEQUENCE: 87
caggtgcagc tgcaggagtc gggcccagga ctggtgaagc cttcacagac cctgtccctc      60
acctgcactg tctctggcta caccttcacc aactactatg tattctgggt ccgccaggct     120
ccagggaagg ggctggagtg ggtcagtgac attaatcctg tcaatggtga tactaacttc     180
aatgagaaat tcaagaacag agtcaccata tcagtagaca cgtccaagaa ccagttctcc     240
ctgaagctga gctctgtgac cgccgcggac acggctgtgt attactgtgc gagaggggt      300 tatactatgg actactgggg ccaggga                                         327

<210> SEQ ID NO 88
<211> LENGTH: 327
<212> TYPE: DNA
<213> ORGANISM: Artificial Sequence
<220> FEATURE:
<223> OTHER INFORMATION: heavy chain variable region

<400> SEQUENCE: 88
caggtgcagc tgcaggagtc gggcccagga ctggtgaagc cttcacagac cctgtccctc      60
acctgcactg tctctggcta caccttcacc aactactatg tattctgggt gcgacaggct     120
cgtggacaac gccttgagtg gataggtgac attaatcctg tcaatggtga tactaacttc     180
```
aatgagaaat tcaagaacag actcaccatc tccaaggaca cctccaaaaa ccaggtggtc        240
cttacaatga ccaacatgga ccctgtggac acagccacgt attactgtgc aagagggggt        300
tatactatgg actactgggg ccaggga                                           327

<210> SEQ ID NO 89
<211> LENGTH: 327
<212> TYPE: DNA
<213> ORGANISM: Artificial Sequence
<220> FEATURE:
<223> OTHER INFORMATION: heavy chain variable region

<400> SEQUENCE: 89
caggtgcagc tgcaggagtc gggcccagga ctggtgaagc ctggggctac agtgaaaatc        60
tcctgcaagg tttctggcta caccttcacc aactactatg tattctgggt gcgacaggct       120
cgtggacaac gccttgagtg dataggtgac attaatcctg tcaatggtga tactaacttc       180
aatgagaaat tcaagaacag agtcacgatt accgcggaca atccacgag cacagcctac        240 atggagctga gcagcctgag atctgaggac acggccgtgt attactgtgc gagaggggt        300 tatactatgg actactgggg ccaggga                                           327

<210> SEQ ID NO 90
<211> LENGTH: 327
<212> TYPE: DNA
<213> ORGANISM: Artificial Sequence
<220> FEATURE:
<223> OTHER INFORMATION: heavy chain variable region

<400> SEQUENCE: 90
cagatcacct tgaaggagtc tggtcctacg ctggtgaaac ccacacagac cctcacgctg        60
acctgcacct tctctggcta caccttcacc aactactatg tattctggat caggcagtcc       120
ccatcgagag gccttgagtg gctgggtgac attaatcctg tcaatggtga tactaacttc       180
aatgagaaat tcaagaacag attcaccatc tccagagaca cgccaagaa ctcactgtat        240 ctgcaaatga cagcctgag agccgaggac acggctgtgt attactgtgc gagaggggt        300 tatactatgg actactgggg ccaggga                                           327

<210> SEQ ID NO 91
<211> LENGTH: 327
<212> TYPE: DNA
<213> ORGANISM: Artificial Sequence
<220> FEATURE:
<223> OTHER INFORMATION: heavy chain variable region

<400> SEQUENCE: 91
caggtgcagc tgcaggagtc gggcccagga ctggtgaagc cttcacagac cctgtccctc        60
acctgcactg tctctggcta caccttcacc aactactatg tattctgggt gcgacaggct       120
cgtggacaac gccttgagtg gataggtgac attaatcctg tcaatggtga tactaacttc       180
aatgagaaat tcaagaacag actcaccatc tccaaggaca cctccaaaaa ccaggtggtc       240
cttacaatga ccaacatgga ccctgtggac acagccacgt attactgtgc aagagggggt       300
tatactatgg actactgggg ccaggga                                           327

<210> SEQ ID NO 92
<211> LENGTH: 327
<212> TYPE: DNA
<213> ORGANISM: Artificial Sequence
<220> FEATURE:

<223> OTHER INFORMATION: heavy chain variable region

<400> SEQUENCE: 92

```
caggtgcagc tgcaggagtc gggcccagga ctggtgaagc cttcacagac cctgtccctc    60
acctgcactg tctctggcta caccttcacc aactactatg tattctgggt gcgacaggct   120
cgtggacaac gccttgagtg gataggtgac attaatcctg tcaatggtga tactaacttc   180
aatgagaaat tcaagaacag actcaccatc tccaaggaca cctccaaaaa ccaggtggtc   240
cttacaatga ccaacatgga ccctgtggac acagccacgt attactgtgc aagaggggt    300
tatactatgg actactgggg ccaggga                                       327
```

<210> SEQ ID NO 93
<211> LENGTH: 327
<212> TYPE: DNA
<213> ORGANISM: Artificial Sequence
<220> FEATURE:
<223> OTHER INFORMATION: heavy chain variable region

<400> SEQUENCE: 93

```
caggtgcagc tgcaggagtc gggcccagga ctggtgaagc ctggggctac agtgaaaatc    60
tcctgcaagg tttctggcta caccttcacc aactactatg tattctgggt gcgacaggct   120
cgtggacaac gccttgagtg gataggtgac attaatcctg tcaatggtga tactaacttc   180
aatgagaaat tcaagaacag agtcacgatt accgcggaca atccacgag cacagcctac   240
atggagctga gcagcctgag atctgaggac acggccgtgt attactgtgc gagaggggt    300
tatactatgg actactgggg ccaggga                                       327
```

<210> SEQ ID NO 94
<211> LENGTH: 327
<212> TYPE: DNA
<213> ORGANISM: Artificial Sequence
<220> FEATURE:
<223> OTHER INFORMATION: heavy chain variable region

<400> SEQUENCE: 94

```
caggtgcagc tgcaggagtc gggcccagga ctggtgaagc ctggggctac agtgaaaatc    60
tcctgcaagg tttctggcta caccttcacc aactactatg tattctgggt gcgacaggct   120
cgtggacaac gccttgagtg gataggtgac attaatcctg tcaatggtga tactaacttc   180
aatgagaaat tcaagaacag agtcacgatt accgcggaca atccacgag cacagcctac   240
atggagctga gcagcctgag atctgaggac acggccgtgt attactgtgc gagaggggt    300
tatactatgg actactgggg ccaggga                                       327
```

<210> SEQ ID NO 95
<211> LENGTH: 327
<212> TYPE: DNA
<213> ORGANISM: Artificial Sequence
<220> FEATURE:
<223> OTHER INFORMATION: heavy chain variable region

<400> SEQUENCE: 95

```
gaagtgcagc tggtgcagtc tggagcagag gtgaaaaagc ccggggagtc tctgaggatc    60
tcctgtaagg gttctggcta caccttcacc aactactatg tattctggat caggcagtcc   120
ccatcgagag gccttgagtg gctgggtgac attaatcctg tcaatggtga tactaacttc   180
aatgagaaat tcaagaacag agtcacgatt accgcggaca atccacgag cacagcctac   240
atggagctga gcagcctgag atctgaggac acggccgtgt attactgtgc gagaggggt    300
```

```
tatactatgg actactgggg ccaggga                                            327

<210> SEQ ID NO 96
<211> LENGTH: 327
<212> TYPE: DNA
<213> ORGANISM: Artificial Sequence
<220> FEATURE:
<223> OTHER INFORMATION: heavy chain variable region

<400> SEQUENCE: 96
caggtgcagc tgcaggagtc gggcccagga ctggtgaagc cttcacagac cctgtccctc         60
acctgcactg tctctggcta caccttcacc aactactatg tattctgggt gcgacaggct        120
cgtggacaac gccttgagtg dataggtgac attaatcctg tcaatggtga tactaacttc        180
aatgagaaat tcaagaacag agtcaccatc tcagccgaca gtccatcag caccgcctac         240 ctgcagtgga gcagcctgaa ggcctcggac accgccatgt attactgtgc gagaggggt         300 tatactatgg actactgggg ccaggga                                            327

<210> SEQ ID NO 97
<211> LENGTH: 327
<212> TYPE: DNA
<213> ORGANISM: Artificial Sequence
<220> FEATURE:
<223> OTHER INFORMATION: heavy chain variable region

<400> SEQUENCE: 97
caggtgcagc tgcaggagtc gggcccagga ctggtgaagc cttcacagac cctgtccctc         60
acctgcactg tctctggcta caccttcacc aactactatg tattctgggt gcgacaggct        120
cgtggacaac gccttgagtg gataggtgac attaatcctg tcaatggtga tactaacttc        180
aatgagaaat tcaagaacag actcaccatc tccaaggaca cctccaaaaa ccaggtggtc        240
cttacaatga ccaacatgga ccctgtggac acagccacgt attactgtgc aagaggggt        300 tatactatgg actactgggg ccaggga                                            327

<210> SEQ ID NO 98
<211> LENGTH: 327
<212> TYPE: DNA
<213> ORGANISM: Artificial Sequence
<220> FEATURE:
<223> OTHER INFORMATION: heavy chain variable region

<400> SEQUENCE: 98
caggtgcagc tgcaggagtc gggcccagga ctggtgaagc cttcacagac cctgtccctc         60
acctgcactg tctctggcta caccttcacc aactactatg tattctgggt gcgacaggct        120
cgtggacaac gccttgagtg gataggtgac attaatcctg tcaatggtga tactaacttc        180
aatgagaaat tcaagaacag agtcaccatc tcagccgaca gtccatcag caccgcctac         240 ctgcagtgga gcagcctgaa ggcctcggac accgccatgt attactgtgc gagaggggt         300 tatactatgg actactgggg ccaggga                                            327

<210> SEQ ID NO 99
<211> LENGTH: 327
<212> TYPE: DNA
<213> ORGANISM: Artificial Sequence
<220> FEATURE:
<223> OTHER INFORMATION: heavy chain variable region

<400> SEQUENCE: 99
```

```
gaggtccagc tggtacagtc tggggctgag gtgaagaagc ctggggctac agtgaaaatc    60
tcctgcaagg tttctggcta caccttcacc aactactatg tattctggat ccgccagccc   120
ccagggaagg ggctggagtg gattggtgac attaatcctg tcaatggtga tactaacttc   180
aatgagaaat tcaagaacag agtcacgatt accgcggaca atccacgag cacagcctac    240 atggagctga gcagcctgag atctgaggac acggccgtgt attactgtgc gagaggggt    300 tatactatgg actactgggg ccaggga                                       327

<210> SEQ ID NO 100
<211> LENGTH: 327
<212> TYPE: DNA
<213> ORGANISM: Artificial Sequence
<220> FEATURE:
<223> OTHER INFORMATION: heavy chain variable region

<400> SEQUENCE: 100
gaagtgcagc tggtgcagtc tggagcagag gtgaaaaagc ccggggagtc tctgaggatc    60
tcctgtaagg gttctggcta caccttcacc aactactatg tattctggat caggcagtcc   120
ccatcgagag gccttgagtg gctgggtgac attaatcctg tcaatggtga tactaacttc   180
aatgagaaat tcaagaacag agtcacgatt accgcggaca atccacgag cacagcctac    240 atggagctga gcagcctgag atctgaggac acggccgtgt attactgtgc gagaggggt    300 tatactatgg actactgggg ccaggga                                       327

<210> SEQ ID NO 101
<211> LENGTH: 327
<212> TYPE: DNA
<213> ORGANISM: Artificial Sequence
<220> FEATURE:
<223> OTHER INFORMATION: heavy chain variable region

<400> SEQUENCE: 101
gaagtgcagc tggtgcagtc tggagcagag gtgaaaaagc ccggggagtc tctgaggatc    60
tcctgtaagg gttctggcta caccttcacc aactactatg tattctggat caggcagtcc   120
ccatcgagag gccttgagtg gctgggtgac attaatcctg tcaatggtga tactaacttc   180
aatgagaaat tcaagaacag agtcacgatt accgcggaca atccacgag cacagcctac    240 atggagctga gcagcctgag atctgaggac acggccgtgt attactgtgc gagaggggt    300 tatactatgg actactgggg ccaggga                                       327

<210> SEQ ID NO 102
<211> LENGTH: 327
<212> TYPE: DNA
<213> ORGANISM: Artificial Sequence
<220> FEATURE:
<223> OTHER INFORMATION: heavy chain variable region

<400> SEQUENCE: 102
cagatcacct tgaaggagtc tggtcctacg ctggtgaaac ccacacagac cctcacgctg    60
acctgcacct tctctggcta caccttcacc aactactatg tattctgggt gcgacaggcc   120
cctggacaag ggcttgagtg gatgggtgac attaatcctg tcaatggtga tactaacttc   180
aatgagaaat tcaagaacag agtcacgatt accgcggaca atccacgag cacagcctac    240 atggagctga gcagcctgag atctgaggac acggccgtgt attactgtgc gagaggggt    300 tatactatgg actactgggg ccaggga                                       327
```

```
<210> SEQ ID NO 103
<211> LENGTH: 327
<212> TYPE: DNA
<213> ORGANISM: Artificial Sequence
<220> FEATURE:
<223> OTHER INFORMATION: heavy chain variable region

<400> SEQUENCE: 103
caggtgcagc tgcaggagtc gggcccagga ctggtgaagc cttcacagac cctgtccctc    60
acctgcactg tctctggcta caccttcacc aactactatg tattctgggt gcgacaggct   120
cgtggacaac gccttgagtg gataggtgac attaatcctg tcaatggtga tactaacttc   180
aatgagaaat tcaagaacag actcaccatc tccaaggaca cctccaaaaa ccaggtggtc   240
cttacaatga ccaacatgga ccctgtggac acagccacgt attactgtgc aagagggggt   300
tatactatgg actactgggg ccaggga                                        327

<210> SEQ ID NO 104
<211> LENGTH: 327
<212> TYPE: DNA
<213> ORGANISM: Artificial Sequence
<220> FEATURE:
<223> OTHER INFORMATION: heavy chain variable region

<400> SEQUENCE: 104
caggtgcagc tgcaggagtc gggcccagga ctggtgaagc cttcacagac cctgtccctc    60
acctgcactg tctctggcta caccttcacc aactactatg tattctgggt gcgacaggct   120
cgtggacaac gccttgagtg gataggtgac attaatcctg tcaatggtga tactaacttc   180
aatgagaaat tcaagaacag actcaccatc tccaaggaca cctccaaaaa ccaggtggtc   240
cttacaatga ccaacatgga ccctgtggac acagccacgt attactgtgc aagagggggt   300
tatactatgg actactgggg ccaggga                                        327

<210> SEQ ID NO 105
<211> LENGTH: 327
<212> TYPE: DNA
<213> ORGANISM: Artificial Sequence
<220> FEATURE:
<223> OTHER INFORMATION: heavy chain variable region

<400> SEQUENCE: 105
caggtgcagc tgcaggagtc gggcccagga ctggtgaagc cttcacagac cctgtccctc    60
acctgcactg tctctggcta caccttcacc aactactatg tattctgggt gcgacaggct   120
cgtggacaac gccttgagtg gataggtgac attaatcctg tcaatggtga tactaacttc   180
aatgagaaat tcaagaacag actcaccatc tccaaggaca cctccaaaaa ccaggtggtc   240
cttacaatga ccaacatgga ccctgtggac acagccacgt attactgtgc aagagggggt   300
tatactatgg actactgggg ccaggga                                        327

<210> SEQ ID NO 106
<211> LENGTH: 327
<212> TYPE: DNA
<213> ORGANISM: Artificial Sequence
<220> FEATURE:
<223> OTHER INFORMATION: heavy chain variable region

<400> SEQUENCE: 106
caggtgcagc tgcaggagtc gggcccagga ctggtgaagc ctggggctac agtgaaaatc    60
tcctgcaagg tttctggcta caccttcacc aactactatg tattctgggt gcgacaggct   120
```

```
cgtggacaac gccttgagtg gataggtgac attaatcctg tcaatggtga tactaacttc    180
aatgagaaat tcaagaacag agtcacgatt accgcggaca atccacgag cacagcctac     240 atggagctga gcagcctgag atctgaggac acggccgtgt attactgtgc gagaggggt     300 tatactatgg actactgggg ccaggga                                        327
```

<210> SEQ ID NO 107
<211> LENGTH: 219
<212> TYPE: PRT
<213> ORGANISM: Artificial Sequence
<220> FEATURE:
<223> OTHER INFORMATION: complete light chain

<400> SEQUENCE: 107

```
Asp Val Val Met Thr Gln Thr Pro Leu Ser Leu Ser Val Ser Leu Gly
1               5                   10                  15

Asp Gln Ala Ser Ile Ser Cys Arg Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 108
<211> LENGTH: 660
<212> TYPE: DNA
<213> ORGANISM: Artificial Sequence
<220> FEATURE:
<223> OTHER INFORMATION: complete light chain

<400> SEQUENCE: 108

```
gatgttgtta tgacccaaac tccactctcc ctgtctgtca gtcttggaga tcaagcctcc    60
atctcttgca gatctagtca gagccttgta cacagtaatg gaaacaccta tttacattgg   120
tacctgcaga agccaggcca gtctccaaag ctcctgatct acaaagtttc ctaccgattt   180
tctggggtcc cagacaggtt cagtggcagt ggatcaggga cagatttcac actcaagatc   240
agcagagtgg aggctgagga tctgggagtt tatttctgct ctcaaaatac acatgttcct   300
```

```
cggacgttcg gccaagggac caaggtggaa atcaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttga    660

<210> SEQ ID NO 109
<211> LENGTH: 446
<212> TYPE: PRT
<213> ORGANISM: Artificial Sequence
<220> FEATURE:
<223> OTHER INFORMATION: complete heavy chain

<400> SEQUENCE: 109

Glu Val Gln Leu Gln Gln Phe Gly Ala Glu Leu Val Lys Pro Gly Ala
1               5                   10                  15

Ser Met Lys Leu Ser Cys Lys Ala Ser Gly Tyr Thr Phe Thr Asn Tyr
            20                  25                  30

Tyr Val Phe Trp Val Lys Gln Arg Pro Gly Gln Gly Leu Glu Trp Ile
        35                  40                  45

Gly Asp Ile Asn Pro Val Asn Gly Asp Thr Asn Phe Asn Glu Lys Phe
    50                  55                  60

Lys Asn Lys Ala Thr Leu Thr Val Asp Lys Ser Ser Thr Thr Thr Tyr
65                  70                  75                  80

Leu Gln Leu Ser Ser Leu Thr Ser Glu Asp Ser Ala Val Tyr Tyr Cys
                85                  90                  95

Thr Arg Gly Gly Tyr Thr Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 110
<211> LENGTH: 1341
<212> TYPE: PRT
<213> ORGANISM: Artificial Sequence
<220> FEATURE:
<223> OTHER INFORMATION: complete heavy chain

<400> SEQUENCE: 110

Gly Ala Gly Gly Thr Cys Cys Ala Gly Cys Thr Gly Cys Ala Gly Cys
1               5                   10                  15

Ala Gly Thr Thr Thr Gly Gly Gly Gly Cys Thr Gly Ala Ala Cys Thr
                20                  25                  30

Gly Gly Thr Gly Ala Ala Gly Cys Cys Thr Gly Gly Gly Gly Cys Thr
                35                  40                  45

Thr Cys Ala Ala Thr Gly Ala Ala Gly Thr Thr Gly Thr Cys Cys Thr
            50                  55                  60

Gly Cys Ala Ala Gly Gly Cys Thr Thr Cys Thr Gly Gly Cys Thr Ala
65                  70                  75                  80

Cys Ala Cys Cys Thr Thr Cys Ala Cys Cys Ala Ala Cys Thr Ala Cys
                85                  90                  95

Thr Ala Thr Gly Thr Ala Thr Cys Thr Gly Gly Gly Thr Gly Ala Ala
                100                 105                 110

Ala Ala Cys Ala Gly Gly Gly Cys Cys Thr Gly Gly Ala Cys Ala Ala
            115                 120                 125

Ala Gly Gly Cys Cys Thr Thr Gly Ala Gly Thr Gly Gly Ala Thr Thr
        130                 135                 140

Gly Gly Ala Gly Ala Cys Ala Thr Thr Ala Thr Cys Cys Thr Gly Gly
145                 150                 155                 160

Thr Cys Ala Ala Thr Gly Gly Thr Gly Ala Thr Ala Cys Thr Ala Ala
                165                 170                 175

Cys Thr Thr Cys Ala Ala Thr Gly Ala Gly Ala Ala Gly Thr Thr Cys
                180                 185                 190

Ala Ala Gly Ala Ala Cys Ala Ala Gly Gly Cys Cys Ala Cys Ala Cys
            195                 200                 205

Thr Gly Ala Cys Thr Gly Thr Ala Gly Ala Cys Ala Ala Gly Thr Cys
        210                 215                 220
```

```
Cys Thr Cys Cys Ala Cys Ala Cys Ala Ala Cys Ala Thr Ala Cys
225                 230                 235                 240

Thr Thr Gly Cys Ala Ala Cys Thr Cys Ala Gly Cys Ala Gly Cys Cys
                245                 250                 255

Thr Gly Ala Cys Ala Thr Cys Thr Gly Ala Gly Ala Cys Thr Cys
            260                 265                 270

Thr Gly Cys Gly Gly Thr Cys Thr Ala Thr Ala Cys Thr Gly Thr
        275                 280                 285

Ala Cys Ala Ala Gly Ala Gly Gly Gly Gly Thr Ala Thr Ala
    290                 295                 300

Cys Thr Ala Thr Gly Gly Ala Cys Thr Ala Cys Thr Gly Gly Gly
305                 310                 315                 320

Cys Cys Ala Gly Gly Ala Ala Cys Gly Cys Thr Gly Gly Thr Cys
            325                 330                 335

Ala Cys Cys Gly Thr Cys Ala Gly Cys Thr Cys Ala Gly Cys Cys Thr
            340                 345                 350

Cys Cys Ala Cys Ala Ala Gly Gly Cys Cys Ala Thr Cys Cys
        355                 360                 365

Gly Gly Thr Cys Thr Thr Cys Cys Cys Cys Thr Gly Gly Cys Ala
370                 375                 380

Cys Cys Cys Thr Cys Cys Thr Cys Cys Ala Ala Gly Ala Gly Cys Ala
385                 390                 395                 400

Cys Cys Thr Cys Thr Gly Gly Gly Gly Cys Ala Cys Ala Gly Cys
            405                 410                 415

Gly Gly Cys Cys Cys Thr Gly Gly Gly Cys Thr Gly Cys Thr Gly
        420                 425                 430

Gly Thr Cys Ala Ala Gly Gly Ala Cys Thr Ala Cys Thr Cys Cys
        435                 440                 445

Cys Cys Gly Ala Ala Cys Cys Gly Gly Thr Gly Ala Cys Gly Gly Thr
        450                 455                 460

Gly Thr Cys Gly Thr Gly Gly Ala Ala Cys Thr Cys Ala Gly Gly Cys
465                 470                 475                 480

Gly Cys Cys Cys Thr Gly Ala Cys Cys Ala Gly Cys Gly Gly Cys Gly
            485                 490                 495

Thr Gly Cys Ala Cys Ala Cys Cys Thr Thr Cys Cys Cys Gly Gly Cys
        500                 505                 510

Thr Gly Thr Cys Cys Thr Ala Cys Ala Gly Thr Cys Thr Cys Ala
        515                 520                 525

Gly Gly Ala Cys Thr Cys Thr Ala Cys Thr Cys Cys Cys Thr Cys Ala
530                 535                 540

Gly Cys Ala Gly Cys Gly Thr Gly Gly Thr Gly Ala Cys Cys Gly Thr
545                 550                 555                 560

Gly Cys Cys Cys Thr Cys Cys Ala Gly Cys Ala Gly Cys Thr Thr Gly
            565                 570                 575

Gly Gly Cys Ala Cys Cys Cys Ala Gly Ala Cys Cys Thr Ala Cys Ala
            580                 585                 590

Thr Cys Thr Gly Cys Ala Ala Cys Gly Thr Gly Ala Ala Thr Cys Ala
            595                 600                 605

Cys Ala Ala Gly Cys Cys Ala Gly Cys Ala Ala Cys Ala Cys Cys
        610                 615                 620

Ala Ala Gly Gly Thr Gly Gly Ala Cys Ala Ala Gly Ala Ala Gly
625                 630                 635                 640
```

-continued

```
Thr Thr Gly Ala Gly Cys Cys Cys Ala Ala Ala Thr Cys Thr Thr Gly
                645                 650                 655

Thr Gly Ala Cys Ala Ala Ala Ala Cys Thr Cys Ala Cys Ala Cys Ala
            660                 665                 670

Thr Gly Cys Cys Cys Ala Cys Cys Gly Thr Gly Cys Cys Cys Ala Gly
        675                 680                 685

Cys Ala Cys Cys Thr Gly Ala Ala Cys Thr Cys Cys Thr Gly Gly Gly
    690                 695                 700

Gly Gly Gly Ala Cys Cys Gly Thr Cys Ala Gly Thr Cys Thr Thr Cys
705                 710                 715                 720

Cys Thr Cys Thr Thr Cys Cys Cys Cys Cys Cys Ala Ala Ala Ala Cys
                725                 730                 735

Cys Cys Ala Ala Gly Gly Ala Cys Ala Cys Cys Cys Thr Cys Ala Thr
            740                 745                 750

Gly Ala Thr Cys Thr Cys Cys Cys Gly Gly Ala Cys Cys Cys Cys Thr
        755                 760                 765

Gly Ala Gly Gly Thr Cys Ala Cys Ala Thr Gly Cys Gly Thr Gly Gly
    770                 775                 780

Thr Gly Gly Thr Gly Gly Ala Cys Gly Thr Gly Ala Gly Cys Cys Ala
785                 790                 795                 800

Cys Gly Ala Ala Gly Ala Cys Cys Cys Thr Gly Ala Gly Gly Thr Cys
                805                 810                 815

Ala Ala Gly Thr Thr Cys Ala Ala Cys Thr Gly Gly Thr Ala Cys Gly
            820                 825                 830

Thr Gly Gly Ala Cys Gly Gly Cys Gly Thr Gly Gly Ala Gly Gly Thr
        835                 840                 845

Gly Cys Ala Thr Ala Ala Thr Gly Cys Cys Ala Ala Gly Ala Cys Ala
    850                 855                 860

Ala Ala Gly Cys Cys Gly Cys Gly Gly Gly Ala Gly Gly Ala Gly Cys
865                 870                 875                 880

Ala Gly Thr Ala Cys Ala Ala Cys Ala Gly Cys Ala Cys Gly Thr Ala
                885                 890                 895

Cys Cys Gly Thr Gly Thr Gly Gly Thr Cys Ala Gly Cys Gly Thr Cys
            900                 905                 910

Cys Thr Cys Ala Cys Cys Gly Thr Cys Cys Thr Gly Cys Ala Cys Cys
        915                 920                 925

Ala Gly Gly Ala Cys Thr Gly Gly Cys Thr Gly Ala Ala Thr Gly Gly
    930                 935                 940

Cys Ala Ala Gly Gly Ala Gly Thr Ala Cys Ala Ala Gly Thr Gly Cys
945                 950                 955                 960

Ala Ala Gly Gly Thr Cys Ala Gly Cys Ala Ala Cys Ala Ala Ala Gly
                965                 970                 975

Cys Cys Cys Thr Cys Cys Cys Ala Gly Cys Cys Cys Cys Cys Ala Thr
            980                 985                 990

Cys Gly Ala Gly Ala Ala Ala Ala  Cys Cys Ala Thr Cys  Thr Cys Cys
        995                 1000                1005

Ala Ala  Ala Gly Cys Cys Ala  Ala Ala Gly Gly Gly  Cys Ala Gly
    1010                1015                1020

Cys Cys  Cys Cys Gly Ala Gly  Ala Ala Cys Cys Ala  Cys Ala Gly
    1025                1030                1035

Gly Thr  Gly Thr Ala Cys Ala  Cys Cys Cys Thr Gly  Cys Cys Cys
    1040                1045                1050

Cys Cys  Ala Thr Cys Cys Cys  Gly Gly Gly Ala Thr  Gly Ala Gly

```
                1055                1060                1065
Cys Thr Gly Ala Cys Cys Ala Gly Ala Ala Cys Cys Ala Gly
        1070                1075                1080
Gly Thr Cys Ala Gly Cys Cys Thr Gly Ala Cys Cys Thr Gly Cys
        1085                1090                1095
Cys Thr Gly Gly Thr Cys Ala Ala Gly Gly Cys Thr Thr Cys
        1100                1105                1110
Thr Ala Thr Cys Cys Cys Ala Gly Cys Gly Ala Cys Ala Thr Cys
        1115                1120                1125
Gly Cys Cys Gly Thr Gly Gly Ala Gly Thr Gly Gly Gly Ala Gly
        1130                1135                1140
Ala Gly Cys Ala Ala Thr Gly Gly Gly Cys Ala Gly Cys Cys Gly
        1145                1150                1155
Gly Ala Gly Ala Ala Cys Ala Ala Cys Thr Ala Cys Ala Ala Gly
        1160                1165                1170
Ala Cys Cys Ala Cys Gly Cys Cys Thr Cys Cys Cys Gly Thr Gly
        1175                1180                1185
Cys Thr Gly Gly Ala Cys Thr Cys Cys Gly Ala Cys Gly Gly Cys
        1190                1195                1200
Thr Cys Cys Thr Thr Cys Thr Thr Cys Cys Thr Cys Thr Ala Cys
        1205                1210                1215
Ala Gly Cys Ala Ala Gly Cys Thr Cys Ala Cys Cys Gly Thr Gly
        1220                1225                1230
Gly Ala Cys Ala Ala Gly Ala Gly Cys Ala Gly Gly Thr Gly Gly
        1235                1240                1245
Cys Ala Gly Cys Ala Gly Gly Gly Ala Ala Cys Gly Thr Cys
        1250                1255                1260
Thr Thr Cys Thr Cys Ala Thr Gly Cys Thr Cys Cys Gly Thr Gly
        1265                1270                1275
Ala Thr Gly Cys Ala Thr Gly Ala Gly Gly Cys Thr Cys Thr Gly
        1280                1285                1290
Cys Ala Cys Ala Ala Cys Cys Ala Cys Thr Ala Cys Ala Cys Gly
        1295                1300                1305
Cys Ala Gly Ala Ala Gly Ala Gly Cys Cys Thr Cys Thr Cys Cys
        1310                1315                1320
Cys Thr Gly Thr Cys Thr Cys Cys Gly Gly Gly Thr Ala Ala Ala
        1325                1330                1335
Thr Gly Ala
    1340

<210> SEQ ID NO 111
<211> LENGTH: 354
<212> TYPE: PRT
<213> ORGANISM: Artificial Sequence
<220> FEATURE:
<223> OTHER INFORMATION: complete heavy chain

<400> SEQUENCE: 111

Glu Val Gln Leu Gln Gln Phe Gly Ala Glu Leu Val Lys Pro Gly Ala
1               5                   10                  15

Ser Met Lys Leu Ser Cys Lys Ala Ser Gly Tyr Thr Phe Thr Asn Tyr
                20                  25                  30

Tyr Val Phe Trp Val Lys Gln Arg Pro Gly Gln Gly Leu Glu Trp Ile
            35                  40                  45

Gly Asp Ile Asn Pro Val Asn Gly Asp Thr Asn Phe Asn Glu Lys Phe
```

```
                    50                  55                  60
Lys Asn Lys Ala Thr Leu Thr Val Asp Lys Ser Thr Thr Thr Tyr
 65                  70                  75                  80

Leu Gln Leu Ser Ser Leu Thr Ser Glu Asp Ser Ala Val Tyr Tyr Cys
                 85                  90                  95

Thr Arg Gly Gly Tyr Thr Met Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Gln Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg

<210> SEQ ID NO 112
<211> LENGTH: 442
<212> TYPE: PRT
<213> ORGANISM: Artificial Sequence
<220> FEATURE:
<223> OTHER INFORMATION: complete heavy chain

<400> SEQUENCE: 112

Gln Val Gln Leu Gln Glu Ser Gly Pro Gly Leu Val Lys Pro Ser Gln
  1               5                  10                  15

Thr Leu Ser Leu Thr Cys Thr Val Ser Gly Tyr Thr Phe Thr Asn Tyr
                 20                  25                  30

Tyr Val Phe Trp Val Arg Gln Ala Arg Gly Gln Arg Leu Glu Trp Ile
             35                  40                  45

Gly Asp Ile Asn Pro Val Asn Gly Asp Thr Asn Phe Asn Glu Lys Phe
     50                  55                  60
```

Lys Asn Arg Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
             85                  90                  95

Ala Arg Gly Gly Tyr Thr Met Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
            195                 200                 205

Lys Val Asp Lys Thr Val Glu Arg Lys Cys Val Glu Cys Pro Pro
210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
            275                 280                 285

Glu Gln Phe Asn Ser Thr Phe Arg Val Val Ser Val Leu Thr Val Val
            290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
            325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Asn Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
            420                 425                 430

Gln Lys Ser Leu Ser Leu Ser Pro Gly Lys
            435                 440

<210> SEQ ID NO 113
<211> LENGTH: 443
<212> TYPE: PRT
<213> ORGANISM: Artificial Sequence
<220> FEATURE:

<223> OTHER INFORMATION: complete heavy chain

<400> SEQUENCE: 113

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Tyr Thr Phe Thr Asn Tyr
             20                  25                  30

Tyr Val Phe Trp Val Arg Gln Ala Arg Gly Gln Arg Leu Glu Trp Ile
         35                  40                  45

Gly Asp Ile Asn Pro Val Asn Gly Asp Thr Asn Phe Asn Glu Lys Phe
     50                  55                  60

Lys Asn Arg Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Gly Tyr Thr Met Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400
```

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
            435                 440

<210> SEQ ID NO 114
<211> LENGTH: 1341
<212> TYPE: PRT
<213> ORGANISM: Artificial Sequence
<220> FEATURE:
<223> OTHER INFORMATION: complete heavy chain

<400> SEQUENCE: 114

Gly Ala Gly Gly Thr Cys Cys Ala Gly Cys Thr Gly Cys Ala Gly Cys
1               5                   10                  15

Ala Gly Thr Thr Thr Gly Gly Gly Cys Thr Gly Ala Ala Cys Thr
            20                  25                  30

Gly Gly Thr Gly Ala Ala Gly Cys Thr Gly Gly Gly Cys Thr
            35                  40                  45

Thr Cys Ala Ala Thr Gly Ala Ala Gly Thr Thr Gly Thr Cys Cys Thr
        50                  55                  60

Gly Cys Ala Ala Gly Gly Cys Thr Thr Cys Thr Gly Cys Thr Ala
65                  70                  75                  80

Cys Ala Cys Cys Thr Thr Cys Ala Cys Cys Ala Ala Cys Thr Ala Cys
                85                  90                  95

Thr Ala Thr Gly Thr Ala Thr Thr Cys Thr Gly Gly Gly Thr Gly Ala
            100                 105                 110

Ala Ala Cys Ala Gly Ala Gly Gly Cys Cys Thr Gly Gly Ala Cys Ala
            115                 120                 125

Ala Gly Gly Cys Cys Thr Thr Gly Ala Gly Thr Gly Gly Ala Thr Thr
            130                 135                 140

Gly Gly Ala Gly Ala Cys Ala Thr Thr Ala Ala Thr Cys Cys Thr Gly
145                 150                 155                 160

Thr Cys Ala Ala Thr Gly Gly Thr Gly Ala Thr Ala Cys Thr Ala Ala
                165                 170                 175

Cys Thr Thr Cys Ala Ala Thr Gly Ala Gly Ala Ala Ala Thr Thr Cys
                180                 185                 190

Ala Ala Gly Ala Gly Cys Ala Ala Gly Gly Cys Cys Ala Cys Ala Cys
                195                 200                 205

Thr Gly Ala Cys Thr Gly Thr Ala Gly Ala Cys Ala Ala Gly Thr Cys
            210                 215                 220

Cys Thr Cys Cys Ala Cys Cys Ala Cys Ala Gly Cys Cys Thr Ala Cys
225                 230                 235                 240

Thr Thr Gly Cys Ala Ala Cys Thr Cys Ala Gly Cys Ala Gly Cys Cys
                245                 250                 255

Thr Gly Ala Cys Ala Thr Cys Thr Gly Ala Gly Gly Ala Cys Thr Cys
            260                 265                 270

Thr Gly Cys Gly Gly Thr Cys Thr Ala Thr Thr Ala Cys Thr Gly Thr
            275                 280                 285

Ala Cys Ala Ala Gly Ala Gly Gly Gly Gly Thr Ala Thr Ala
            290                 295                 300

Cys Thr Ala Thr Gly Gly Ala Cys Thr Ala Cys Thr Gly Gly Gly Gly
305                 310                 315                 320

```
Cys Cys Ala Gly Gly Ala Ala Cys Gly Cys Thr Gly Gly Thr Cys
                325             330             335
Ala Cys Cys Gly Thr Cys Ala Gly Cys Thr Cys Ala Gly Cys Cys Thr
            340             345             350
Cys Cys Ala Cys Cys Ala Ala Gly Gly Gly Cys Cys Ala Thr Cys
            355             360             365
Gly Gly Thr Cys Thr Thr Cys Cys Cys Cys Thr Gly Gly Cys Ala
            370             375             380
Cys Cys Cys Thr Cys Thr Cys Cys Ala Gly Ala Gly Cys Ala
385             390             395             400
Cys Cys Thr Cys Thr Gly Gly Gly Gly Cys Ala Cys Ala Gly Cys
            405             410             415
Gly Gly Cys Cys Cys Thr Gly Gly Cys Thr Gly Cys Cys Thr Gly
            420             425             430
Gly Thr Cys Ala Ala Gly Gly Ala Cys Thr Ala Cys Thr Cys Cys
            435             440             445
Cys Cys Gly Ala Ala Cys Cys Gly Gly Thr Gly Ala Cys Gly Gly Thr
            450             455             460
Gly Thr Cys Gly Thr Gly Gly Ala Ala Cys Thr Cys Ala Gly Gly Cys
465             470             475             480
Gly Cys Cys Cys Thr Gly Ala Cys Cys Ala Gly Cys Gly Gly Cys Gly
            485             490             495
Thr Gly Cys Ala Cys Ala Cys Cys Thr Thr Cys Cys Cys Gly Gly Cys
            500             505             510
Thr Gly Thr Cys Cys Thr Ala Cys Ala Gly Thr Cys Cys Thr Cys Ala
            515             520             525
Gly Gly Ala Cys Thr Cys Thr Ala Cys Thr Cys Cys Cys Thr Cys Ala
            530             535             540
Gly Cys Ala Gly Cys Gly Thr Gly Gly Thr Gly Ala Cys Cys Gly Thr
545             550             555             560
Gly Cys Cys Cys Thr Cys Cys Ala Gly Cys Ala Gly Cys Thr Thr Gly
            565             570             575
Gly Gly Cys Ala Cys Cys Cys Ala Gly Ala Cys Cys Thr Ala Cys Ala
            580             585             590
Thr Cys Thr Gly Cys Ala Ala Cys Gly Thr Gly Ala Ala Thr Cys Ala
            595             600             605
Cys Ala Ala Gly Cys Cys Cys Ala Gly Cys Ala Ala Cys Ala Cys Cys
            610             615             620
Ala Ala Gly Gly Thr Gly Gly Ala Cys Ala Ala Gly Ala Ala Ala Gly
625             630             635             640
Thr Thr Gly Ala Gly Cys Cys Cys Ala Ala Ala Thr Cys Thr Thr Gly
            645             650             655
Thr Gly Ala Cys Ala Ala Ala Ala Cys Thr Cys Ala Cys Ala Cys Ala
            660             665             670
Thr Gly Cys Cys Cys Ala Cys Cys Gly Thr Gly Cys Cys Cys Ala Gly
            675             680             685
Cys Ala Cys Cys Thr Gly Ala Ala Cys Thr Cys Cys Thr Gly Gly Gly
            690             695             700
Gly Gly Gly Ala Cys Cys Gly Thr Cys Ala Gly Thr Cys Thr Thr Cys
705             710             715             720
Cys Thr Cys Thr Thr Cys Cys Cys Cys Cys Cys Ala Ala Ala Ala Cys
            725             730             735
Cys Cys Ala Ala Gly Gly Ala Cys Ala Cys Cys Cys Thr Cys Ala Thr
```

```
                     740                 745                 750
Gly Ala Thr Cys Thr Cys Cys Cys Gly Gly Ala Cys Cys Cys Cys Thr
                755                 760                 765
Gly Ala Gly Gly Thr Cys Ala Cys Ala Thr Gly Cys Gly Thr Gly Gly
                770                 775                 780
Thr Gly Gly Thr Gly Gly Ala Cys Gly Thr Gly Ala Gly Cys Cys Ala
785                 790                 795                 800
Cys Gly Ala Ala Gly Ala Cys Cys Thr Gly Ala Gly Gly Thr Cys
                805                 810                 815
Ala Ala Gly Thr Thr Cys Ala Ala Cys Thr Gly Gly Thr Ala Cys Gly
                820                 825                 830
Thr Gly Gly Ala Cys Gly Gly Cys Gly Thr Gly Gly Ala Gly Gly Thr
                835                 840                 845
Gly Cys Ala Thr Ala Ala Thr Gly Cys Cys Ala Ala Gly Ala Cys Ala
                850                 855                 860
Ala Ala Gly Cys Cys Gly Cys Gly Gly Gly Ala Gly Gly Ala Gly Cys
865                 870                 875                 880
Ala Gly Thr Ala Cys Cys Ala Gly Ala Gly Cys Ala Cys Gly Thr Ala
                885                 890                 895
Cys Cys Gly Thr Gly Thr Gly Gly Thr Cys Ala Gly Cys Gly Thr Cys
                900                 905                 910
Cys Thr Cys Ala Cys Cys Gly Thr Cys Cys Thr Gly Cys Ala Cys Cys
                915                 920                 925
Ala Gly Gly Ala Cys Thr Gly Gly Cys Thr Gly Ala Ala Thr Gly Gly
                930                 935                 940
Cys Ala Ala Gly Gly Ala Gly Thr Ala Cys Ala Ala Gly Thr Gly Cys
945                 950                 955                 960
Ala Ala Gly Gly Thr Cys Ala Gly Cys Ala Ala Cys Ala Ala Ala Gly
                965                 970                 975
Cys Cys Cys Thr Cys Cys Ala Gly Cys Cys Cys Cys Cys Ala Thr
                980                 985                 990
Cys Gly Ala Gly Ala Ala Ala Ala Cys Cys Ala Thr Cys Thr Cys Cys
                995                1000                1005
Ala Ala Ala Gly Cys Cys Ala Ala Gly Gly Gly Cys Ala Gly
                1010                1015                1020
Cys Cys Cys Cys Gly Ala Gly Ala Ala Cys Cys Ala Cys Ala Gly
                1025                1030                1035
Gly Thr Gly Thr Ala Cys Ala Cys Cys Cys Thr Gly Cys Cys Cys
                1040                1045                1050
Cys Cys Ala Thr Cys Cys Gly Gly Gly Ala Thr Gly Ala Gly
                1055                1060                1065
Cys Thr Gly Ala Cys Cys Ala Ala Gly Ala Ala Cys Cys Ala Gly
                1070                1075                1080
Gly Thr Cys Ala Gly Cys Cys Thr Gly Ala Cys Cys Thr Gly Cys
                1085                1090                1095
Cys Thr Gly Gly Thr Cys Ala Ala Ala Gly Gly Cys Thr Thr Cys
                1100                1105                1110
Thr Ala Thr Cys Cys Cys Ala Gly Cys Gly Ala Cys Ala Thr Cys
                1115                1120                1125
Gly Cys Cys Gly Thr Gly Gly Ala Gly Thr Gly Gly Gly Ala Gly
                1130                1135                1140
Ala Gly Cys Ala Ala Thr Gly Gly Gly Cys Ala Gly Cys Cys Gly
                1145                1150                1155
```

Gly Ala Gly Ala Ala Cys Ala Ala Cys Thr Ala Cys Ala Ala Gly
            1160                1165                1170

Ala Cys Cys Ala Cys Gly Cys Cys Thr Cys Cys Cys Gly Thr Gly
    1175                1180                1185

Cys Thr Gly Gly Ala Cys Thr Cys Cys Gly Ala Cys Gly Gly Cys
    1190                1195                1200

Thr Cys Cys Thr Thr Cys Thr Thr Cys Cys Thr Cys Thr Ala Cys
    1205                1210                1215

Ala Gly Cys Ala Ala Gly Cys Thr Cys Ala Cys Cys Gly Thr Gly
    1220                1225                1230

Gly Ala Cys Ala Ala Gly Ala Gly Cys Ala Gly Gly Thr Gly Gly
    1235                1240                1245

Cys Ala Gly Cys Ala Gly Gly Gly Gly Ala Ala Cys Gly Thr Cys
    1250                1255                1260

Thr Thr Cys Thr Cys Ala Thr Gly Cys Thr Cys Cys Gly Thr Gly
    1265                1270                1275

Ala Thr Gly Cys Ala Thr Gly Ala Gly Gly Cys Thr Cys Thr Gly
    1280                1285                1290

Cys Ala Cys Ala Ala Cys Cys Ala Cys Thr Ala Cys Ala Cys Gly
    1295                1300                1305

Cys Ala Gly Ala Ala Gly Ala Gly Cys Cys Thr Cys Thr Cys Cys
    1310                1315                1320

Cys Thr Gly Thr Cys Thr Cys Cys Gly Gly Gly Thr Ala Ala Ala
    1325                1330                1335

Thr Gly Ala
    1340

<210> SEQ ID NO 115
<211> LENGTH: 1326
<212> TYPE: PRT
<213> ORGANISM: Artificial Sequence
<220> FEATURE:
<223> OTHER INFORMATION: complete heavy chain

<400> SEQUENCE: 115

Cys Ala Gly Gly Thr Gly Cys Ala Gly Cys Thr Gly Cys Ala Gly
1               5                   10                  15

Ala Gly Thr Cys Gly Gly Gly Cys Cys Cys Ala Gly Gly Ala Cys Thr
                20                  25                  30

Gly Gly Thr Gly Ala Ala Gly Cys Cys Thr Thr Cys Ala Cys Ala Gly
            35                  40                  45

Ala Cys Cys Cys Thr Gly Thr Cys Cys Cys Thr Cys Ala Cys Cys Thr
    50                  55                  60

Gly Cys Ala Cys Thr Gly Thr Cys Thr Cys Thr Gly Gly Cys Thr Ala
65                  70                  75                  80

Cys Ala Cys Cys Thr Thr Cys Ala Cys Cys Ala Ala Cys Thr Ala Cys
                85                  90                  95

Thr Ala Thr Gly Thr Ala Thr Cys Thr Gly Gly Gly Thr Gly Cys
            100                 105                 110

Gly Ala Cys Ala Gly Gly Cys Thr Cys Gly Thr Gly Gly Ala Cys Ala
        115                 120                 125

Ala Cys Gly Cys Cys Thr Thr Gly Ala Gly Thr Gly Gly Ala Thr Ala
    130                 135                 140

Gly Gly Thr Gly Ala Cys Ala Thr Thr Ala Ala Thr Cys Cys Thr Gly
145                 150                 155                 160

-continued

```
Thr Cys Ala Ala Thr Gly Gly Thr Gly Ala Thr Ala Cys Thr Ala Ala
                165                 170                 175
Cys Thr Thr Cys Ala Ala Thr Gly Ala Gly Ala Ala Ala Thr Thr Cys
                180                 185                 190
Ala Ala Gly Ala Ala Cys Ala Gly Ala Gly Thr Cys Ala Cys Cys Ala
                195                 200                 205
Thr Cys Thr Cys Ala Gly Cys Cys Gly Ala Cys Ala Ala Gly Thr Cys
                210                 215                 220
Cys Ala Thr Cys Ala Gly Cys Ala Cys Cys Gly Cys Cys Thr Ala Cys
225                 230                 235                 240
Cys Thr Gly Cys Ala Gly Thr Gly Gly Ala Gly Cys Ala Gly Cys Cys
                245                 250                 255
Thr Gly Ala Ala Gly Gly Cys Cys Thr Cys Gly Gly Ala Cys Ala Cys
                260                 265                 270
Cys Gly Cys Cys Ala Thr Gly Thr Ala Thr Thr Ala Cys Thr Gly Thr
                275                 280                 285
Gly Cys Gly Ala Gly Ala Gly Gly Gly Gly Thr Thr Ala Thr Ala Ala
                290                 295                 300
Cys Thr Ala Thr Gly Gly Ala Cys Thr Ala Cys Thr Gly Gly Gly Gly
305                 310                 315                 320
Cys Cys Ala Gly Gly Gly Ala Ala Cys Gly Cys Thr Gly Gly Thr Cys
                325                 330                 335
Ala Cys Cys Gly Thr Cys Ala Gly Cys Thr Cys Ala Gly Cys Cys Thr
                340                 345                 350
Cys Cys Ala Cys Ala Ala Gly Gly Cys Cys Cys Ala Thr Cys Gly Gly
                355                 360                 365
Thr Cys Thr Thr Cys Cys Cys Cys Cys Thr Gly Gly Cys Ala Cys Cys
                370                 375                 380
Cys Cys Thr Gly Cys Thr Cys Cys Ala Gly Gly Ala Gly Cys Ala Cys
385                 390                 395                 400
Cys Thr Cys Cys Gly Ala Gly Ala Gly Cys Ala Cys Ala Gly Cys Gly
                405                 410                 415
Gly Cys Cys Cys Thr Gly Gly Gly Cys Thr Gly Cys Cys Thr Gly Gly
                420                 425                 430
Thr Cys Ala Ala Gly Gly Ala Cys Thr Ala Cys Thr Thr Cys Cys Cys
                435                 440                 445
Cys Gly Ala Ala Cys Cys Gly Gly Thr Gly Ala Cys Gly Gly Thr Gly
                450                 455                 460
Thr Cys Gly Thr Gly Gly Ala Ala Cys Thr Cys Ala Gly Gly Cys Gly
465                 470                 475                 480
Cys Cys Thr Cys Thr Gly Ala Cys Cys Ala Gly Cys Gly Gly Cys Gly
                485                 490                 495
Thr Gly Cys Ala Cys Ala Cys Thr Thr Cys Cys Cys Gly Gly Cys Thr
                500                 505                 510
Thr Gly Thr Cys Cys Thr Ala Cys Ala Gly Thr Cys Cys Thr Cys Ala
                515                 520                 525
Gly Gly Ala Cys Thr Cys Thr Ala Cys Thr Cys Cys Cys Thr Cys Ala
                530                 535                 540
Gly Cys Ala Gly Cys Gly Thr Gly Gly Thr Gly Ala Cys Cys Gly Thr
                545                 550                 555                 560
Gly Cys Cys Cys Thr Cys Cys Ala Gly Cys Ala Ala Cys Thr Thr Cys
                565                 570                 575
```

-continued

```
Gly Gly Cys Ala Cys Cys Ala Gly Ala Cys Thr Ala Cys Ala
            580             585             590

Cys Cys Thr Gly Cys Ala Ala Cys Gly Thr Ala Gly Thr Cys Ala
            595             600             605

Cys Ala Ala Gly Cys Cys Ala Gly Cys Ala Ala Cys Ala Cys Cys
            610             615             620

Ala Ala Gly Gly Thr Gly Gly Ala Cys Ala Ala Gly Ala Cys Ala Gly
625             630             635             640

Thr Thr Gly Ala Gly Cys Gly Cys Ala Ala Thr Gly Thr Thr Gly
            645             650             655

Thr Gly Thr Cys Gly Ala Gly Thr Gly Cys Cys Ala Cys Cys Gly
            660             665             670

Thr Gly Cys Cys Cys Ala Gly Cys Ala Cys Cys Ala Cys Thr Gly
            675             680             685

Thr Gly Gly Cys Ala Gly Gly Ala Cys Cys Gly Thr Cys Ala Gly Thr
            690             695             700

Cys Thr Thr Cys Cys Thr Cys Thr Thr Cys Cys Cys Cys Cys Ala
705             710             715             720

Ala Ala Ala Cys Cys Cys Ala Ala Gly Gly Ala Cys Ala Cys Cys Cys
            725             730             735

Thr Cys Ala Thr Gly Ala Thr Cys Thr Cys Cys Cys Gly Gly Ala Cys
            740             745             750

Cys Cys Cys Thr Gly Ala Gly Gly Thr Cys Ala Cys Gly Thr Gly Cys
            755             760             765

Gly Thr Gly Gly Thr Gly Gly Thr Gly Gly Ala Cys Gly Thr Gly Ala
            770             775             780

Gly Cys Cys Ala Cys Gly Ala Ala Gly Ala Cys Cys Cys Thr Gly Ala
785             790             795             800

Gly Gly Thr Cys Cys Ala Gly Thr Thr Cys Ala Ala Cys Thr Gly Gly
            805             810             815

Thr Ala Cys Gly Thr Gly Gly Ala Cys Gly Gly Cys Gly Thr Gly Gly
            820             825             830

Ala Gly Gly Thr Gly Cys Ala Thr Ala Ala Thr Gly Cys Cys Ala Ala
            835             840             845

Gly Ala Cys Ala Ala Ala Gly Cys Cys Ala Cys Gly Gly Gly Ala Gly
            850             855             860

Gly Ala Gly Cys Ala Gly Thr Thr Cys Ala Ala Cys Ala Gly Cys Ala
865             870             875             880

Cys Gly Thr Thr Cys Cys Gly Thr Gly Thr Gly Gly Thr Cys Ala Gly
            885             890             895

Cys Gly Thr Cys Cys Thr Cys Ala Cys Cys Gly Thr Cys Gly Thr Gly
            900             905             910

Cys Ala Cys Cys Ala Gly Gly Ala Cys Thr Gly Gly Cys Thr Gly Ala
            915             920             925

Ala Cys Gly Gly Cys Ala Ala Gly Gly Ala Gly Thr Ala Cys Ala Ala
            930             935             940

Gly Thr Gly Cys Ala Ala Gly Gly Thr Gly Thr Cys Cys Ala Ala Cys
945             950             955             960

Ala Ala Ala Gly Gly Cys Cys Thr Cys Cys Cys Ala Gly Cys Cys Cys
            965             970             975

Cys Cys Ala Thr Cys Gly Ala Gly Ala Ala Ala Cys Cys Ala Thr
            980             985             990

Cys Thr Cys Cys Ala Ala Ala Ala  Cys Cys Ala Ala Ala  Gly Gly Gly
```

```
                995                 1000                1005
Cys Ala Gly Cys Cys Cys  Gly Ala Gly Ala Ala  Cys Cys Ala
    1010                 1015                 1020

Cys Ala Gly Gly Thr Gly  Thr Ala Cys Ala Cys  Cys Thr Gly
    1025                 1030                 1035

Cys Cys Cys Cys Ala Thr  Cys Cys Cys Gly Gly  Gly Ala Gly
    1040                 1045                 1050

Gly Ala Gly Ala Thr Gly  Ala Cys Cys Ala Ala  Gly Ala Ala Cys
    1055                 1060                 1065

Cys Ala Gly Gly Thr Cys  Ala Gly Cys Cys Thr  Gly Ala Cys Cys
    1070                 1075                 1080

Thr Gly Cys Cys Thr Gly  Gly Thr Cys Ala Ala  Ala Gly Gly Cys
    1085                 1090                 1095

Thr Thr Cys Thr Ala Cys  Cys Cys Cys Ala Gly  Cys Gly Ala Cys
    1100                 1105                 1110

Ala Thr Cys Gly Cys Cys  Gly Thr Gly Ala Gly  Thr Gly Gly
    1115                 1120                 1125

Gly Ala Gly Ala Gly Cys  Ala Ala Thr Gly Gly  Gly Cys Ala Gly
    1130                 1135                 1140

Cys Cys Gly Gly Ala Gly  Ala Ala Cys Ala Ala  Cys Thr Ala Cys
    1145                 1150                 1155

Ala Ala Cys Ala Cys Cys  Ala Cys Ala Cys Cys  Thr Cys Cys Cys
    1160                 1165                 1170

Ala Thr Gly Cys Thr Gly  Gly Ala Cys Thr Cys  Cys Gly Ala Cys
    1175                 1180                 1185

Gly Gly Cys Thr Cys Cys  Thr Thr Cys Thr Thr  Cys Cys Thr Cys
    1190                 1195                 1200

Thr Ala Cys Ala Gly Cys  Ala Ala Gly Cys Thr  Cys Ala Cys Cys
    1205                 1210                 1215

Gly Thr Gly Gly Ala Cys  Ala Ala Gly Ala Gly  Cys Ala Gly Gly
    1220                 1225                 1230

Thr Gly Gly Cys Ala Gly  Cys Ala Gly Gly Gly  Ala Ala Cys
    1235                 1240                 1245

Gly Thr Cys Thr Thr Cys  Thr Cys Ala Thr Gly  Cys Thr Cys Cys
    1250                 1255                 1260

Gly Thr Gly Ala Thr Gly  Cys Ala Thr Gly Ala  Gly Gly Cys Thr
    1265                 1270                 1275

Cys Thr Gly Cys Ala Cys  Ala Cys Cys Ala Cys  Thr Ala Cys
    1280                 1285                 1290

Ala Cys Gly Cys Ala Gly  Ala Ala Gly Ala Gly  Cys Cys Thr Cys
    1295                 1300                 1305

Thr Cys Cys Cys Thr Gly  Thr Cys Thr Cys Cys  Gly Gly Gly Thr
    1310                 1315                 1320

Ala Ala Ala
    1325

<210> SEQ ID NO 116
<211> LENGTH: 1329
<212> TYPE: PRT
<213> ORGANISM: Artificial Sequence
<220> FEATURE:
<223> OTHER INFORMATION: complete heavy chain

<400> SEQUENCE: 116

Cys Ala Gly Gly Thr Gly Cys Ala Gly Cys Thr Gly Cys Ala Gly Gly
```

-continued

```
1               5                   10                  15
Ala Gly Thr Cys Gly Gly Cys Cys Cys Ala Gly Ala Cys Thr
                20                  25                  30
Gly Gly Thr Gly Ala Ala Gly Cys Cys Thr Thr Cys Ala Cys Ala Gly
                35                  40                  45
Ala Cys Cys Thr Gly Thr Cys Cys Cys Thr Cys Ala Cys Cys Thr
                50                  55                  60
Gly Cys Ala Cys Thr Gly Thr Cys Thr Cys Thr Gly Gly Cys Thr Ala
65                  70                  75                  80
Cys Ala Cys Cys Thr Thr Cys Ala Cys Ala Ala Cys Thr Ala Cys
                85                  90                  95
Thr Ala Thr Gly Thr Ala Thr Cys Thr Gly Gly Gly Thr Gly Cys
                100

```
Gly Thr Cys Ala Ala Gly Gly Ala Cys Thr Ala Cys Thr Cys Cys
            435                 440                 445
Cys Cys Gly Ala Ala Cys Cys Gly Gly Thr Gly Ala Cys Gly Gly Thr
            450                 455                 460
Gly Thr Cys Gly Thr Gly Gly Ala Ala Cys Thr Cys Ala Gly Gly Cys
465                 470                 475                 480
Gly Cys Cys Cys Thr Gly Ala Cys Cys Ala Gly Cys Gly Gly Cys Gly
                485                 490                 495
Thr Gly Cys Ala Cys Ala Cys Cys Thr Thr Cys Cys Cys Gly Gly Cys
                500                 505                 510
Thr Gly Thr Cys Cys Thr Ala Cys Ala Gly Thr Cys Cys Thr Cys Ala
            515                 520                 525
Gly Gly Ala Cys Thr Cys Thr Ala Cys Thr Cys Cys Cys Thr Cys Ala
            530                 535                 540
Gly Cys Ala Gly Cys Gly Thr Gly Gly Thr Gly Ala Cys Cys Gly Thr
545                 550                 555                 560
Gly Cys Cys Cys Thr Cys Cys Ala Gly Cys Ala Gly Cys Thr Thr Gly
                565                 570                 575
Gly Gly Cys Ala Cys Gly Ala Ala Gly Ala Cys Cys Thr Ala Cys Ala
                580                 585                 590
Cys Cys Thr Gly Cys Ala Ala Cys Gly Thr Ala Gly Ala Thr Cys Ala
            595                 600                 605
Cys Ala Ala Gly Cys Cys Cys Ala Gly Cys Ala Ala Cys Ala Cys Cys
            610                 615                 620
Ala Ala Gly Gly Thr Gly Gly Ala Cys Ala Ala Gly Ala Gly Ala Gly
625                 630                 635                 640
Thr Thr Gly Ala Gly Thr Cys Cys Ala Ala Ala Thr Ala Thr Gly Gly
                645                 650                 655
Thr Cys Cys Cys Cys Cys Ala Thr Gly Cys Cys Cys Ala Cys Cys Gly
                660                 665                 670
Thr Gly Cys Cys Cys Ala Gly Cys Ala Cys Cys Thr Gly Ala Gly Thr
            675                 680                 685
Thr Cys Cys Thr Gly Gly Gly Gly Gly Ala Cys Cys Ala Thr Cys Ala
            690                 695                 700
Gly Thr Cys Thr Thr Cys Cys Thr Gly Thr Thr Cys Cys Cys Cys Cys
705                 710                 715                 720
Cys Cys Ala Ala Ala Ala Cys Cys Cys Ala Ala Gly Gly Ala Cys Ala
                725                 730                 735
Cys Thr Cys Thr Cys Ala Thr Gly Ala Thr Cys Thr Cys Cys Cys Gly
            740                 745                 750
Gly Ala Cys Cys Cys Cys Thr Gly Ala Gly Gly Thr Cys Ala Cys Gly
                755                 760                 765
Thr Gly Cys Gly Thr Gly Gly Thr Gly Gly Thr Gly Gly Ala Cys Gly
770                 775                 780
Thr Gly Ala Gly Cys Cys Ala Gly Gly Ala Ala Gly Ala Cys Cys Cys
785                 790                 795                 800
Cys Gly Ala Gly Gly Thr Cys Cys Ala Gly Thr Thr Cys Ala Ala Cys
                805                 810                 815
Thr Gly Gly Thr Ala Cys Gly Thr Gly Gly Ala Thr Gly Gly Cys Gly
            820                 825                 830
Thr Gly Gly Ala Gly Gly Thr Gly Cys Ala Thr Ala Ala Thr Gly Cys
            835                 840                 845
```

```
Cys Ala Ala Gly Ala Cys Ala Ala Gly Cys Gly Cys Gly
    850                 855                 860
Gly Ala Gly Gly Ala Gly Cys Ala Gly Thr Thr Cys Ala Ala Cys Ala
865                 870                 875                 880
Gly Cys Ala Cys Gly Thr Ala Cys Cys Gly Thr Gly Thr Gly Thr
                885                 890                 895
Cys Ala Gly Cys Gly Thr Cys Cys Thr Cys Ala Cys Cys Gly Thr Cys
                900                 905                 910
Cys Thr Gly Cys Ala Cys Ala Gly Gly Ala Cys Thr Gly Gly Cys
                915                 920                 925
Thr Gly Ala Ala Cys Gly Gly Cys Ala Ala Gly Gly Ala Gly Thr Ala
930                 935                 940
Cys Ala Ala Gly Thr Gly Cys Ala Ala Gly Gly Thr Gly Thr Cys Cys
945                 950                 955                 960
Ala Ala Cys Ala Ala Ala Gly Gly Cys Cys Thr Cys Cys Cys Gly Thr
                965                 970                 975
Cys Cys Thr Cys Cys Ala Thr Cys Gly Ala Gly Ala Ala Ala Ala Cys
                980                 985                 990
Cys Ala Thr Cys Thr Cys Cys Ala  Ala Ala Gly Cys Cys  Ala Ala Ala
                995                 1000                1005
Gly Gly  Gly Cys Ala Gly Cys  Cys Cys Cys Gly Ala  Gly Ala Gly
1010                1015                1020
Cys Cys  Ala Cys Ala Gly Gly  Thr Gly Thr Ala Cys  Ala Cys Cys
1025                1030                1035
Cys Thr  Gly Cys Cys Cys Cys  Cys Ala Thr Cys Cys  Cys Ala Gly
1040                1045                1050
Gly Ala  Gly Gly Ala Gly Ala  Thr Gly Ala Cys Cys  Ala Ala Gly
1055                1060                1065
Ala Ala Cys Cys Ala Gly Gly  Thr Cys Ala Gly Cys  Cys Thr Gly
1070                1075                1080
Ala Cys  Cys Thr Gly Cys Cys  Thr Gly Gly Thr Cys  Ala Ala Ala
1085                1090                1095
Gly Gly  Cys Thr Thr Cys Thr  Ala Cys Cys Cys Cys  Ala Gly Cys
1100                1105                1110
Gly Ala  Cys Ala Thr Cys Gly  Cys Cys Gly Thr Gly  Gly Ala Gly
1115                1120                1125
Thr Gly  Gly Gly Ala Gly Ala  Gly Cys Ala Ala Thr  Gly Gly Gly
1130                1135                1140
Cys Ala  Gly Cys Cys Gly Gly  Ala Gly Ala Ala Cys  Ala Ala Cys
1145                1150                1155
Thr Ala  Cys Ala Ala Gly Ala  Cys Cys Ala Cys Gly  Cys Cys Thr
1160                1165                1170
Cys Cys  Cys Gly Thr Gly Cys  Thr Gly Gly Ala Cys  Thr Cys Cys
1175                1180                1185
Gly Ala  Cys Gly Gly Cys Thr  Cys Cys Thr Thr Cys  Thr Thr Cys
1190                1195                1200
Cys Thr  Cys Thr Ala Cys Ala  Gly Cys Ala Gly Gly  Cys Thr Ala
1205                1210                1215
Ala Cys  Cys Gly Thr Gly Gly  Ala Cys Ala Ala Gly  Ala Gly Cys
1220                1225                1230
Ala Gly  Gly Thr Gly Gly Cys  Ala Gly Gly Ala Gly  Gly Gly Gly
1235                1240                1245
Ala Ala  Thr Gly Thr Cys Thr  Thr Cys Thr Cys Ala  Thr Gly Cys
```

```
                    1250                1255                1260
Thr Cys  Cys Gly Thr Gly Ala  Thr Gly Cys Ala Thr  Gly Ala Gly
            1265                1270                1275

Gly Cys  Thr Cys Thr Gly Cys  Ala Cys Ala Ala Cys  Cys Ala Cys
            1280                1285                1290

Thr Ala  Cys Ala Cys Ala Cys  Ala Gly Ala Ala Gly  Ala Gly Cys
            1295                1300                1305

Cys Thr  Cys Thr Cys Cys Cys  Thr Gly Thr Cys Thr  Cys Thr Gly
            1310                1315                1320

Gly Gly  Thr Ala Ala Ala
            1325

<210> SEQ ID NO 117
<211> LENGTH: 113
<212> TYPE: PRT
<213> ORGANISM: Artificial Sequence
<220> FEATURE:
<223> OTHER INFORMATION: light chain constant region

<400> SEQUENCE: 117

Thr Lys Val Glu Ile Lys Arg Thr Val Ala Ala Pro Ser Val Phe Ile
1               5                   10                  15

Phe Pro Pro Ser Asp Glu Gln Leu Lys Ser Gly Thr Ala Ser Val Val
            20                  25                  30

Cys Leu Leu Asn Asn Phe Tyr Pro Arg Glu Ala Lys Val Gln Trp Lys
        35                  40                  45

Val Asp Asn Ala Leu Gln Ser Gly Asn Ser Gln Glu Ser Val Thr Glu
50                  55                  60

Gln Asp Ser Lys Asp Ser Thr Tyr Ser Leu Ser Ser Thr Leu Thr Leu
65                  70                  75                  80

Ser Lys Ala Asp Tyr Glu Lys His Lys Val Tyr Ala Cys Glu Val Thr
                85                  90                  95

His Gln Gly Leu Ser Ser Pro Val Thr Lys Ser Phe Asn Arg Gly Glu
            100                 105                 110

Cys

<210> SEQ ID NO 118
<211> LENGTH: 337
<212> TYPE: PRT
<213> ORGANISM: Artificial Sequence
<220> FEATURE:
<223> OTHER INFORMATION: heavy chain constant region

<400> SEQUENCE: 118

Thr Leu Val Thr Val Ser Ser Ala Ser Thr Lys Gly Pro Ser Val Phe
1               5                   10                  15

Pro Leu Ala Pro Ser Ser Lys Ser Thr Ser Gly Gly Thr Ala Ala Leu
            20                  25                  30

Gly Cys Leu Val Lys Asp Tyr Phe Pro Glu Pro Val Thr Val Ser Trp
        35                  40                  45

Asn Ser Gly Ala Leu Thr Ser Gly Val His Thr Phe Pro Ala Val Leu
50                  55                  60

Gln Ser Ser Gly Leu Tyr Ser Leu Ser Ser Val Val Thr Val Pro Ser
65                  70                  75                  80

Ser Ser Leu Gly Thr Gln Thr Tyr Ile Cys Asn Val Asn His Lys Pro
                85                  90                  95

Ser Asn Thr Lys Val Asp Lys Lys Val Glu Pro Lys Ser Cys Asp Lys
```

```
                    100                 105                 110
Thr His Thr Cys Pro Pro Cys Pro Ala Pro Glu Leu Leu Gly Gly Pro
                115                 120                 125

Ser Val Phe Leu Phe Pro Pro Lys Pro Lys Asp Thr Leu Met Ile Ser
        130                 135                 140

Arg Thr Pro Glu Val Thr Cys Val Val Val Asp Val Ser His Glu Asp
145                 150                 155                 160

Pro Glu Val Lys Phe Asn Trp Tyr Val Asp Gly Val Glu Val His Asn
                165                 170                 175

Ala Lys Thr Lys Pro Arg Glu Glu Gln Tyr Asn Ser Thr Tyr Arg Val
                180                 185                 190

Val Ser Val Leu Thr Val Leu His Gln Asp Trp Leu Asn Gly Lys Glu
                195                 200                 205

Tyr Lys Cys Lys Val Ser Asn Lys Ala Leu Pro Ala Pro Ile Glu Lys
                210                 215                 220

Thr Ile Ser Lys Ala Lys Gly Gln Pro Arg Glu Pro Gln Val Tyr Thr
225                 230                 235                 240

Leu Pro Pro Ser Arg Asp Glu Leu Thr Lys Asn Gln Val Ser Leu Thr
                245                 250                 255

Cys Leu Val Lys Gly Phe Tyr Pro Ser Asp Ile Ala Val Glu Trp Glu
                260                 265                 270

Ser Asn Gly Gln Pro Glu Asn Asn Tyr Lys Thr Thr Pro Pro Val Leu
                275                 280                 285

Asp Ser Asp Gly Ser Phe Phe Leu Tyr Ser Lys Leu Thr Val Asp Lys
                290                 295                 300

Ser Arg Trp Gln Gln Gly Asn Val Phe Ser Cys Ser Val Met His Glu
305                 310                 315                 320

Ala Leu His Asn His Tyr Thr Gln Lys Ser Leu Ser Leu Ser Pro Gly
                325                 330                 335

Lys

<210> SEQ ID NO 119
<211> LENGTH: 245
<212> TYPE: PRT
<213> ORGANISM: Artificial Sequence
<220> FEATURE:
<223> OTHER INFORMATION: heavy chain constant region

<400> SEQUENCE: 119

Thr Leu Val Thr Val Ser Ser Ala Ser Thr Lys Gly Pro Ser Val Phe
1               5                   10                  15

Pro Leu Ala Pro Ser Ser Lys Ser Thr Ser Gly Gly Thr Ala Ala Leu
                20                  25                  30

Gly Cys Leu Val Lys Asp Tyr Phe Pro Glu Pro Val Thr Val Ser Trp
            35                  40                  45

Asn Ser Gly Ala Leu Thr Ser Gly Val His Thr Phe Pro Ala Val Leu
        50                  55                  60

Gln Ser Ser Gly Leu Tyr Ser Leu Ser Ser Val Val Thr Val Pro Ser
65                  70                  75                  80

Ser Ser Leu Gly Thr Gln Thr Tyr Ile Cys Asn Val Asn His Lys Pro
                85                  90                  95

Ser Asn Thr Lys Val Asp Lys Lys Val Glu Pro Lys Ser Cys Asp Lys
                100                 105                 110

Thr His Thr Cys Pro Pro Cys Pro Ala Pro Glu Leu Leu Gly Gly Pro
                115                 120                 125
```

Ser Val Phe Leu Phe Pro Pro Lys Pro Lys Asp Thr Leu Met Ile Ser
130                 135                 140

Arg Thr Pro Glu Val Thr Cys Val Val Val Asp Val Ser His Glu Asp
145                 150                 155                 160

Pro Glu Val Lys Phe Asn Trp Tyr Val Asp Gly Val Glu Val His Asn
                165                 170                 175

Ala Lys Thr Lys Pro Arg Glu Glu Gln Tyr Gln Ser Thr Tyr Arg Val
            180                 185                 190

Val Ser Val Leu Thr Val Leu His Gln Asp Trp Leu Asn Gly Lys Glu
        195                 200                 205

Tyr Lys Cys Lys Val Ser Asn Lys Ala Leu Pro Ala Pro Ile Glu Lys
    210                 215                 220

Thr Ile Ser Lys Ala Lys Gly Gln Pro Arg Glu Pro Gln Val Tyr Thr
225                 230                 235                 240

Leu Pro Pro Ser Arg
                245

<210> SEQ ID NO 120
<211> LENGTH: 337
<212> TYPE: PRT
<213> ORGANISM: Artificial Sequence
<220> FEATURE:
<223> OTHER INFORMATION: heavy chain constant region

<400> SEQUENCE: 120

Trp Gly Gln Gly Thr Leu Val Thr Val Ser Ala Ser Thr Lys Gly
1               5                   10                  15

Pro Ser Val Phe Pro Leu Ala Pro Cys Ser Arg Ser Thr Ser Glu Ser
                20                  25                  30

Thr Ala Ala Leu Gly Cys Leu Val Lys Asp Tyr Phe Pro Glu Pro Val
            35                  40                  45

Thr Val Ser Trp Asn Ser Gly Ala Leu Thr Ser Gly Val His Thr Phe
        50                  55                  60

Pro Ala Val Leu Gln Ser Ser Gly Leu Tyr Ser Leu Ser Ser Val Val
65                  70                  75                  80

Thr Val Pro Ser Ser Asn Phe Gly Thr Gln Thr Tyr Thr Cys Asn Val
                85                  90                  95

Asp His Lys Pro Ser Asn Thr Lys Val Asp Lys Thr Val Glu Arg Lys
                100                 105                 110

Cys Cys Val Glu Cys Pro Pro Cys Pro Ala Pro Pro Val Ala Gly Pro
            115                 120                 125

Ser Val Phe Leu Phe Pro Pro Lys Pro Lys Asp Thr Leu Met Ile Ser
130                 135                 140

Arg Thr Pro Glu Val Thr Cys Val Val Val Asp Val Ser His Glu Asp
145                 150                 155                 160

Pro Glu Val Gln Phe Asn Trp Tyr Val Asp Gly Val Glu Val His Asn
                165                 170                 175

Ala Lys Thr Lys Pro Arg Glu Glu Gln Phe Asn Ser Thr Phe Arg Val
            180                 185                 190

Val Ser Val Leu Thr Val Val His Gln Asp Trp Leu Asn Gly Lys Glu
        195                 200                 205

Tyr Lys Cys Lys Val Ser Asn Lys Gly Leu Pro Ala Pro Ile Glu Lys
    210                 215                 220

Thr Ile Ser Lys Thr Lys Gly Gln Pro Arg Glu Pro Gln Val Tyr Thr
225                 230                 235                 240

Leu Pro Pro Ser Arg Glu Glu Met Thr Lys Asn Gln Val Ser Leu Thr
            245                 250                 255

Cys Leu Val Lys Gly Phe Tyr Pro Ser Asp Ile Ala Val Glu Trp Glu
            260                 265                 270

Ser Asn Gly Gln Pro Glu Asn Asn Tyr Asn Thr Thr Pro Pro Met Leu
            275                 280                 285

Asp Ser Asp Gly Ser Phe Phe Leu Tyr Ser Lys Leu Thr Val Asp Lys
            290                 295                 300

Ser Arg Trp Gln Gln Gly Asn Val Phe Ser Cys Ser Val Met His Glu
305                 310                 315                 320

Ala Leu His Asn His Tyr Thr Gln Lys Ser Leu Ser Leu Ser Pro Gly
            325                 330                 335

Lys

<210> SEQ ID NO 121
<211> LENGTH: 334
<212> TYPE: PRT
<213> ORGANISM: Artificial Sequence
<220> FEATURE:
<223> OTHER INFORMATION: heavy chain constant region

<400> SEQUENCE: 121

Thr Thr Val Thr Val Ser Ser Ala Ser Thr Lys Gly Pro Ser Val Phe
1               5                   10                  15

Pro Leu Ala Pro Cys Ser Arg Ser Thr Ser Glu Ser Thr Ala Ala Leu
            20                  25                  30

Gly Cys Leu Val Lys Asp Tyr Phe Pro Glu Pro Val Thr Val Ser Trp
            35                  40                  45

Asn Ser Gly Ala Leu Thr Ser Gly Val His Thr Phe Pro Ala Val Leu
            50                  55                  60

Gln Ser Ser Gly Leu Tyr Ser Leu Ser Ser Val Val Thr Val Pro Ser
65                  70                  75                  80

Ser Ser Leu Gly Thr Lys Thr Tyr Thr Cys Asn Val Asp His Lys Pro
            85                  90                  95

Ser Asn Thr Lys Val Asp Lys Arg Val Glu Ser Lys Tyr Gly Pro Pro
            100                 105                 110

Cys Pro Pro Cys Pro Ala Pro Glu Phe Leu Gly Gly Pro Ser Val Phe
            115                 120                 125

Leu Phe Pro Pro Lys Pro Lys Asp Thr Leu Met Ile Ser Arg Thr Pro
            130                 135                 140

Glu Val Thr Cys Val Val Val Asp Val Ser Gln Glu Asp Pro Glu Val
145                 150                 155                 160

Gln Phe Asn Trp Tyr Val Asp Gly Val Glu Val His Asn Ala Lys Thr
            165                 170                 175

Lys Pro Arg Glu Glu Gln Phe Asn Ser Thr Tyr Arg Val Val Ser Val
            180                 185                 190

Leu Thr Val Leu His Gln Asp Trp Leu Asn Gly Lys Glu Tyr Lys Cys
            195                 200                 205

Lys Val Ser Asn Lys Gly Leu Pro Ser Ser Ile Glu Lys Thr Ile Ser
            210                 215                 220

Lys Ala Lys Gly Gln Pro Arg Glu Pro Gln Val Tyr Thr Leu Pro Pro
225                 230                 235                 240

Ser Gln Glu Glu Met Thr Lys Asn Gln Val Ser Leu Thr Cys Leu Val
            245                 250                 255

```
Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
            275                 280                 285

Gly Ser Phe Phe Leu Tyr Ser Arg Leu Thr Val Asp Lys Ser Arg Trp
            290                 295                 300

Gln Glu Gly Asn Val Phe Ser Cys Ser Val Met His Glu Ala Leu His
305                 310                 315                 320

Asn His Tyr Thr Gln Lys Ser Leu Ser Leu Ser Leu Gly Lys
            325                 330

<210> SEQ ID NO 122
<211> LENGTH: 443
<212> TYPE: PRT
<213> ORGANISM: Artificial Sequence
<220> FEATURE:
<223> OTHER INFORMATION: full length heavy chain variable domain and a
      constant domain amino acid sequence.

<400> SEQUENCE: 122

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
            35                  40                  45

Gly Asp Ile Asn Pro Val Asn Gly Asp Thr Asn Phe Asn Glu Lys Phe
            50                  55                  60

Lys Asn Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Gly Gly Tyr Thr Met Asp Tyr Trp Gly Gln Gly Thr Thr Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Pro
            210                 215                 220

Cys Pro Ala Pro Glu Phe Glu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285
```

```
Glu Glu Gln Phe Asn Ser Thr Tyr Arg Val Val Ser Val Leu Thr Val
    290                 295                 300
Leu His Gln Asp Trp Leu Asn Gly Lys Glu Tyr Lys Cys Lys Val Ser
305                 310                 315                 320
Asn Lys Gly Leu Pro Ser Ser Ile Glu Lys Thr Ile Ser Lys Ala Lys
                325                 330                 335
Gly Gln Pro Arg Glu Pro Gln Val Tyr Thr Leu Pro Pro Ser Gln Glu
            340                 345                 350
Glu Met Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Val Leu Asp Ser Asp Gly Ser Phe
385                 390                 395                 400
Phe Leu Tyr Ser Arg Leu Thr Val Asp Lys Ser Arg Trp Gln Glu Gly
                405                 410                 415
Asn Val Phe Ser Cys Ser Val Met His Glu Ala Leu His Asn His Tyr
            420                 425                 430
Thr Gln Lys Ser Leu Ser Leu Ser Leu Gly Lys
        435                 440
```

<210> SEQ ID NO 123
<211> LENGTH: 1329
<212> TYPE: DNA
<213> ORGANISM: Artificial Sequence
<220> FEATURE:
<223> OTHER INFORMATION: IgG4 S228P L235E Heavy Chain Nucleic Acid
      Sequence

<400> SEQUENCE: 123

```
caggtgcagc tgcaggagtc gggcccagga ctggtgaagc cttcacagac cctgtccctc      60
acctgcactg tctctggcta cccttcacc aactactatg tattctgggt gcgacaggct     120
cgtggacaac gccttgagtg gataggtgac attaatcctg tcaatggtga ctaacttc      180
aatgagaaat tcaagaacag agtcaccatc tcagccgaca gtccatcag caccgcctac     240
ctgcagtgga gcagcctgaa ggcctcggac accgccatgt attactgtgc gagaggggt      300
tatactatgg actactgggg ccagggcacc ccgtgaccg tgtcctccgc ttccaccaag     360
ggcccatccg tcttccccct ggcgccctgc tccaggagca cctccgagag cacagccgcc     420
ctgggctgcc tggtcaagga ctacttcccc gaaccggtga cggtgtcgtg aactcaggc      480
gccctgacca gcggcgtgca caccttcccg gctgtcctac agtcctcagg actctactcc     540
ctcagcagcg tggtgaccgt gccctccagc agcttgggca cgaagaccta cacctgcaac     600
gtagatcaca agcccagcaa caccaaggtg acaagagag ttgagtccaa atatggtccc      660
ccatgcccac cgtgccca cctgagttc gagggggac catcagtctt cctgttcccc         720
ccaaaaccca aggacactct catgatctcc cggaccctg aggtcacgtg cgtggtggtg      780
gacgtgagcc aggaagaccc cgaggtccag ttcaactggt acgtggatgg cgtggaggtg     840
cataatgcca agacaaagcc gcgggaggag cagttcaaca gcacgtaccg tgtggtcagc     900
gtcctcaccg tcctgcacca ggactggctg aacggcaagg agtacaagtg caaggtgtcc     960
aacaaaggcc tcccgtcctc catcgagaaa accatctcca agccaaagg gcagccccga    1020
gagccacagg tgtacaccct gccccatcc caggaggaga tgaccaagaa ccaggtcagc     1080
ctgacctgcc tggtcaaagg cttctacccc agcgacatcg ccgtggagtg ggagagcaat    1140
```

```
gggcagccgg agaacaacta caagaccacg cctcccgtgc tggactccga cggctccttc    1200
ttcctctaca gcaggctaac cgtggacaag agcaggtggc aggagggaa tgtcttctca     1260 tgctccgtga tgcatgaggc tctgcacaac cactacacac agaagagcct ctccctgtct    1320
ctgggtaaa                                                            1329
```

<210> SEQ ID NO 124
<211> LENGTH: 334
<212> TYPE: PRT
<213> ORGANISM: Artificial Sequence
<220> FEATURE:
<223> OTHER INFORMATION: Framework 4 + Heavy Chain Constant IgG4 S228P
     L235E Domain

<400> SEQUENCE: 124

```
Thr Thr Val Thr Val Ser Ser Ala Ser Thr Lys Gly Pro Ser Val Phe
1               5                   10                  15

Pro Leu Ala Pro Cys Ser Arg Ser Thr Ser Glu Ser Thr Ala Ala Leu
            20                  25                  30

Gly Cys Leu Val Lys Asp Tyr Phe Pro Glu Pro Val Thr Val Ser Trp
        35                  40                  45

Asn Ser Gly Ala Leu Thr Ser Gly Val His Thr Phe Pro Ala Val Leu
    50                  55                  60

Gln Ser Ser Gly Leu Tyr Ser Leu Ser Ser Val Val Thr Val Pro Ser
65                  70                  75                  80

Ser Ser Leu Gly Thr Lys Thr Tyr Thr Cys Asn Val Asp His Lys Pro
                85                  90                  95

Ser Asn Thr Lys Val Asp Lys Arg Val Glu Ser Lys Tyr Gly Pro Pro
            100                 105                 110

Cys Pro Pro Cys Pro Ala Pro Glu Phe Glu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser Gln Glu Asp Pro Glu Val
145                 150                 155                 160

Gln Phe Asn Trp Tyr Val Asp Gly Val Glu Val His Asn Ala Lys Thr
                165                 170                 175

Lys Pro Arg Glu Glu Gln Phe Asn Ser Thr Tyr Arg Val Val Ser Val
            180                 185                 190

Leu Thr Val Leu His Gln Asp Trp Leu Asn Gly Lys Glu Tyr Lys Cys
        195                 200                 205

Lys Val Ser Asn Lys Gly Leu Pro Ser Ser Ile Glu Lys Thr Ile Ser
    210                 215                 220

Lys Ala Lys Gly Gln Pro Arg Glu Pro Gln Val Tyr Thr Leu Pro Pro
225                 230                 235                 240

Ser Gln Glu Glu Met Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Arg Leu Thr Val Asp Lys Ser Arg Trp
    290                 295                 300
```

-continued

```
Gln Glu Gly Asn Val Phe Ser Cys Ser Val Met His Glu Ala Leu His
305                 310                 315                 320

Asn His Tyr Thr Gln Lys Ser Leu Ser Leu Ser Leu Gly Lys
                325                 330
```

THERAPEUTIC CD47 ANTIBODIES

CROSS REFERENCE TO RELATED APPLICATIONS

This application is a Continuation of U.S. application Ser. No. 14/737,053, filed Jun. 11, 2015, which is a Continuation-in-part of U.S. application Ser. No. 14/302,348, filed Jun. 11, 2014, which is a Continuation-in-part of PCT Application Serial No. PCT/US2013/074766, filed Dec. 12, 2013, U.S. Provisional Application Ser. No. 61/833,691, filed Jun. 11, 2013, and U.S. Provisional Application Ser. No. 61/736,301, filed Dec. 12, 2012, the contents of each of which are herein incorporated by reference in their entirety.

INCORPORATION OF SEQUENCE LISTING

The present application is being filed along with a Sequence Listing in electronic format. The Sequence Listing is provided as a file entitled, "VLX0001-201CIP2 US_SequenceListing", created on Jun. 11, 2015, which is 168,755 bytes in size. The information in the electronic format of the Sequence Listing is incorporated herein by reference in its entirety.

BACKGROUND OF THE INVENTION

The present disclosure relates to antibodies that bind CD47, including that of humans and other mammalian species, and their use in treating conditions and disorders, such as ischemia-reperfusion injury (IRI) and cancers, mediated by this receptor.

CD47 is a cell surface receptor comprised of an extracellular IgV set domain, a 5 membrane spanning transmembrane domain, and a cytoplasmic tail that is alternatively spliced. Two ligands bind CD47: thrombospondin-1 (TSP1), and signal inhibitory receptor protein alpha (SIRPalpha). TSP1 binding to CD47 activates the heterotrimeric G protein Gi, which leads to suppression of intracellular cyclic AMP (cAMP) levels. In addition, the TSP1-CD47 pathway opposes the beneficial effects of the nitric oxide pathway in all vascular cells. The nitric oxide (NO) pathway consists of any of three nitric oxide synthase enzymes (NOS I, NOS II and NOS III) that generate bioactive gas NO using arginine as a substrate. NO can act within the cell in which it is produced, or in neighboring cells, to activate the enzyme soluble guanylyl cyclase that produces the messenger molecule cyclic GMP (cGMP). The proper functioning of the NO-cGMP pathway is essential for protecting the cardiovascular system against stresses including, but not limited to, those resulting from wounding, inflammation, hypertension, metabolic syndrome, ischemia, and ischemia-reperfusion injury (IRI). In the context of these cellular stresses, the inhibition of the NO-cGMP pathway by the TSP1-CD47 system exacerbates the effects of stress. This is a particular problem in the cardiovascular system where both cGMP and cAMP play important protective roles. There are many cases in which ischemia and reperfusion injury cause or contribute to disease, trauma, and poor outcomes of surgical procedures.

SIRPalpha is expressed on hematopoietic cells, including macrophages and dendritic cells. When it engages CD47 on a potential phagocytic target cell, phagocytosis is slowed or prevented. The CD47-SIRPalpha interaction effectively sends a "don't eat me" signal to the phagocyte. Thus, blocking the SIRPalpha-CD47 interaction with a monoclonal antibody in this therapeutic context can provide an effective anti-cancer therapy by promoting, i.e., increasing, the uptake and clearance of cancer cells by the host's immune system by increasing phagocytosis. This mechanism is effective in leukemias, lymphomas, and many types of solid tumors.

U.S. Pat. No. 8,236,313 contemplates antibodies that could be useful in the field of ischemia and blood flow to reverse and/or prevent tissue ischemia and related and associated tissue and cell damage, including antibodies that block CD47.

U.S. Pat. No. 8,101,719 discloses humanized antibodies that bind to CD47 for use in treating hematological disorders. Objects of the invention include humanized anti-CD47 antibodies and small antibody fragments exhibiting reduced antigenicity while retaining their CD47 binding activity and apoptosis-inducing activity. Such antibodies and small fragments are contemplated for use in treating hematological disorders such as various types of leukemias, malignant lymphoma, aplastic anemia, myelodysplastic syndromes, and polycythemia vera.

PCT International Publication WO 2011/143624 discloses chimeric and humanized anti-CD47 monoclonal antibodies for use as reagents for the diagnosis and immunotherapy of diseases associated with CD47 in humans, particularly in cancer therapy, for example to increase phagocytosis of cancer cells expressing CD47. Preferred antibodies are non-activating, i.e., block ligand binding, but do not signal. Disclosed humanized B6H12 and 5F9 antibodies bound soluble human CD47; B6H12 also bound human CD47 on the surface of human CD47-transfected YB2/0 cells. Humanized B6H12 and 5F9 antibodies enabled phagocytosis of CFSE-labeled HL-60 cells by mouse bone marrow- or peripheral blood-derived macrophages in vitro, respectively. Humanized B6H12 utilized human VH-3-7 and VK3-11 frameworks.

U.S. 2013/0142786 discloses non-activating anti-CD47 antibodies that increase the phagocytosis of CD47 expressing cells and these humanized or chimeric anti-CD47 antibodies can be used for therapeutic purposes, particularly in cancer therapy. Amino acid sequences of murine and humanized mAb B6H12, 5F9, and 8B6 heavy and light chain variable regions are disclosed.

Han et al. (2000) *J. Biol. Chem.* 275(48):37984-37992 discloses the production of mouse anti-CD47 monoclonal antibodies 400 (IgG2b), 410 (IgG1), 420 (IgG2a), 430 (IgG2a), 440 (IgG1), 450 (IgG2a), 460 (IgG1), 470 (IgG2a), and 480 (IgG1) generated by immunizing CD47-deficient mice with the extracellular domain of human CD47. No amino acid sequences of these antibodies, or their CDRs, are disclosed. Of these nine mAbs, three blocked macrophage fusion: 430, 450, and 470. Han et al. discloses no data either demonstrating or suggesting that CD47 plays a role in ischemia-reperfusion injury, autoimmune or inflammatory diseases, or cancer.

PCT International Publication WO 2013/119714 discloses anti-CD47 antibodies that do not cause a significant level of hemagglutination of human red blood cells.

There exists a need for antibodies to human CD47 that selectively block the binding of TSP1 to CD47 to promote the beneficial effects of nitric oxide-cGMP signaling and cAMP signaling in the cardiovascular system in settings in which IRI plays a role in pathogenesis. These situations/diseases include organ transplantation, acute kidney injury, cardiopulmonary bypass surgery, pulmonary hypertension, sickle cell disease, myocardial infarction, stroke, surgical resections and reconstructive surgery, reattachment of digits/body parts, skin grafting, and trauma. There is also a need for antibodies that block the binding of SIRPalpha to CD47, thus providing novel anti-cancer therapies.

Antibody compounds of the present disclosure meet these needs. They bind to epitopes in the extracellular IgV domain of CD47, variously inhibiting the binding of SIRPalpha and TSP1 to CD47 and receptor activation. Antibodies that block TSP1 and SIRPalpha binding should be therapeutically useful in preventing, treating, or reducing many forms of IRI and treating cancers. Antibodies that block SIRPalpha binding promote phagocytosis of cancer cells. In view of these properties, SIRPalpha blocking antibody compounds should be therapeutically useful in treating a variety of cancers, including hematological cancers and solid tumors.

SUMMARY OF THE INVENTION

Antibody compounds disclosed herein meet these needs by exhibiting the following desirable therapeutic activities:
Binding to CD47 of multiple mammalian species;
Blocking SIRPalpha and TSP1 binding to CD47;
Promoting phagocytosis of cancer cells; and
Reversing TSP1 inhibition of nitric oxide signaling.

The present antibodies are useful in reducing, preventing, and/or treating CD47-mediated diseases or conditions (e.g., ischemia reperfusion injury and cancers).

They bind to epitopes in the extracellular IgV domain of CD47, inhibiting TSP1 and SIRPalpha binding to CD47, while inducing little or no agonist activity and promoting tumor cell phagocytic clearance. In view of these properties, antibody compounds of the present disclosure should be therapeutically useful in treating many forms of IRI and cancers.

In addition, the present antibody compounds can possess a number of other desirable properties, including broad reactivity with CD47 of a wide variety of mammalian species, including that of human, mouse, rat, pig, cynomolgus monkey, and dog, making these antibodies useful in both human and veterinary medicine. This feature is further advantageous in that it facilitates preclinical studies including, but not limited to, safety and efficacy studies, in a variety of mammalian species, and therefore the development of such antibodies as human and veterinary therapeutics.

Accordingly, the present disclosure provides:

[1] A monoclonal antibody, or antigen-binding fragment thereof, that:
(i) specifically binds human, rat, mouse, pig, cynomolgus monkey, and dog CD47;
(ii) blocks SIRPalpha and TSP1 binding to CD47;
(iii) promotes phagocytosis of cancer cells; and
(iv) reverses TSP1 inhibition of nitric oxide signaling.

[2] The monoclonal antibody or antigen-binding fragment thereof of [1], which is chimeric or humanized.

[3] The monoclonal antibody, or antigen-binding fragment thereof, of [1] or [2], which comprises three light chain complementarity determining regions (LCDRs 1-3) and three heavy chain complementarity determining regions (HCDRs 1-3), wherein:
LCDR 1 comprises the amino acid sequence RSSQSLVHSNGNTYLH (SEQ ID NO:1);
LCDR 2 comprises the amino acid sequence KVSYRFS (SEQ ID NO:2); and
LCDR 3 comprises the amino acid sequence SQNTHVPRT (SEQ ID NO:3);
HCDR 1 comprises the amino acid sequence GYTFTNYYVF (SEQ ID NO:4);
HCDR 2 comprises the amino acid sequence DINPVNGDTNFNEKFKN (SEQ ID NO:5); and
HCDR 3 comprises the amino acid sequence GGYTMDY (SEQ ID NO:6).

[4] The monoclonal antibody, or antigen-binding fragment thereof, of any one of [1]-[3], which comprises a light chain variable region (LCVR) and a heavy chain variable region (HCVR), wherein said LCVR and said HCVR comprise, respectively, amino acid sequences selected from among the following combinations of LCVRs and HCVRs:
SEQ ID NO:7 and SEQ ID NO:57;
SEQ ID NO:8 and SEQ ID NO:58;
SEQ ID NO:9 and SEQ ID NO:59;
SEQ ID NO:10 and SEQ ID NO:60;
SEQ ID NO:11 and SEQ ID NO:61;
SEQ ID NO:12 and SEQ ID NO:62;
SEQ ID NO:13 and SEQ ID NO:63;
SEQ ID NO:14 and SEQ ID NO:64;
SEQ ID NO:15 and SEQ ID NO:65;
SEQ ID NO:16 and SEQ ID NO:66;
SEQ ID NO:17 and SEQ ID NO:67;
SEQ ID NO:18 and SEQ ID NO:68;
SEQ ID NO:19 and SEQ ID NO:69;
SEQ ID NO:20 and SEQ ID NO:70;
SEQ ID NO:21 and SEQ ID NO:71;
SEQ ID NO:22 and SEQ ID NO:72;
SEQ ID NO:23 and SEQ ID NO:73;
SEQ ID NO:24 and SEQ ID NO:74;
SEQ ID NO:25 and SEQ ID NO:75;
SEQ ID NO:26 and SEQ ID NO:76;
SEQ ID NO:27 and SEQ ID NO:77;
SEQ ID NO:28 and SEQ ID NO:78;
SEQ ID NO:29 and SEQ ID NO:79;
SEQ ID NO:30 and SEQ ID NO:80; and
SEQ ID NO:31 and SEQ ID NO:81,
wherein each one of LCVR SEQ ID NOs:7-31 further comprises a constant domain having the amino acid sequence shown in SEQ ID NO:117, and wherein each one of HCVR SEQ ID NOs:57-81 comprises a constant domain selected from among SEQ ID NO:118, SEQ ID NO:119, SEQ ID NO:120, SEQ ID NO:121, and SEQ ID NO:124.

[5] A monoclonal antibody, or antigen-binding fragment thereof, that competes with said monoclonal antibody or antigen-binding fragment thereof of any one of [1]-[4] for binding to CD47, especially human CD47.

[6] A pharmaceutical composition, comprising said monoclonal antibody or antigen-binding fragment thereof, or competing antibody or antigen binding fragment thereof, of any one of [1]-[5], and a pharmaceutically or physiologically acceptable carrier, diluent, or excipient.

[7] A monoclonal antibody or antigen-binding fragment thereof, or competing antibody or antigen binding fragment thereof, of any one of [1]-[5] for use in human therapy or therapy of companion/pet animals, working animals, sport animals, zoo animals, or therapy of other valuable animals kept in captivity.

[8] The monoclonal antibody or antigen-binding fragment thereof, or competing antibody or antigen binding fragment thereof, of any one of [1]-[5] for use in treating ischemia-reperfusion injury, or an autoimmune or inflammatory disease, in a human or companion/pet animal, working animal, sport animal, zoo animal, or other valuable animal kept in captivity.

[9] The monoclonal antibody or antigen-binding fragment thereof, or competing antibody or antigen binding fragment thereof, of [8], wherein said ischemia-reperfusion injury occurs in organ transplantation, acute kidney injury, cardiopulmonary bypass surgery, pulmonary hypertension, sickle cell disease, myocardial infarction, stroke, surgical resections and reconstructive surgery, reattachment of an appendage or other body part, skin grafting, or trauma.

[10] The monoclonal antibody, or antigen-binding fragment thereof, or competing antibody or antigen binding fragment thereof, of [8], wherein said autoimmune or inflammatory disease is selected from the group consisting of arthritis, multiple sclerosis, psoriasis, Crohn's disease, inflammatory bowel disease, lupus, Grave's disease and Hashimoto's thyroiditis, and ankylosing spondylitis.

[11] The monoclonal antibody or antigen-binding fragment thereof, or competing antibody or antigen binding fragment thereof, of any one of [1]-[5] for use in treating a susceptible cancer.

[12] The monoclonal antibody or antigen binding fragment thereof, or competing antibody or antigen binding fragment thereof, of [11], which promotes phagocytosis of cells of said susceptible cancer.

[13] The monoclonal antibody or antigen binding fragment thereof, or competing antibody or antigen binding fragment thereof, of [11] or [12], wherein said susceptible cancer is selected from the group consisting of a leukemia, a lymphoma, ovarian cancer, breast cancer, endometrial cancer, colon cancer (colorectal cancer), rectal cancer, bladder cancer, lung cancer (non-small cell lung cancer, adenocarcinoma of the lung, squamous cell carcinoma of the lung), bronchial cancer, bone cancer, prostate cancer, pancreatic cancer, gastric cancer, hepatocellular carcinoma (liver cancer, hepatoma), gall bladder cancer, bile duct cancer, esophageal cancer, renal cell carcinoma, thyroid cancer, squamous cell carcinoma of the head and neck (head and neck cancer), testicular cancer, cancer of the endocrine gland, cancer of the adrenal gland, cancer of the pituitary gland, cancer of the skin, cancer of soft tissues, cancer of blood vessels, cancer of brain, cancer of nerves, cancer of eyes, cancer of meninges, cancer of oropharynx, cancer of hypopharynx, cancer of cervix, and cancer of uterus, glioblastoma, medulloblastoma, astrocytoma, glioma, meningioma, gastrinoma, neuroblastoma, melanoma, myelodysplastic syndrome, and sarcomas including, but not limited to, osteosarcoma, Ewing sarcoma, leiomyosarcoma, synovial sarcoma, alveolar soft part sarcoma, angiosarcoma, liposarcoma, fibrosarcoma, rhabdomyosarcoma, and chrondrosarcoma.

[14] The monoclonal antibody or antigen binding fragment thereof, or competing antibody or antigen binding fragment thereof, of any one of [11]-[13], wherein said leukemia is selected from the group consisting of systemic mastocytosis, acute lymphocytic (lymphoblastic) leukemia (ALL), T cell-ALL, acute myeloid leukemia (AML), myelogenous leukemia, chronic lymphocytic leukemia (CLL), multiple myeloma (MM), chronic myeloid leukemia (CML), myeloproliferative disorder/neoplasm, myelodysplastic syndrome, monocytic cell leukemia, and plasma cell leukemia; lymphomas, including histiocytic lymphoma and T cell lymphoma, B cell lymphomas, including Hodgkin's lymphoma and non-Hodgkin's lymphoma, such as low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, and Waldenstrom's Macroglobulinemia

[15] Use of said monoclonal antibody or antigen-binding fragment thereof, or competing antibody or antigen binding fragment thereof, of any one of [1]-[5] to treat ischemia-reperfusion injury, or an autoimmune or inflammatory disease, in a human or companion/pet animal, working animal, sport animal, zoo animal, or other valuable animal kept in captivity.

[16] Use of said monoclonal antibody or antigen-binding fragment thereof, or competing antibody or antigen binding fragment thereof, of any one of [1]-[5] to treat a susceptible cancer.

[17] Use of said monoclonal antibody or antigen-binding fragment thereof, or competing antibody or antigen binding fragment thereof, of any one of [1]-[5] for the manufacture of a medicament to treat ischemia-reperfusion injury, or an autoimmune or inflammatory disease, in a human or companion/pet animal, working animal, sport animal, zoo animal, or other valuable animal kept in captivity.

[18] The use of [17], wherein said ischemia-reperfusion injury occurs in organ transplantation, acute kidney injury, cardiopulmonary bypass surgery, pulmonary hypertension, sickle cell disease, myocardial infarction, stroke, surgical resections and reconstructive surgery, reattachment of an appendage or other body part, skin grafting, and trauma.

[19] The use of [17] or [18], wherein said autoimmune or inflammatory disease is selected from among arthritis, multiple sclerosis, psoriasis, Crohn's disease, inflammatory bowel disease, lupus, Grave's disease and Hashimoto's thyroiditis, and ankylosing spondylitis.

[20] Use of said monoclonal antibody or antigen-binding fragment thereof, or competing antibody or antigen binding fragment thereof, of any one of [1]-[5] for the manufacture of a medicament to treat a susceptible cancer.

[21] A method of treating ischemia or ischemia-reperfusion injury in a patient in need thereof, comprising administering to said patient an effective amount of said monoclonal antibody or antigen-binding fragment thereof, or competing antibody or antigen binding fragment thereof, of any one of [1]-[5].

[22] The method of [21], wherein said patient is about to be subjected to, or is experiencing, ischemia or ischemia-reperfusion injury.

[23] The method of [21] or [22], wherein said patient is a human.

[24] The method of [21] or [22], wherein said patient is a companion/pet animal, working animal, sport animal, zoo animal, or other valuable animal kept in captivity.

[25] The method of any one of [21]-[24], wherein said ischemia occurs because said patient will undergo, or is undergoing, a surgery selected from the group consisting of integument surgery, soft tissue surgery, composite tissue surgery, cosmetic surgery, surgical resections, reconstructive surgery, skin graft surgery, and limb reattachment surgery.

[26] The method of [25], wherein said skin graft is an autograft.

[27] The method of any one of [21]-[24], wherein said ischemia occurs because said patient will undergo, or is undergoing, organ transplant surgery.

[28] The method of any one of [21]-[24], wherein said ischemia-reperfusion injury occurs in organ transplantation, acute kidney injury, cardiopulmonary bypass surgery, pulmonary hypertension, sickle cell disease, myocardial infarction, stroke, surgical resection, reconstructive surgery, reattachment of an appendage or other body part, or skin grafting.

[29] The method of any one of [21]-[28], wherein said monoclonal antibody or antigen-binding fragment thereof, or competing monoclonal antibody or antigen binding fragment thereof, is administered before, during, or after said subject undergoes ischemia or surgery, or a combination of any of these time periods.

[30] The method of any one of [21]-[29], further comprising administering to said patient an effective amount of a nitric oxide donor, precursor, or both; a nitric oxide generating topical agent; an agent that activates soluble guanylyl cyclase; an agent that inhibits cyclic nucleotide phosphodiesterases; or any combination of any of the foregoing.

[31] The method of [30], wherein said nitric oxide donor or precursor is selected from the group consisting of NO gas, isosorbide dinitrate, nitrite, nitroprusside, nitroglycerin, 3-Morpholino-sydnonimine (SIN-1), S-nitroso-N-acetylpenicillamine (SNAP), Diethylenetriamine/NO (DETA/NO), S-nitrosothiols, Bidil®, and arginine; and said agent that inhibits cyclic nucleotide phosphodiesterases is selected from the group consisting of sildenafil, tadalafil, vardenafil udenafil, and avanafil.

[32] A method of increasing tissue perfusion in a subject in need thereof, comprising administering to said subject an effective amount of a monoclonal antibody, or antigen-binding fragment thereof, or competing antibody or antigen binding fragment thereof, of any one of [1]-[5].

[33] The method of [32], wherein said subject has, or is at risk of developing, at least one disease or condition selected from the group consisting of ischemia-reperfusion injury, myocardial infarction, myocardial ischemia, stroke, cerebral ischemia, sickle cell anemia, and pulmonary hypertension.

[34] The method of [32], wherein said subject has, or is at risk of developing, at least one disease or condition selected from the group consisting of hypertension, atherosclerosis, vasculopathy, ischemia secondary to diabetes, and peripheral vascular disease.

[35] The method of [32], wherein the need for increased tissue perfusion arises because said subject has had, is having, or will have, a surgery selected from the group consisting of integument surgery, soft tissue surgery, composite tissue surgery, skin graft surgery, resection of a solid organ, and reattachment or an appendage or other body part.

[36] The method of [35], wherein said skin graft is an autograft.

[37] The method of [32], wherein the need for increased tissue perfusion arises because said subject has had, is having, or will have, organ transplant surgery.

[38] The method of any one of [32]-[37], further comprising administering to said subject an effective amount of a nitric oxide donor, precursor, or both; a nitric oxide generating topical agent; an agent that activates soluble guanylyl cyclase; an agent that inhibits cyclic nucleotide phosphodiesterases; or any combination of any of the foregoing.

[39] The method of [38], wherein said nitric oxide donor or precursor is selected from the group consisting of NO gas, isosorbide dinitrate, nitrite, nitroprusside, nitroglycerin, 3-Morpholino-sydnonimine (SIN-1), S-nitroso-N-acetylpenicillamine (SNAP), Diethylenetriamine/NO (DETA/NO), S-nitrosothiols, Bidil®, and arginine; and said agent that inhibits cyclic nucleotide phosphodiesterases is selected from the group consisting of sildenafil, tadalafil, vardenafil udenafil, and avanafil.

[40] A method of transplanting a donor organ from an organ donor to an organ recipient, comprising any single step, any combination of steps, or all steps selected from the group consisting of steps i)-iii):

i) administering to said organ donor prior to, during, both prior to and during, after, or any combination thereof, donation of said donor organ an effective amount of said monoclonal antibody or antigen-binding fragment thereof of any one of [1]-[5], and/or a monoclonal antibody, or antigen-binding fragment thereof, that competes with said monoclonal antibody or antigen-binding fragment thereof of any one of [1]-[5] for binding to CD47;

ii) contacting said donor organ prior to, during, both prior to and during, after, or any combination thereof, transplantation to said organ recipient, and an effective amount of said monoclonal antibody or antigen-binding fragment thereof of any one of [1]-[5], and/or a monoclonal antibody, or antigen-binding fragment thereof, that competes with said monoclonal antibody or antigen-binding fragment thereof of any one of [1]-[5] for binding to CD47; and iii) administering to said organ recipient prior to, during, both prior to and during, after, or any combination thereof, transplantation of said donor organ to said organ recipient, an effective amount of said monoclonal antibody or antigen-binding fragment thereof of any one of [1]-[5], and/or a monoclonal antibody, or antigen-binding fragment thereof, that competes with said monoclonal antibody or antigen-binding fragment thereof of any one of [1]-[5] for binding to CD47.

[41] The method of [40], wherein said monoclonal antibody or antigen-binding fragment thereof of any one of [1]-[5], or monoclonal antibody, or antigen-binding fragment thereof, that competes with said monoclonal antibody or antigen-binding fragment thereof of any one of [1]-[5] for binding to CD47, reduces ischemia reperfusion injury in said donor organ.

[42] The method of [40] or [41], further comprising administering to said organ donor, said donor organ, said organ recipient, or any combination thereof, an effective amount of a nitric oxide donor, precursor, or both; a nitric oxide generating topical agent; an agent that activates soluble guanylyl cyclase; or an agent that inhibits cyclic nucleotide phosphodiesterases; or any combination of any of the foregoing.

[43] The method of [42], wherein said nitric oxide donor or precursor is selected from the group consisting of NO gas, isosorbide dinitrate, nitrite, nitroprusside, nitroglycerin, 3-Morpholino-sydnonimine (SIN-1), S-nitroso-N-acetylpenicillamine (SNAP), Diethylenetriamine/NO (DETA/NO), S-nitrosothiols, Bidil®, and arginine; and said agent that inhibits cyclic nucleotide phosphodiesterases is selected from the group consisting of sildenafil, tadalafil, vardenafil, udenafil, and avanafil.

[44] A method of treating an autoimmune or inflammatory disease in a patient in need thereof, comprising administering to said patient an effective amount of said monoclonal antibody, or antigen-binding fragment thereof, or competing antibody or antigen binding fragment thereof, of any one of [1]-[5].

[45] The method of [44], wherein said autoimmune or inflammatory disease is selected from the group consisting of arthritis, multiple sclerosis, psoriasis, Crohn's disease, inflammatory bowel disease, lupus, Grave's disease and Hashimoto's thyroiditis, and ankylosing spondylitis.

[46] The method of [44] or [45], wherein said patient is a human.

[47] The method of [44] or [45], wherein said patient is a companion/pet animal, working animal, sport animal, zoo animal, or other valuable animal kept in captivity.

[48] The method of any one of [44]-[47], further comprising administering to said patient an effective amount of a nitric oxide donor, precursor, or both; a nitric oxide generating topical agent; an agent that activates soluble guanylyl cyclase; an agent that inhibits cyclic nucleotide phosphodiesterases; or any combination of any of the foregoing.

[49] The method of [48], wherein said nitric oxide donor or precursor is selected from the group consisting of NO gas, isosorbide dinitrate, nitrite, nitroprusside, nitroglycerin, 3-Morpholino-sydnonimine (SIN-1), S-nitroso-N-acetylpenicillamine (SNAP), Diethylenetriamine/NO (DETA/NO), S-nitrosothiols, Bidil®, and arginine; and said agent that inhibits cyclic nucleotide phosphodiesterases is selected from the group consisting of sildenafil, tadalafil, vardenafil, udenafil, and avanafil.

[50] A method of treating a susceptible cancer in a human or companion/pet animal, working animal, sport animal, zoo animal, or other valuable animal kept in captivity in need thereof, comprising administering thereto an effective amount of a monoclonal antibody or antigen binding fragment thereof, or competing antibody or antigen binding fragment thereof, of any one of [1]-[5].

[51] The method of [50], wherein said susceptible cancer is selected from the group consisting of a leukemia, a lymphoma, ovarian cancer, breast cancer, endometrial cancer, colon cancer (colorectal cancer), rectal cancer, bladder cancer, lung cancer (non-small cell lung cancer, adenocarcinoma of the lung, squamous cell carcinoma of the lung), bronchial cancer, bone cancer, prostate cancer, pancreatic cancer, gastric cancer, hepatocellular carcinoma (liver cancer, hepatoma), gall bladder cancer, bile duct cancer, esophageal cancer, renal cell carcinoma, thyroid cancer, squamous cell carcinoma of the head and neck (head and neck cancer), testicular cancer, cancer of the endocrine gland, cancer of the adrenal gland, cancer of the pituitary gland, cancer of the skin, cancer of soft tissues, cancer of blood vessels, cancer of brain, cancer of nerves, cancer of eyes, cancer of meninges, cancer of oropharynx, cancer of hypopharynx, cancer of cervix, and cancer of uterus, glioblastoma, meduloblastoma, astrocytoma, glioma, meningioma, gastrinoma, neuroblastoma, melanoma, myelodysplastic syndrome, and sarcomas including, but not limited to, osteosarcoma, Ewing sarcoma, leiomyosarcoma, synovial sarcoma, alveolar soft part sarcoma, angiosarcoma, liposarcoma, fibrosarcoma, rhabdomyosarcoma, and chrondrosarcoma.

[52] The method of [51], wherein said leukemia is selected from the group consisting of systemic mastocytosis, acute lymphocytic (lymphoblastic) leukemia (ALL), T cell-ALL, acute myeloid leukemia (AML), myelogenous leukemia, chronic lymphocytic leukemia (CLL), multiple myeloma (MM), chronic myeloid leukemia (CML), myeloproliferative disorder/neoplasm, myelodysplastic syndrome, monocytic cell leukemia, and plasma cell leukemia; lymphomas, including histiocytic lymphoma and T cell lymphoma, B cell lymphomas, including Hodgkin's lymphoma and non-Hodgkin's lymphoma, such as low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, and Waldenstrom's Macroglobulinemia. [53] The method of any one of [50]-[52], wherein said monoclonal antibody or antigen-binding fragment thereof, or competing antibody or antigen binding fragment thereof, of any one of [1]-[5] increases phagocytosis of cells of said susceptible cancer.

[54] The method of [53], wherein said monoclonal antibody or antigen-binding fragment thereof, or competing antibody or antigen binding fragment thereof, of any one of [1]-[5], increases phagocytosis of cells of said susceptible cancer and inhibits SIRPalpha binding to CD47.

[55] A humanized monoclonal antibody, or antigen-binding fragment thereof, that specifically binds human CD47.

[56] The use or method of any one of the previously described embodiments, further comprising administering to said patient an anti-tumor therapeutic treatment selected from the group consisting of surgery, radiation, an anti-tumor or anti-neoplastic agent, and combinations of any of the foregoing.

[57] The use or method of [56], wherein said an anti-tumor or anti-neoplastic agent is a small chemical molecule or a biologic therapeutic.

[58] The use or method of [57], wherein said small chemical molecule or biologic therapeutic is selected from the group consisting of an alkylating agent; an antimetabolite; a natural product; a miscellaneous agent used in cancer therapy; a hormone; an antagonist; a monoclonal antibody or antigen-binding fragment thereof; a cytokine; an antisense oligonucleotide; an siRNA; or a miRNA.

[59] A method of enhancing the therapeutic effect of a soluble guanylyl cyclase activator, comprising administering to a patient in need thereof:
  i) an effective amount of a soluble guanylyl cyclase activator, and
  ii) a monoclonal antibody or antigen-binding fragment thereof, or competing antibody or antigen-binding fragment thereof, of any one of [1]-[5] in an amount effective to enhance said therapeutic effect of said soluble guanylyl cyclase activator.

[60] The method of [59], wherein said therapeutic effect comprises treatment of ischemia-reperfusion injury, or an autoimmune or inflammatory disease, in a human or companion/pet animal, working animal, sport animal, zoo animal, or other valuable animal kept in captivity.

[61] The method of [60], wherein said ischemia-reperfusion injury occurs in organ transplantation, acute kidney injury, cardiopulmonary bypass surgery, pulmonary hypertension, sickle cell disease, myocardial infarction, stroke, surgical resections and reconstructive surgery, reattachment of an appendage or other body part, skin grafting, or trauma.

[62] The method of [60], wherein said autoimmune or inflammatory disease is selected from the group consisting of arthritis, multiple sclerosis, psoriasis, Crohn's disease, inflammatory bowel disease, lupus, Grave's disease and Hashimoto's thyroiditis, and ankylosing spondylitis.

[63] Use of said monoclonal antibody or antigen-binding fragment thereof, or competing antibody or antigen-binding fragment thereof, of any one of [1]-[5] for the manufacture of a medicament to enhance the therapeutic effect of a soluble guanylyl cyclase activator.

[64] The use of [63], wherein said therapeutic effect comprises treatment of ischemia-reperfusion injury, or an autoimmune or inflammatory disease, in a human or companion/pet animal, working animal, sport animal, zoo animal, or other valuable animal kept in captivity.

[65] The use of [64], wherein said ischemia-reperfusion injury occurs in organ transplantation, acute kidney injury, cardiopulmonary bypass surgery, pulmonary hypertension, sickle cell disease, myocardial infarction, stroke, surgical resections and reconstructive surgery, reattachment of an appendage or other body part, skin grafting, and trauma.

[66] The use of [64], wherein said autoimmune or inflammatory disease is selected from the group consisting of arthritis, multiple sclerosis, psoriasis, Crohn's disease, inflammatory bowel disease, lupus, Grave's disease and Hashimoto's thyroiditis, and ankylosing spondylitis.

[67] A method of increasing the level of cGMP in vascular cells, comprising administering to said cells:
  i) an effective amount of a soluble guanylyl cyclase activator, and
  ii) a monoclonal antibody or antigen-binding fragment thereof, or competing antibody or antigen-binding fragment thereof, of any one of [1]-[5] in an amount effective to increase the level of cGMP in said vascular cells.

[68] The monoclonal antibody or antigen-binding fragment thereof, or competing antibody or antigen-binding fragment thereof, of any one of [1]-[5], which is an IgG isotype selected from among IgG1 isotype, IgG2 isotype, IgG3 isotype, and IgG4 isotypes

[69] A pharmaceutical composition, comprising said monoclonal antibody or antigen-binding fragment thereof, or competing antibody or antigen-binding fragment thereof, of [68], and a pharmaceutically or physiologically acceptable carrier, diluent, or excipient.

[70] The monoclonal antibody or antigen-binding fragment thereof, or competing antibody or antigen-binding fragment thereof, of [68] for use in human therapy or therapy of companion/pet animals, working animals, sport animals, zoo animals, or therapy of other valuable animals kept in captivity.

[71] The monoclonal antibody or antigen-binding fragment thereof, or competing antibody or antigen-binding fragment thereof, of [68] for use in treating ischemia-reperfusion injury, or an autoimmune or inflammatory disease, in a human or companion/pet animal, working animal, sport animal, zoo animal, or other valuable animal kept in captivity.

[72] The monoclonal antibody or antigen-binding fragment thereof, or competing antibody or antigen-binding fragment thereof, of [68] for use in treating a susceptible cancer.

[73] Use of said monoclonal antibody or antigen-binding fragment thereof, or competing antibody or antigen-binding fragment thereof, of [68] to treat ischemia-reperfusion injury, or an autoimmune or inflammatory disease, in a human or companion/pet animal, working animal, sport animal, zoo animal, or other valuable animal kept in captivity.

[74] Use of said monoclonal antibody or antigen-binding fragment thereof, or competing antibody or antigen-binding fragment thereof, of [68] to treat a susceptible cancer. [75] Use of said monoclonal antibody or antigen-binding fragment thereof, or competing antibody or antigen-binding fragment thereof, of [68] for the manufacture of a medicament to treat ischemia-reperfusion injury, or an autoimmune or inflammatory disease, in a human or companion/pet animal, working animal, sport animal, zoo animal, or other valuable animal kept in captivity.

[76] Use of said monoclonal antibody or antigen-binding fragment thereof, or competing antibody or antigen-binding fragment thereof, of [68] for the manufacture of a medicament to treat a susceptible cancer.

Expressly encompassed herein is the use of the monoclonal antibodies or antigen-binding fragments thereof of [68]-[76] in any of the methods, uses, compositions, or any other embodiments disclosed herein.

[77] The monoclonal antibody or antigen-binding fragment thereof, or competing antibody or antigen-binding fragment thereof, of any one of [1]-[5], wherein said monoclonal antibody or antigen-binding fragment thereof, or competing antibody or antigen-binding fragment thereof, is human IgG1 isotype, the human IgG1 constant region is modified at amino acid Asn297 to prevent to glycosylation; and/or at amino acid Leu 234 and/or Leu235 to alter Fc receptor interactions; and/or to enhance FcRn binding; and/or to alter antibody-dependent cellular cytotoxicity and/or complement-dependent cytotoxicity; and/or to induce heterodimerization, optionally further by introduction of a disulfide bond;

i. when said monoclonal antibody or antigen-binding fragment thereof, or competing antibody or antigen-binding fragment thereof, is human IgG2 isotype, the human IgG2 constant region is modified at amino acid Asn297 to prevent to glycosylation; and/or to enhance FcRn binding; and/or to alter antibody-dependent cellular cytotoxicity and/or complement-dependent cytotoxicity; and/or to induce heterodimerization, optionally further by introduction of a disulfide bond;

ii. when said monoclonal antibody or antigen-binding fragment thereof, or competing antibody or antigen-binding fragment thereof, is human IgG3 isotype, the human IgG3 constant region is modified at amino acid Asn297 to prevent to glycosylation; and/or at amino acid 435 to extend half-life; and/or to enhance FcRn binding; and/or to alter antibody-dependent cellular cytotoxicity and/or complement-dependent cytotoxicity; and/or to induce heterodimerization, optionally further by introduction of a disulfide bond;

iii. when said monoclonal antibody or antigen-binding fragment thereof, or competing antibody or antigen-binding fragment thereof, is human IgG4 isotype, the human IgG4 constant region is modified within the hinge region to prevent or reduce strand exchange; and/or at amino acid 235 to alter Fc receptor interactions; and/or at amino acid Asn297 to prevent glycosylation; and/or to enhance FcRn binding; and/or to alter antibody-dependent cellular cytotoxicity; and/or complement-dependent cytotoxicity; and/or to induce heterodimerization, optionally further by introduction of a disulfide bond.

[78] The monoclonal antibody or antigen-binding fragment thereof, or competing antibody or antigen-binding fragment thereof, of [77], wherein:
  i. when said monoclonal antibody or antigen-binding fragment thereof, or competing antibody or antigen-binding fragment thereof, is human IgG1 isotype, the human IgG1 constant region is modified at amino acid Asn297 to prevent to glycosylation by modification of Asn297→Ala (N297A) or Asn297→Gln(N297Q); and/or at amino acid Leu 234 by modification of Leu234→Ala (L234A) and/or Leu235 by modification of Leu235→Glu (L235E) or Leu235→Ala (L235A) or at both amino acid 234 and 235 by modification of Leu234→Ala and Leu235→Ala to alter Fc receptor interactions; and/or to enhance FcRn binding by modification of Met252→Tyr, Ser254→Thr, Thr256→Glu, Met428→Leu, or Asn434→Ser; and/or to alter antibody-dependent cellular cytotoxicity and/or complement-dependent cytotoxicity; and/or to induce heterodimerization by modification of Thr366→Trp, and optionally further by introduction of a disulfide bond by modification of Ser354→Cys and Tyr349→Cys on opposite CH3 domains;

ii. when said monoclonal antibody or antigen-binding fragment thereof, or competing antibody or antigen-binding fragment thereof, is human IgG2 isotype, the human IgG2 constant region is modified at amino acid Asn297 to prevent to glycosylation by modification of Asn297→Ala or Asn297→Gln; and/or to enhance FcRn binding by modification of Met252→Tyr, Ser254→Thr, Thr256→Glu, Met428→Leu, or Asn434→Ser; and/or to alter antibody-dependent cellular cytotoxicity and/or complement-dependent cytotoxicity; and/or to induce heterodimerization by modification of Thr366→Trp, and optionally further by introduction of a disulfide bond by modification of Ser354→Cys and Tyr349→Cys on opposite CH3 domains;

iii. when said monoclonal antibody or antigen-binding fragment thereof, or competing antibody or antigen-binding fragment thereof, is human IgG3 isotype, the human IgG3 constant region is modified at amino acid Asn297 to prevent to glycosylation by modification of Asn297→Ala or Asn297→Gln; and/or at amino acid 435 to extend half-life by modification of Arg435→His; and/or to enhance FcRn binding by modification of Met252→Tyr, Ser254→Thr, Thr256→Glu, Met428→Leu, or Asn434→Ser; and/or to alter antibody-dependent cellular cytotoxicity and/or complement-dependent cytotoxicity; and/or to induce heterodimerization by modification of Thr366→Trp, and optionally further by introduction of a disulfide bond by modification of Ser354→Cys and Tyr349→Cys on opposite CH3 domains;

iv. when said monoclonal antibody or antigen-binding fragment thereof, or competing antibody or antigen-binding fragment thereof, is human IgG4 isotype, the human IgG4 constant region is modified within the hinge region to prevent or reduce strand exchange by modification of Ser228→Pro; and/or at amino acid 235 to alter Fc receptor interactions by modification of Leu235→Glu, or by modification within the hinge and at amino acid 235 by modifying Ser228→Pro and Leu235→Glu; and/or at amino acid Asn297 to prevent glycosylation by modification of Asn297→Ala; and/or and/or to enhance FcRn binding by modification of Met252→Tyr, Ser254→Thr, Thr256→Glu, Met428→Leu, or Asn434→Ser; and/or to alter antibody-dependent cellular cytotoxicity and/or complement-dependent cytotoxicity; and/or to induce heterodimerization by modification of Thr366→Trp, and optionally further by introduction of a disulfide bond by modification of Ser354→Cys and Tyr349→Cys on opposite CH3 domains.

Expressly encompassed herein is the use of the monoclonal antibodies or antigen binding fragments thereof of [77]-[78] in any of the methods, uses, compositions, or any other embodiments disclosed herein.

Further scope of the applicability of the present antibody compounds and methods will become apparent from the detailed description provided below. However, it should be understood that the detailed description and specific examples, while indicating particular embodiments of the disclosure, are given by way of illustration only since various changes and modifications within the spirit and scope of the disclosure will become apparent to those skilled in the art from this detailed description.

BRIEF DESCRIPTION OF THE DRAWINGS

The above and other aspects, features, and advantages of the present disclosure will be better understood from the following detailed descriptions taken in conjunction with the accompanying drawing(s), all of which are given by way of illustration only, and are not limitative of the present disclosure, in which.

DETAILED DESCRIPTION OF THE INVENTION

Figure 1A:
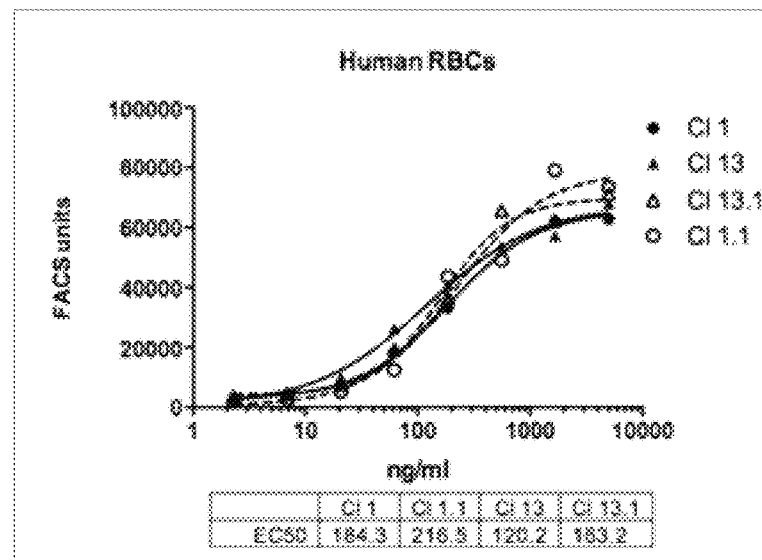
FIGS. 1A, 1B, 1C, and 1D show cross species binding curves to human, mouse, rat, and porcine RBCs, respectively, generated using various concentrations of purified antibodies from clones (Cl) Cl 1, Cl 1.1 (hum01 IgG1 N297Q), Cl 13, and Cl 13.1 (hum13 IgG1 N297Q) as described in Example 3. Clones Cl 1 and Cl 13 are as described in Table 3. Clones Cl 1.1 and Cl 13.1 are Fc mutants of clones Cl 1 and Cl 13, respectively, modified to reduce Fc effector function. Each has an Asn297→Gln (N297Q) mutation in the Fc domain (Sazinsky et al. (2008) *PNAS* 105(51):20167-20172). All of these clones exhibit concentration-dependent binding to all of the species of RBCs tested. RBCs are incubated for 60 minutes on ice with various concentrations of purified antibodies from clones Cl 1, Cl 1.1, Cl 13, and Cl 13.1. Cells are then washed with cold PBS containing EDTA, incubated for an additional hour on ice with FITC labeled donkey anti-human antibody, washed, and antibody binding is analyzed using a BD FACS Aria Cell Sorter (Becton Dickinson) or a C6 Accuri Flow Cytometer (Becton Dickinson).
Figure 1B:
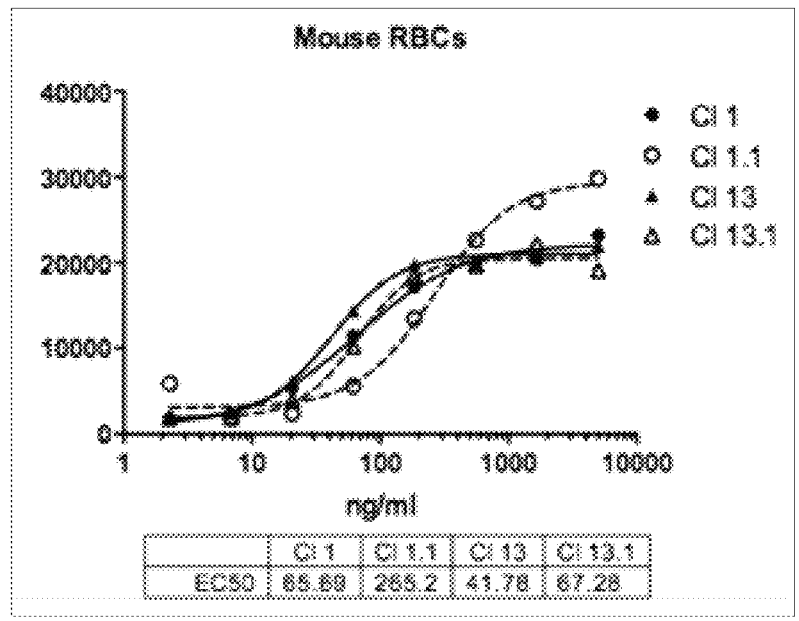
Figure 1C:
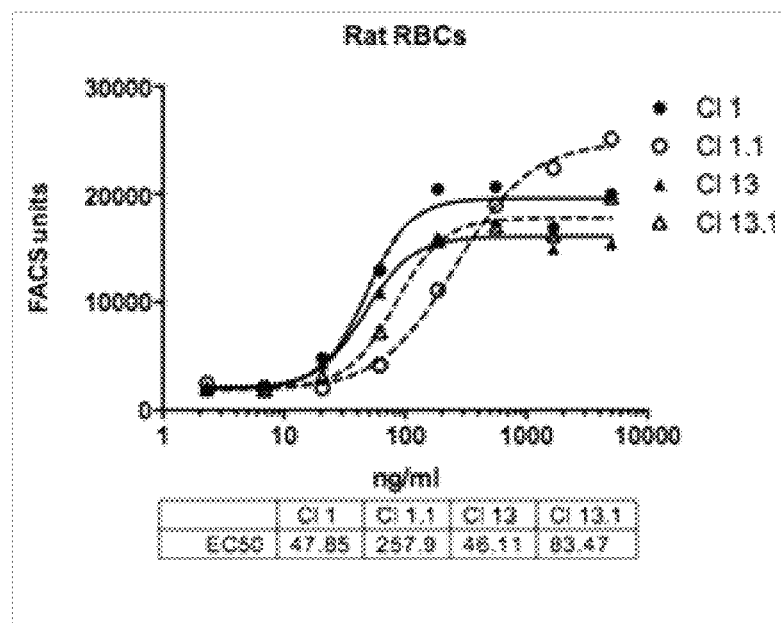
Figure 1D:
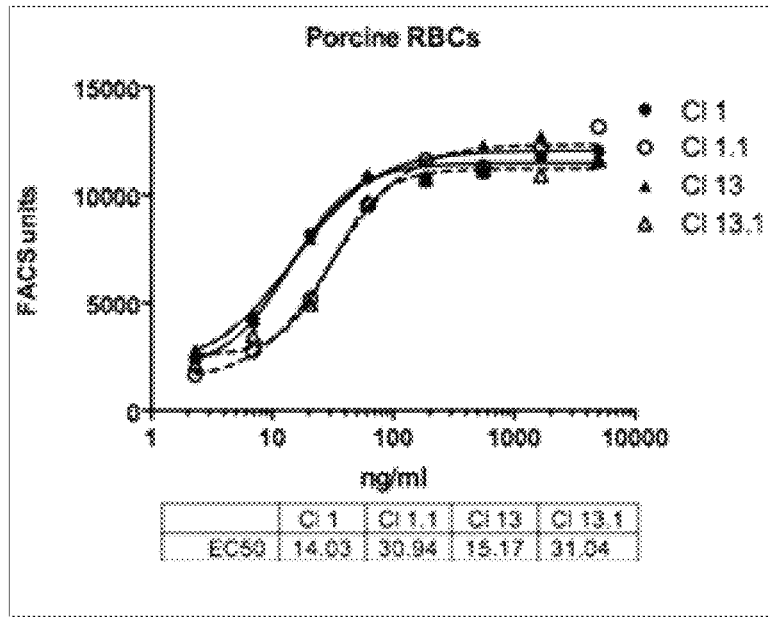

The following detailed description is provided to aid those skilled in the art in practicing the various embodiments of the present disclosure described herein, including all the methods, uses, compositions, etc., described herein. Even so, the following detailed description should not be construed to unduly limit the present disclosure, as modifications and variations in the embodiments herein discussed may be made by those of ordinary skill in the art without departing from the spirit or scope of the present discoveries.

Any feature, or combination of features, described herein is(are) included within the scope of the present disclosure, provided that the features included in any such combination are not mutually inconsistent as will be apparent from the context, this specification, and the knowledge of one of ordinary skill in the art. Additional advantages and aspects of the present disclosure are apparent in the following detailed description and claims.

The contents of all publications, patent applications, patents, and other references mentioned herein are incorporated by reference herein in their entirety. In case of conflict, the present specification, including explanations of terms, will control.

Antibody compounds of the present disclosure can bind to epitopes in the extracellular IgV domain of CD47, inhibiting TSP1 and SIRPalpha binding to CD47 and receptor activation, while inducing little or no agonist activity, and promoting tumor cell phagocytic clearance. In view of these properties, antibody compounds of the present disclosure should be therapeutically useful in treating many forms of IRI and cancers.

The present antibody compounds can also possess a number of other desirable properties, including broad reactivity with CD47 of a wide variety of mammalian species, including that of human, mouse, rat, pig, cynomolgus monkey, and/or dog, i.e., any individual one of these mammalian species, or various combinations thereof, making these antibodies useful in both human and veterinary medicine. This broad reactivity is further advantageous in that it facilitates preclinical studies including, but not limited to, safety and efficacy studies, in a variety of mammalian species, and therefore the development of such antibodies as human and veterinary therapeutics.

Thus, antibody compounds of the present disclosure exhibit the following desirable therapeutic activities:
Binding to CD47 of multiple mammalian species;
Blocking SIRPalpha and TSP1 binding to CD47;
Promoting phagocytosis of cancer cells; and
Reversing TSP1 inhibition of nitric oxide signaling
and are therefore useful in treating ischemia reperfusion injury and cancers.

Definitions

The following definitions are provided to aid the reader in understanding the various aspects of the present disclosure. Unless defined otherwise, all technical and scientific terms used herein have the same meaning as commonly understood by those of ordinary skill in the art to which this disclosure pertains.

A full-length antibody as it exists naturally is an immunoglobulin molecule comprising two heavy (H) chains and two light (L) chains interconnected by disulfide bonds. The amino terminal portion of each chain includes a variable region of about 100-110 or more amino acids primarily responsible for antigen recognition via the complementarity determining regions (CDRs) contained therein. The carboxy-terminal portion of each chain defines a constant region primarily responsible for effector function.

The CDRs are interspersed with regions that are more conserved, termed framework regions ("FR"). Each light chain variable region (LCVR) and heavy chain variable region (HCVR) is composed of 3 CDRs and 4 FRs, arranged from amino-terminus to carboxy-terminus in the following order: FR1, CDR1, FR2, CDR2, FR3, CDR3, FR4. The 3 CDRs of the light chain are referred to as "LCDR1, LCDR2, and LCDR3" and the 3 CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions are in accordance with the well-known Kabat numbering convention. While the light chain CDRs and heavy chain CDRs disclosed herein are numbered 1, 2, and 3, respectively, it is not necessary that they be employed in the corresponding antibody compound light and heavy chain variable regions in that numerical order, i.e., they can be present in any numerical order in a light or heavy chain variable region, respectively.

Light chains are classified as kappa or lambda, and are characterized by a particular constant region as known in the art. Heavy chains are classified as gamma, mu, alpha, delta, or epsilon, and define the isotype of an antibody as IgG, IgM, IgA, IgD, or IgE, respectively. IgG antibodies can be further divided into subclasses, e.g., IgG1, IgG2, IgG3, IgG4. Each heavy chain type is characterized by a particular constant region with a sequence well known in the art.

The monoclonal antibodies and other antibody compounds useful in the methods and compositions described herein can be any of these isotypes. Furthermore, any of these isotypes can comprise amino acid modifications as follows.

In some embodiments, the antibody constant region is of human IgG1 isotype.

In some embodiments, the human IgG1 constant region is modified at amino acid Asn297 (Kabat Numbering) to prevent to glycosylation of the antibody. For example, this modification can be Asn297→Ala (N297A) or Asn297→Gln (N297Q) (Sazinsky et al. (2008) *PNAS* 105 (51):20167-20172).

In some embodiments, the constant region of the antibody is modified at amino acid Leu234 (Kabat Numbering) to alter Fc receptor interactions. For example, this modification can be Leu234→Ala (L234A).

In some embodiments, the constant region of the antibody is modified at amino acid Leu235 (Kabat Numbering) to alter Fc receptor interactions. For example, this modification can be Leu235→Glu (L235E) or Leu235→Ala (L235A).

In some embodiments, the constant region of the antibody is altered at both amino acid 234 and 235. For example, these modifications can be Leu234→Ala and Leu235→Ala (L234A/L235A) (EU index of Kabat et al. (1991) *Sequences of Proteins of Immunological Interest*).

In some embodiments, the constant region of the antibody is of human IgG2 isotype.

In some embodiments, the human IgG2 constant region is modified at amino acid Asn297 (Kabat Numbering) to prevent to glycosylation of the antibody. For example, this modification can be Asn297→Ala (N297A) or Asn297→Gln(N297Q).

In some embodiments, the constant region of the antibody is of human IgG3 isotype.

In some embodiments, the human IgG3 constant region is modified at amino acid Asn297 (Kabat Numbering) to prevent to glycosylation of the antibody. For example, this modification can be Asn297→Ala (N297A) or Asn297→Gln(N297Q).

In some embodiments, the human IgG3 constant region is modified at amino acid 435 to extend the half-life. For example, this modification can be Arg435→His (R435H) (EU index of Kabat et al. (1991) *Sequences of Proteins of Immunological Interest*).

In some embodiments, the constant region of the antibody is of human IgG4 isotype.

In some embodiments, the human IgG4 constant region is modified within the hinge region to prevent or reduce strand exchange. For example, this modification can be Ser228→Pro (S228P) (Angal et al. (1993) *Molecular Immunology* 30(1):105-108).

In other embodiments, the human IgG4 constant region is modified at amino acid 235 to alter Fc receptor interactions. For example, this can be Leu235→Glu (L235E).

In some embodiments, the human IgG4 constant region is modified within the hinge and at amino acid 228 and in the Fc at amino acid 235. For example, this can be Ser228→Pro and Leu235→Glu (S228P/L235E).

In some embodiments, the human IgG4 constant region is modified at amino acid Asn297 (Kabat Numbering) to prevent to glycosylation of the antibody. For example, this can be Asn297→Ala (N297A). (EU index of Kabat et al. (1991) *Sequences of Proteins of Immunological Interest*).

In some embodiments, the human IgG constant region is modified to enhance FcRn binding. Examples of Fc mutations that enhance binding to FcRn are Met252→Tyr, Ser254→Thr, Thr256→Glu (M252Y, S254T, and T256E, respectively) (Kabat numbering, Dall'Acqua et al. (2006) *J. Biol. Chem.* 281(33) 23514-23524), or Met428→Leu and Asn434→Ser (M428L, N434S) (Zalevsky et al. (2010) *Nature Biotech.* 28(2):157-159). (EU index of Kabat et al. (1991) *Sequences of Proteins of Immunological Interest*).

In some embodiments, the human IgG constant region is modified to alter antibody-dependent cellular cytotoxicity (ADCC) and/or complement-dependent cytotoxicity (CDC), e.g., the amino acid modifications described in Natsume et al. (2008) *Cancer Res.* 68(10):3863-72; Idusogie et al. (2001) *J. Immunol.* 166(4):2571-5; Moore et al. (2010) *mAbs* 2(2):181-189; Lazar et al. (2006) *PNAS* 103(11):4005-4010; Shields et al. (2001) *J. Biol. Chem.* 276(9):6591-6604; Stavenhagen et al. (2007) *Cancer Res.* 67(18):8882-8890; Stavenhagen et al. (2008) *Advan. Enzyme Regul.* 48:152-164; Alegre et al. (1992) *J. Immunol.* 148:3461-3468; reviewed in Kaneko and Niwa (2011) *Biodrugs* 25(1):1-11.

In some embodiments, the human IgG constant region is modified to induce heterodimerization. For example, having an amino acid modification within the CH3 domain at Thr366, which when replaced with a more bulky amino acid, such as Trp (T366W), is able to preferentially pair with a second CH3 domain having amino acid modifications to less bulky amino acids at positions Thr366, Leu368, and Tyr407, e.g., Ser, Ala, and Val, respectively (T366S/L368A/Y407V). Heterodimerization via CH3 modifications can be further stabilized by the introduction of a disulfide bond, for example by changing Ser354 to Cys (S354C) and Tyr349 to Cys (Y349C) on opposite CH3 domains (reviewed in Carter (2001) *Journal of Immunological Methods* 248:7-15).

As used herein, the term "monoclonal antibody" (mAb) as applied to the present antibody compounds refers to an antibody that is derived from a single copy or clone including, for example, any eukaryotic, prokaryotic, or phage clone, and not the method by which it is produced. mAbs of the present disclosure preferably exist in a homogeneous or substantially homogeneous population, and can be chimeric or humanized. Complete mAbs contain two heavy chains and two light chains.

"Antigen binding fragments" of such monoclonal antibodies may be desirable for certain applications due to their small size and consequent superior tissue distribution, and include, for example, Fab fragments, Fab' fragments, F(ab')$_2$ fragments, Fd fragments, single chain Fv fragments (ScFv), and one-armed antibodies comprising a light chain and a heavy chain. Preferred antigen binding fragments are those that bind to the antigen recognized by the intact antibody. Fc fragments can also be obtained. Monoclonal antibodies and antigen-binding fragments thereof of the present disclosure can be produced, for example, by recombinant technologies, phage display technologies, synthetic technologies, e.g., CDR-grafting, or combinations of such technologies, or other technologies known in the art, including proteolytic digestion of intact antibodies.

"Antibody compounds" refers to mAbs, antigen-binding fragments thereof such as Fabs, etc., and competing antibodies, disclosed herein that specifically bind CD47 of various species, including human, rat, mouse, pig, cynomolgus monkey, and dog CD47, and that exhibit the properties disclosed herein. Thus, the term "mAb" as used herein with respect to antibodies encompassed by the present disclosure includes Fabs and competing antibodies. Additional antibody compounds exhibiting similar functional properties according to the present disclosure can be generated by conventional methods. For example, mice can be immunized with human CD47 or fragments thereof, the resulting antibodies can be recovered and purified, and determination of whether they possess binding and functional properties similar to or the same as the antibody compounds disclosed herein can be assessed by the methods disclosed in Examples 3, 4, and 5, below. Antigen-binding fragments can also be prepared by conventional methods. Methods for producing and purifying antibodies and antigen-binding fragments are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15, ISBN 0-87969-314-2.

The phrase "humanized antibodies" refers to monoclonal antibodies and antigen binding fragments thereof, including the antibody compounds disclosed herein, that have binding and functional properties according to the disclosure similar to those disclosed herein, and that have framework and constant regions that are substantially human or fully human surrounding CDRs derived from a non-human antibody. "Framework region" or "framework sequence" refers to any one of framework regions 1 to 4. Humanized antibodies and antigen binding fragments encompassed by the present disclosure include molecules wherein any one or more of framework regions 1 to 4 is substantially or fully human, i.e., wherein any of the possible combinations of individual substantially or fully human framework regions 1 to 4, is present. For example, this includes molecules in which framework region 1 and framework region 2, framework region 1 and framework region 3, framework region 1, 2, and 3, etc., are substantially or fully human Substantially human frameworks are those that have at least 80% sequence identity to a known human germline framework sequence. Preferably, the substantially human frameworks have at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, to a framework sequence disclosed herein, or to a known human germline framework sequence.

CDRs encompassed by the present disclosure include not only those specifically disclosed herein, but also CDR sequences having sequence identities of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a CDR sequence disclosed herein. Alternatively, CDRs encompassed by the present disclosure include not only those specifically disclosed herein, but also CDR sequences having 1, 2, 3, 4, 5, or 6 amino acid changes at corresponding positions compared to CDR sequences disclosed herein. Such sequence identical, or amino acid modified, CDRs preferably bind to the antigen recognized by the intact antibody.

As used herein, the phrase "sequence identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., *SIAM J. Applied Math.*, 48: 1073 (1988). Methods to determine identity are designed to give the largest match between the sequences tested. Moreover, methods to determine identity are codified in publicly available computer programs.

Optimal alignment of sequences for comparison can be conducted, for example, by the local homology algorithm of Smith & Waterman, by the homology alignment algorithms, by the search for similarity method or, by computerized implementations of these algorithms (GAP, BESTFIT, PASTA, and TFASTA in the GCG Wisconsin Package, available from Accelrys, Inc., San Diego, Calif., United States of America), or by visual inspection. See generally, (Altschul, S. F. et al., *J. Mol. Biol.* 215: 403-410 (1990) and Altschul et al. *Nucl. Acids Res.* 25: 3389-3402 (1997)).

One example of an algorithm that is suitable for determining percent sequence identity and sequence similarity is the BLAST algorithm, which is described in (Altschul, S., et al., NCBI NLM NIH Bethesda, Md. 20894; & Altschul, S., et al., *J. Mol. Biol.* 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold.

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always; 0) and N (penalty score for mismatching residues; always; 0). For amino acid sequences, a scoring matrix is used to calculate the cumulative score. Extension of the word hits in each direction are halted when: the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix.

In addition to calculating percent sequence identity, the BLAST algorithm also performs a statistical analysis of the similarity between two sequences. One measure of similarity provided by the BLAST algorithm is the smallest sum probability (P (N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in one embodiment less than about 0.1, in another embodiment less than about 0.01, and in still another embodiment less than about 0.001.

Fully human frameworks are those that are identical to a known human germline framework sequence. Human framework germline sequences can be obtained from ImMunoGeneTics (IMGT) via their website or from *The Immunoglobulin FactsBook* by Marie-Paule Lefranc and Gerard Lefranc, Academic Press, 2001, ISBN 012441351. For example, germline light chain frameworks can be selected from the group consisting of: A11, A17, A18, A19, A20, A27, A30, LI, L1I, L12, L2, L5, L15, L6, L8, O12, O2, and O8, and germline heavy chain framework regions can be selected from the group consisting of: VH2-5, VH2-26, VH2-70, VH3-20, VH3-72, VHI-46, VH3-9, VH3-66, VH3-74, VH4-31, VHI-18, VHI-69, VI-13-7, VH3-11, VH3-15, VH3-21, VH3-23, VH3-30, VH3-48, VH4-39, VH4-59, and VH5-5I.

Humanized antibodies in addition to those disclosed herein exhibiting similar functional properties according to the present disclosure can be generated using several different methods. In one approach, the parent antibody compound CDRs are grafted into a human framework that has a high sequence identity with the parent antibody compound framework. The sequence identity of the new framework will generally be at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identical to the sequence of the corresponding framework in the parent antibody compound. In the case of frameworks having fewer than 100 amino acid residues, one, two, three, four, five, six, seven, eight, nine, or ten amino acid residues can be changed. This grafting may result in a reduction in binding affinity compared to that of the parent antibody. If this is the case, the framework can be back-mutated to the parent framework at certain positions based on specific criteria disclosed by Queen et al. (1991) *Proc. Natl. Acad. Sci*. USA 88:2869. Additional references describing methods useful in humanizing mouse antibodies include U.S. Pat. Nos. 4,816,397; 5,225,539; and 5,693,761; computer programs ABMOD and ENCAD as described in Levitt (1983) *J. Mol. Biol*. 168:595-620; and the method of Winter and co-workers (Jones et al. (1986) *Nature* 321:522-525; Riechmann et al. (1988) *Nature* 332:323-327; and Verhoeyen et al. (1988) *Science* 239:1534-1536.

The identification of residues to consider for back-mutation can be carried out as follows: When an amino acid falls under the following category, the framework amino acid of the human germ-line sequence that is being used (the "acceptor framework") is replaced by a framework amino acid from a framework of the parent antibody compound (the "donor framework"): (a) the amino acid in the human framework region of the acceptor framework is unusual for human frameworks at that position, whereas the corresponding amino acid in the donor immunoglobulin is typical for human frameworks at that position; (b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model.

When each of the amino acids in the human framework region of the acceptor framework and a corresponding amino acid in the donor framework is generally unusual for human frameworks at that position, such amino acid can be replaced by an amino acid typical for human frameworks at that position. This back-mutation criterion enables one to recover the activity of the parent antibody compound.

Another approach to generating human engineered antibodies exhibiting similar functional properties to the antibody compounds disclosed herein involves randomly mutating amino acids within the grafted CDRs without changing the framework, and screening the resultant molecules for binding affinity and other functional properties that are as good as or better than those of the parent antibody compounds. Single mutations can also be introduced at each amino acid position within each CDR, followed by assessing the effects of such mutations on binding affinity and other functional properties. Single mutations producing improved properties can be combined to assess their effects in combination with one another.

Further, a combination of both of the foregoing approaches is possible. After CDR grafting, one can back-mutate specific framework regions in addition to introducing amino acid changes in the CDRs. This methodology is described in Wu et al. (1999) *J. Mol. Biol*. 294:151-162.

The method described in Example 1 below can also be employed.

Applying the teachings of the present disclosure, a person skilled in the art can use common techniques, e.g., site-directed mutagenesis, to substitute amino acids within the presently disclosed CDR and framework sequences and thereby generate further variable region amino acid sequences derived from the present sequences. Up to all naturally occurring amino acids can be introduced at a specific substitution site, including conservative amino acid substitutions as are well known to those of ordinary skill in the art. The methods disclosed herein can then be used to screen these additional variable region amino acid sequences to identify sequences having the indicated in vitro and/or in vivo functions. In this way, further sequences suitable for preparing human engineered antibodies and antigen-binding portions thereof in accordance with the present disclosure can be identified. In some embodiments, amino acid substitution within the frameworks can include one, two, three, four, five, six, seven, eight, nine, or ten positions within any one or more of the 4 light chain and/or heavy chain framework regions disclosed herein. In some embodiments, amino acid substitution within the CDRs is restricted to one, two, three, four, or five positions within any one or more of the 3 light chain and/or heavy chain CDRs. Combinations of the various changes within these framework regions and CDRs described above are also possible.

That the functional properties of the antibody compounds generated by introducing the amino acid modifications discussed above conform to, and are comparable to, those exhibited by the specific molecules disclosed herein can be confirmed by the methods disclosed in the Examples below.

The terms "specifically binds", "bind specifically", "specific binding", and the like as applied to the present antibody compounds refer to the ability of a specific binding agent (such as an antibody) to bind to a target molecular species in preference to binding to other molecular species with which the specific binding agent and target molecular species are admixed. A specific binding agent is said specifically to recognize a target molecular species when it can bind specifically to that target.

"Binding affinity" is a term that refers to the strength of binding of one molecule to another at a site on the molecule. If a particular molecule will bind to or specifically associate with another particular molecule, these two molecules are said to exhibit binding affinity for each other. Binding affinity is related to the association constant and dissociation constant for a pair of molecules, but it is not critical to the methods herein that these constants be measured or determined. Rather, affinities as used herein to describe interactions between molecules of the described methods are generally apparent affinities (unless otherwise specified) observed in empirical studies, which can be used to compare the relative strength with which one molecule (e.g., an antibody or other specific binding partner) will bind two other molecules (e.g., two versions or variants of a peptide). The concepts of binding affinity, association constant, and dissociation constant are well known.

The term "epitope" refers to a specific arrangement of amino acids located on a peptide or protein to which an antibody or antibody fragment binds. Epitopes often consist of a chemically active surface grouping of molecules such as amino acids or sugar side chains, and have specific three dimensional structural characteristics as well as specific charge characteristics. Epitopes can be linear, i.e., involving binding to a single sequence of amino acids, or conformational, i.e., involving binding to two or more sequences of amino acids in various regions of the antigen that may not necessarily be contiguous in the linear sequence.

Monoclonal antibodies or antigen-binding fragments thereof encompassed by the present disclosure that "compete" with the molecules disclosed herein are those that bind human CD47 at site(s) that are identical to, or overlapping with, the site(s) at which the present molecules bind. Competing monoclonal antibodies or antigen-binding fragments thereof can be identified, for example, via an antibody competition assay. For example, a sample of purified or partially purified human CD47 extracellular domain can be bound to a solid support. Then, an antibody compound, or antigen binding fragment thereof, of the present disclosure and a monoclonal antibody or antigen-binding fragment thereof suspected of being able to compete with such disclosure antibody compound are added. One of the two molecules is labeled. If the labeled compound and the unlabeled compound bind to separate and discrete sites on CD47, the labeled compound will bind to the same level whether or not the suspected competing compound is present. However, if the sites of interaction are identical or overlapping, the unlabeled compound will compete, and the amount of labeled compound bound to the antigen will be lowered. If the unlabeled compound is present in excess, very little, if any, labeled compound will bind. For purposes of the present disclosure, competing monoclonal antibodies or antigen-binding fragments thereof are those that decrease the binding of the present antibody compounds to CD47 by about 50%, about 60%, about 70%, about 80%, about 85%, about 86%, about 87%, about 88%, about 89%, about 90%, about 91%, about 92%, about 93%, about 94%, about 95%, about 96%, about 97%, about 98%, or about 99%. Details of procedures for carrying out such competition assays are well known in the art and can be found, for example, in Harlow and Lane (1988) *Antibodies, A Laboratory Manual*, Cold Spring Harbor Laboratory Press, Cold Spring Harbor, N.Y., pages 567-569, ISBN 0-87969-314-2. Such assays can be made quantitative by using purified antibodies. A standard curve is established by titrating one antibody against itself, i.e., the same antibody is used for both the label and the competitor. The capacity of an unlabeled competing monoclonal antibody or antigen-binding fragment thereof to inhibit the binding of the labeled molecule to the plate is titrated. The results are plotted, and the concentrations necessary to achieve the desired degree of binding inhibition are compared.

Whether monoclonal antibodies or antigen-binding fragments thereof that compete with antibody compounds of the present disclosure in such competition assays possess the same or similar functional properties of the present antibody compounds can be determined via these methods in conjunction with the methods described in Examples 3-5, below. In various embodiments, competing antibodies for use in the therapeutic methods encompassed herein possess biological activities as described herein in the range of from about 50% to about 100% or about 125%, or more, compared to that of the antibody compounds disclosed herein. In some embodiments, competing antibodies possess about 50%, about 60%, about 70%, about 80%, about 85%, about 90%, about 91%, about 92%, about 93%, about 94%, about 95%, about 96%, about 97%, about 98%, about 99%, or identical biological activity compared to that of the antibody compounds disclosed herein as determined by the methods disclosed in the Examples presented below.

The term "treating" (or "treat" or "treatment") means slowing, interrupting, arresting, controlling, stopping, reducing, or reversing the progression or severity of a sign, symptom, disorder, condition, or disease, but does not necessarily involve a total elimination of all disease-related signs, symptoms, conditions, or disorders. The term "treating" and the like refer to a therapeutic intervention that ameliorates a sign, symptom, etc., of a disease or pathological condition after it has begun to develop.

Acute events and chronic conditions can be treated. In an acute event, an antibody or antigen binding fragment thereof is administered at the onset of a symptom, disorder, condition, disease, or procedure, and is discontinued when the acute event ends, or in the case of organ transplantation to the organ, at the time of organ harvest and/or to the transplant recipient at the time of organ transplantation. In contrast, a chronic symptom, disorder, condition, or disease is treated over a more protracted time frame.

The term "effective amount" refers to the amount or dose of an antibody compound of the present disclosure which, upon single or multiple dose administration to a patient or organ, provides the desired treatment or prevention.

The precise effective amount for any particular subject will depend upon their size and health, the nature and extent of their condition, and the therapeutics or combination of therapeutics selected for administration. The effective amount for a given patient is determined by routine experimentation and is within the judgment of a clinician. In some embodiments, an effective dose will generally be from about 0.01 mg/kg to about 50 mg/kg, or about 0.05 mg/kg to about 10 mg/kg of the compositions of the present disclosure in the individual to which it is administered. Therapeutically effective amounts of the present antibody compounds can also comprise an amount in the range of from about 0.1 mg/kg to about 150 mg/kg, from about 0.1 mg/kg to about 100 mg/kg, or from about 0.1 mg/kg to about 50 mg/kg per single dose administered to a harvested organ or to a patient. Known antibody-based pharmaceuticals provide guidance in this respect. For example, Herceptin™ is administered by intravenous infusion of a 21 mg/ml solution, with an initial loading dose of 4 mg/kg body weight and a weekly maintenance dose of 2 mg/kg body weight; Rituxan™ is administered weekly at 375 mg/m$^2$; etc.

A therapeutically effective amount for any individual patient can be determined by the health care provider by monitoring the effect of the antibody compounds on a biomarker, such as serum biomarkers of injury of the treated organ, including but not limited to liver, kidney, lung, intestine, pancreas and heart, changes in pulmonary artery pressures, cell surface CD47 expression in tumor or non-tumor tissues, tumor regression, circulating tumor cells or tumor stem cells, etc. Analysis of the data obtained by these methods permits modification of the treatment regimen during therapy so that optimal amounts of antibody compounds of the present disclosure, whether employed alone or in combination with one another, or in combination with another therapeutic agent, or both, are administered, and so that the duration of treatment can be determined as well. In this way, the dosing/treatment regimen can be modified over the course of therapy so that the lowest amounts of antibody compounds used alone or in combination that exhibit satisfactory efficacy are administered, and so that administration of such compounds is continued only so long as is necessary to successfully treat the patient. Known antibody-based pharmaceuticals provide guidance relating to frequency of administration e.g., whether a pharmaceutical should be delivered daily, weekly, monthly, etc. Frequency and dosage may also depend on the severity of symptoms.

The antibody compounds of the present disclosure can be used as medicaments in human and veterinary medicine, administered by a variety of routes. Veterinary applications include the treatment of companion/pet animals, such as cats and dogs; working animals, such as guide or service dogs, and horses; sport animals, such as horses and dogs; zoo animals, such as primates, cats such as lions and tigers, bears, etc.; and other valuable animals kept in captivity.

Antibody compounds can be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal, intravesiciular or rectal routes. Hypo sprays may also be used to administer the pharmaceutical compositions. Typically, the therapeutic compositions can be prepared as injectables, either as liquid solutions or suspensions. Solid forms suitable for solution in, or suspension in, liquid vehicles prior to injection can also be prepared.

Direct delivery of the compositions can generally be accomplished by injection, subcutaneously, intraperitoneally, intravenously, or intramuscularly, or delivered to the interstitial space of a tissue. The compositions can also be administered into a lesion such as a tumor. Dosage treatment may be a single dose schedule or a multiple dose schedule.

In some embodiments, such compositions are formulated for parenteral administration by, for example, intravenous, intramuscular, subcutaneous, etc., administration by infusion, injection, implantation, etc., as is well known in the art. Examples include bolus injection or continuous infusion. Intratumoral administration, for example by injection, is also contemplated.

Such pharmaceutical compositions can be prepared by methods well known in the art. See, e.g., *Remington: The Science and Practice of Pharmacy,* 21$^{st}$ Edition (2005), Lippincott Williams & Wilkins, Philadelphia, Pa., and comprise one or more antibody compounds disclosed herein, and a pharmaceutically or veterinary acceptable, e.g., physiologically acceptable, carrier, diluent, or excipient.

Combination Therapies

The therapeutic methods encompassed herein include the use of the antibodies disclosed herein alone, and/or in combinations with one another, and/or with antigen-binding fragments thereof, and/or with competing antibodies exhibiting appropriate biological/therapeutic activity, as well, i.e., all possible combinations of these antibody compounds.

In addition, the present therapeutic methods also encompass the use of these antibodies, antigen-binding fragments thereof, competing antibodies, etc., and combinations thereof further in combination with: (1) any one or more of the nitric oxide donor, precursor, or nitric oxide generating topical agents, and/or agents that activate soluble guanylyl cyclase, and/or agents that inhibit cyclic nucleotide phosphodiesterases disclosed herein, or (2) any one or more anti-tumor therapeutic treatments selected from surgery, radiation, anti-tumor or anti-neoplastic agents, and combinations of any of these, or (3) equivalents of any of the foregoing of (1) or (2) as would be apparent to one of ordinary skill in the art, in appropriate combination(s) to achieve the desired therapeutic treatment effect for the particular indication.

Combinations of Antibody Compounds

It should be noted that in all of the therapeutic methods disclosed and claimed herein, the monoclonal antibodies or antigen binding fragments thereof, and monoclonal antibodies or antigen binding fragments thereof that compete with these monoclonal antibodies or antigen binding fragments thereof of the present disclosure that bind to CD47, can be used alone, or in any appropriate combinations with one another, to achieve the greatest treatment efficacy.

Further Therapeutic Combinations to Treat IRI-Related Indications

In addition to administering the combinations of antibody compounds as described immediately above, the methods of the present disclosure, for example those related to treatment of IRI-related indications, can further comprise administering to a patient in need thereof an effective amount of a nitric oxide donor, precursor, or both; a nitric oxide generating topical agent; an agent that activates soluble guanylyl cyclase; an agent that inhibits cyclic nucleotide phosphodiesterases; or any combination of any of the foregoing.

In these methods, the nitric oxide donor or precursor can be selected from NO gas, isosorbide dinitrate, nitrite, nitroprusside, nitroglycerin, 3-Morpholinosydnonimine (SIN-1), S-nitroso-N-acetylpenicillamine (SNAP), Diethylenetriamine/NO (DETA/NO), S-nitrosothiols, Bidil®, and arginine.

The agent that activates soluble guanylyl cyclase can be a non-NO (nitric oxide)-based chemical activator of soluble guanylyl cyclase that increases cGMP levels in vascular cells. Such agents bind soluble guanylyl cyclase in a region other than the NO binding motif, and activate the enzyme regardless of local NO or reactive oxygen stress (ROS). Non-limiting examples of chemical activators of soluble guanylyl cyclase include organic nitrates (Artz et al. (2002) *J. Biol. Chem.* 277:18253-18256); protoporphyrin IX (Ignarro et al. (1982) *Proc. Natl. Acad. Sci. USA* 79:2870-2873); YC-1 (Ko et al. (1994) *Blood* 84:4226-4233); BAY 41-2272 and BAY 41-8543 (Stasch et al. (2001 *Nature* 410 (6825): 212-5), CMF-1571, and A-350619 (reviewed in Evgenov et al. (2006) *Nat. Rev. Drug. Discov.* 5:755-768); BAY 58-2667 (Cinaciguat; Frey et al. (2008) *Journal of Clinical Pharmacology* 48 (12): 1400-10); BAY 63-2521 (Riociguat; Mittendorf et al. (2009) *Chemmedchem* 4 (5): 853-65). Additional soluble guanylyl cyclase activators are disclosed in Stasch et al. (2011) *Circulation* 123:2263-2273; Derbyshire and Marietta (2012) *Ann. Rev. Biochem.* 81:533-559, and Nossaman et al. (2012) *Critical Care Research and Practice*, Volume 2012, Article ID 290805, pages 1-12.

The agent that inhibits cyclic nucleotide phosphodiesterases can be selected from sildenafil, tadalafil, vardenafil, udenafil, and avanafil.

Further Therapeutic Combinations to Treat Cancer Indications

In addition to the foregoing, the methods of the present disclosure, for example those related to treatment of cancer indications, can further comprise treating the patient via surgery, radiation, and/or administering to a patient in need thereof an effective amount of a chemical small molecule or biologic drug including, but not limited to, a peptide, polypeptide, protein, nucleic acid therapeutic, etc., conventionally used, or currently being developed, to treat cancer. This includes antibodies and antigen-binding fragments other than those disclosed herein, cytokines, antisense oligonucleotides, siRNAs, miRNAs, etc.

As is well known to those of ordinary skill in the art, combination therapies are often employed in cancer treatment as single-agent therapies or procedures may not be sufficient to treat or cure the disease or condition. Conventional cancer treatments often involve surgery, radiation treatment, the administration of a combination of cytotoxic drugs to achieve additive or synergistic effects, and combinations of any or all of these approaches. Especially useful chemotherapeutic and biologic therapy combinations employ drugs that work via different mechanisms of action, increasing cancer cell control or killing, increasing the ability of the immune system to control cancer cell growth, reducing the likelihood of drug resistance during therapy, and minimizing possible overlapping toxicities by permitting the use of reduced doses of individual drugs.

Classes of conventional anti-tumor/anti-neoplastic agents useful in the combination therapies encompassed by the present methods are disclosed, for example, in *Goodman & Gilman's The Pharmacological Basis of Therapeutics*, Twelfth Edition (2010) L. L. Brunton, B. A. Chabner, and B. C. Knollmann Eds., Section VIII, "Chemotherapy of Neoplastic Diseases", Chapters 60-63, pp. 1665-1770, McGraw-Hill, NY, and include, for example, alkylating agents; antimetabolites; natural products; a variety of miscellaneous agents; hormones and antagonists; and monoclonal antibodies.

Antibody and small molecule drugs that increase the immune response to cancer by modulating co-stimulatory or inhibitory interactions that influence the T cell response to tumor antigens, including inhibitors of immune checkpoints and modulators of co-stimulatory molecules, are also of particular interest in the context of the combination therapeutic methods encompassed herein and include, but are not limited to, other anti-CD47 antibodies. These agents that are involved in the immune response include IL-10 (Interleukin-10, human cytokin synthesis inhibitory factor, CSIF) and Galectins. Administration of therapeutic agents that bind to the CD47 protein, for example, antibodies or small molecules that bind to CD47 and prevent interaction between CD47 and SIRPalpha, are administered to a patient, increasing the clearance of cancer cells via phagocytosis. The therapeutic agent that binds to the CD47 protein is combined with a therapeutic agent such as an antibody, a chemical small molecule or biologic drug disclosed herein, directed against one or more additional cellular targets of CD70 (Cluster of Differentiation 70), CD200 (OX-2 membrane glycoprotein, Cluster of Differentiation 200), CD154 (Cluster of Differentiation 154, CD40L, CD40 ligand, Cluster of Differentiation 40 ligand), CD223 (Lymphocyte-activation gene 3, LAG3, Cluster of Differentiation 223), KIR (Killer-cell immunoglobulin-like receptors), GITR (TNFRSF18, glucocorticoid-induced TNFR-related protein, activation-inducible TNFR family receptor, AITR, Tumor necrosis factor receptor superfamily member 18), CD28 (Cluster of Differentiation 28), CD40 (Cluster of Differentiation 40, Bp50, CDW40, TNFRSF5, Tumor necrosis factor receptor superfamily member 5, p50), CD86 (B7-2, Cluster of Differentiation 86), CD160 (Cluster of Differentiation 160, BY55, NK1, NK28), CD258 (LIGHT, Cluster of Differentiation 258, Tumor necrosis factor ligand superfamily member 14, TNFSF14, HVEML, HVEM ligand, herpesvirus entry mediator ligand, LTg), CD270 (HVEM, Tumor necrosis factor receptor superfamily member 14, herpesvirus entry mediator, Cluster of Differentiation 270, LIGHTR, HVEA), CD275 (ICOSL, ICOS ligand, Inducible T-cell Costimulator ligand, Cluster of Differentiation 275), CD276 (B7-H3, B7 homolog 3, Cluster of Differentiation 276), OX40L (OX40 Ligand), B7-H4 (B7 homolog 4, VTCN1, V-set domain-containing T-cell activation inhibitor 1), GITRL (Glucocorticoid-induced tumor necrosis factor receptor-ligand, glucocorticoid-induced TNFR-ligand), 4-1BBL (4-1BB ligand), CD3 (Cluster of Differentiation 3, T3D), CD25 (IL2Rα, Cluster of Differentiation 25, Interleukin-2 Receptor α chain, IL-2 Receptor α chain), CD48 (Cluster of Differentiation 48, B-lymphocyte activation marker, BLAST-1, signaling lymphocytic activation molecule 2, SLAMF2), CD66a (Ceacam-1, Carcinoembryonic antigen-related cell adhesion molecule 1, biliary glycoprotein, BGP, BGP1, BGPI, Cluster of Differentiation 66a), CD80 (B7-1, Cluster of Differentiation 80), CD94 (Cluster of Differentiation 94), NKG2A (Natural killer group 2A, killer cell lectin-like receptor subfamily D member 1, KLRD1), CD96 (Cluster of Differentiation 96, TActILE, T cell activation increased late expression), CD112 (PVRL2, nectin, Poliovirus receptor-related 2, herpesvirus entry mediator B, HVEB, nectin-2, Cluster of Differentiation 112), CD115 (CSF1R, Colony stimulating factor 1 receptor, macrophage colony-stimulating factor receptor, M-CSFR, Cluster of Differentiation 115), CD205 (DEC-205, LY75, Lymphocyte antigen 75, Cluster of Differentiation 205), CD226 (DNAM1, Cluster of Differentiation 226, DNAX Accessory Molecule-1, PTA1, platelet and T cell activation antigen 1), CD244 (Cluster of Differentiation 244, Natural killer cell receptor 2B4), CD262 (DR5, TrailR2, TRAIL-R2, Tumor necrosis factor receptor superfamily member 10b, TNFRSF10B, Cluster of Differentiation 262, KILLER, TRICK2, TRICKB, ZTNFR9, TRICK2A, TRICK2B), CD284 (Toll-like Receptor-4, TLR4, Cluster of Differentiation 284), CD288 (Toll-like Receptor-8, TLR8, Cluster of Differentiation 288), TNFSF15 (Tumor necrosis factor superfamily member 15, Vascular endothelial growth inhibitor, VEGI, TL1A), TDO2 (Tryptophan 2,3-dioxygenase, TPH2, TRPO), IGF-1R (Type 1 Insulin-like Growth Factor), GD2 (Disialoganglioside 2), TMIGD2 (Transmembrane and immunoglobulin domain-containing protein 2), RGMB (RGM domain family, member B), VISTA (V-domain immunoglobulin-containing suppressor of T-cell activation, B7-H5, B7 homolog 5), BTNL2 (Butyrophilin-like protein 2), Btn (Butyrophilin family), TIGIT (T cell immunoreceptor with Ig and ITIM domains, Vstm3, WUCAM), Siglecs (Sialic acid binding Ig-like lectins), Neurophilin, VEGFR (Vascular endothelial growth factor receptor), ILT family (LIRs, immunoglobulin-like transcript family, leukocyte immunoglobulin-like receptors), NKG families (Natural killer group families, C-type lectin transmembrane receptors), MICA (MHC class I polypeptide-related sequence A), TGFβ (Transforming growth factor β), STING pathway (Stimulator of interferon gene pathway), Arginase (Arginine amidinase, canavanase, L-arginase, arginine transamidinase), EGFRvIII (Epidermal growth factor receptor variant III), and HHLA2 (B7-H7, B7y, HERV-H LTR-associating protein 2, B7 homolog 7), inhibitors of PD-1 (Programmed cell death protein 1, PD-1, CD279, Cluster of Differentiation 279), PD-L1 (B7-H1, B7 homolog 1, Programmed death-ligand 1, CD274, cluster of Differentiation 274), PD-L2 (B7-DC, Programmed cell death 1 ligand 2, PDCD1LG2, CD273, Cluster of Differentiation 273), CTLA-4 (Cytotoxic T-lymphocyte-associated protein 4, CD152, Cluster of Differentiation 152), BTLA (B- and T-lymphocyte attenuator, CD272, Cluster of Differentiation 272), Indoleamine 2,3-dioxygenase (IDO, IDO1), TIM3 (HAVCR2, Hepatitis A virus cellular receptor 2, T cell immunoglobulin mucin-3, KIM-3, Kidney injury molecule 3, TIMD-3, T cell immunoglobulin mucin-domain 3), A2A adenosine receptor (ADO receptor), CD39 (ectonucleoside triphosphate diphosphohydrolase-1, Cluster of Differentiation 39, ENTPD1), and CD73 (Ecto-5'-nucleotidase, 5'-nucleotidase, 5'-NT, Cluster of Differentiation 73), including antibodies and small molecules, and agonists of CD27 (Cluster of Differentiation 27), ICOS (CD278, Cluster of Differentiation 278, Inducible T-cell Co-stimulator), CD137 (4-1BB, Cluster of Differentiation 137, tumor necrosis factor receptor superfamily member 9, TNFRSF9), OX40 (CD134, Cluster of Differentiation 134), and TNFSF25 (Tumor necrosis factor receptor superfamily member 25), including small molecules and antibodies, are also specifically contemplated herein. YERVOY® (ipilimumab; Bristol-Meyers Squibb) is an example of an approved anti-CTLA-4 antibody.

KEYTRUDA® (pembrolizumab; Merck) and OPDIVO® (nivolumab; Bristol-Meyers Squibb Company) are examples of approved anti-PD-1 antibodies.

Another useful class of compounds for the combination therapies contemplated herein includes modulators of SIRPalpha/CD47 binding such as antibodies to SIRPalpha, as well as soluble protein fragments of this ligand, or CD47 itself, acting as "decoy" molecules inhibiting binding of, or interfering with binding of, SIRPalpha to CD47.

The present disclosure encompasses therapeutic methods comprising not only the administration of any of the individual monoclonal antibodies, antigen binding fragments thereof, or competing antibodies disclosed herein with any one or more of the molecules discussed immediately above, but also combinations of the disclosed monoclonal antibodies, antigen-binding fragments thereof, and competing antibodies in combinations with any one or more of the molecules discussed immediately above, i.e., all possible permutations and combinations of the presently disclosed molecules. The term "tumor" refers to all neoplastic cell growth and proliferation, whether malignant or benign, and all pre-cancerous and cancerous cells and tissues. The terms "cancer", "cancerous", and "tumor" are not mutually exclusive as used herein.

The terms "cancer" and "cancerous" refer to or describe the physiological condition in mammals that is typically characterized by aberrant cell growth/proliferation. Examples of cancers include, but are not limited to, carcinomas, lymphomas, blastomas, sarcomas, and leukemias.

The term "susceptible cancer" as used herein refers to a cancer, cells of which express CD47 and that are responsive to treatment with an antibody or antigen binding fragment thereof, or competing antibody or antigen binding fragment thereof, of the present disclosure. Exemplary susceptible cancers include, but are not limited to, leukemias, including systemic mastocytosis, acute lymphocytic (lymphoblastic) leukemia (ALL), T cell-ALL, acute myeloid leukemia (AML), myelogenous leukemia, chronic lymphocytic leukemia (CLL), multiple myeloma (MM), chronic myeloid leukemia (CML), myeloproliferative disorder/neoplasm, myelodysplastic syndrome, monocytic cell leukemia, and plasma cell leukemia; lymphomas, including histiocytic lymphoma and T cell lymphoma, B cell lymphomas, including Hodgkin's lymphoma and non-Hodgkin's lymphoma, such as low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, and Waldenstrom's Macroglobulinemia, ovarian cancer, breast cancer, endometrial cancer, colon cancer (colorectal cancer), rectal cancer, bladder cancer, lung cancer (non-small cell lung cancer, adenocarcinoma of the lung, squamous cell carcinoma of the lung), bronchial cancer, bone cancer, prostate cancer, pancreatic cancer, gastric cancer, hepatocellular carcinoma (liver cancer, hepatoma), gall bladder cancer, bile duct cancer, esophageal cancer, renal cell carcinoma, thyroid cancer, squamous cell carcinoma of the head and neck (head and neck cancer), testicular cancer, cancer of the endocrine gland, cancer of the adrenal gland, cancer of the pituitary gland, cancer of the skin, cancer of soft tissues, cancer of blood vessels, cancer of brain, cancer of nerves, cancer of eyes, cancer of meninges, cancer of oropharynx, cancer of hypopharynx, cancer of cervix, and cancer of uterus, glioblastoma, medulloblastoma, astrocytoma, glioma, meningioma, gastrinoma, neuroblastoma, melanoma, myelodysplastic syndrome, and sarcomas including, but not limited to, osteosarcoma, Ewing sarcoma, leiomyosarcoma, synovial sarcoma, alveolar soft part sarcoma, angiosarcoma, liposarcoma, fibrosarcoma, rhabdomyosarcoma, and chondrosarcoma.

"Phagocytosis" of cancer cells refers to the engulfment and digestion of such cells by macrophages, and the eventual digestion or degradation of these cancer cells and their release extracellularly, or intracellularly, to undergo further processing. Anti-CD47 monoclonal antibodies that block SIRPalpha binding to CD47, the "don't eat me" signal which is highly expressed on cancer cells as compared with normal cells, induce macrophage phagocytosis of cancer cells. SIR-Palpha binding to CD47 on cancer cells would otherwise allow these cells to escape macrophage phagocytosis.

The terms "promote", "promoting", and the like are used herein synonymously with "increase", "increasing", etc.

"Ischemia" refers to a vascular phenomenon in which a decrease in the blood supply to a bodily organ, tissue, or part is caused, for instance, by constriction or obstruction of one or more blood vessels. Ischemia sometimes results from vasoconstriction or thrombosis or embolism. Ischemia can lead to direct ischemic injury, tissue damage due to cell death caused by reduced oxygen supply. Ischemia can occur acutely, as during surgery, or from trauma to tissue incurred in accidents, injuries and war settings, or following harvest of organs intended for subsequent transplantation, for example. It can also occur sub-acutely, as found in atherosclerotic peripheral vascular disease, where progressive narrowing of blood vessels leads to inadequate blood flow to tissues and organs.

When a tissue is subjected to ischemia, a sequence of chemical events is initiated that may ultimately lead to cellular dysfunction and necrosis. If ischemia is ended by the restoration of blood flow, a second series of injurious events ensue, producing additional injury. Thus, whenever there is a transient decrease or interruption of blood flow in a subject, the resultant injury involves two components—the direct injury occurring during the ischemic interval, and the indirect or reperfusion injury that follows.

"Ischemic stroke" can be caused by several different kinds of diseases. The most common problem is narrowing of the arteries in the neck or head. This is most often caused by atherosclerosis, or gradual cholesterol deposition. If the arteries become too narrow, blood cells may collect in them and form blood clots (thrombi). These blood clots can block the artery where they are formed (thrombosis), or can dislodge and become trapped in arteries closer to the brain (embolism). Cerebral stroke can occur when atherosclerotic plaque separates away partially from the vessel wall and occludes the flow of blood through the blood vessel.

"Reperfusion" refers to restoration of blood flow to tissue that is ischemic, due to decrease in blood flow. Reperfusion is a procedure for treating infarction or other ischemia, by enabling viable ischemic tissue to recover, thus limiting further necrosis. However, reperfusion can itself further damage the ischemic tissue, causing reperfusion injury.

In addition to the immediate injury that occurs during deprivation of blood flow, "ischemic/reperfusion injury" involves tissue injury that occurs after blood flow is restored. Current understanding is that much of this injury is caused by chemical products, free radicals, and active biological agents released by the ischemic tissues.

"Nitric oxide donor, precursor, or nitric oxide generating topical agent" refers to a compound or agent that either delivers NO, or that can be converted to NO through enzymatic or non-enzymatic processes. Examples include, but are not limited to, NO gas, isosorbide dinitrite, nitrite, nitroprusside, nitroglycerin, 3-Morpholinosydnonimine (SIN-1), S-nitroso-N-acetyl-penicillamine (SNAP), Diethylenetriamine/NO (DETA/NO), S-nitrosothiols, Bidil®, and arginine.

"Soluble guanylyl cyclase (sGC)" is the receptor for nitric oxide in vascular smooth muscle. In the cardiovascular system, nitric oxide is endogenously generated by endothelial nitric oxide synthase from L-arginine, and activates soluble guanylyl cyclase in adjacent vascular smooth muscle cells to increase cGMP levels, inducing vascular relaxation. Nitric oxide binds to the normally reduced heme moiety of soluble guanylyl cyclase, and increases the formation of cGMP from GTP, leading to a decrease in intracellular calcium, vasodilation, and anti-inflammatory effects. Oxidation of the heme iron on sGC decreases responsiveness of the enzyme to nitric oxide, and promotes vasoconstriction. The nitric oxide-sGC-cGMP pathway therefore plays an important role in cardiovascular diseases. Nitrogen-containing compounds such as sodium azide, sodium nitrite, hydroxylamine, nitroglycerin, and sodium nitroprusside have been shown to stimulate sGC, causing an increase in cGMP, and vascular relaxation. In contrast to stimulators of sGC, which bind to reduced sGC, activators of sGC activate the oxidized or heme-deficient sGC enzyme that is not responsive to nitric oxide, i.e., they stimulate sGC independent of redox state. While stimulators of sGC can enhance the sensitivity of reduced sGC to nitric oxide, activators of sGC can increase sGC enzyme activity even when the enzyme is oxidized and is therefore less, or unresponsive, to nitric oxide. Thus, sGC activators are non-nitric oxide based. Note the reviews of Nossaman et al. (2012) *Critical Care Research and Practice*, Volume 2012, article 290805, and Derbyshire and Marietta (2012) *Ann. Rev. Biochem.* 81:533-559.

"An agent that activates soluble guanylyl cyclase" refers, for example, to organic nitrates (Artz et al. (2002) *J. Biol. Chem.* 277:18253-18256); protoporphyrin IX (Ignarro et al. (1982) *Proc. Natl. Acad. Sci. USA* 79:2870-2873); YC-1 (Ko et al. (1994) *Blood* 84:4226-4233); BAY 41-2272 and BAY 41-8543 (Stasch et al. (2001 *Nature* 410 (6825): 212-5), CMF-1571, and A-350619 (reviewed in Evgenov et al. (2006) *Nat. Rev. Drug. Discov.* 5:755-768); BAY 58-2667 (Cinaciguat; Frey et al. (2008) *Journal of Clinical Pharmacology* 48 (12): 1400-10); BAY 63-2521 (Riociguat; Mittendorf et al. (2009) *Chemmedchem* 4 (5): 853-65). Additional soluble guanylyl cyclase activators are disclosed in Stasch et al. (2011) *Circulation* 123:2263-2273; Derbyshire and Marietta (2012) *Ann. Rev. Biochem.* 81:533-559, and Nossaman et al. (2012) *Critical Care Research and Practice*, Volume 2012, Article ID 290805, pages 1-12.

Examples of "an agent that inhibits cyclic nucleotide phosphodiesterases" include sildenafil, tadalafil, vardenafil, udenafil, and avanafil.

The singular terms "a", "an", and "the" include plural referents unless context clearly indicates otherwise. Similarly, the word "or" is intended to include "and" unless the context clearly indicates otherwise. Hence, comprising A or B means including A, or B, or A and B.

The term "about" as used herein is a flexible word with a meaning similar to "approximately" or "nearly". The term "about" indicates that exactitude is not claimed, but rather a contemplated variation. Thus, as used herein, the term "about" means within 1 or 2 standard deviations from the specifically recited value, or ± a range of up to 20%, up to 15%, up to 10%, up to 9%, up to 8%, up to 7%, up to 6%, up to 5%, up to 4%, up to 3%, up to 2%, or up to 1% compared to the specifically recited value.

The term "comprising" as used in a claim herein is open-ended, and means that the claim must have all the features specifically recited therein, but that there is no bar on additional features that are not recited being present as well. The term "comprising" leaves the claim open for the inclusion of unspecified ingredients even in major amounts. The term "consisting essentially of" in a claim means that the invention necessarily includes the listed ingredients, and is open to unlisted ingredients that do not materially affect the basic and novel properties of the invention. A "consisting essentially of" claim occupies a middle ground between closed claims that are written in a closed "consisting of" format and fully open claims that are drafted in a "comprising' format". These terms can be used interchangeably herein if, and when, this may become necessary.

Furthermore, the use of the term "including", as well as other related forms, such as "includes" and "included", is not limiting.

CD47 and Ischemia-Reperfusion Injury (IRI)

Following periods of tissue ischemia, the initiation of blood flow causes damage referred to as "ischemia-reperfusion injury" or IRI. IRI contributes to poor outcomes in many surgical procedures where IRI occurs due to the necessity to stop blood flow for a period of time, in many forms/causes of trauma in which blood flow is interrupted and later restored by therapeutic intervention and in procedures required for organ transplantation, cardio/pulmonary bypass procedures, reattachment of severed body parts, reconstructive and cosmetic surgeries and other situations involving stopping and restarting blood flow. Ischemia itself causes many physiological changes that, by themselves would eventually lead to cell and tissue necrosis and death. Reperfusion poses its own set of damaging events including generation of reactive oxygen species, thrombosis, inflammation and cytokine mediated damage. The pathways that are limited by the TSP1-CD47 system are precisely those that would be of most benefit in combating the damage of IRI. Thus, blocking the TSP1-CD47 pathway, as with the antibody compounds disclosed herein, will provide more robust functioning of these endogenous protective pathways.

The humanized anti-CD47 antibodies, antigen binding fragments thereof, and competing antibodies and antigen binding fragments thereof, of the present disclosure can be used in the methods disclosed in U.S. Pat. No. 8,236,313, the contents of which are herein incorporated by reference in their entirety.

CD47 and Cancer

CD47 has been identified as a novel therapeutic target in hematologic cancers (Majeti et al. (2009) *Cell* 138(2):286-99), as well as in solid tumors such as colon, prostate, breast, and brain cancers (Willingham et al. (2012) *Proc Natl Acad Sci USA* 109(17):6662-7). Many human cancers up-regulate cell surface expression of CD47, and those expressing the highest levels of CD47 are the most aggressive and the most lethal for patients. Increased CD47 expression is thought to protect cancer cells from phagocytic clearance by sending a "don't eat me" signal to macrophages via SIRPalpha, an inhibitory receptor that prevents phagocytosis of CD47-bearing cells (Jaiswal et al. (2009) *Cell* 138(2):271-851; Chao et al. (2010) *Science Translational Medicine* 2(63): 63ra94). Thus, the increase of CD47 expression by many cancers provides them with a cloak of "selfness" that slows their phagocytic clearance by macrophages and dendritic cells. Anti-CD47 mAbs (CD47mAbs) that block the CD47/SIRPalpha interaction enhance phagocytosis of cancer cells in vitro and contribute to control of tumor burden in published human to mouse xenograft tumor models.

Antibodies that block CD47 and prevent its binding to SIRPalpha ("blocking mAbs") have shown efficacy in human tumor in mouse (xenograft) tumor models. Such blocking CD47mAbs exhibiting this property promote (increase) the phagocytosis of cancer cells by macrophages, which can reduce tumor burden (Majeti et al. (2009) *Cell* 138(2):286-99) and may ultimately lead to generation of an adaptive immune response to the tumor (Tseng et al. (2013) *Proc Natl Acad Sci USA*. 110(27):11103-8).

Therapeutic Indications

IRI-Related and Autoimmune/Inflammatory Conditions

Administration of a CD47 mAb or antigen binding fragment thereof disclosed herein can be used to treat a number of diseases and conditions in which IRI is a contributing feature, and to treat various autoimmune and inflammatory diseases. These include: organ transplantation in which a mAb or antigen binding fragment thereof of the present disclosure is administered to the donor prior to organ harvest, to the harvested donor organ, to the organ preservation solution, to the recipient patient, or to any combination thereof; skin grafting; surgical resections or tissue reconstruction in which such mAb or fragment is administered either locally by injection to the affected tissue or parenterally to the patient; reattachment of body parts; treatment of traumatic injury; pulmonary hypertension; sickle cell disease (crisis); myocardial infarction; stroke; surgically-induced ischemia; acute kidney disease/kidney failure; any other condition in which IRI occurs and contributes to the pathogenesis of disease; and autoimmune/inflammatory diseases, including arthritis, multiple sclerosis, psoriasis, Crohn's disease, inflammatory bowel disease, lupus, Grave's disease and Hashimoto's thyroiditis, and ankylosing spondylitis.

CD47 mAbs and antigen binding fragments thereof of the present disclosure can also be used to increase tissue perfusion in a subject in need of such treatment. Such subjects can be identified by diagnostic procedures indicating a need for increased tissue perfusion. In addition, the need for increased tissue perfusion may arise because the subject has had, is having, or will have, a surgery selected from integument surgery, soft tissue surgery, composite tissue surgery, skin graft surgery, resection of a solid organ, organ transplant surgery, or reattachment or an appendage or other body part.

Susceptible Cancers

Presently disclosed mAbs and antigen binding fragments thereof effective as cancer therapeutics can be administered to patients, preferably parenterally, with susceptible hematologic cancers and solid tumors including, but not limited to, leukemias, including systemic mastocytosis, acute lymphocytic (lymphoblastic) leukemia (ALL), T cell-ALL, acute myeloid leukemia (AML), myelogenous leukemia, chronic lymphocytic leukemia (CLL), multiple myeloma (MM), chronic myeloid leukemia (CML), myeloproliferative disorder/neoplasm, myelodysplastic syndrome, monocytic cell leukemia, and plasma cell leukemia; lymphomas, including histiocytic lymphoma and T cell lymphoma, B cell lymphomas, including Hodgkin's lymphoma and non-Hodgkin's lymphoma, such as low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, and Waldenstrom's Macroglobulinemia, ovarian cancer, breast cancer, endometrial cancer, colon cancer (colorectal cancer), rectal cancer, bladder cancer, lung cancer (non-small cell lung cancer, adenocarcinoma of the lung, squamous cell carcinoma of the lung), bronchial cancer, bone cancer, prostate cancer, pancreatic cancer, gastric cancer, hepatocellular carcinoma (liver cancer, hepatoma), gall bladder cancer, bile duct cancer, esophageal cancer, renal cell carcinoma, thyroid cancer, squamous cell carcinoma of the head and neck (head and neck cancer), testicular cancer, cancer of the endocrine gland, cancer of the adrenal gland, cancer of the pituitary gland, cancer of the skin, cancer of soft tissues, cancer of blood vessels, cancer of brain, cancer of nerves, cancer of eyes, cancer of meninges, cancer of oropharynx, cancer of hypopharynx, cancer of cervix, and cancer of uterus, glioblastoma, medulloblastoma, astrocytoma, glioma, meningioma, gastrinoma, neuroblastoma, melanoma, myelodysplastic syndrome, and sarcomas including, but not limited to, osteosarcoma, Ewing sarcoma, leiomyosarcoma, synovial sarcoma, alveolar soft part sarcoma, angiosarcoma, liposarcoma, fibrosarcoma, rhabdomyosarcoma, and chondrosarcoma.

In certain cases, it may be advantageous to administer the mAb directly to the cancer by injection into the tumor.

Since CD47 expression is up-regulated on many cancers, it may also be desirable to use one or more of the disclosed mAbs as imaging and diagnostic agents when labeled with radioactive or other tracers known to those skilled in the art of in vivo imaging of cancers/tumors.

The following examples describe various aspects of the present disclosure, but should not be considered as limiting the disclosure only to these particularly disclosed embodiments. The materials and methods employed in these examples are for illustrative purposes, and are not intended to limit the practice of the present disclosure thereto. Any materials and methods similar or equivalent to those described herein as would be apparent to one of ordinary skill in the art can be used in the practice or testing of the present compounds and methods.

Example 1

Production of CD47 Antibodies

The humanized antibodies disclosed herein comprise frameworks derived from the human genome. The collection covers the diversity found in the human germ line sequences, yielding functionally expressed antibodies in vivo. The complementarity determining regions (CDRs) in the light and heavy chain variable regions of the target chimeric, non-human antibody VxP037-01LC/VxP037-01HC (SEQ ID NO:7/SEQ ID NO:57) are determined following commonly accepted rules disclosed, for example, in "Protein Sequence and Structure Analysis of Antibody Variable Domains", In: *Antibody Engineering Lab Manual*, eds. S. Duebel and R. Kontermann, Springer-Verlag, Heidelberg (2001)). The CDR fragments are synthesized and combined with pools of frameworks to generate full length variable domains. The humanized variable domains are then combined with a secretion signal and human kappa and human IgG1 constant domains, and cloned into a mammalian expression system (e.g., OptiCHO System, Life Technologies, Carlsbad, Calif.) to generate a library of humanized IgG1, IgG2, and IgG4 variants. An aliquot of the library is sequenced to ensure high diversity and integrity of the reading frames of the individual clones. Aliquots of the humanized variant library are then re-arrayed as single clones into 96 well plates, mini-prepped (e.g., 96 well Miniprep Kit, Qiagen Hilden, Germany), and transfected into CHO cells (Lipofectamine transfection protocol as recommended by Life Technologies, Carlsbad, Calif.). Transfected CHO cells are grown in DMEM medium with 10% 1-BS (both from Life Technologies, Carlsbad, Calif.) at 37° C. under 5% $CO_2$. The humanized variants are expressed as full length IgG1 molecules, and secreted into the medium.

The cell culture supernatant containing the humanized IgG variants is then screened for binding to the target antigen, CD47. In parallel, the concentration of each variant is determined in order to calculate specific activity for each clone. The specific activity of each clone is compared to the specific activity of chimeric clone VxP037-01LC-Pro/VxP037-01HC-Pro (SEQ ID NO:107/SEQ ID NO:109) expressed on the same plate, and normalized. Top hits from each plate are re-arrayed and re-screened for confirmation. The final candidates are selected by specific activity, functional activity, expression level, and sequence diversity, as well as other criteria, as described below.

A non-glycosylated version (IgG1-N297Q) was created by site directed mutagenesis of heavy chain position 297 to change the asparagine to glutamine (pVxP037-01-HC-IgG1 N297Q-Pro; SEQ ID NO:111). IgG2, IgG4-S228P and IgG4-2SS8P-L235E isotypes were constructed by cloning the heavy chain variable domain in frame with the human IgG2 and IgG4-S228P constant domains (pVxK7b-037-hum01-HC-IgG2-Pro, SEQ ID NO:112 or pVxK7b-037-hum01-HC_IgG4 S228P-Pro, SEQ ID NO:113, pVxK7b-037-hum01-HC-IgG4 S228P L235E-Pro, SEQ ID NO: 122).

Example 2

CD47 Antibody Sequences

The amino acid sequences of the light chain and heavy chain variable regions, the complete light and heavy chains, and the respective encoding nucleotide sequences of the foregoing, of the present human engineered antibodies are listed below in the section entitled "Amino Acid and Nucleic Acid Sequences."

Also included in this list are complete light chain sequences (SEQ ID NO:107/SEQ ID NO:108), complete heavy chain amino acid and respectively encoding nucleotide sequences of humanized IgG1 (SEQ ID NO:109/SEQ ID NO:110), complete heavy chain amino acid and respectively encoding nucleotide sequences of humanized IgG1 with a N→Q mutation at amino acid position 297 (SEQ ID NO:111/SEQ ID NO:114), IgG2 (SEQ ID NO:112/SEQ ID NO:115), and IgG4 (SEQ ID NO:113/SEQ ID NO:116) antibodies.

SEQ ID NO:117 shows the amino acid sequence of framework 4+the light chain constant domain amino acid sequence of chimeric complete light chain amino acid sequence SEQ ID NO:107.

SEQ ID NOs: 118, 119, 120, 121, and 124 show the amino acid sequences of framework 4+the heavy chain constant domain amino acid sequences of complete heavy chain amino acid sequences SEQ ID NOs:109, 111, 112, 113, and 122 respectively.

All the light chain variable regions SEQ ID NOs: 7-31 can further comprise SEQ ID NO:117, and all the heavy chain amino acid sequences SEQ ID NOs:57-81 can further comprise any of SEQ ID NOs:118, 119, 120, 121, and 124 thereby describing complete antibody sequences encompassed by this disclosure.

The light chain and heavy chain CDR amino acid sequences are shown in Tables 1 and 2, respectively.

TABLE 1

Light Chain CDRs.

| CDR1 | CDR2 | CDR3 |
|---|---|---|
| RSSQSLVHSNGNTYLH (SEQ ID NO: 1) | KVSYRFS (SEQ ID NO: 2) | SQNTHVPRT (SEQ ID NO: 3) |

TABLE 2

Heavy Chain CDRs.

| CDR1 | CDR2 | CDR3 |
|---|---|---|
| GYTFTNYYVF (SEQ ID NO: 4) | DINPVNGDTNFNEKFKN (SEQ ID NO: 5) | GGYTMDY (SEQ ID NO: 6) |

Example 3

Binding of Antibodies to CD47 of Different Species

Cross species reactivity of humanized antibodies of the present disclosure is determined using freshly isolated red blood cells (RBCs), which display CD47 on their surface, from human, mouse, rat, pig, cynomolgus monkey, and dog according to the methods disclosed in Kamel et al. (2010) *Blood. Transfus.* 8(4):260-266.

Supernatants containing secreted antibodies are collected from CHO cells transiently transfected with plasmids encoding antibody clones and used as collected, or antibodies are further purified from the supernatants using standard methods. Transfected CHO cells are grown in F-12 medium containing 10% heat inactivated fetal bovine serum (Bio-West; S01520). Antibody concentration in the supernatants is determined utilizing a quantitative ELISA. ELISA plates are coated with a donkey anti-human FC antibody (Sigma; Catalog #12136) at 10 µg/ml overnight at 4° C. (Promega; Catalog # W4031). Plates are washed with PBS, and then blocked with casein blocking solution (ThermoScientific; Catalog #37532) for 60 minutes at room temperature. Plates are again washed with PBS, tissue culture supernatants are added, and the plates are incubated for 60 minutes at room temperature. Plates are then washed three times with PBS and incubated with peroxidase-conjugated goat anti-human IgG (Jackson Immunoresearch Labs; Catalog #109-035-003) for 60 minutes at room temperature. Plates are washed three times with PBS, and the peroxidase substrate 3,3'-5, 5'-tetramethylbenzidine is added (Sigma; Catalog # T4444). Reactions are terminated by the addition of HCl to 0.7N, and absorbance at 450 nM is determined using a Tecan model Infinite M200 plate reader.

RBCs are incubated for 60 minutes on ice with tissue culture supernatants containing the secreted humanized antibodies at a concentration of 10 ng/ml in a solution of phosphate buffered saline, pH 7.2, 2.5 mM EDTA (PBS+E), or with various concentrations of purified antibodies. Cells are then washed with cold PBS+E, and incubated for an additional hour on ice with FITC labeled donkey anti-human antibody (Jackson Immuno Research Labs, West Grove, Pa.; Catalogue #709-096-149) in PBS+E. Cells are then washed with PBS+E, and antibody binding is analyzed using a BD FACSAria Cell Sorter (Becton Dickinson) or a C6 Accuri Flow Cytometer (Becton Dickinson). Antibody binding is quantitated by comparison of mean fluorescence values relative to that of chimeric antibody >VxP037-01LC (SEQ ID NO:7))/>VxP037-01HC (SEQ ID NO:57). The mean fluorescence value for each antibody is divided by the mean fluorescence value for the chimeric antibody.

The results obtained from the supernatants are shown in Table 3, where "Chimera" represents chimeric antibody >VxP037-01LC (SEQ ID NO:7))/>VxP037-01HC (SEQ ID NO:57; complete sequences VxP037-01LC-Pro/ VxP037-01HC-Pro (SEQ ID NO:107/SEQ ID NO:109)), Clone 1 represents >pVxK7b-037-hum01-LC (SEQ ID NO:8)/>pVxK7b-037-hum01-HC (SEQ ID NO:58), Clone 2 represents >pVxK7b-037-hum02-LC (SEQ ID NO:9)/>p-VxK7b-037-hum02-HC (SEQ ID NO:59), and so on similarly for remaining clones 3-24. Each antibody also contains a light chain constant domain (SEQ ID:117) and a heavy chain constant domain selected from among SEQ ID NO:118, SEQ ID NO:119, SEQ ID NO:120, and SEQ ID NO:121.

TABLE 3

Binding of Humanized Antibodies to CD47 on the Surface of Red Blood Cells of Different Mammalian Species.

| Clone No. | Human | Mouse | Rat | Pig | Dog |
|---|---|---|---|---|---|
| Chimera | 1.0 | 1.0 | 1.0 | 1.0 | 1.0 |
| 1 | 1.1 | 1.7 | 2.7 | 1.3 | 1.0 |
| 2 | 1.0 | 1.2 | 2.6 | 1.2 | 1.0 |
| 3 | 0.7 | 0.9 | 1.7 | 0.9 | 0.9 |
| 4 | 0.6 | 0.6 | 1.0 | 0.6 | 0.6 |
| 5 | 1.0 | 1.0 | 2.2 | 1.2 | 1.1 |
| 6 | 0.9 | 1.2 | 2.1 | 1.1 | 1.1 |
| 7 | 0.5 | 0.4 | 0.8 | 0.9 | 0.8 |
| 8 | 0.7 | 0.7 | 1.2 | 0.8 | 0.8 |
| 9 | 1.2 | 1.4 | 3.7 | 1.6 | 1.0 |
| 10 | 1.1 | 1.2 | 2.9 | 1.5 | 1.1 |
| 11 | 0.8 | 0.7 | 1.2 | 1.2 | 0.8 |
| 12 | 0.8 | 0.6 | 1.3 | 1.4 | 0.9 |
| 13 | 1.2 | 1.3 | 3.1 | 1.4 | 1.0 |
| 14 | 1.1 | 1.5 | 3.2 | 1.4 | 1.3 |
| 15 | 1.0 | 1.3 | 2.4 | 1.2 | 1.1 |
| 16 | 0.9 | 1.0 | 2.1 | 1.1 | 1.1 |
| 17 | 0.8 | 0.9 | 2.1 | 1.3 | 1.3 |
| 18 | 1.0 | 1.3 | 2.2 | 1.2 | 1.5 |
| 19 | 0.7 | 1.0 | 2.6 | 1.3 | 1.2 |
| 20 | 1.3 | 1.5 | 1.9 | 1.7 | 1.1 |
| 21 | 1.2 | 1.2 | 2.8 | 1.4 | 1.1 |
| 22 | 1.1 | 1.2 | 2.8 | 1.4 | 1.0 |
| 23 | 1.2 | 1.4 | 3.3 | 1.7 | 1.1 |
| 24 | 0.8 | 0.7 | 1.2 | 1.1 | 1.0 |

Figure 9:
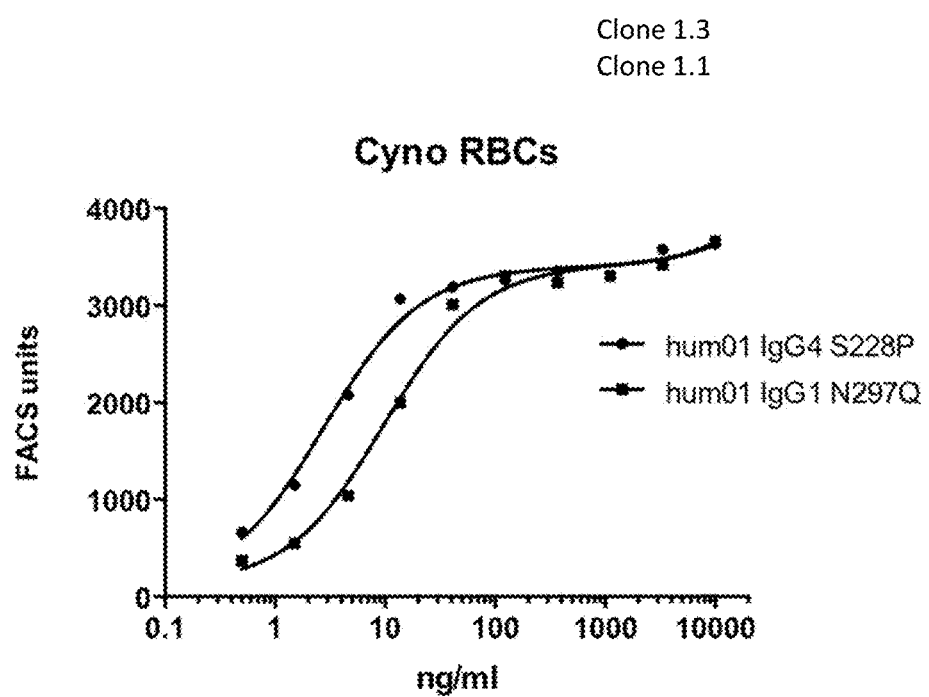
FIG. 9 shows binding of Clone 1.1 (IgG1 N297Q) and clone 1.3 (IgG4 S228P) to cynomolgus monkey RBCs by FACS (described previously). Both mAbs exhibited similar binding affinities to cynomolgus RBCs.

FIG. 1 shows cross species binding curves to human, mouse, rat, and porcine RBCs (panels A, B, C, and D, respectively, generated using various concentrations of purified antibodies from clones Cl 1, Cl 1.1, Cl 13, and Cl 13.1. Clones Cl 1 and Cl 13 are as described above in Table 3. Clones Cl 1.1 and Cl 13.1 are Fc mutants of clones Cl 1 and Cl 13, respectively, modified to reduce effector function. Each has an Asn297→Gln (N297Q) mutation in the Fc domain (Sazinsky et al. (2008) *PNAS* 105(51):20167-20172). All of these clones exhibit concentration-dependent binding to all of the species of RBCs tested. These clones also bind to cynomolgus monkey RBCs as shown in FIG. 9 by the concentration-dependent binding of Clones 1.1 (IgG 1 N297Q mutation) and 1.3 (IgG4 S228P mutation).

Table 4 shows the apparent affinities of these clones to human RBCs determined by non-linear fits (Prism Graph-Pad software) of the median fluorescence intensities at various antibody concentrations. Clones 1, 1.1, 13, and 13.1 all have apparent Kd values in the low nanomolar range.

TABLE 4

Binding Affinity of Humanized Antibodies to CD47 on Human RBCs.

|  | Clone 1 | Clone 1.1 | Clone 13 | Clone 13.1 |
|---|---|---|---|---|
| Kd (ng/ml) | 226.2 | 307.1 | 86.4 | 182.9 |
| Kd (apparent) nM | 1.51 | 2.04 | 0.58 | 1.21 |

Binding activities of humanized clones 1, 3, 5, 8, 13, 14, 17, 20 and 23, either IgG1 N297Q (Clone 1.1, Clone 13.1, etc.) or an IgG4 S228P L235E (Clones 1.2, etc.), to human and mouse CD47 were determined using cell-based ELISA assays with either human OV10 or mouse 4T1 cells expressing cell surface CD47. OV10 cells are grown in IMDM medium containing 10% heat inactivated fetal bovine serum (BioWest; S01520) and 4T1 cells are grown in RMPI medium containing 10% heat inactivated fetal bovine serum (BioWest; S01520). One day before assay, $3 \times 10^4$ cells are plated in 96 well cell bind plates (Corning #3300, VWR #66025-626) so that they are 95-100% confluent at the time of assay. Cells are washed and various concentrations of purified antibodies added in either IMDM or RPMI at 37° C. for 1 hour in 95% $O_2$/5% $CO_2$. Cells are then washed with media and incubated for an additional hour at 37° C. with HRP labeled secondary anti-human antibody (Promega) diluted 1/2500 in media. Cells are washed three times with PBS, and the peroxidase substrate 3,3',5,5'-tetramethylbenzidine is added (Sigma; Catalog # T4444). Reactions are terminated by the addition of HCl to 0.7N, and absorbance at 450 nM is determined using a Tecan model Infinite M200 plate reader. The apparent binding affinities of these clones to human and mouse cells is determined by non-linear fits (Prism GraphPad software). As shown in Table 5, all of the humanized clones bind to both human and mouse tumor cells with apparent affinities in the picomolar range. Agglutination of human RBCs is assessed following incubation of human RBCs with various concentrations of humanized blocking only clones. Blood is diluted (1:50) and washed 3 times with PBS/EDTA/BSA. RBCs are added to U-bottomed 96 well plates with equal volumes of the antibodies (75 µl) and incubated for 3 hrs at 37° C. and overnight at 4° C. As shown in Table 3, while all clones bind similarly to human RBCs, they exhibit different agglutination activities. Clones 3.1, 3.2, 13.1, 13.2, 20.1, and 20.2 cause agglutination of human RBCs, whereas Clones 1.1 (IgG1 N297Q), 1.2 (IgG4 S228P L235E), 5.1, 5.2, 8.1, 8.2, 14.1, 14.2, 17.1, 17.2, 23.1 and 23.2 do not.

Example 4

Antibodies to CD47 Enhance Phagocytosis

To assess the effect of humanized CD47 mAbs on phagocytosis of tumor cells by marcrophages in vitro the following method is employed using flow cytometry, essentially as described by Willingham et al. (2012) *Proc Nail Acad Sci USA* 109(17):6662-7 and Tseng et al. (2013) *Proc Nail Acad Sci USA* 110(27):11103-8.

Human derived macrophages are derived from leukapheresis of healthy human peripheral blood incubated in human AB serum (Sigma Aldrich) for 24 hours in culture. After 24 hours, all non-adherent cells are removed and the remaining adherent macrophages are incubated in RPMI medium (10% fetal bovine serum (FBS; Hyclone) and antibiotics) for two weeks. In additional experiments, human macrophages are derived from human peripheral blood and incubated in AIM-V media (Life Technologies) for 7-10 days. For the in vitro phagocytosis assay, macrophages are re-plated at a concentration of $5 \times 10^4$ cells per well in 1 ml of RPMI media in a 24 well plate and allowed to adhere for 24 hours. Once the effector macrophages have adhered to the culture dish, the target cancer cells (Jurkat) are labeled with 1 µM 5(6)-Carboxyfluorescein diacetate N-succinimidyl ester (CFSE; Sigma Aldrich) and added to the macrophage cultures at a concentration of $2 \times 10^5$ cells in 1 ml of RPMI media (4:1 target to effector ratio). CD47mAbs (1-10 µg/ml) are added immediately upon mixture of target and effector cells and allowed to incubate at 37° C. for 2-3 hours. After 2-3 hours, all non-phagocytosed cells are removed and the remaining cells are washed three times with phosphate

TABLE 5

Humanized Blocking-Only mAb. CD47 Binding Affinity and Red Blood Cell Hemagglutination.

| | | Human OV10-ELISA Kd [pM] | Mouse 4T1_ELISA Kd [pM] | Hemagglutination Human RBC |
|---|---|---|---|---|
| hum01 IgG1 N297Q | Clone 1.1 | 147.7 | 131.6 | No |
| hum01 IgG4 S228P L235E | Clone 1.2 | 150.5 | 175.5 | No |
| hum13 IgG1 N297Q | Clone 13.1 | 88.6 | 86.7 | Yes |
| hum13 IgG4 S228P L235E | Clone 13.2 | 107.8 | 177.8 | Yes |
| hum03 IgG1 N297Q | Clone 3.1 | 115.3 | 131.7 | Yes |
| hum03 IgG4 S228P L235E | Clone 3.2 | 129.3 | 202 | Yes |
| hum05 IgG1 N297Q | Clone 5.1 | 124.7 | 112.4 | No |
| hum05 IgG4 S228P L235E | Clone 5.2 | 107.5 | 171.8 | No |
| hum08 IgG1 N297Q | Clone 8.1 | 114.9 | 205 | No |
| hum08 IgG4 S228P L235E | Clone 8.2 | 121.4 | 94.9 | No |
| hum14 IgG1 N297Q | Clone 14.1 | 96.2 | 94.9 | No |
| hum14 IgG4 S228P L235E | Clone 14.2 | 89.9 | 101.8 | No |
| hum17 IgG1 N297Q | Clone 17.1 | 85.5 | 197.9 | No |
| hum17 IgG4 S228P L235E | Clone 17.2 | 120.9 | 147 | No |
| hum20 IgG1 N297Q | Clone 20.1 | 120.9 | 236.9 | Yes |
| hum20 IgG4 S228P L235E | Clone 20.2 | 113.5 | 354 | Yes |
| hum23 IgG1 N297Q | Clone 23.1 | 99.6 | 92.2 | No |
| hum23 IgG4 S228P L235E | Clone 23.2 | 194.6 | 192.2 | No |

These data demonstrate that all of the humanized CD47 mAb clones disclosed herein bind to CD47 of a variety of different mammalian species in addition to human CD47, confirming the useful cross-species reactivity of these antibodies and that certain of these antibodies do not cause agglutination of human RBCs buffered saline (PBS; Sigma Aldrich). Cells are trypsinized, collected into microcentrifuge tubes and incubated in 100 ng of allophycocyanin (APC) labeled CD14 antibodies (BD biosciences) for 30 minutes. Cells are washed once and analyzed by flow cytometry (Accuri C6; BD biosciences) for the percentage of CD14 positive cells that are also CFSE positive indicating complete phagocytosis.

Figure 2:
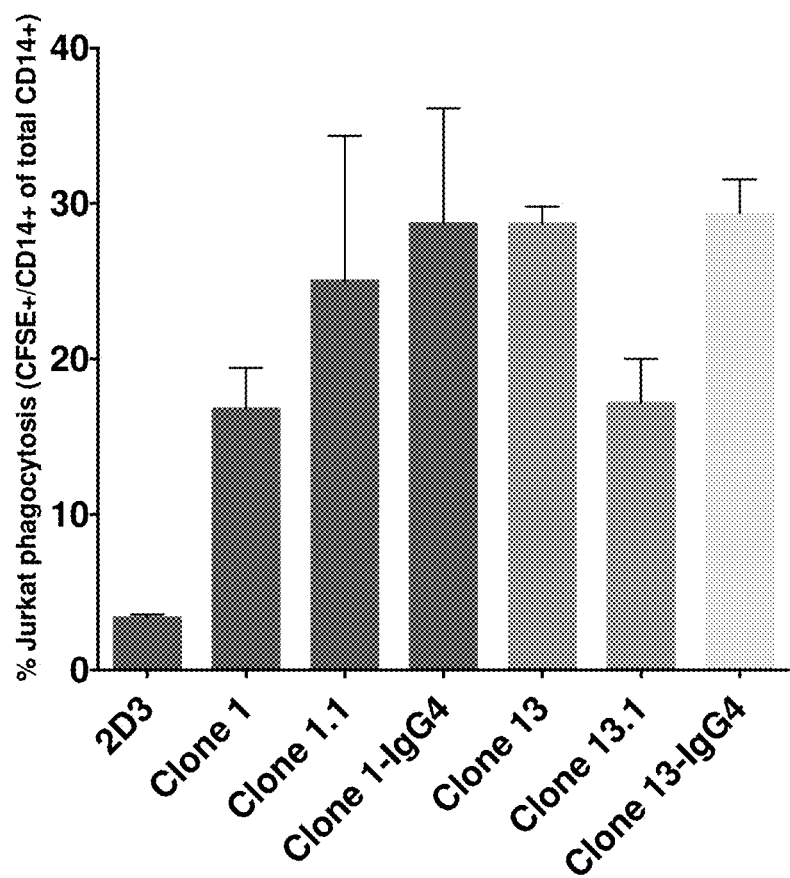
FIG. 2 shows CD47 mAb-mediated phagocytosis of Jurkat cells. Target (Jurkat) and effector (human macrophages) are combined at a target effector ratio of 4:1, 10 µg/ml of the CD47 mAbs added and incubated for 2 hours at 37 C. Percent phagocytosis is determined by flow cytometry as the percentage of $CFSE^+/CD14^+$ cells from the total $CD14^+$ population. All of the clones, Clone 1, Clone 1.1, Clone 1-IgG4 (Clone 1 IgG4 S228P, Clone 1.3), Clone 13, Clone 13.1, and Clone 13-IgG4 (Clone 13 IgG4 S228P, Clone 13.3), except the negative control mAb 2D3, increase phagocytosis of the Jurkat cells by the macrophages irrespective of their affinity to activate Fc receptors.
Figure 10:
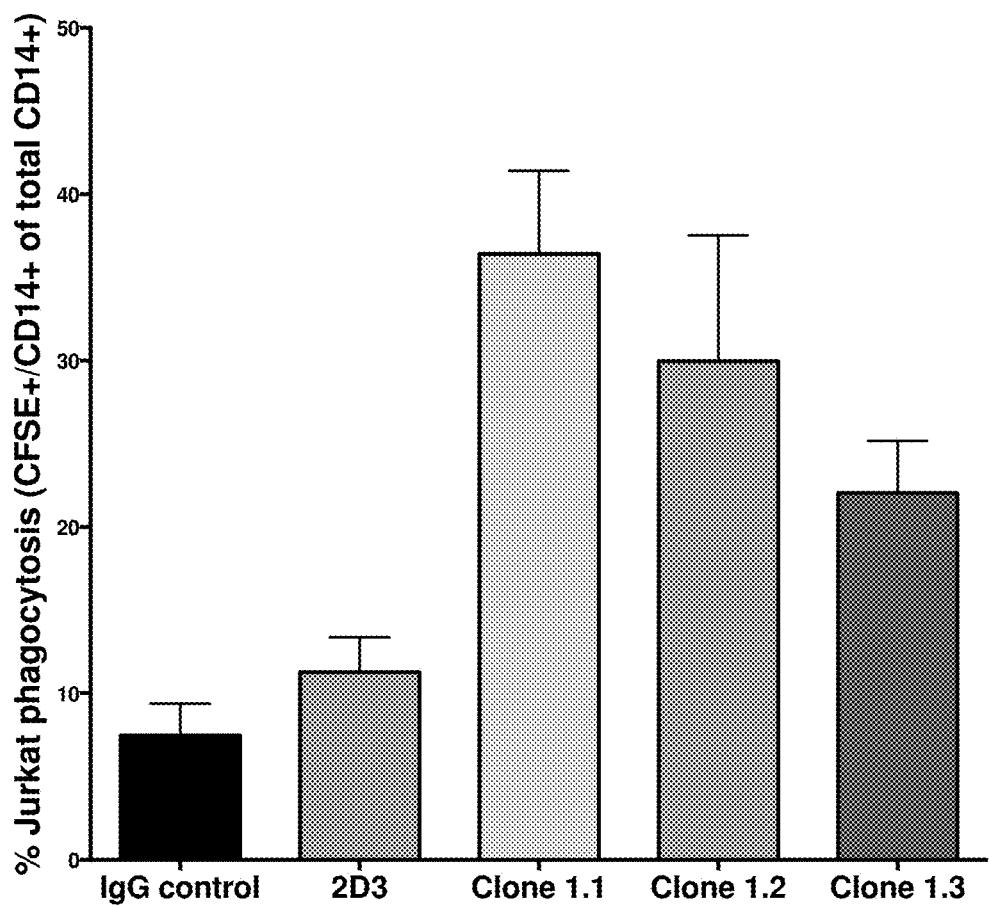
FIG. 10 shows that Clones 1.1, 1.2 (IgG4 with mutations of residue S228 to P and of residue L235 to E to reduce Fc effector function, and 1.3 (IgG4 with mutation of residue S228 to P) increase phagocytosis of Jurkat cells by human macrophages while control IgG or the mouse 2D3 antibody that binds to CD47, but does not block the CD47/SIRPalpha interaction, do not.

As shown in FIG. 2, both Clone 1 and Clone 13 humanized IgG1 mAbs increase phagocytosis of Jurkat cells by human macrophages grown in serum. Clones 1.1 and Clone 13.1 are identical to Clones 1 and 13 except for a mutation of residue N297 to Q that reduces the affinity of the IgG1 molecule to the Fc receptor. The IgG4 versions of Clone 1 and Clone 13 with a mutation of residue S228 to P to reduce chain strand exchange (also designated as Clones 1.3 and 13.3) also increase phagocytosis of Jurkat cells. The IgG4 isotype also has reduced affinity for activating Fc receptors. As shown in FIG. 10, the IgG4 version of Clone 1 with a mutation of residue S228 to P and a further mutation of residue L235 to E to reduce Fc effector function (designated as Clone 1.2) also increases phagocytosis of Jurkat cells.

Therefore, all isotypes/mutants of Clone 1 and 13 enhance phagocytosis via blocking the CD47/SIRPalpha interaction.

Example 5

Antibodies to CD47 Regulate Nitric Oxide Signaling

The purpose of this experiment is to demonstrate that humanized antibody clones of the present disclosure exhibit the ability to reverse TSP1-mediated inhibition of NO-stimulated cGMP synthesis as, for example, described previously using mouse monoclonal antibodies to CD47 as disclosed by Isenberg et al. (2006) *J. Biol. Chem.* 281: 26069-80.

The method employed to measure cGMP is as described by the manufacturer (CatchPoint Cyclic-GMP Fluorescent Assay Kit, Molecular Devices, Sunnyvale, Calif.). Jurkat JE6.1 cells (ATCC, Manassas, Va.; Catalog # TIB-152) are used as these cells retain the NO-cGMP signaling pathway when grown in culture and exhibit a robust and reproducible inhibitory response to TSP1 ligation of CD47. Cells are grown in Iscove's modified Dulbeccco's medium containing 5% (v/v) heat inactivated fetal bovine serum (BioWest; Catalogue # S01520), 100 units/mL penicillin, 100 µg mL streptomycin (Sigma; Catalogue # P4222) at densities less than $1 \times 10^6$ cells/mL. For the cGMP assay, cells are plated in 96 well tissue culture plates at a density of $1 \times 10^5$ cells/ml in Iscoves modified Dulbecco's medium containing 5% (v/v) heat inactivated fetal bovine serum (BioWest; Catalog # S01520), 100 units/mL penicillin, 100 µg/mL streptomycin (Sigma; # P4222) for 24 hours and then transferred to serum free medium overnight.

The humanized antibodies as disclosed herein, purified from transient transfections in CHO cells as described above in Example 3, as well as the control chimeric antibody, are then added at a final concentration of 20 ng/ml, followed 15 minutes later by 0 or 1 µg/ml human TSP1 (Athens Research and Technology, Athens, Ga., Catalogue #16-20-201319). After an additional 15 minutes, the NO donor, diethylamine (DEA) NONOate (Cayman Chemical, Ann Arbor, Mich., Catalog #82100), is added to half the wells at a final concentration of 1 µM. Five minutes later, the cells are lysed with buffer supplied in the cGMP kit, and aliquots of each well are assayed for cGMP content.

Figure 3:
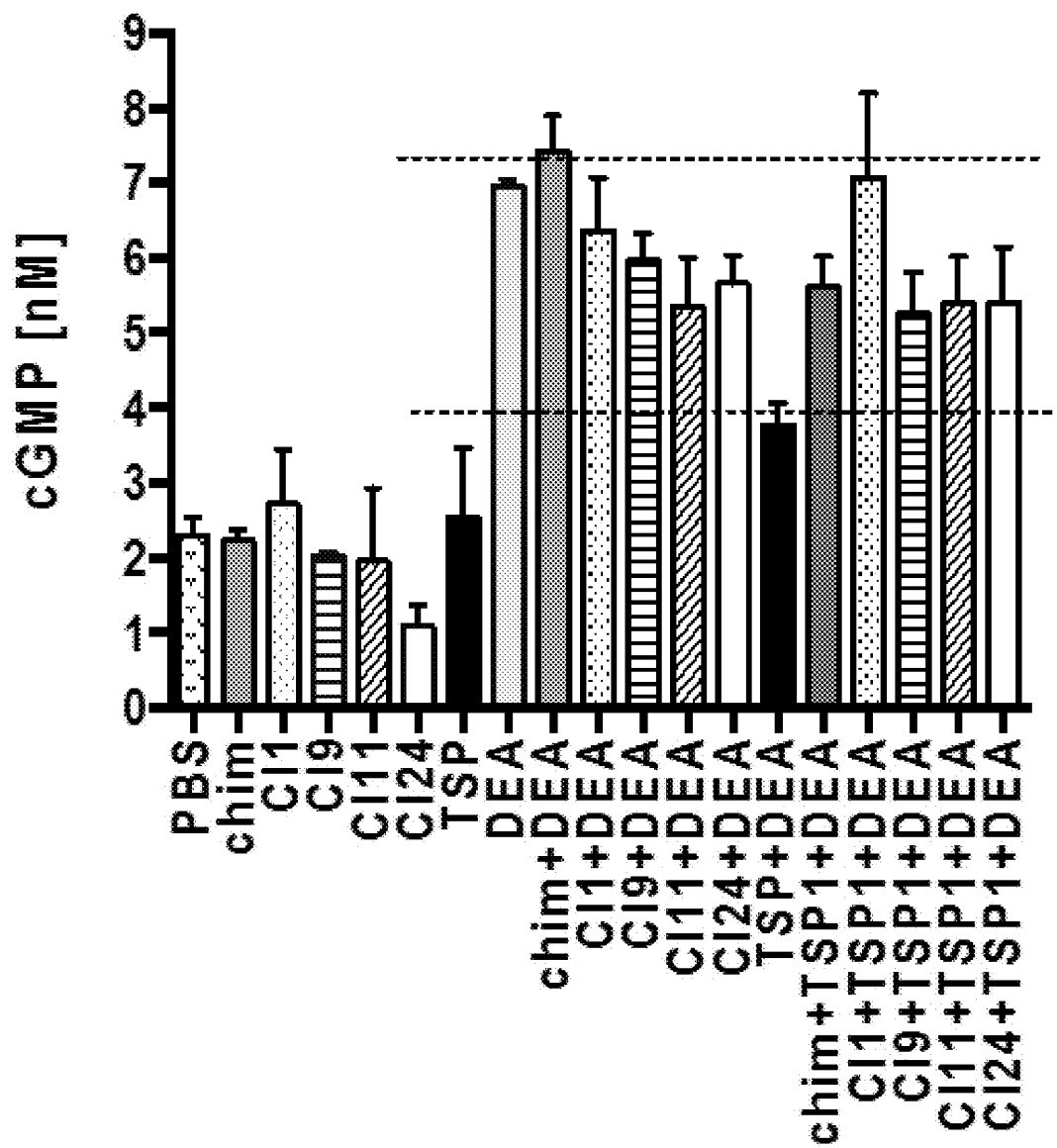
FIG. 3 shows reversal of TSP1 inhibition of NO-stimulated cGMP production by humanized antibodies of the present disclosure. As described in Example 5, Jurkat JE6.1 cells are incubated overnight in serum-free medium and then incubated with humanized antibodies of the present disclosure or the control chimeric mAb, and with or without TSP1, followed by treatment with or without a NO donor. Cells are lysed 5 minutes later and cGMP is measured. None of the present humanized antibody clones tested, or the control chimeric mAb, has an effect on basal cGMP levels. The control chimeric antibody reverses the TSP1 inhibition, as do humanized Clones 1, 9, 11, and 24 disclosed herein (Cl 1; Cl 9; Cl 11; Cl 24, respectively). PBS: phosphate buffered saline; TSP or TSP1: thrombospondin-1; DEA: diethylamine NONOate; chim: chimeric antibody>VxP037-01LC (SEQ ID NO:7))/>VxP037-01HC (SEQ ID NO:57).
Figure 4:
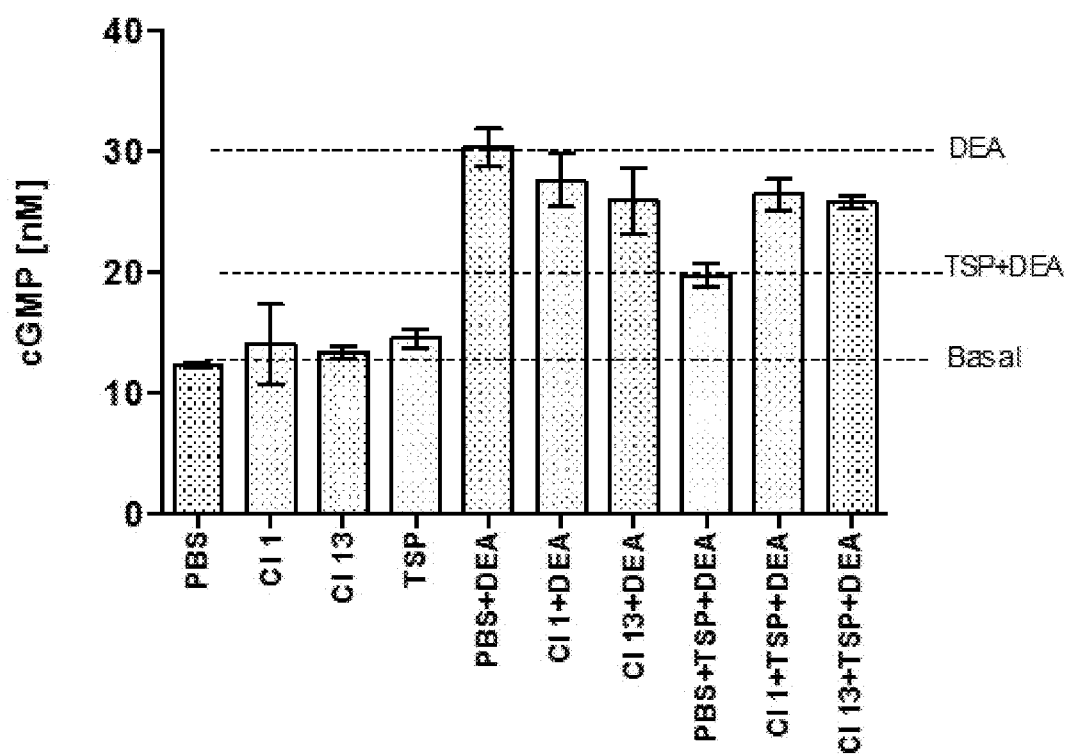
FIG. 4 shows reversal of TSP1 inhibition of NO-stimulated cGMP production by humanized antibodies of the present disclosure. As described in Example 5, Jurkat JE6.1 cells are incubated overnight in serum-free medium and then incubated with purified humanized Clone 1 and 13 antibodies, or PBS as the control, and with or without TSP1, followed by treatment with or without a NO donor. Cells are lysed 5 minutes later and cGMP is measured. The humanized antibody clones or PBS have no effect on basal cGMP levels. The humanized Clones 1 and 13 reverse the TSP1 inhibition, while PBS has no effect. PBS: phosphate buffered saline; TSP or TSP1: thrombospondin-1; DEA: diethylamine NONOate.

As shown in FIGS. 3 and 4, none of the present humanized antibody clones tested, or the chimeric control mAb, has an effect on basal cGMP levels. As expected, the chimeric antibody VxP037-01LC-Pro/VxP037-01HC-Pro (SEQ ID NO:107/SEQ ID NO:109)) reverses the TSP1 inhibition.

Humanized Clones 1, 9, 11, 13, and 24 of the present disclosure also significantly reverse TSP1 inhibition, demonstrating that they have the ability to increase NO signaling (FIGS. 3 and 4), suggesting their utility in protecting the cardiovascular system against stresses including, but not limited to, those resulting from wounding, inflammation, hypertension, metabolic syndrome, ischemia, and ischemia-reperfusion injury (IRI).

Example 6

Reduction of Ischemia-Reperfusion Injury In Vivo

The purpose of this experiment is to demonstrate that a humanized antibody clone disclosed herein, i.e., Clone 1, that is shown to regulate nitric oxide signaling in vitro in Example 5, is effective in reducing IRI and kidney damage in vivo in a rat kidney transplant model under standard conditions, i.e., with no warm ischemic time but with cold ischemic time. IRI significantly contributes to delayed graft function and inflammation leading to graft loss, and is exacerbated by the thrombospondin-1/CD47 system through inhibition of nitric oxide signaling.

A syngeneic rat renal transplantation model of IRI with bilaterally nephrectomized recipients is used to evaluate the effect of the anti-CD47 monoclonal antibody Clone 1 on graft function following transplantation as described in Schumacher et al. (2003) *Microsurg.* 23:389-394 and Karatzas et al. (2007) *Microsug.* 27:668-672.

Male Lewis rats weighing 275-300 g are obtained from Charles River Laboratories (Wilmington, Mass.). Donor kidneys are flushed with 50 µg of purified Clone 1 or vehicle (phosphate buffered saline, pH 7.2), and stored at 4° C. in University of Wisconsin preservation solution (UW) for 6 hours prior to transplantation. Two days following transplantation, kidney function is assessed by measuring serum creatinine by standard methodology.

Figure 5:
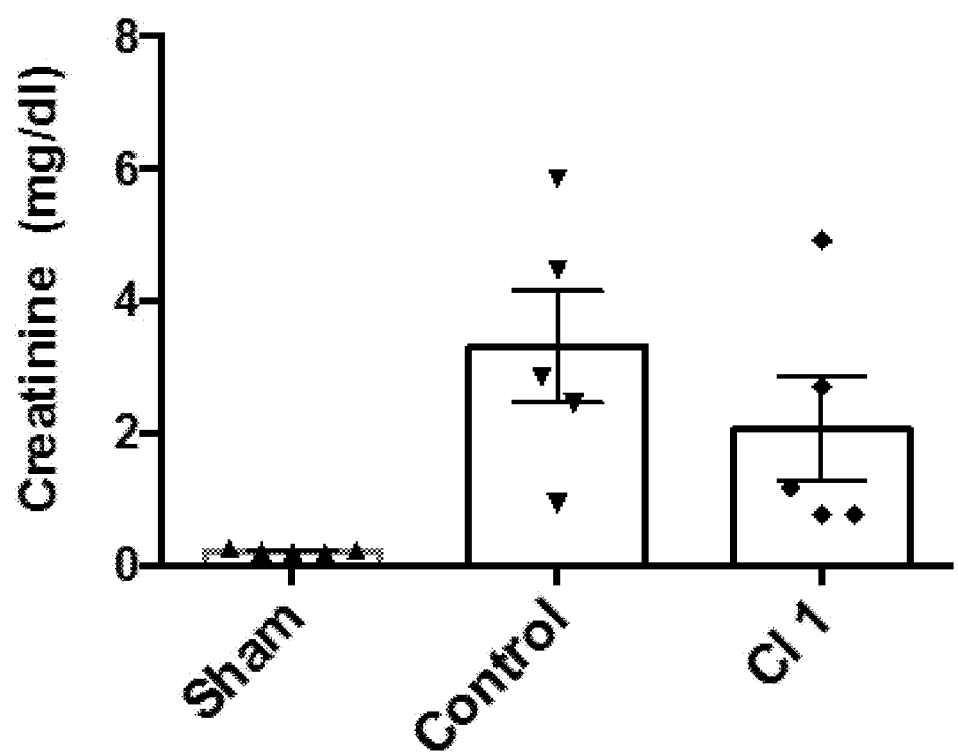
FIG. 5 shows that treatment of a donor kidney with Clone 1 (Cl 1) at the time of organ harvest is effective in reducing IRI and kidney damage in vivo in a rat kidney transplantation model as assessed by measuring serum creatinine. A syngeneic rat renal transplantation model of IRI with bilaterally nephrectomized recipients is used to evaluate the effect of the anti-CD47 monoclonal antibody Clone 1 on graft function following transplantation. Male Lewis rats weighing 275-300 g are used as both donor and recipient animals. Donor kidneys are flushed with 50 µg of purified Clone 1 or vehicle (phosphate buffered saline, pH 7.2), stored at 4° C. in University of Wisconsin preservation (WU) solution for 6 hours, and then transplanted. Two days following transplantation, kidney function is assessed by measuring serum creatinine. Treatment of donor kidneys with Clone 1 results in improved kidney function compared to controls as measured by a reduction in serum creatinine.

As shown in FIG. 5, CD47mAb Clone 1 perfusion of donor kidneys results in improved kidney function compared to controls as measured by a reduction in serum creatinine.

An additional experiment is shown that also demonstrates the ability of CD47mAbs of the present disclosure to improve kidney function of extended criteria organs that have also undergone a 60 minute period of warm ischemic time in addition to a 6 hour cold ischemic time. Male Lewis rats weighing 275-300 g underwent 60 minutes of warm ischemia, prior to flushing the donor kidneys with 50 µg of purified Clone 1.1 or an IgG control mAb. Kidneys are stored at 4° C. in University of Wisconsin preservation solution (UW) for 6 hours prior to transplantation. In this experiment, survival is monitored over a 7 day time period.

Figure 6:
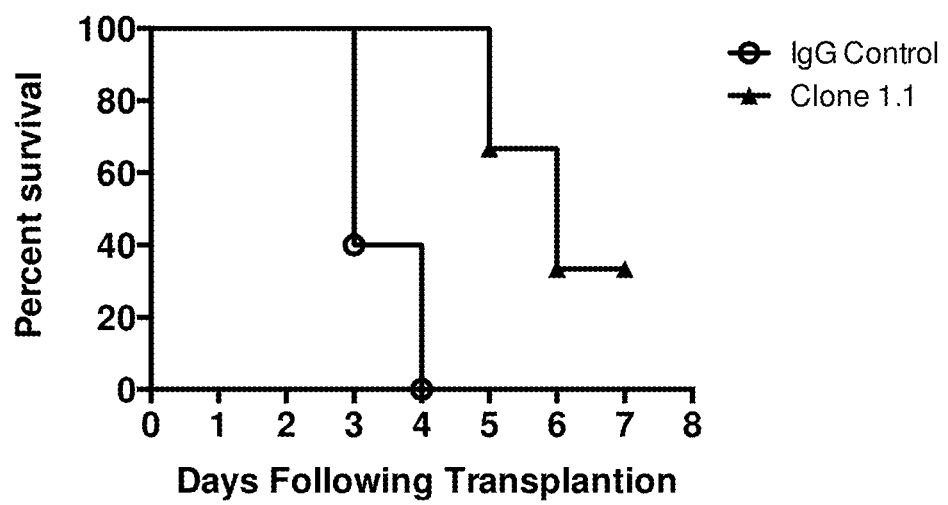
FIG. 6 shows the survival in a DCD (donation after cardiac death) rat kidney transplant model. Male Lewis rats weighing 275-300 g underwent 60 minutes of warm ischemia, prior to flushing the donor kidneys with 50 µg of purified Clone 1.1 or an IgG control mAb. Kidneys are then stored at 4° C. in University of Wisconsin preservation solution (UW) for 6 hours prior to transplantation. In this experiment, survival is monitored over a 7 day time period. All animals that received the IgG control mAb-treated kidney died within 4 days. In contrast, survival is significantly prolonged in the animals that received the Clone1.1 treated kidney, with 30% of the animals surviving for the 7 day duration of the experiment. This shows that with extended periods of warm ischemia, treatment of donor kidneys with Clone 1.1 reduces IRI and increases survival of the recipient.

As shown in FIG. 6, all animals that received the IgG control mAb-treated kidney die within 4 days. In contrast, survival is significantly increased in the animals that received the Clone1.1 treated kidney, with 30% of the animals surviving for the 7 day duration of the experiment.

Together, these experiments show that with both standard and extended criteria donor kidneys, Clone 1 and Clone 1.1 reduce IRI and increase kidney function and survival outcomes, respectively.

Example 7

Acute Promyelocytic Leukemia (APL) Anti-Tumor Activity In Vivo

The purpose of this experiment is to demonstrate that a humanized antibody clone disclosed herein, i.e., Clone 13, reduces tumor burden in vivo in a mouse leukemia model.

The anti-tumor activity of the anti-CD47mAb Clone13 (Cl 13; clone number as described above in Examples 2 and 3) is determined in a syngeneic murine model of Acute Promyelocytic Leukemia (APL) as described in Ramirez et al. (2009) Blood 113:6206-6214.

Murine APL cells (B6APL1) are injected intravenously into C57BL/6 mice that are randomized into three groups (5-10 mice per group): Group 1: no APL; Group 2: APL with no treatment; Group 3: APL with anti-CD47mAb Cl 13 treatment. Antibody treatment is initiated on the day of tumor inoculation (day 0), and given in single doses of 10 µg/dose (0.4 mg/kg) in phosphate buffered saline, pH 7.2, by intraperitoneal injection on days 0, 3, and 6.

Tumor burden is evaluated at day 25 following tumor cell inoculation. Blood samples from each mouse are analyzed for white blood cell count using an automated hemocytometer, and circulating APL cells (representing the tumor burden) are quantified by flow cytometry ($CD34_+$/$CD117_+$ cells).

Figure 7:
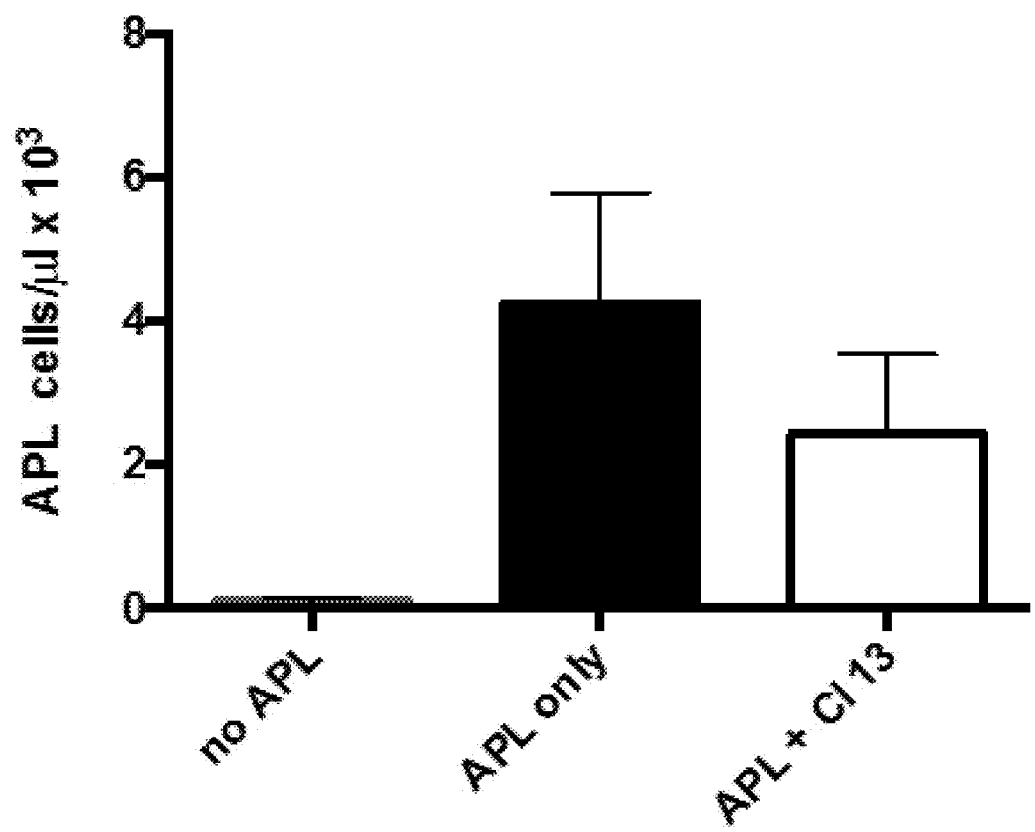
FIG. 7 shows that purified, humanized antibody Clone 13 (Cl 13) reduces tumor burden in vivo in a syngeneic mouse Acute Promyelocytic Leukemia (APL) model. Murine APL cells (B6APL1) are injected intravenously into C57BL/6 mice randomized into three groups (5-10 mice per group): Group 1: no APL; Group 2: APL with no treatment; Group 3: APL treated with anti-CD47mAb Cl 13. Antibody treatment is initiated on the day of tumor inoculation (day 0), and given in single doses of 10 µg/dose (0.4 mg/kg) by intraperitoneal injection on days 0, 3, and 6. Circulating APL cells (representing the tumor burden) are evaluated at day 25 following tumor inoculation by flow cytometry ($CD34^+$/$CD117^+$ cells). Mice treated with Cl 13 have reduced tumor burden compared to untreated mice at 25 days after tumor inoculation, demonstrating anti-tumor activity of this humanized clone.

As shown in FIG. 7, mice treated with Cl 13 have reduced tumor burden compared to untreated mice at 25 days after tumor inoculation, thus demonstrating anti-tumor activity of this humanized clone.

Example 8

HepG2 Anti-Tumor Activity In Vivo

The purpose of this experiment is to demonstrate that a humanized antibody clone disclosed herein, i.e., Clone 1.1, reduces tumor burden in vivo in a mouse xenograft model of human hepatocellular carcinoma (HCC).

Male NSG mice are obtained from The Jackson Laboratory (Bar Harbor, Me.) and housed in cages in temperature and light-controlled environments with access to water and food ad libitum. For the heterotopic xenograft model, HepG2-luc2 cells (Perkin Elmer, Waltham, Mass. #134280) are suspended in DMEM containing 25% (v/v), and 1,000,000 cells implanted subcutaneously into the dorsal subcutaneous space of 4- to 8-wk-old NSG mice. After 2 weeks of growth, antibody treatment is begun with twice-weekly intraperitoneal injections of 15 mg/kg of either anti-CD47 antibody Clone 1.1 or an IgG control for 6 weeks. Tumor volumes are calculated twice weekly using (length×width)/ 0.6. After 6 weeks of treatment, animals are euthanized and tumors were resected, weighed, and fixed in 10% formalin.

Figure 8:
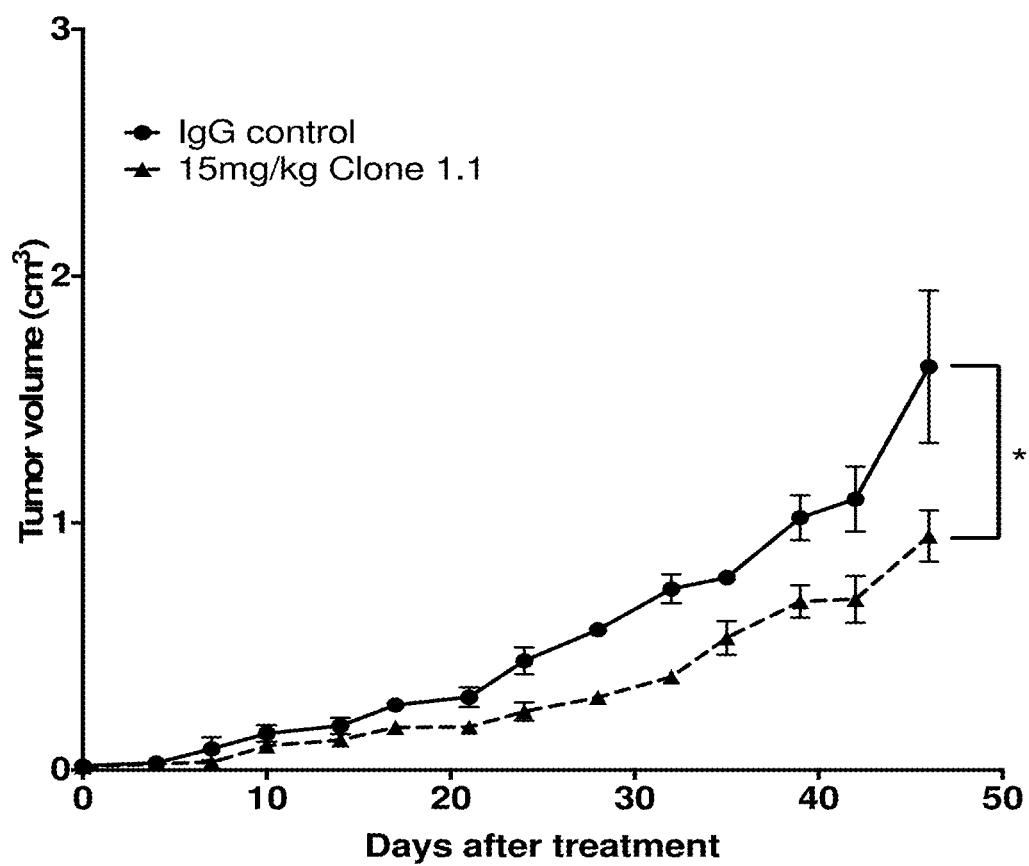
FIG. 8 shows that treatment with the CD47 mAb Clone 1.1 significantly reduced tumor growth of the human HepG2 hepatocellular carcinoma model. Male NSG mice are obtained from The Jackson Laboratory (Bar Harbor, Me.) and housed in cages in temperature and light-controlled environments with access to water and food ad libitum. For the heterotopic xenograft model, HepG2-luc2 cells (Perkin Elmer, Waltham, Mass. #134280) are suspended in DMEM containing 25% (v/v), and 1,000,000 cells implanted subcutaneously into the dorsal subcutaneous space of 4- to 8-wk-old NSG mice. After 2 weeks of growth, antibody treatment is begun with twice-weekly intraperitoneal injections of 15 mg/kg of either anti-CD47 antibody Clone 1.1 or an IgG control for 6 weeks. Tumor volumes are calculated twice weekly using (length×width)/0.6. After 6 weeks of treatment, animals are euthanized and tumors were resected, weighed, and fixed in 10% formalin.

As shown in FIG. 8, treatment with the CD47 mAb Clone 1.1 significantly reduced tumor growth of the HepG2 tumors ($p<0.01$), demonstrating anti-tumor efficacy on solid tumors.

Embodiments of the disclosure being thus described, it will be obvious that the same may be varied in many ways. Such variations are not to be regarded as a departure from the spirit and scope of the disclosure, and all such modifications as would be obvious to one skilled in the art are intended to be included within the scope of the following claims.

Example 9

Antibodies to CD47 Block CD47/SIRPalpha Binding

To assess the effect of humanized CD47 mAbs on binding of CD47 to SIRPalpha in vitro the following method is employed using binding of CD47 expressing Jurkat cells to SIRPalpha bound to plates.

Figure 11:
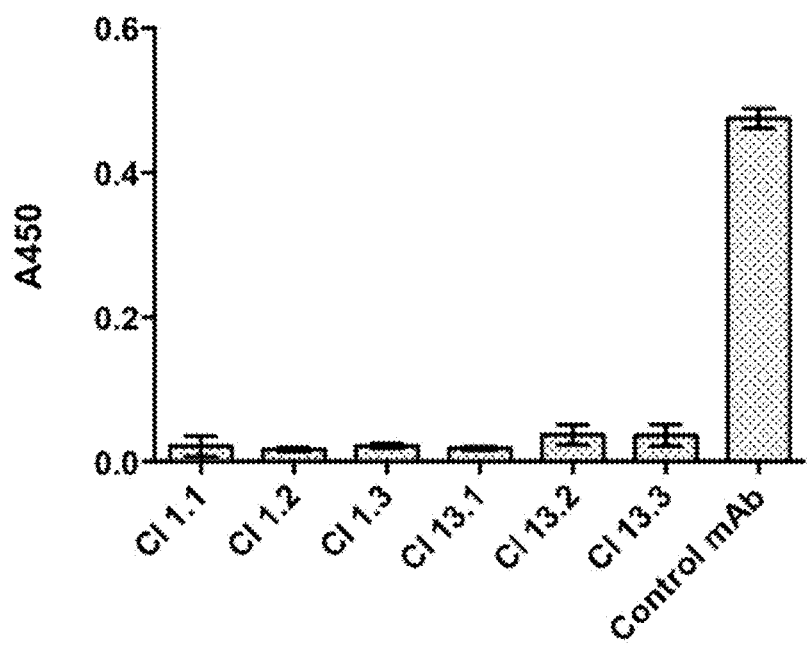
FIG. 11 shows Clones 1.1, 1.2, 1.3, 13.1, 13.2 and 13.3 all block the interaction of CD47 (expressed on the Jurkat cells) with SIPRalpha while a control antibody that does not bind to CD47 did not block the CD47/SIRPalpha interaction. Absorbance was read at 450 nm.

Polystyrene 96 well tissue culture plates were coated for 60 minutes at 37 degrees with 2 µg/ml SIRP-Fc fusion protein (R and D Systems, cat #4546-SA). Unbound SIRP-Fc fusion was removed and nonspecific protein binding sites were blocked with casein for 60 minutes at 37 degrees (ThermoScientific cat #37528). Blocking solution was removed and plates were washed with PBS. Jurkat cells in RPMI growth medium containing 10% FBS were added (100,000 cells/well), with or without CD47 antibodies at 1 ug/ml. Cells were incubated at 37 degrees for 60 minutes. Cells were aspirated and wells gently washed twice with PBS. Growth medium containing WST-1 reagent was added and plates incubated at 37 degrees for 2 hrs (Cayman Scientific cat #10008883). Absorbance was read at 450 nm. As shown in FIG. 11, Clones 1.1, 1.2, 1.3, 13.1, 13.2 and 13.3 all block the interaction of CD47 (expressed on the Jurkat cells) with SIPRalpha while a control antibody that does not bind to CD47 does not block the CD47/SIRPalpha interaction.

Amino Acid and Nucleic Acid Sequences
Light Chain Variable Region Amino Acid Sequences
    Murine Sequence

```
>VxP037-01LC: Underlined amino acid sequences
represent CDRs
                                     (SEQ ID NO: 7)
DVVMTQTPLSLSVSLGDQASISCRSSQSLVHSNGNTYLHWYLQKPGQSPK

LLIYKVSYRFSGVPDRFSGSGSGTDFTLKISRVEAEDLGVYFCSQNTHVP

RTFGQG
```

Humanized Light Chain Sequences

```
>pVxK7b-037-hum01-LC
                                     (SEQ ID NO: 8)
DIVMTQTPLSLPVTPGEPASISCRSSQSLVHSNGNTYLHWYQQKPGKAPK

LLIYKVSYRFSGVPDRFSGSGSGTDFTLKISRVEAEDVGVYYCSQNTHVP

RTFGQG

>pVxK7b-037-hum02-LC
                                     (SEQ ID NO: 9)
DVVMTQSPLSLPVTLGQPASISCRSSQSLVHSNGNTYLHWYQQKPGQAPR

LLIYKVSYRFSGVPSRFSGSGSGTEFTLTISSLQPDDFATYYCSQNTHVP

RTFGQG

>pVxK7b-037-hum03-LC
                                     (SEQ ID NO: 10)
DVVMTQSPLSLPVTLGQPASISCRSSQSLVHSNGNTYLHWYQQKPGKAPK

LLIYKVSYRFSGVPDRFSGSGSGTDFTLKISRVEAEDVGVYYCSQNTHVP

RTFGQG

>pVxK7b-037-hum04-LC
                                     (SEQ ID NO: 11)
DIQMTQSPSSLSASVGDRVTITCRSSQSLVHSNGNTYLHWYLQKPGQSPQ

LLIYKVSYRFSGIPARFSGSGSGTEFTLTISSLQSEDFAVYYCSQNTHVP

RTFGQG

>pVxK7b-037-hum05-LC
                                     (SEQ ID NO: 12)
DIVMTQTPLSLPVTPGEPASISCRSSQSLVHSNGNTYLHWYLQKPGQSPQ

LLIYKVSYRFSGVPDRFSGSGSGTDFTLKISRVEAEDVGVYYCSQNTHVP

RTFGQG
```

-continued

>pVxK7b-037-hum06-LC
(SEQ ID NO: 13)
DIQMTQSPSSLSASVGDRVTITCRSSQSLVHSNGNTYLHWYLQKPGQSPQ
LLIYKVSYRFSGIPARFSGSGSGTEFTLTISSLQSEDFAVYYCSQNTHVP
RTFGQG >pVxK7b-037-hum07-LC
(SEQ ID NO: 14)
DIVMTQTPLSLPVTPGEPASISCRSSQSLVHSNGNTYLHWYLQKPGQSPQ
LLIYKVSYRFSGVPDRFSGSGSGTDFTLKISRVEAEDVGVYYCSQNTHVP
RTFGQG >pVxK7b-037-hum08-LC
(SEQ ID NO: 15)
DIVMTQTPLSLPVTPGEPASISCRSSQSLVHSNGNTYLHWYQQKPGKAPK
LLIYKVSYRFSGVPDRFSGSGSGTDFTLKISRVEAEDVGVYYCSQNTHVP
RTFGQG >pVxK7b-037-hum09-LC
(SEQ ID NO: 16)
DVVMTQSPLSLPVTLGQPASISCRSSQSLVHSNGNTYLHWYQQKPGKAPK
LLIYKVSYRFSGVPDRFSGSGSGTDFTLKISRVEAEDVGVYYCSQNTHVP
RTFGQG >pVxK7b-037-hum10-LC
(SEQ ID NO: 17)
DIVMTQTPLSLPVTPGEPASISCRSSQSLVHSNGNTYLHWYLQKPGQSPQ
LLIYKVSYRFSGVPDRFSGSGSGTDFTLKISRVEAEDVGVYYCSQNTHVP
RTFGQG >pVxK7b-037-hum11-LC
(SEQ ID NO: 18)
EIVLTQSPATLSVSPGERATLSCRSSQSLVHSNGNTYLHWYQQKPGQAPR
LLIYKVSYRFSGVPSRFSGSGSGTDFTFTISSLEAEDAATYYCSQNTHVP
RTFGQG >pVxK7b-037-hum12-LC
(SEQ ID NO: 19)
DIVMTQTPLSLPVTPGEPASISCRSSQSLVHSNGNTYLHWYQQKPGKAPK
LLIYKVSYRFSGVPDRFSGSGSGTDFTLKISRVEAEDVGVYYCSQNTHVP
RTFGQG >pVxK7b-037-hum13-LC
(SEQ ID NO: 20)
DIVMTQTPLSLPVTPGEPASISCRSSQSLVHSNGNTYLHWYQQKPGKAPK
LLIYKVSYRFSGVPDRFSGSGSGTDFTLKISRVEAEDVGVYYCSQNTHVP
RTFGQG >pVxK7b-037-hum14-LC
(SEQ ID NO: 21)
DVVMTQSPLSLPVTLGQPASISCRSSQSLVHSNGNTYLHWYQQKPGKAPK
LLIYKVSYRFSGVPDRFSGSGSGTDFTLKISRVEAEDVGVYYCSQNTHVP
RTFGQG >pVxK7b-037-hum15-LC
(SEQ ID NO: 22)
AIQLTQSPSSLSASVGDRVTITCRSSQSLVHSNGNTYLHWYQQKPGQAPR
LLIYKVSYRFSGVPSRFSGSGSGTEFTLTISSLQPDDFATYYCSQNTHVP
RTFGQG >pVxK7b-037-hum16-LC
(SEQ ID NO: 23)
AIQLTQSPSSLSASVGDRVTITCRSSQSLVHSNGNTYLHWYQQKPGQAPR
LLIYKVSYRFSGVPDRFSGSGSGTDFTLKISRVEAEDVGVYYCSQNTHVP
RTFGQG >pVxK7b-037-hum17-LC
(SEQ ID NO: 24)
AIQLTQSPSSLSASVGDRVTITCRSSQSLVHSNGNTYLHWYQQKPGQAPR
LLIYKVSYRFSGVPDRFSGSGSGTDFTLKISRVEAEDVGVYYCSQNTHVP
RTFGQG >pVxK7b-037-hum18-LC
(SEQ ID NO: 25)
EIVLTQSPATLSVSPGERATLSCRSSQSLVHSNGNTYLHWYQQKPGQAPR
LLIYKVSYRFSGVPSRFSGSGSGTDFTFTISSLEAEDAATYYCSQNTHVP
RTFGQG >pVxK7b-037-hum19-LC
(SEQ ID NO: 26)
DVVMTQSPLSLPVTLGQPASISCRSSQSLVHSNGNTYLHWYQQKPGKAPK
LLIYKVSYRFSGVPDRFSGSGSGTDFTLKISRVEAEDVGVYYCSQNTHVP
RTFGQG >pVxK7b-037-hum20-LC
(SEQ ID NO: 27)
DIVMTQTPLSLPVTPGEPASISCRSSQSLVHSNGNTYLHWYLQKPGQSPQ
LLIYKVSYRFSGVPDRFSGSGSGTDFTLKISRVEAEDVGVYYCSQNTHVP
RTFGQG >pVxK7b-037-hum21-LC
(SEQ ID NO: 28)
AIQLTQSPSSLSASVGDRVTITCRSSQSLVHSNGNTYLHWYQQKPGQAPR
LLIYKVSYRFSGVPDRFSGSGSGTDFTLKISRVEAEDVGVYYCSQNTHVP
RTFGQG >pVxK7b-037-hum22-LC
(SEQ ID NO: 29)
EIVLTQSPATLSVSPGERATLSCRSSQSLVHSNGNTYLHWYQQKPGQAPR
LLIYKVSYRFSGVPSRFSGSGSGTDFTFTISSLEAEDAATYYCSQNTHVP
RTFGQG >pVxK7b-037-hum23-LC
(SEQ ID NO: 30)
DIVMTQTPLSLPVTPGEPASISCRSSQSLVHSNGNTYLHWYQQKPGKAPK
LLIYKVSYRFSGVPDRFSGSGSGTDFTLKISRVEAEDVGVYYCSQNTHVP
RTFGQG >pVxK7b-037-hum24-LC
(SEQ ID NO: 31)
AIQLTQSPSSLSASVGDRVTITCRSSQSLVHSNGNTYLHWYQQKPGQAPR
LLIYKVSYRFSGVPSRFSGSGSGTEFTLTISSLQPDDFATYYCSQNTHVP
RTFGQG Murine Light Chain Variable Region Nucleic Acid Sequence >VxP037-01LC
(SEQ ID NO: 32)
GATGTTGTTATGACCCAAACTCCACTCTCCCTGTCTGTCAGTCTTGGAGA
TCAAGCCTCCATCTCTTGCAGATCTAGTCAGAGCCTTGTACACAGTAATG

GAAACACCTATTTACATTGGTACCTGCAGAAGCCAGGCCAGTCTCCAAAG

CTCCTGATCTACAAAGTTTCCTACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTTCTGCTCTCAAAATACACATGTTCCT

CGGACGTTCGGCCAAGGAG

Humanized Light Chain Variable Region Nucleic Acid Sequences

>pVxK7b-037-hum01-LC (SEQ ID NO: 33)
GATATTGTGATGACCCAGACTCCACTCTCCCTGCCCGTCACCCCTGGAGA

GCCGGCCTCCATCTCCTGCAGATCTAGTCAGAGCCTTGTACACAGTAATG

GAAACACCTATTTACATTGGTATCAGCAGAAACCAGGGAAAGCTCCTAAG

CTCCTGATCTATAAAGTTTCCTACCGATTTTCTGGGGTCCCAGACAGGTT

CAGTGGCAGTGGGTCAGGCACTGATTTCACACTGAAAATCAGCAGGGTGG

AGGCTGAGGATGTTGGAGTTTATTACTGTTCTCAAAATACACATGTTCCT

CGGACGTTCGGCCAAGGG

>pVxK7b-037-hum02-LC (SEQ ID NO: 34)
GATGTTGTGATGACTCAGTCTCCACTCTCCCTGCCCGTCACCCTTGGACA

GCCGGCCTCCATCTCCTGCAGATCTAGTCAGAGCCTTGTACACAGTAATG

GAAACACCTATTTACATTGGTACCAGCAGAAACCTGGCCAGGCTCCCAGG

CTCCTCATCTATAAAGTTTCCTACCGATTTTCTGGGGTCCCATCAAGGTT

CAGCGGCAGTGGATCTGGGACAGAATTCACTCTCACCATCAGCAGCCTGC

AGCCTGATGATTTTGCAACTTATTACTGTTCTCAAAATACACATGTTCCT

CGGACGTTCGGCCAAGGG

>pVxK7b-037-hum03-LC (SEQ ID NO: 35)
GATGTTGTGATGACTCAGTCTCCACTCTCCCTGCCCGTCACCCTTGGACA

GCCGGCCTCCATCTCCTGCAGATCTAGTCAGAGCCTTGTACACAGTAATG

GAAACACCTATTTACATTGGTATCAGCAGAAACCAGGGAAAGCTCCTAAG

CTCCTGATCTATAAAGTTTCCTACCGATTTTCTGGGGTCCCAGACAGGTT

CAGTGGCAGTGGGTCAGGCACTGATTTCACACTGAAAATCAGCAGGGTGG

AGGCTGAGGATGTTGGAGTTTATTACTGTTCTCAAAATACACATGTTCCT

CGGACGTTCGGCCAAGGG

>pVxK7b-037-hum04-LC (SEQ ID NO: 36)
GACATCCAGATGACCCAGTCTCCATCCTCCCTGTCTGCATCTGTAGGAGA

CAGAGTCACCATCACTTGCAGATCTAGTCAGAGCCTTGTACACAGTAATG

GAAACACCTATTTACATTGGTACCTGCAGAAGCCAGGGCAGTCTCCACAG

CTCCTGATCTATAAAGTTTCCTACCGATTTTCTGGGATCCCAGCCAGGTT

CAGTGGCAGTGGGTCTGGGACAGAGTTCACTCTCACCATCAGCAGCCTGC

AGTCTGAAGATTTTGCAGTTTATTACTGTTCTCAAAATACACATGTTCCT

CGGACGTTCGGCCAAGGG

>pVxK7b-037-hum05-LC (SEQ ID NO: 37)
GATATTGTGATGACCCAGACTCCACTCTCCCTGCCCGTCACCCCTGGAGA

GCCGGCCTCCATCTCCTGCAGATCTAGTCAGAGCCTTGTACACAGTAATG

GAAACACCTATTTACATTGGTACCTGCAGAAGCCAGGGCAGTCTCCACAG

CTCCTGATCTATAAAGTTTCCTACCGATTTTCTGGGGTCCCAGACAGGTT

CAGTGGCAGTGGGTCAGGCACTGATTTCACACTGAAAATCAGCAGGGTGG

AGGCTGAGGATGTTGGAGTTTATTACTGTTCTCAAAATACACATGTTCCT

CGGACGTTCGGCCAAGGG

>pVxK7b-037-hum06-LC (SEQ ID NO: 38)
GACATCCAGATGACCCAGTCTCCATCCTCCCTGTCTGCATCTGTAGGAGA

CAGAGTCACCATCACTTGCAGATCTAGTCAGAGCCTTGTACACAGTAATG

GAAACACCTATTTACATTGGTACCTGCAGAAGCCAGGGCAGTCTCCACAG

CTCCTGATCTATAAAGTTTCCTACCGATTTTCTGGGATCCCAGCCAGGTT

CAGTGGCAGTGGGTCTGGGACAGAGTTCACTCTCACCATCAGCAGCCTGC

AGTCTGAAGATTTTGCAGTTTATTACTGTTCTCAAAATACACATGTTCCT

CGGACGTTCGGCCAAGGG

>pVxK7b-037-hum07-LC (SEQ ID NO: 39)
GATATTGTGATGACCCAGACTCCACTCTCCCTGCCCGTCACCCCTGGAGA

GCCGGCCTCCATCTCCTGCAGATCTAGTCAGAGCCTTGTACACAGTAATG

GAAACACCTATTTACATTGGTACCTGCAGAAGCCAGGGCAGTCTCCACAG

CTCCTGATCTATAAAGTTTCCTACCGATTTTCTGGGGTCCCAGACAGGTT

CAGTGGCAGTGGGTCAGGCACTGATTTCACACTGAAAATCAGCAGGGTGG

AGGCTGAGGATGTTGGAGTTTATTACTGTTCTCAAAATACACATGTTCCT

CGGACGTTCGGCCAAGGG

>pVxK7b-037-hum08-LC (SEQ ID NO: 40)
GATATTGTGATGACCCAGACTCCACTCTCCCTGCCCGTCACCCCTGGAGA

GCCGGCCTCCATCTCCTGCAGATCTAGTCAGAGCCTTGTACACAGTAATG

GAAACACCTATTTACATTGGTATCAGCAGAAACCAGGGAAAGCTCCTAAG

CTCCTGATCTATAAAGTTTCCTACCGATTTTCTGGGGTCCCAGACAGGTT

CAGTGGCAGTGGGTCAGGCACTGATTTCACACTGAAAATCAGCAGGGTGG

AGGCTGAGGATGTTGGAGTTTATTACTGTTCTCAAAATACACATGTTCCT

CGGACGTTCGGCCAAGGG

>pVxK7b-037-hum09-LC (SEQ ID NO: 41)
GATGTTGTGATGACTCAGTCTCCACTCTCCCTGCCCGTCACCCTTGGACA

GCCGGCCTCCATCTCCTGCAGATCTAGTCAGAGCCTTGTACACAGTAATG

GAAACACCTATTTACATTGGTATCAGCAGAAACCAGGGAAAGCTCCTAAG

CTCCTGATCTATAAAGTTTCCTACCGATTTTCTGGGGTCCCAGACAGGTT

CAGTGGCAGTGGGTCAGGCACTGATTTCACACTGAAAATCAGCAGGGTGG

AGGCTGAGGATGTTGGAGTTTATTACTGTTCTCAAAATACACATGTTCCT

CGGACGTTCGGCCAAGGG

>pVxK7b-037-hum10-LC
(SEQ ID NO: 42)
GATATTGTGATGACCCAGACTCCACTCTCCCTGCCCGTCACCCCTGGAGA

GCCGGCCTCCATCTCCTGCAGATCTAGTCAGAGCCTTGTACACAGTAATG

GAAACACCTATTTACATTGGTACCTGCAGAAGCCAGGGCAGTCTCCACAG

CTCCTGATCTATAAAGTTTCCTACCGATTTTCTGGGGTCCCAGACAGGTT

CAGTGGCAGTGGGTCAGGCACTGATTTCACACTGAAAATCAGCAGGGTGG

AGGCTGAGGATGTTGGAGTTTATTACTGTTCTCAAAATACACATGTTCCT

CGGACGTTCGGCCAAGGG

>pVxK7b-037-hum11-LC
(SEQ ID NO: 43)
GAAATTGTGTTGACACAGTCTCCAGCCACCCTGTCTGTGTCTCCAGGGGA

AAGAGCCACCCTCTCCTGCAGATCTAGTCAGAGCCTTGTACACAGTAATG

GAAACACCTATTTACATTGGTACCAGCAGAAACCTGGCCAGGCTCCCAGG

CTCCTCATCTATAAAGTTTCCTACCGATTTTCTGGGGTCCCCTCGAGGTT

CAGTGGCAGTGGATCTGGGACAGATTTCACCTTTACCATCAGTAGCCTGG

AAGCTGAAGATGCTGCAACATATTACTGTTCTCAAAATACACATGTTCCT

CGGACGTTCGGCCAAGGG

>pVxK7b-037-hum12-LC
(SEQ ID NO: 44)
GATATTGTGATGACCCAGACTCCACTCTCCCTGCCCGTCACCCCTGGAGA

GCCGGCCTCCATCTCCTGCAGATCTAGTCAGAGCCTTGTACACAGTAATG

GAAACACCTATTTACATTGGTATCAGCAGAAACCAGGGAAAGCTCCTAAG

CTCCTGATCTATAAAGTTTCCTACCGATTTTCTGGGGTCCCAGACAGGTT

CAGTGGCAGTGGGTCAGGCACTGATTTCACACTGAAAATCAGCAGGGTGG

AGGCTGAGGATGTTGGAGTTTATTACTGTTCTCAAAATACACATGTTCCT

CGGACGTTCGGCCAAGGG

>pVxK7b-037-hum13-LC
(SEQ ID NO: 45)
GATATTGTGATGACCCAGACTCCACTCTCCCTGCCCGTCACCCCTGGAGA

GCCGGCCTCCATCTCCTGCAGATCTAGTCAGAGCCTTGTACACAGTAATG

GAAACACCTATTTACATTGGTATCAGCAGAAACCAGGGAAAGCTCCTAAG

CTCCTGATCTATAAAGTTTCCTACCGATTTTCTGGGGTCCCAGACAGGTT

CAGTGGCAGTGGGTCAGGCACTGATTTCACACTGAAAATCAGCAGGGTGG

AGGCTGAGGATGTTGGAGTTTATTACTGTTCTCAAAATACACATGTTCCT

CGGACGTTCGGCCAAGGG

>pVxK7b-037-hum14-LC
(SEQ ID NO: 46)
GATGTTGTGATGACTCAGTCTCCACTCTCCCTGCCCGTCACCCTTGGACA

GCCGGCCTCCATCTCCTGCAGATCTAGTCAGAGCCTTGTACACAGTAATG

GAAACACCTATTTACATTGGTATCAGCAGAAACCAGGGAAAGCTCCTAAG

CTCCTGATCTATAAAGTTTCCTACCGATTTTCTGGGGTCCCAGACAGGTT

CAGTGGCAGTGGGTCAGGCACTGATTTCACACTGAAAATCAGCAGGGTGG

AGGCTGAGGATGTTGGAGTTTATTACTGTTCTCAAAATACACATGTTCCT

CGGACGTTCGGCCAAGGG

>pVxK7b-037-hum15-LC
(SEQ ID NO: 47)
GCCATCCAGTTGACCCAGTCTCCATCCTCCCTGTCTGCATCTGTAGGAGA

CAGAGTCACCATCACTTGCAGATCTAGTCAGAGCCTTGTACACAGTAATG

GAAACACCTATTTACATTGGTACCAGCAGAAACCTGGCCAGGCTCCCAGG

CTCCTCATCTATAAAGTTTCCTACCGATTTTCTGGGGTCCCATCAAGGTT

CAGCGGCAGTGGATCTGGGACAGAATTCACTCTCACCATCAGCAGCCTGC

AGCCTGATGATTTTGCAACTTATTACTGTTCTCAAAATACACATGTTCCT

CGGACGTTCGGCCAAGGG

>pVxK7b-037-hum16-LC
(SEQ ID NO: 48)
GCCATCCAGTTGACCCAGTCTCCATCCTCCCTGTCTGCATCTGTAGGAGA

CAGAGTCACCATCACTTGCAGATCTAGTCAGAGCCTTGTACACAGTAATG

GAAACACCTATTTACATTGGTACCAGCAGAAACCTGGCCAGGCTCCCAGG

CTCCTCATCTATAAAGTTTCCTACCGATTTTCTGGGGTCCCAGACAGGTT

CAGTGGCAGTGGGTCAGGCACTGATTTCACACTGAAAATCAGCAGGGTGG

AGGCTGAGGATGTTGGAGTTTATTACTGTTCTCAAAATACACATGTTCCT

CGGACGTTCGGCCAAGGG

>pVxK7b-037-hum17-LC
(SEQ ID NO: 49)
GCCATCCAGTTGACCCAGTCTCCATCCTCCCTGTCTGCATCTGTAGGAGA

CAGAGTCACCATCACTTGCAGATCTAGTCAGAGCCTTGTACACAGTAATG

GAAACACCTATTTACATTGGTACCAGCAGAAACCTGGCCAGGCTCCCAGG

CTCCTCATCTATAAAGTTTCCTACCGATTTTCTGGGGTCCCAGACAGGTT

CAGTGGCAGTGGGTCAGGCACTGATTTCACACTGAAAATCAGCAGGGTGG

AGGCTGAGGATGTTGGAGTTTATTACTGTTCTCAAAATACACATGTTCCT

CGGACGTTCGGCCAAGGG

>pVxK7b-037-hum18-LC
(SEQ ID NO: 50)
GAAATTGTGTTGACACAGTCTCCAGCCACCCTGTCTGTGTCTCCAGGGGA

AAGAGCCACCCTCTCCTGCAGATCTAGTCAGAGCCTTGTACACAGTAATG

GAAACACCTATTTACATTGGTACCAGCAGAAACCTGGCCAGGCTCCCAGG

CTCCTCATCTATAAAGTTTCCTACCGATTTTCTGGGGTCCCCTCGAGGTT

CAGTGGCAGTGGATCTGGGACAGATTTCACCTTTACCATCAGTAGCCTGG

AAGCTGAAGATGCTGCAACATATTACTGTTCTCAAAATACACATGTTCCT

CGGACGTTCGGCCAAGGG

>pVxK7b-037-hum19-LC
(SEQ ID NO: 51)
GATGTTGTGATGACTCAGTCTCCACTCTCCCTGCCCGTCACCCTTGGACA

GCCGGCCTCCATCTCCTGCAGATCTAGTCAGAGCCTTGTACACAGTAATG

GAAACACCTATTTACATTGGTATCAGCAGAAACCAGGGAAAGCTCCTAAG

CTCCTGATCTATAAAGTTTCCTACCGATTTTCTGGGGTCCCAGACAGGTT

CAGTGGCAGTGGGTCAGGCACTGATTTCACACTGAAAATCAGCAGGGTGG

AGGCTGAGGATGTTGGAGTTTATTACTGTTCTCAAAATACACATGTTCCT

CGGACGTTCGGCCAAGGG

```
>pVxK7b-037-hum20-LC
                                       (SEQ ID NO: 52)
GATATTGTGATGACCCAGACTCCACTCTCCCTGCCCGTCACCCCTGGAGA

GCCGGCCTCCATCTCCTGCAGATCTAGTCAGAGCCTTGTACACAGTAATG

GAAACACCTATTTACATTGGTACCTGCAGAAGCCAGGGCAGTCTCCACAG

CTCCTGATCTATAAAGTTTCCTACCGATTTTCTGGGGTCCCAGACAGGTT

CAGTGGCAGTGGGTCAGGCACTGATTTCACACTGAAAATCAGCAGGGTGG

AGGCTGAGGATGTTGGAGTTTATTACTGTTCTCAAAATACACATGTTCCT

CGGACGTTCGGCCAAGGG

>pVxK7b-037-hum21-LC
                                       (SEQ ID NO: 53)
GCCATCCAGTTGACCCAGTCTCCATCCTCCCTGTCTGCATCTGTAGGAGA

CAGAGTCACCATCACTTGCAGATCTAGTCAGAGCCTTGTACACAGTAATG

GAAACACCTATTTACATTGGTACCAGCAGAAACCTGGCCAGGCTCCCAGG

CTCCTCATCTATAAAGTTTCCTACCGATTTTCTGGGGTCCCAGACAGGTT

CAGTGGCAGTGGGTCAGGCACTGATTTCACACTGAAAATCAGCAGGGTGG

AGGCTGAGGATGTTGGAGTTTATTACTGTTCTCAAAATACACATGTTCCT

CGGACGTTCGGCCAAGGG

>pVxK7b-037-hum22-LC
                                       (SEQ ID NO: 54)
GAAATTGTGTTGACACAGTCTCCAGCCACCCTGTCTGTGTCTCCAGGGGA

AAGAGCCACCCTCTCCTGCAGATCTAGTCAGAGCCTTGTACACAGTAATG

GAAACACCTATTTACATTGGTACCAGCAGAAACCTGGCCAGGCTCCCAGG

CTCCTCATCTATAAAGTTTCCTACCGATTTTCTGGGGTCCCCTCGAGGTT

CAGTGGCAGTGGATCTGGGACAGATTTCACCTTTACCATCAGTAGCCTGG

AAGCTGAAGATGCTGCAACATATTACTGTTCTCAAAATACACATGTTCCT

CGGACGTTCGGCCAAGGG

>pVxK7b-037-hum23-LC
                                       (SEQ ID NO: 55)
GATATTGTGATGACCCAGACTCCACTCTCCCTGCCCGTCACCCCTGGAGA

GCCGGCCTCCATCTCCTGCAGATCTAGTCAGAGCCTTGTACACAGTAATG

GAAACACCTATTTACATTGGTATCAGCAGAAACCAGGGAAAGCTCCTAAG

CTCCTGATCTATAAAGTTTCCTACCGATTTTCTGGGGTCCCAGACAGGTT

CAGTGGCAGTGGGTCAGGCACTGATTTCACACTGAAAATCAGCAGGGTGG

AGGCTGAGGATGTTGGAGTTTATTACTGTTCTCAAAATACACATGTTCCT

CGGACGTTCGGCCAAGGG

>pVxK7b-037-hum24-LC
                                       (SEQ ID NO: 56)
GCCATCCAGTTGACCCAGTCTCCATCCTCCCTGTCTGCATCTGTAGGAGA

CAGAGTCACCATCACTTGCAGATCTAGTCAGAGCCTTGTACACAGTAATG

GAAACACCTATTTACATTGGTACCAGCAGAAACCTGGCCAGGCTCCCAGG

CTCCTCATCTATAAAGTTTCCTACCGATTTTCTGGGTCCCATCAAGGTT

CAGCGGCAGTGGATCTGGGACAGAATTCACTCTCACCATCAGCAGCCTGC

AGCCTGATGATTTTGCAACTTATTACTGTTCTCAAAATACACATGTTCCT

CGGACGTTCGGCCAAGGG
```

Heavy Chain Variable Region Amino Acid Sequences

Murine Heavy Chain Variable Region Amino Acid Sequence: Underlined Amino Acid Sequences Indicate CDRs

```
>VxP037-01HC
                                       (SEQ ID NO: 57)
EVQLQQFGAELVKPGASMKLSCKASGYTFTNYYVFWVKQRPGQGLEWIGD

INPVNGDTNFNEKFKNKATLTVDKSSTTTYLQLSSLTSEDSAVYYCTRGG

YTMDYWGQG
```

Humanized Heavy Chain Variable Region Amino Acid Sequences

```
>pVxK7b-037-hum01-HC
                                       (SEQ ID NO: 58)
QVQLQESGPGLVKPSQTLSLTCTVSGYTFTNYYVFWVRQARGQRLEWIGD

INPVNGDTNFNEKFKNRVTISADKSISTAYLQWSSLKASDTAMYYCARGG

YTMDYWGQG

>pVxK7b-037-hum02-HC
                                       (SEQ ID NO: 59)
QVQLQESGPGLVKPSQTLSLTCTVSGYTFTNYYVFWVRQARGQRLEWIGD

INPVNGDTNFNEKFKNRVTISADKSISTAYLQWSSLKASDTAMYYCARGG

YTMDYWGQG

>pVxK7b-037-hum03-HC
                                       (SEQ ID NO: 60)
EVQLVQSGAEVKKPGESLRISCKGSGYTFTNYYVFWVRQARGQRLEWIGD

INPVNGDTNFNEKFKNRVTITADKSTSTAYMELSSLRSEDTAVYYCARGG

YTMDYWGQG

>pVxK7b-037-hum04-HC
                                       (SEQ ID NO: 61)
QVQLQESGPGLVKPSQTLSLTCTVSGYTFTNYYVFWVRQAPGKGLEWVSD

INPVNGDTNFNEKFKNRVTISVDTSKNQFSLKLSSVTAADTAVYYCARGG

YTMDYWGQG

>pVxK7b-037-hum05-HC
                                       (SEQ ID NO: 62)
QVQLQESGPGLVKPSQTLSLTCTVSGYTFTNYYVFWVRQAPGKGLEWVSD

INPVNGDTNFNEKFKNRVTISVDTSKNQFSLKLSSVTAADTAVYYCARGG

YTMDYWGQG

>pVxK7b-037-hum06-HC
                                       (SEQ ID NO: 63)
QVQLQESGPGLVKPSQTLSLTCTVSGYTFTNYYVFWVRQARGQRLEWIGD

INPVNGDTNFNEKFKNRLTISKDTSKNQVVLTMTNMDPVDTATYYCARGG

YTMDYWGQG

>pVxK7b-037-hum07-HC
                                       (SEQ ID NO: 64)
QVQLQESGPGLVKPGATVKISCKVSGYTFTNYYVFWVRQARGQRLEWIGD

INPVNGDTNFNEKFKNRVTITADKSTSTAYMELSSLRSEDTAVYYCARGG

YTMDYWGQG

>pVxK7b-037-hum08-HC
                                       (SEQ ID NO: 65)
QITLKESGPTLVKPTQTLTLTCTFSGYTFTNYYVFWIRQSPSRGLEWLGD

INPVNGDTNFNEKFKNRFTISRDNAKNSLYLQMNSLRAEDTAVYYCARGG

YTMDYWGQG
```

-continued

>pVxK7b-037-hum09-HC
(SEQ ID NO: 66)
QVQLQESGPGLVKPSQTLSLTCTVSGYTFTNYYVFWVRQARGQRLEWIGD
INPVNGDTNFNEKFKNRLTISKDTSKNQVVLTMTNMDPVDTATYYCARGG
YTMDYWGQG >pVxK7b-037-hum10-HC
(SEQ ID NO: 67)
QVQLQESGPGLVKPSQTLSLTCTVSGYTFTNYYVFWVRQARGQRLEWIGD
INPVNGDTNFNEKFKNRLTISKDTSKNQVVLTMTNMDPVDTATYYCARGG
YTMDYWGQG >pVxK7b-037-hum11-HC
(SEQ ID NO: 68)
QVQLQESGPGLVKPGATVKISCKVSGYTFTNYYVFWVRQARGQRLEWIGD
INPVNGDTNFNEKFKNRVTITADKSTSTAYMELSSLRSEDTAVYYCARGG
YTMDYWGQG >pVxK7b-037-hum12-HC
(SEQ ID NO: 69)
QVQLQESGPGLVKPGATVKISCKVSGYTFTNYYVFWVRQARGQRLEWIGD
INPVNGDTNFNEKFKNRVTITADKSTSTAYMELSSLRSEDTAVYYCARGG
YTMDYWGQG >pVxK7b-037-hum13-HC
(SEQ ID NO: 70)
EVQLVQSGAEVKKPGESLRISCKGSGYTFTNYYVFWIRQSPSRGLEWLGD
INPVNGDTNFNEKFKNRVTITADKSTSTAYMELSSLRSEDTAVYYCARGG
YTMDYWGQG >pVxK7b-037-hum14-HC
(SEQ ID NO: 71)
QVQLQESGPGLVKPSQTLSLTCTVSGYTFTNYYVFWVRQARGQRLEWIGD
INPVNGDTNFNEKFKNRVTISADKSISTAYLQWSSLKASDTAMYYCARGG
YTMDYWGQG >pVxK7b-037-hum15-HC
(SEQ ID NO: 72)
QVQLQESGPGLVKPSQTLSLTCTVSGYTFTNYYVFWVRQARGQRLEWIGD
INPVNGDTNFNEKFKNRLTISKDTSKNQVVLTMTNMDPVDTATYYCARGG
YTMDYWGQG >pVxK7b-037-hum16-HC
(SEQ ID NO: 73)
QVQLQESGPGLVKPSQTLSLTCTVSGYTFTNYYVFWVRQARGQRLEWIGD
INPVNGDTNFNEKFKNRVTISADKSISTAYLQWSSLKASDTAMYYCARGG
YTMDYWGQG >pVxK7b-037-hum17-HC
(SEQ ID NO: 74)
EVQLVQSGAEVKKPGATVKISCKVSGYTFTNYYVFWIRQPPGKGLEWIGD
INPVNGDTNFNEKFKNRVTITADKSTSTAYMELSSLRSEDTAVYYCARGG
YTMDYWGQG >pVxK7b-037-hum18-HC
(SEQ ID NO: 75)
EVQLVQSGAEVKKPGESLRISCKGSGYTFTNYYVFWIRQSPSRGLEWLGD
INPVNGDTNFNEKFKNRVTITADKSTSTAYMELSSLRSEDTAVYYCARGG
YTMDYWGQG >pVxK7b-037-hum19-HC
(SEQ ID NO: 76)
EVQLVQSGAEVKKPGESLRISCKGSGYTFTNYYVFWIRQSPSRGLEWLGD
INPVNGDTNFNEKFKNRVTITADKSTSTAYMELSSLRSEDTAVYYCARGG
YTMDYWGQG >pVxK7b-037-hum20-HC
(SEQ ID NO: 77)
QITLKESGPTLVKPTQTLTLTCTFSGYTFTNYYVFWVRQAPGQGLEWMGD
INPVNGDTNFNEKFKNRVTITADKSTSTAYMELSSLRSEDTAVYYCARGG
YTMDYWGQG >pVxK7b-037-hum21-HC
(SEQ ID NO: 78)
QVQLQESGPGLVKPSQTLSLTCTVSGYTFTNYYVFWVRQARGQRLEWIGD
INPVNGDTNFNEKFKNRLTISKDTSKNQVVLTMTNMDPVDTATYYCARGG
YTMDYWGQG >pVxK7b-037-hum22-HC
(SEQ ID NO: 79)
QVQLQESGPGLVKPSQTLSLTCTVSGYTFTNYYVFWVRQARGQRLEWIGD
INPVNGDTNFNEKFKNRLTISKDTSKNQVVLTMTNMDPVDTATYYCARGG
YTMDYWGQG >pVxK7b-037-hum23-HC
(SEQ ID NO: 80)
QVQLQESGPGLVKPSQTLSLTCTVSGYTFTNYYVFWVRQARGQRLEWIGD
INPVNGDTNFNEKFKNRLTISKDTSKNQVVLTMTNMDPVDTATYYCARGG
YTMDYWGQG >pVxK7b-037-hum24-HC
(SEQ ID NO: 81)
QVQLQESGPGLVKPGATVKISCKVSGYTFTNYYVFWVRQARGQRLEWIGD
INPVNGDTNFNEKFKNRVTITADKSTSTAYMELSSLRSEDTAVYYCARGG
YTMDYWGQG Murine Heavy Chain Variable Region Nucleic Acid Sequence >VxP037-01HC
(SEQ ID NO: 82)
GAGGTCCAGCTGCAGCAGTTTGGGGCTGAACTGGTGAAGCCTGGGGCTTC
AATGAAGTTGTCCTGCAAGGCTTCTGGCTACACCTTCACCAACTACTATG
TATTCTGGGTGAAACAGAGGCCTGGACAAGGCCTTGAGTGGATTGGAGAC
ATTAATCCTGTCAATGGTGATACTAACTTCAATGAGAAATTCAAGAACAA
GGCCACACTGACTGTAGACAAGTCCTCCACCACAACATACTTGCAACTCA
GCAGCCTGACATCTGAGGACTCTGCGGTCTATTACTGTACAAGAGGGGGT
TATACTATGGACTACTGGGGTCAAGGA Humanized Heavy Chain Variable Region Nucleic Acid Sequences >pVxK7b-037-hum01-HC
(SEQ ID NO: 83)
CAGGTGCAGCTGCAGGAGTCGGGCCCAGGACTGGTGAAGCCTTCACAGAC
CCTGTCCCTCACCTGCACTGTCTCTGGCTACACCTTCACCAACTACTATG
TATTCTGGGTGCGACAGGCTCGTGGACAACGCCTTGAGTGGATAGGTGAC

ATTAATCCTGTCAATGGTGATACTAACTTCAATGAGAAATTCAAGAACAG

AGTCACCATCTCAGCCGACAAGTCCATCAGCACCGCCTACCTGCAGTGGA

GCAGCCTGAAGGCCTCGGACACCGCCATGTATTACTGTGCGAGAGGGGGT

TATACTATGGACTACTGGGGCCAGGGA

>pVxK7b-037-hum02-HC (SEQ ID NO: 84)
CAGGTGCAGCTGCAGGAGTCGGGCCCAGGACTGGTGAAGCCTTCACAGAC

CCTGTCCCTCACCTGCACTGTCTCTGGCTACACCTTCACCAACTACTATG

TATTCTGGGTGCGACAGGCTCGTGGACAACGCCTTGAGTGGATAGGTGAC

ATTAATCCTGTCAATGGTGATACTAACTTCAATGAGAAATTCAAGAACAG

AGTCACCATCTCAGCCGACAAGTCCATCAGCACCGCCTACCTGCAGTGGA

GCAGCCTGAAGGCCTCGGACACCGCCATGTATTACTGTGCGAGAGGGGGT

TATACTATGGACTACTGGGGCCAGGGA

>pVxK7b-037-hum03-HC (SEQ ID NO: 85)
GAAGTGCAGCTGGTGCAGTCTGGAGCAGAGGTGAAAAAGCCCGGGGAGTC

TCTGAGGATCTCCTGTAAGGGTTCTGGCTACACCTTCACCAACTACTATG

TATTCTGGGTGCGACAGGCTCGTGGACAACGCCTTGAGTGGATAGGTGAC

ATTAATCCTGTCAATGGTGATACTAACTTCAATGAGAAATTCAAGAACAG

AGTCACGATTACCGCGGACAAATCCACGAGCACAGCCTACATGGAGCTGA

GCAGCCTGAGATCTGAGGACACGGCCGTGTATTACTGTGCGAGAGGGGGT

TATACTATGGACTACTGGGGCCAGGGA

>pVxK7b-037-hum04-HC (SEQ ID NO: 86)
CAGGTGCAGCTGCAGGAGTCGGGCCCAGGACTGGTGAAGCCTTCACAGAC

CCTGTCCCTCACCTGCACTGTCTCTGGCTACACCTTCACCAACTACTATG

TATTCTGGGTCCGCCAGGCTCCAGGGAAGGGGCTGGAGTGGGTCAGTGAC

ATTAATCCTGTCAATGGTGATACTAACTTCAATGAGAAATTCAAGAACAG

AGTCACCATATCAGTAGACACGTCCAAGAACCAGTTCTCCCTGAAGCTGA

GCTCTGTGACCGCCGCGGACACGGCTGTGTATTACTGTGCGAGAGGGGGT

TATACTATGGACTACTGGGGCCAGGGA

>pVxK7b-037-hum05-HC (SEQ ID NO: 87)
CAGGTGCAGCTGCAGGAGTCGGGCCCAGGACTGGTGAAGCCTTCACAGAC

CCTGTCCCTCACCTGCACTGTCTCTGGCTACACCTTCACCAACTACTATG

TATTCTGGGTCCGCCAGGCTCCAGGGAAGGGGCTGGAGTGGGTCAGTGAC

ATTAATCCTGTCAATGGTGATACTAACTTCAATGAGAAATTCAAGAACAG

AGTCACCATATCAGTAGACACGTCCAAGAACCAGTTCTCCCTGAAGCTGA

GCTCTGTGACCGCCGCGGACACGGCTGTATTACTGTGCGAGAGGGGGT

TATACTATGGACTACTGGGGCCAGGGA

>pVxK7b-037-hum06-HC (SEQ ID NO: 88)
CAGGTGCAGCTGCAGGAGTCGGGCCCAGGACTGGTGAAGCCTTCACAGAC

CCTGTCCCTCACCTGCACTGTCTCTGGCTACACCTTCACCAACTACTATG

TATTCTGGGTGCGACAGGCTCGTGGACAACGCCTTGAGTGGATAGGTGAC

ATTAATCCTGTCAATGGTGATACTAACTTCAATGAGAAATTCAAGAACAG

ACTCACCATCTCCAAGGACACCTCCAAAAACCAGGTGGTCCTTACAATGA

CCAACATGGACCCTGTGGACACAGCCACGTATTACTGTGCAAGAGGGGGT

TATACTATGGACTACTGGGGCCAGGGA

>pVxK7b-037-hum07-HC (SEQ ID NO: 89)
CAGGTGCAGCTGCAGGAGTCGGGCCCAGGACTGGTGAAGCCTGGGGCTAC

AGTGAAAATCTCCTGCAAGGTTTCTGGCTACACCTTCACCAACTACTATG

TATTCTGGGTGCGACAGGCTCGTGGACAACGCCTTGAGTGGATAGGTGAC

ATTAATCCTGTCAATGGTGATACTAACTTCAATGAGAAATTCAAGAACAG

AGTCACGATTACCGCGGACAAATCCACGAGCACAGCCTACATGGAGCTGA

GCAGCCTGAGATCTGAGGACACGGCCGTGTATTACTGTGCGAGAGGGGGT

TATACTATGGACTACTGGGGCCAGGGA

>pVxK7b-037-hum08-HC (SEQ ID NO: 90)
CAGATCACCTTGAAGGAGTCTGGTCCTACGCTGGTGAAACCCACACAGAC

CCTCACGCTGACCTGCACCTTCTCTGGCTACACCTTCACCAACTACTATG

TATTCTGGATCAGGCAGTCCCCATCGAGAGGCCTTGAGTGGCTGGGTGAC

ATTAATCCTGTCAATGGTGATACTAACTTCAATGAGAAATTCAAGAACAG

ATTCACCATCTCCAGAGACAACGCCAAGAACTCACTGTATCTGCAAATGA

ACAGCCTGAGAGCCGAGGACACGGCTGTGTATTACTGTGCGAGAGGGGGT

TATACTATGGACTACTGGGGCCAGGGA

>pVxK7b-037-hum09-HC (SEQ ID NO: 91)
CAGGTGCAGCTGCAGGAGTCGGGCCCAGGACTGGTGAAGCCTTCACAGAC

CCTGTCCCTCACCTGCACTGTCTCTGGCTACACCTTCACCAACTACTATG

TATTCTGGGTGCGACAGGCTCGTGGACAACGCCTTGAGTGGATAGGTGAC

ATTAATCCTGTCAATGGTGATACTAACTTCAATGAGAAATTCAAGAACAG

ACTCACCATCTCCAAGGACACCTCCAAAAACCAGGTGGTCCTTACAATGA

CCAACATGGACCCTGTGGACACAGCCACGTATTACTGTGCAAGAGGGGGT

TATACTATGGACTACTGGGGCCAGGGA

>pVxK7b-037-hum10-HC (SEQ ID NO: 92)
CAGGTGCAGCTGCAGGAGTCGGGCCCAGGACTGGTGAAGCCTTCACAGAC

CCTGTCCCTCACCTGCACTGTCTCTGGCTACACCTTCACCAACTACTATG

TATTCTGGGTGCGACAGGCTCGTGGACAACGCCTTGAGTGGATAGGTGAC

ATTAATCCTGTCAATGGTGATACTAACTTCAATGAGAAATTCAAGAACAG

ACTCACCATCTCCAAGGACACCTCCAAAAACCAGGTGGTCCTTACAATGA

CCAACATGGACCCTGTGGACACAGCCACGTATTACTGTGCAAGAGGGGGT

TATACTATGGACTACTGGGGCCAGGGA

>pVxK7b-037-hum11-HC (SEQ ID NO: 93)
CAGGTGCAGCTGCAGGAGTCGGGCCCAGGACTGGTGAAGCCTGGGGCTAC

AGTGAAAATCTCCTGCAAGGTTTCTGGCTACACCTTCACCAACTACTATG

TATTCTGGGTGCGACAGGCTCGTGGACAACGCCTTGAGTGGATAGGTGAC

ATTAATCCTGTCAATGGTGATACTAACTTCAATGAGAAATTCAAGAACAG

AGTCACGATTACCGCGGACAAATCCACGAGCACAGCCTACATGGAGCTGA
GCAGCCTGAGATCTGAGGACACGGCCGTGTATTACTGTGCGAGAGGGGT
TATACTATGGACTACTGGGGCCAGGGA

>pVxK7b-037-hum12-HC
(SEQ ID NO: 94)
CAGGTGCAGCTGCAGGAGTCGGGCCCAGGACTGGTGAAGCCTGGGCTAC
AGTGAAAATCTCCTGCAAGGTTTCTGGCTACACCTTCACCAACTACTATG
TATTCTGGGTGCGACAGGCTCGTGGACAACGCCTTGAGTGGATAGGTGAC
ATTAATCCTGTCAATGGTGATACTAACTTCAATGAGAAATTCAAGAACAG
AGTCACGATTACCGCGGACAAATCCACGAGCACAGCCTACATGGAGCTGA
GCAGCCTGAGATCTGAGGACACGGCCGTGTATTACTGTGCGAGAGGGGT
TATACTATGGACTACTGGGGCCAGGGA >pVxK7b-037-hum13-HC
(SEQ ID NO: 95)
GAAGTGCAGCTGGTGCAGTCTGGAGCAGAGGTGAAAAAGCCCGGGGAGTC
TCTGAGGATCTCCTGTAAGGGTTCTGGCTACACCTTCACCAACTACTATG
TATTCTGGATCAGGCAGTCCCCATCGAGAGGCCTTGAGTGGCTGGGTGAC
ATTAATCCTGTCAATGGTGATACTAACTTCAATGAGAAATTCAAGAACAG
AGTCACGATTACCGCGGACAAATCCACGAGCACAGCCTACATGGAGCTGA
GCAGCCTGAGATCTGAGGACACGGCCGTGTATTACTGTGCGAGAGGGGT
TATACTATGGACTACTGGGGCCAGGA >pVxK7b-037-hum14-HC
(SEQ ID NO: 96)
CAGGTGCAGCTGCAGGAGTCGGGCCCAGGACTGGTGAAGCCTTCACAGAC
CCTGTCCCTCACCTGCACTGTCTCTGGCTACACCTTCACCAACTACTATG
TATTCTGGGTGCGACAGGCTCGTGGACAACGCCTTGAGTGGATAGGTGAC
ATTAATCCTGTCAATGGTGATACTAACTTCAATGAGAAATTCAAGAACAG
AGTCACCATCTCAGCCGACAAGTCCATCAGCACCGCCTACCTGCAGTGGA
GCAGCCTGAAGGCCTCGGACACCGCCATGTATTACTGTGCGAGAGGGGGT
TATACTATGGACTACTGGGGCCAGGGA >pVxK7b-037-hum15-HC
(SEQ ID NO: 97)
CAGGTGCAGCTGCAGGAGTCGGGCCCAGGACTGGTGAAGCCTTCACAGAC
CCTGTCCCTCACCTGCACTGTCTCTGGCTACACCTTCACCAACTACTATG
TATTCTGGGTGCGACAGGCTCGTGGACAACGCCTTGAGTGGATAGGTGAC
ATTAATCCTGTCAATGGTGATACTAACTTCAATGAGAAATTCAAGAACAG
ACTCACCATCTCCAAGGACACCTCCAAAAACCAGGTGGTCCTTACAATGA
CCAACATGGACCCTGTGGACACAGCCACGTATTACTGTGCAAGAGGGGGT
TATACTATGGACTACTGGGGCCAGGGA >pVxK7b-037-hum16-HC
(SEQ ID NO: 98)
CAGGTGCAGCTGCAGGAGTCGGGCCCAGGACTGGTGAAGCCTTCACAGAC
CCTGTCCCTCACCTGCACTGTCTCTGGCTACACCTTCACCAACTACTATG
TATTCTGGGTGCGACAGGCTCGTGGACAACGCCTTGAGTGGATAGGTGAC
ATTAATCCTGTCAATGGTGATACTAACTTCAATGAGAAATTCAAGAACAG
AGTCACCATCTCAGCCGACAAGTCCATCAGCACCGCCTACCTGCAGTGGA
GCAGCCTGAAGGCCTCGGACACCGCCATGTATTACTGTGCGAGAGGGGGT
TATACTATGGACTACTGGGGCCAGGGA >pVxK7b-037-hum17-HC
(SEQ ID NO: 99)
GAGGTCCAGCTGGTACAGTCTGGGGCTGAGGTGAAGAAGCCTGGGGCTAC
AGTGAAAATCTCCTGCAAGGTTTCTGGCTACACCTTCACCAACTACTATG
TATTCTGGATCCGCCAGCCCCAGGGAAGGGGCTGGAGTGGATTGGTGAC
ATTAATCCTGTCAATGGTGATACTAACTTCAATGAGAAATTCAAGAACAG
AGTCACGATTACCGCGGACAAATCCACGAGCACAGCCTACATGGAGCTGA
GCAGCCTGAGATCTGAGGACACGGCCGTGTATTACTGTGCGAGAGGGGGT
TATACTATGGACTACTGGGGCCAGGGA >pVxK7b-037-hum18-HC
(SEQ ID NO: 100)
GAAGTGCAGCTGGTGCAGTCTGGAGCAGAGGTGAAAAAGCCCGGGGAGTC
TCTGAGGATCTCCTGTAAGGGTTCTGGCTACACCTTCACCAACTACTATG
TATTCTGGATCAGGCAGTCCCCATCGAGAGGCCTTGAGTGGCTGGGTGAC
ATTAATCCTGTCAATGGTGATACTAACTTCAATGAGAAATTCAAGAACAG
AGTCACGATTACCGCGGACAAATCCACGAGCACAGCCTACATGGAGCTGA
GCAGCCTGAGATCTGAGGACACGGCCGTGTATTACTGTGCGAGAGGGGGT
TATACTATGGACTACTGGGGCCAGGGA >pVxK7b-037-hum19-HC
(SEQ ID NO: 101)
GAAGTGCAGCTGGTGCAGTCTGGAGCAGAGGTGAAAAAGCCCGGGGAGTC
TCTGAGGATCTCCTGTAAGGGTTCTGGCTACACCTTCACCAACTACTATG
TATTCTGGATCAGGCAGTCCCCATCGAGAGGCCTTGAGTGGCTGGGTGAC
ATTAATCCTGTCAATGGTGATACTAACTTCAATGAGAAATTCAAGAACAG
AGTCACGATTACCGCGGACAAATCCACGAGCACAGCCTACATGGAGCTGA
GCAGCCTGAGATCTGAGGACACGGCCGTGTATTACTGTGCGAGAGGGGGT
TATACTATGGACTACTGGGGCCAGGGA >pVxK7b-037-hum20-HC
(SEQ ID NO: 102)
CAGATCACCTTGAAGGAGTCTGGTCCTACGCTGGTGAAACCCACACAGAC
CCTCACGCTGACCTGCACCTTCTCTGGCTACACCTTCACCAACTACTATG
TATTCTGGGTGCGACAGGCCCCTGGACAAGGGCTTGAGTGGATGGGTGAC
ATTAATCCTGTCAATGGTGATACTAACTTCAATGAGAAATTCAAGAACAG
AGTCACGATTACCGCGGACAAATCCACGAGCACAGCCTACATGGAGCTGA
GCAGCCTGAGATCTGAGGACACGGCCGTGTATTACTGTGCGAGAGGGGGT
TATACTATGGACTACTGGGGCCAGGGA >pVxK7b-037-hum21-HC
(SEQ ID NO: 103)
CAGGTGCAGCTGCAGGAGTCGGGCCCAGGACTGGTGAAGCCTTCACAGAC
CCTGTCCCTCACCTGCACTGTCTCTGGCTACACCTTCACCAACTACTATG
TATTCTGGGTGCGACAGGCTCGTGGACAACGCCTTGAGTGGATAGGTGAC
ATTAATCCTGTCAATGGTGATACTAACTTCAATGAGAAATTCAAGAACAG
ACTCACCATCTCCAAGGACACCTCCAAAAACCAGGTGGTCCTTACAATGA -continued

CCAACATGGACCCTGTGGACACAGCCACGTATTACTGTGCAAGAGGGGGT

TATACTATGGACTACTGGGGCCAGGGA

>pVxK7b-037-hum22-HC
(SEQ ID NO: 104)
CAGGTGCAGCTGCAGGAGTCGGGCCCAGGACTGGTGAAGCCTTCACAGAC

CCTGTCCCTCACCTGCACTGTCTCTGGCTACACCTTCACCAACTACTATG

TATTCTGGGTGCGACAGGCTCGTGGACAACGCCTTGAGTGGATAGGTGAC

ATTAATCCTGTCAATGGTGATACTAACTTCAATGAGAAATTCAAGAACAG

ACTCACCATCTCCAAGGACACCTCCAAAAACCAGGTGGTCCTTACAATGA

CCAACATGGACCCTGTGGACACAGCCACGTATTACTGTGCAAGAGGGGGT

TATACTATGGACTACTGGGGCCAGGGA

>pVxK7b-037-hum23-HC
(SEQ ID NO: 105)
CAGGTGCAGCTGCAGGAGTCGGGCCCAGGACTGGTGAAGCCTTCACAGAC

CCTGTCCCTCACCTGCACTGTCTCTGGCTACACCTTCACCAACTACTATG

TATTCTGGGTGCGACAGGCTCGTGGACAACGCCTTGAGTGGATAGGTGAC

ATTAATCCTGTCAATGGTGATACTAACTTCAATGAGAAATTCAAGAACAG

ACTCACCATCTCCAAGGACACCTCCAAAAACCAGGTGGTCCTTACAATGA

CCAACATGGACCCTGTGGACACAGCCACGTATTACTGTGCAAGAGGGGGT

TATACTATGGACTACTGGGGCCAGGGA

>pVxK7b-037-hum24-HC
(SEQ ID NO: 106)
CAGGTGCAGCTGCAGGAGTCGGGCCCAGGACTGGTGAAGCCTGGGGCTAC

AGTGAAAATCTCCTGCAAGGTTTCTGGCTACACCTTCACCAACTACTATG

TATTCTGGGTGCGACAGGCTCGTGGACAACGCCTTGAGTGGATAGGTGAC

ATTAATCCTGTCAATGGTGATACTAACTTCAATGAGAAATTCAAGAACAG

AGTCACGATTACCGCGGACAAATCCACGAGCACAGCCTACATGGAGCTGA

GCAGCCTGAGATCTGAGGACACGGCCGTGTATTACTGTGCGAGAGGGGGT

TATACTATGGACTACTGGGGCCAGGGA

Chimeric Complete Light Chain Amino Acid Sequence

>VxP037-01-LC-Pro, below, represents a full length chimeric light chain variable domain (SEQ ID NO:7)+a constant domain amino acid sequence. The underlined amino acid sequence=framework 4+the constant domain. All full length humanized light chain sequences can contain a light chain variable region sequence selected from SEQ ID NOs: 7-31 in combination with framework 4+the same constant domain as VxP037-01-LC-Pro. However, while present, this constant domain is not shown for all the complete humanized light chain amino acid sequences.

>VxP037-01-LC-Pro
(SEQ ID NO: 107)
DVVMTQTPLSLSVSLGDQASISCRSSQSLVHSNGNTYLHWYLQKPGQSPK

LLIYKVSYRFSGVPDRFSGSGSGTDFTLKISRVEAEDLGVYFCSQNTHVP

RTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Chimeric Complete Light Chain Nucleic Acid Sequence

The underlined nucleic acid sequence encodes the underlined protein sequence in >VxP037-01-LC-Pro, above.

>VxP037-01-LC-DNA
(SEQ ID NO: 108)
GATGTTGTTATGACCCAAACTCCACTCTCCCTGTCTGTCAGTCTTGGAGA

TCAAGCCTCCATCTCTTGCAGATCTAGTCAGAGCCTTGTACACAGTAATG

GAAACACCTATTTACATTGGTACCTGCAGAAGCCAGGCCAGTCTCCAAAG

CTCCTGATCTACAAAGTTTCCTACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTTCTGCTCTCAAAATACACATGTTCCT

CGGACGTTCGGCCAAGGGACCAAGGTGGAAATCAAACGTACGGTGGCTGC

ACCATCTGTCTTCATCTTCCCGCCATCTGATGAGCAGTTGAAATCTGGAA

CTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

GTCACCCATCAGGGCCTGAGCTCGCCCGTCACAAAGAGCTTCAACAGGGG

AGAGTGTTGA

Chimeric and Humanized Complete Heavy Chain Amino Acid Sequences

>VxP037-01-HC-Pro, below, represents a full length chimeric heavy chain variable domain (SEQ ID NO:57)+a constant domain amino acid sequence. The underlined amino acid sequence=framework 4+the constant IgG1 domain. All full length humanized heavy chain sequences can contain a heavy chain variable region sequence selected from SEQ ID NOs:57-81 in combination with framework 4+the same constant domain as VxP037-01-HC-Pro. However, while present, this constant domain is not shown for all the complete humanized heavy chain amino acid sequences.

Chimeric Complete Heavy Chain Amino Acid Sequence

>VxP037-01-HC-Pro
(SEQ ID NO: 109)
EVQLQQFGAELVKPGASMKLSCKASGYTFTNYYVFWVKQRPGQGLEWIGD

INPVNGDTNFNEKFKNKATLTVDKSSTTTYLQLSSLTSEDSAVYYCTRGG

YTMDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

Chimeric Complete Heavy Chain Nucleic Acid Sequence

The underlined nucleic acid sequence encodes the underlined protein sequence in >VxP037-01-HC-Pro, above.

>VxP037-01-HC-DNA
(SEQ ID NO: 110)
GAGGTCCAGCTGCAGCAGTTTGGGGCTGAACTGGTGAAGCCTGGGGCTTC

AATGAAGTTGTCCTGCAAGGCTTCTGGCTACACCTTCACCAACTACTATG

TATTCTGGGTGAAACAGAGGCCTGGACAAGGCCTTGAGTGGATTGGAGAC

ATTAATCCTGTCAATGGTGATACTAACTTCAATGAGAAATTCAAGAACAA

GGCCACACTGACTGTAGACAAGTCCTCCACCACAACATACTTGCAACTCA

GCAGCCTGACATCTGAGGACTCTGCGGTCTATTACTGTACAAGAGGGGGT

TATACTATGGACTACTGGGGCCAGGGAACGCTGGTCACCGTCAGCTCAGC

CTCCACCAAGGGCCCATCGGTCTTCCCCCTGGCACCCTCCTCCAAGAGCA

CCTCTGGGGGCACAGCGGCCCTGGGCTGCCTGGTCAAGGACTACTTCCCC

GAACCGGTGACGGTGTCGTGGAACTCAGGCGCCCTGACCAGCGGCGTGCA

CACCTTCCCGGCTGTCCTACAGTCCTCAGGACTCTACTCCCTCAGCAGCG

TGGTGACCGTGCCCTCCAGCAGCTTGGGCACCCAGACCTACATCTGCAAC

GTGAATCACAAGCCCAGCAACACCAAGGTGGACAAGAAAGTTGAGCCCAA

ATCTTGTGACAAAACTCACACATGCCCACCGTGCCCAGCACCTGAACTCC

TGGGGGGACCGTCAGTCTTCCTCTTCCCCCCAAAACCCAAGGACACCCTC

ATGATCTCCCGGACCCCTGAGGTCACATGCGTGGTGGTGGACGTGAGCCA

CGAAGACCCTGAGGTCAAGTTCAACTGGTACGTGGACGGCGTGGAGGTGC

ATAATGCCAAGACAAAGCCGCGGGAGGAGCAGTACAACAGCACGTACCGT

GTGGTCAGCGTCCTCACCGTCCTGCACCAGGACTGGCTGAATGGCAAGGA

GTACAAGTGCAAGGTCAGCAACAAAGCCCTCCCAGCCCCCATCGAGAAAA

CCATCTCCAAAGCCAAAGGGCAGCCCCGAGAACCACAGGTGTACACCCTG

CCCCCATCCCGGGATGAGCTGACCAAGAACCAGGTCAGCCTGACCTGCCT

GGTCAAAGGCTTCTATCCCAGCGACATCGCCGTGGAGTGGGAGAGCAATG

GGCAGCCGGAGAACAACTACAAGACCACGCCTCCCGTGCTGGACTCCGAC

GGCTCCTTCTTCCTCTACAGCAAGCTCACCGTGGACAAGAGCAGGTGGCA

GCAGGGGAACGTCTTCTCATGCTCCGTGATGCATGAGGCTCTGCACAACC

ACTACACGCAGAAGAGCCTCTCCCTGTCTCCGGGTAAATGA

Complete IgG1 N2970, IgG2, IgG4 S228P, and IgG4 S228P L235E Heavy Chain Amino Acid Sequences >VxP037-01-HC-IgG1 N297Q-Pro, below, represents a full length heavy chain variable domain (SEQ ID NO:57)+a constant domain amino acid sequence. The underlined amino acid sequence=framework 4+the constant IgG1 constant domain containing a N→Q mutation at amino acid position 297. All full length humanized heavy chain sequences can contain a heavy chain variable region sequence selected from SEQ ID NOs:57-81 in combination with framework 4+the same constant domain as >VxP037-01-HC-IgG1 N297Q-Pro. However, while present, this constant domain is not shown for all the complete humanized heavy chain amino acid sequences.

>VxP037-01-HC-IgG1-N297Q-Pro
(SEQ ID NO: 111)
EVQLQQFGAELVKPGASMKLSCKASGYTFTNYYVFWVKQRPGQGLEWIGD

INPVNGDTNFNEKFKNKATLTVDKSSTTTYLQLSSLTSEDSAVYYCTRGG

YTMDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYQSTYR

VVSVLTVLHQDWLNGKEYKCKVSNKALPAPIEKTISKAKGQPREPQVYTL

PPSR

>pVxK7b-037-hum01-HC-IgG2-Pro, below, represents a full length heavy chain variable domain (SEQ ID NO:58)+a constant domain amino acid sequence. The underlined amino acid sequence=framework 4+the constant IgG2 domain. All full length humanized heavy chain sequences can contain a heavy chain variable region sequence selected from SEQ ID NOs:57-81 in combination with framework 4+the same constant domain as >pVxK7b-037-hum01-HC-IgG2-Pro. However, while present, this constant domain is not shown for all the complete humanized heavy chain amino acid sequences.

>pVxK7b-037-hum01-HC-IgG2-Pro
(SEQ ID NO: 112)
QVQLQESGPGLVKPSQTLSLTCTVSGYTFTNYYVFWVRQARGQRLEWIGD

INPVNGDTNFNEKFKNRVTISADKSISTAYLQWSSLKASDTAMYYCARGG

YTMDYWGQGTLVTVSSASTKGPSVFPLAPCSRSTSESTAALGCLVKDYFP

EPVTVSWNSGALTSGVHTFPAVLQSSGLYSLSSVVTVPSSNFGTQTYTCN

VDHKPSNTKVDKTVERKCCVECPPCPAPPVAGPSVFLFPPKPKDTLMISR

TPEVTCVVVDVSHEDPEVQFNWYVDGVEVHNAKTKPREEQFNSTFRVVSV

LTVVHQDWLNGKEYKCKVSNKGLPAPIEKTISKTKGQPREPQVYTLPPSR

EEMTKNQVSLTCLVKGFYPSDIAVEWESNGQPENNYNTTPPMLDSDGSFF

LYSKLTVDKSRWQQGNVFSCSVMHEALHNHYTQKSLSLSPGK

>pVxK7b-037-hum01-HC-IgG4 S228P-Pro, below, represents a full length heavy chain variable domain (SEQ ID NO:58)+a constant domain amino acid sequence. The underlined amino acid sequence=framework 4+the constant IgG4 S228P domain. All full length humanized heavy chain sequences can contain a heavy chain variable region sequence selected from SEQ ID NOs:57-81 in combination with framework 4+the same constant domain as >pVxK7b-037-hum01-HC-IgG4 S228P-Pro. However, while present, this constant domain is not shown for all the complete humanized heavy chain amino acid sequences.

>pVxK7b-037-hum01-HC-IgG4 S228P-Pro
(SEQ ID NO: 113)
QVQLQESGPGLVKPSQTLSLTCTVSGYTFTNYYVFWVRQARGQRLEWIGD

INPVNGDTNFNEKFKNRVTISADKSISTAYLQWSSLKASDTAMYYCARGG

YTMDYWGQGTTVTVSSASTKGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYGPPCPPCPAPEFLGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK

>pVxK7b-037-hum01-HC-IgG4 S228P L235E-Pro, below, represents a full length heavy chain variable domain (SEQ ID NO:58)+a constant domain amino acid sequence. The underlined amino acid sequence=framework 4+the constant IgG4 S228P L235E domain. All full length humanized heavy chain sequences can contain a heavy chain variable region sequence selected from SEQ ID NOs:57-81 in combination with framework 4+the same constant domain as >pVxK7b-037-hum01-HC-IgG4 S228P-L235E-Pro. However, while present, this constant domain is not shown for all the complete humanized heavy chain amino acid sequences.

>pVxK7b-037-hum01-HC-IgG4 S228P L235E-Pro
(SEQ ID NO: 122)
QVQLQESGPGLVKPSQTLSLTCTVSGYTFTNYYVFWVRQARGQRLEWIGD

INPVNGDTNFNEKFKNRVTISADKSISTAYLQWSSLKASDTAMYYCARGG

YTMDYWGQGTTVTVSSASTKGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYGPPCPPCPAPEFEGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK

Complete IgG1 N297Q, IgG2, IgG4 S228P, and IgG4 IgG4 S228P L235E Heavy Chain Nucleic Acid Sequences The underlined nucleic acid sequence encodes the underlined protein sequence in >VxP037-01-HC-IgG1 N297Q-Pro, above.

>VxP037-01-HC-IgG1 N297Q-DNA
(SEQ ID NO: 114)
GAGGTCCAGCTGCAGCAGTTTGGGGCTGAACTGGTGAAGCCTGGGCTTC

AATGAAGTTGTCCTGCAAGGCTTCTGGCTACACCTTCACCAACTACTATG

TATTCTGGGTGAAACAGAGGCCTGGACAAGGCCTTGAGTGGATTGGAGAC

ATTAATCCTGTCAATGGTGATACTAACTTCAATGAGAAATTCAAGAACAA

GGCCACACTGACTGTAGACAAGTCCTCCACCACAACATACTTGCAACTCA

GCAGCCTGACATCTGAGGACTCTGCGGTCTATTACTGTACAAGAGGGGGT

TATACTATGGACTACTGGGGCCAGGGAACGCTGGTCACCGTCAGCTCAGC

CTCCACCAAGGGCCCATCGGTCTTCCCCCTGGCACCCTCCTCCAAGAGCA

CCTCTGGGGGCACAGCGGCCCTGGGCTGCCTGGTCAAGGACTACTTCCCC

GAACCGGTGACGGTGTCGTGGAACTCAGGCGCTCTGACCAGCGGCGTGCA

CACCTTCCCGGCTGTCCTACAGTCCTCAGGACTCTACTCCCTCAGCAGCG

TGGTGACCGTGCCCTCCAGCAGCTTGGGCACCCAGACCTACATCTGCAAC

GTGAATCACAAGCCCAGCAACACCAAGGTGGACAAGAAAGTTGAGCCCAA

ATCTTGTGACAAAACTCACACATGCCCACCGTGCCCAGCACCTGAACTCC

TGGGGGGACCGTCAGTCTTCCTCTTCCCCCCAAAACCCAAGGACACCCTC

ATGATCTCCCGGACCCCTGAGGTCACATGCGTGGTGGTGGACGTGAGCCA

CGAAGACCCTGAGGTCAAGTTCAACTGGTACGTGGACGGCGTGGAGGTGC

ATAATGCCAAGACAAAGCCGCGGGAGGAGCAGTACCAGAGCACGTACCGT

GTGGTCAGCGTCCTCACCGTCCTGCACCAGGACTGGCTGAATGGCAAGGA

GTACAAGTGCAAGGTCAGCAACAAAGCCCTCCCAGCCCCCATCGAGAAAA

CCATCTCCAAAGCCAAAGGGCAGCCCCGAGAACCACAGGTGTACACCCTG

CCCCCATCCCGGGATGAGCTGACCAAGAACCAGGTCAGCCTGACCTGCCT

GGTCAAAGGCTTCTATCCCAGCGACATCGCCGTGGAGTGGGAGAGCAATG

GGCAGCCGGAGAACAACTACAAGACCACGCCTCCCGTGCTGGACTCCGAC

GGCTCCTTCTTCCTCTACAGCAAGCTCACCGTGGACAAGAGCAGGTGGCA

GCAGGGGAACGTCTTCTCATGCTCCGTGATGCATGAGGCTCTGCACAACC

ACTACACGCAGAAGAGCCTCTCCCTGTCTCCGGGTAAATGA

The underlined nucleic acid sequence encodes the underlined protein sequence in >VxP037-hum 01-HC-IgG2-Pro, above.

>pVxK7b-037-hum01-HC-IgG2-DNA
(SEQ ID NO: 115)
CAGGTGCAGCTGCAGGAGTCGGGCCCAGGACTGGTGAAGCCTTCACAGAC

CCTGTCCCTCACCTGCACTGTCTCTGGCTACACCTTCACCAACTACTATG

TATTCTGGGTGCGACAGGCTCGTGGACAACGCCTTGAGTGGATAGGTGAC

ATTAATCCTGTCAATGGTGATACTAACTTCAATGAGAAATTCAAGAACAG

AGTCACCATCTCAGCCGACAAGTCCATCAGCACCGCCTACCTGCAGTGGA

GCAGCCTGAAGGCCTCGGACACCGCCATGTATTACTGTGCGAGAGGGGGT

TATACTATGGACTACTGGGGCCAGGGAACGCTGGTCACCGTCAGCTCAGC

CTCCACCAAGGGCCCATCGGTCTTCCCCCTGGCACCCTGCTCCAGGAGCA

CCTCCGAGAGCACAGCGGCCCTGGGCTGCCTGGTCAAGGACTACTTCCCC

GAACCGGTGACGGTGTCGTGGAACTCAGGCGCTCTGACCAGCGGCGTGCA

CACCTTCCCGGCTGTCCTACAGTCCTCAGGACTCTACTCCCTCAGCAGCG

TGGTGACCGTGCCCTCCAGCAACTTCGGCACCCAGACCTACACCTGCAAC

GTAGATCACAAGCCCAGCAACACCAAGGTGGACAAGACAGTTGAGCGCAA

ATGTTGTGTCGAGTGCCCACCGTGCCCAGCACCACCTGTGGCAGGACCGT

CAGTCTTCCTCTTCCCCCCAAAACCCAAGGACACCCTCATGATCTCCCGG

ACCCCTGAGGTCACGTGCGTGGTGGTGGACGTGAGCCACGAAGACCCCGA

GGTCCAGTTCAACTGGTACGTGGACGGCGTGGAGGTGCATAATGCCAAGA

CAAAGCCACGGGAGGAGCAGTTCAACAGCACGTTCCGTGTGGTCAGCGTC

CTCACCGTCGTGCACCAGGACTGGCTGAACGGCAAGGAGTACAAGTGCAA

GGTGTCCAACAAAGGCCTCCCAGCCCCCATCGAGAAAACCATCTCCAAAA

CCAAAGGGCAGCCCCGAGAACCACAGGTGTACACCCTGCCCCCATCCCGG

GAGGAGATGACCAAGAACCAGGTCAGCCTGACCTGCCTGGTCAAAGGCTT

CTACCCCAGCGACATCGCCGTGGAGTGGGAGAGCAATGGGCAGCCGGAGA

ACAACTACAACACCACACCTCCCATGCTGGACTCCGACGGCTCCTTCTTC

CTCTACAGCAAGCTCACCGTGGACAAGAGCAGGTGGCAGCAGGGGAACGT

-continued

CTTCTCATGCTCCGTGATGCATGAGGCTCTGCACAACCACTACACGCAGA

AGAGCCTCTCCCTGTCTCCGGGTAAA

The underlined nucleic acid sequence encodes the underlined protein sequence in >VxP037-hum 01-HC-IgG4 S228P-Pro, above.

>pVxK7b-037-hum01-HC-IgG4 S228P-DNA
(SEQ ID NO: 116)
CAGGTGCAGCTGCAGGAGTCGGGCCCAGGACTGGTGAAGCCTTCACAGAC

CCTGTCCCTCACCTGCACTGTCTCTGGCTACACCTTCACCAACTACTATG

TATTCTGGGTGCGACAGGCTCGTGGACAACGCCTTGAGTGGATAGGTGAC

ATTAATCCTGTCAATGGTGATACTAACTTCAATGAGAAATTCAAGAACAG

AGTCACCATCTCAGCCGACAAGTCCATCAGCACCGCCTACCTGCAGTGGA

GCAGCCTGAAGGCCTCGGACACCGCCATGTATTACTGTGCGAGAGGGGGT

TATACTATGGACTACTGGGGCCAGGGCACCACCGTGACCGTGTCCTCCGC

TTCCACCAAGGGCCCATCCGTCTTCCCCCTGGCGCCCTGCTCCAGGAGCA

CCTCCGAGAGCACAGCCGCCCTGGGCTGCCTGGTCAAGGACTACTTCCCC

GAACCGGTGACGGTGTCGTGGAACTCAGGCGCCCTGACCAGCGGCGTGCA

CACCTTCCCGGCTGTCCTACAGTCCTCAGGACTCTACTCCCTCAGCAGCG

TGGTGACCGTGCCCTCCAGCAGCTTGGGCACGAAGACCTACACCTGCAAC

GTAGATCACAAGCCCAGCAACACCAAGGTGGACAAGAGAGTTGAGTCCAA

ATATGGTCCCCCATGCCCACCGTGCCCAGCACCTGAGTTCCTGGGGGGAC

CATCAGTCTTCCTGTTCCCCCCAAAACCCAAGGACACTCTCATGATCTCC

CGGACCCCTGAGGTCACGTGCGTGGTGGTGGACGTGAGCCAGGAAGACCC

CGAGGTCCAGTTCAACTGGTACGTGGATGGCGTGGAGGTGCATAATGCCA

AGACAAAGCCGCGGGAGGAGCAGTTCAACAGCACGTACCGTGTGGTCAGC

GTCCTCACCGTCCTGCACCAGGACTGGCTGAACGGCAAGGAGTACAAGTG

CAAGGTGTCCAACAAAGGCCTCCCGTCCTCCATCGAGAAAACCATCTCCA

AGCCAAAGGGCAGCCCCGAGAGCCACAGGTGTACACCCTGCCCCCATCC

CAGGAGGAGATGACCAAGAACCAGGTCAGCCTGACCTGCCTGGTCAAAGG

CTTCTACCCCAGCGACATCGCCGTGGAGTGGGAGAGCAATGGGCAGCCGG

AGAACAACTACAAGACCACGCCTCCCGTGCTGGACTCCGACGGCTCCTTC

TTCCTCTACAGCAGGCTAACCGTGGACAAGAGCAGGTGGCAGGAGGGGAA

TGTCTTCTCATGCTCCGTGATGCATGAGGCTCTGCACAACCACTACACAC

AGAAGAGCCTCTCCCTGTCTCTGGGTAAA

The underlined nucleic acid sequence encodes the underlined protein sequence in >VxP037-hum 01-HC-IgG4 S228P L235E-Pro, above.

> pVxK7b-037-hum01-HC-IgG4 S228P L235E-DNA
(SEQ ID NO: 123)
CAGGTGCAGCTGCAGGAGTCGGGCCCAGGACTGGTGAAGCCTTCACAGAC

CCTGTCCCTCACCTGCACTGTCTCTGGCTACACCTTCACCAACTACTATG

TATTCTGGGTGCGACAGGCTCGTGGACAACGCCTTGAGTGGATAGGTGAC

ATTAATCCTGTCAATGGTGATACTAACTTCAATGAGAAATTCAAGAACAG

AGTCACCATCTCAGCCGACAAGTCCATCAGCACCGCCTACCTGCAGTGGA

GCAGCCTGAAGGCCTCGGACACCGCCATGTATTACTGTGCGAGAGGGGGT

TATACTATGGACTACTGGGGCCAGGGCACCACCGTGACCGTGTCCTCCGC

TTCCACCAAGGGCCCATCCGTCTTCCCCCTGGCGCCCTGCTCCAGGAGCA

CCTCCGAGAGCACAGCCGCCCTGGGCTGCCTGGTCAAGGACTACTTCCCC

GAACCGGTGACGGTGTCGTGGAACTCAGGCGCCCTGACCAGCGGCGTGCA

CACCTTCCCGGCTGTCCTACAGTCCTCAGGACTCTACTCCCTCAGCAGCG

TGGTGACCGTGCCCTCCAGCAGCTTGGGCACGAAGACCTACACCTGCAAC

GTAGATCACAAGCCCAGCAACACCAAGGTGGACAAGAGAGTTGAGTCCAA

ATATGGTCCCCCATGCCCACCGTGCCCAGCACCTGAGTTCGAGGGGGGAC

CATCAGTCTTCCTGTTCCCCCCAAAACCCAAGGACACTCTCATGATCTCC

CGGACCCCTGAGGTCACGTGCGTGGTGGTGGACGTGAGCCAGGAAGACCC

CGAGGTCCAGTTCAACTGGTACGTGGATGGCGTGGAGGTGCATAATGCCA

AGACAAAGCCGCGGGAGGAGCAGTTCAACAGCACGTACCGTGTGGTCAGC

GTCCTCACCGTCCTGCACCAGGACTGGCTGAACGGCAAGGAGTACAAGTG

CAAGGTGTCCAACAAAGGCCTCCCGTCCTCCATCGAGAAAACCATCTCCA

AGCCAAAGGGCAGCCCCGAGAGCCACAGGTGTACACCCTGCCCCCATCC

CAGGAGGAGATGACCAAGAACCAGGTCAGCCTGACCTGCCTGGTCAAAGG

CTTCTACCCCAGCGACATCGCCGTGGAGTGGGAGAGCAATGGGCAGCCGG

AGAACAACTACAAGACCACGCCTCCCGTGCTGGACTCCGACGGCTCCTTC

TTCCTCTACAGCAGGCTAACCGTGGACAAGAGCAGGTGGCAGGAGGGGAA

TGTCTTCTCATGCTCCGTGATGCATGAGGCTCTGCACAACCACTACACAC

AGAAGAGCCTCTCCCTGTCTCTGGGTAAA

Framework 4+Light Chain Constant Domain Amino Acid Sequence (SEQ ID NO: 117)
TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC

Framework 4+Heavy Chain Constant IgG1 Domain (SEQ ID NO: 118)
TLVTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSNTK

VDKKVEPKSCDKTHTCPPCPAPELLGGPSVFLFPPKPKDTLMISRTPEVT

CVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTK

NQVSLTCLVKGFYPSDIAVEWESNGQPENNYKTTPPVLDSDGSFFLYSKL

TVDKSRWQQGNVFSCSVMHEALHNHYTQKSLSLSPGK

Framework 4+Heavy Chain Constant IgG1 N2970 Domain (SEQ ID NO: 119)

TLVTVSSASTKGPSVFPLAPSSKSTSGGTAALGCLVKDYFPEPVTVSWN

SGALTSGVHTFPAVLQSSGLYSLSSVVTVPSSSLGTQTYICNVNHKPSNT

KVDKKVEPKSCDKTHTCPPCPAPELLGGPSVFLFPPKPKDTLMISRTPE

VTCVVVDVSHEDPEVKFNWYVDGVEVHNAKTKPREEQYQSTYRVVSVL

TVLHQDWLNGKEYKCKVSNKALPAPIEKTISKAKGQPREPQVYTLPPSR

Framework 4+Heavy Chain Constant IgG2 Domain (SEQ ID NO: 120)

WGQGTLVTVSSASTKGPSVFPLAPCSRSTSESTAALGCLVKDYFPEPVTV

SWNSGALTSGVHTFPAVLQSSGLYSLSSVVTVPSSNFGTQTYTCNVDHKP

SNTKVDKTVERKCCVECPPCPAPPVAGPSVFLFPPKPKDTLMISRTPEVT

CVVVDVSHEDPEVQFNWYVDGVEVHNAKTKPREEQFNSTFRVVSVLTVVH

QDWLNGKEYKCKVSNKGLPAPIEKTISKTKGQPREPQVYTLPPSREEMTK

NQVSLTCLVKGFYPSDIAVEWESNGQPENNYNTTPPMLDSDGSFFLYSKL

TVDKSRWQQGNVFSCSVMHEALHNHYTQKSLSLSPGK

Framework 4+Heavy Chain Constant IgG4 S228P Domain (SEQ ID NO: 121)

TTVTVSSASTKGPSVFPLAPCSRSTSESTAALGCLVKDYFPEPVTVSWNS

GALTSGVHTFPAVLQSSGLYSLSSVVTVPSSSLGTKTYTCNVDHKPSNTK

VDKRVESKYGPPCPPCPAPEFLGGPSVFLFPPKPKDTLMISRTPEVTCVV

VDVSQEDPEVQFNWYVDGVEVHNAKTKPREEQFNSTYRVVSVLTVLHQDW

LNGKEYKCKVSNKGLPSSIEKTISKAKGQPREPQVYTLPPSQEEMTKNQV

SLTCLVKGFYPSDIAVEWESNGQPENNYKTTPPVLDSDGSFFLYSRLTVD

KSRWQEGNVFSCSVMHEALHNHYTQKSLSLSLGK

Framework 4+Heavy Chain Constant IgG4 S228P L235E Domain (SEQ ID NO: 124)

TTVTVSSASTKGPSVFPLAPCSRSTSESTAALGCLVKDYFPEPVTVSWNS

GALTSGVHTFPAVLQSSGLYSLSSVVTVPSSSLGTKTYTCNVDHKPSNTK

VDKRVESKYGPPCPPCPAPEFEGGPSVFLFPPKPKDTLMISRTPEVTCVV

VDVSQEDPEVQFNWYVDGVEVHNAKTKPREEQFNSTYRVVSVLTVLHQDW

LNGKEYKCKVSNKGLPSSIEKTISKAKGQPREPQVYTLPPSQEEMTKNQV

SLTCLVKGFYPSDIAVEWESNGQPENNYKTTPPVLDSDGSFFLYSRLTVD

KSRWQEGNVFSCSVMHEALHNHYTQKSLSLSLGK

---

What is claimed is:

1. A monoclonal antibody, or antigen-binding fragment thereof, that specifically binds CD47, wherein the monoclonal antibody, or antigen-binding fragment thereof, comprises a light chain variable region (LCVR), SEQ ID NO:20, and a heavy chain variable region (HCVR), SEQ ID NO:70, wherein SEQ ID NO:20 further comprises a light chain constant domain of SEQ ID NO:117, and wherein SEQ ID NO:70 further comprises a heavy chain constant domain selected from among SEQ ID NO:118, SEQ ID NO:119, SEQ ID NO:120, SEQ ID NO:121, and SEQ ID NO:124.

2. The monoclonal antibody, or antigen-binding fragment thereof, of claim 1 which comprises a heavy chain constant domain of SEQ ID NO:118.

* * * * *